US006503741B1

(12) United States Patent
Ashley et al.

(10) Patent No.: US 6,503,741 B1
(45) Date of Patent: Jan. 7, 2003

(54) **POLYKETIDE SYNTHASE GENES FROM *STREPTOMYCES VENEZUELAE***

(75) Inventors: Gary Ashley, Alameda, CA (US); Melanie C. Betlach, Burlingame, CA (US); Mary Betlach, San Francisco, CA (US); Robert McDaniel, Palo Alto, CA (US); Li Tang, Foster City, CA (US)

(73) Assignee: Kosan Biosciences, Inc., Burlingame, CA (US)

( * ) Notice: Subject to any disclaimer, the term of this patent is extended or adjusted under 35 U.S.C. 154(b) by 0 days.

(21) Appl. No.: 09/141,908

(22) Filed: Aug. 28, 1998

Related U.S. Application Data
(60) Provisional application No. 60/087,080, filed on May 28, 1998.

(51) Int. Cl.[7] .............................. C12N 9/00; C12N 1/20; C07H 21/04
(52) U.S. Cl. ............. 435/183; 435/252.33; 435/252.35; 435/254.2; 435/183; 435/189; 435/193; 435/232; 435/320.1; 536/23.2; 536/23.7; 536/23.1
(58) Field of Search ................................. 435/183, 189, 435/190, 252.3, 252.33, 252.35, 254.2, 193, 232, 320.1, 148, 145; 536/23.2, 23.1, 23.7

(56) References Cited

U.S. PATENT DOCUMENTS

| | | | |
|---|---|---|---|
| 4,551,433 A | 11/1985 | DeBoer | 435/253 |
| 4,874,748 A | 10/1989 | Katz et al. | 514/29 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,168,052 A | 12/1992 | Cox et al. | 435/72 |
| 5,252,474 A | 10/1993 | Gewain et al. | 435/172.3 |
| 5,514,544 A | 5/1996 | Rao et al. | 435/6 |
| 5,672,491 A | 9/1997 | Khosla et al. | 435/148 |
| 5,712,146 A | 1/1998 | Khosla et al. | 435/252.35 |
| 5,712,496 A | 1/1998 | Takahashi et al. | 257/64 |
| 5,824,513 A | 10/1998 | Katz et al. | 453/76 |
| 5,998,194 A * | 12/1999 | Summers, Jr. et al. | 435/252.33 |
| 6,200,813 B1 | 3/2001 | Katz et al. | 435/477 |
| 6,265,202 B1 * | 7/2001 | Sherman et al. | 435/252.31 |

FOREIGN PATENT DOCUMENTS

| | | |
|---|---|---|
| EP | 0 238 323 A2 | 9/1987 |
| EP | 0 238 323 B1 | 12/1994 |
| EP | 0 791 655 A2 | 8/1997 |
| EP | 0 791 656 A2 | 8/1997 |
| WO | WO 93/13663 | 7/1993 |
| WO | 95/08548 | 3/1995 |
| WO | 96/40968 | 12/1996 |
| WO | WO 97/02358 | 1/1997 |
| WO | WO 97/13845 | 4/1997 |
| WO | WO 97/22711 | 6/1997 |
| WO | WO 97/23630 | 7/1997 |
| WO | WO 98/01546 | 1/1998 |
| WO | WO 98/01571 | 1/1998 |
| WO | WO 98/27203 | 6/1998 |
| WO | WO 00/00620 | 1/2000 |

OTHER PUBLICATIONS

Malpartida et al. (1984) "Molecular Cloning of the Whole Biosynthetic Pathway of a Streptomyces . . . " Nature 309, 462–464.*

Katz et al. (1993) "polyketide Synthesis: Prospect for Hybrid Antibiotics" Ann. Rev. Microbiol. 47, 875–912.*

Fraley et al. (1983) "Expression of Bacterial Genes in Plant Cells" Proc. Natl. Acad. Sci. USA 80, 4803–4807.*

Weber et al. J. of Bacteriology, vol. 164, No. 1, issued Oct 1985, J.M. Weber et al, "Genetic Analysis of Erythromycin Production in *Streptomyces erythreus*," pp. 425–433, See the entire document.

Weber et al. J. of Bacteriology, vol. 172, No. 5, issued May 1990, J.M. Weber et al, "Organization of a Cluster of Erythromycin Genes in *Saccharomyces erythraea*," pp. 2372–2383. See the entire document.

Bartel, et al., "Biosynthesis of anthraquinones by interspecies cloning of actinorhodin biosynthesis genes in streptomycetes: Clarification of actinorhodin gene functions," *J. Bacteriol* (1990).

Bibb, et al., "Analysis of the nucleotide sequence of the *Streptomyces glaucescens* tcml genes provides key information about the enzymology of polyketide antibiotic biosynthesis," *EMBO J* (1989)8(9):2727–2735.

Brown, M. J. B. et al., "A Mutant Generated by Expression of an Engineered DEBS1 Protein from the Erythromycin–Producing Polyketide Synthase (PKS) in Streptomyces Coelicolor Produces the Triketide as a Lactone, but the Major Product is the Nor–Analogue Derived from Acetate as Starter Acid," *Journal of the Chemical Society*, Chemical Communications, GB, Chemical Society. No. 15, 1995, pp. 1517–1518, XP002044729 ISSN: 0022–4936.

Caballero et al., "Organisation and functions of the actVA region of the actinorhodin biosynthetic gene cluster of *Streptomyces coelicolor*," *Mol Gen Genet* (1991) 230:401–412.

Caffrey et al., FEBS Lett. (1992), 304:225–228.

Cane, D.E. et al., J. Am. Chem. Soc. (1993), 115:522–526.

Cane, D.E. et al., J. Antibiotics (1995), 48:647–651.

(List continued on next page.)

Primary Examiner—Nashaat T. Nashed
(74) Attorney, Agent, or Firm—Ted Apple; Kate Murashige; Kevin Kaster

(57) ABSTRACT

Combinatorial libraries of polyketides can be obtained by suitable manipulation of a host modular polyketide synthase gene cluster such as that which encodes the PKS for picromycin. The combinatorial library is useful as a source of pharmaceutically active compounds. In addition, novel polyketides and antibiotics are prepared using this method.

16 Claims, 30 Drawing Sheets

OTHER PUBLICATIONS

Dalbie–McFarland et al., Proc Natl Acad Sci USA (1982), 79:6409.

Donadio et al., "Biosynthesis of the erythromycin macrolactone and a rational approach for producing hybrid macrolides," *Gene* (1992) 115:97–103.

Donadio et al., Industrial Microorganism, Basic and Applied Molecular Genetics 91993, R.H. Baltz, G.D. Hegeman and PlL. Skatrud (eds)(Amer. Soc. Microbial).

Donadio, S. et al., Proc Natl Acad Sci USA (1993), 90:7119–7123.

Evans, D.A. et al., J. Am. Chem. Soc. (1992), 114: 9434–9453.

Fernandez–Moreno et al., "Nucleotide sequence and deduced functions of a set of cotranscribed genes of *Streptomyces coelicolor* A3(2) including the polyketide synthase for the antibiotic actinorhodin," *J Biol Chem* (1992) 267:19278–19290.

Fernandez–Moreno et al., "the act cluster contains regulatory and antibiotic export genes, direct targets for translational control by the bldA tRNA gene of Streptomyces," *Cell* (1991) 66:769–780.

Floss, "Genetic engineering of hybrid antibiotics—a progress report," *Tetrahydron* (1991) 47(31):6045–6058.

Fu, "Engineered biosynthesis of novel polyketides: Stereochemical course of two reactions catalyzed by a polyketide synthase," *Biochemistry* (1994) 33(31):9321–9326.

Geisselsoder et al., BioTechniques (1987), 5:786.

Hallam, "Nucleotide sequence, transcriptional and deduced function of a gene involved in polyketide antibiotic synthesis in *Streptomyces coelicolor*," *Gene* (1988) 74:305–320.

Hamilton et al., J. Bacteriol (1989), 171:4617.

Hopwood et al., "Product of 'hybrid' antibiotics by genetic engineering," *Nature* (1985) 314 (6012):642–644.

Ireland, R.E. et al., *J. Org. Chem,* (1980), 45:1868–1880.

Jay, E. et al., *J. Org. Chem.* (1984), 259:6311–6317.

Kao, C.M. et al., J. Am. Chem. Soc. (1994), 116:11612–11613.

Kao, C.M et al., Science (1994), 265:509–512.

Khosla, C., et al., "Genetic construction and functional analysis of hybrid polyketide synthases containing heterologous acyl carrier proteins," *J Bacteriol* (1993), 175:2197–2204.

Khosla, Chaitan et al., "Generation of polyketide libraries via combinatorial biosynthesis," Tibtech Sep. 1996 (vol. 14) pp. 335–341.

Khosla, et al., "Targeted gene replacements in a *Streptomyces* polyketide synthase gene cluster: role for the acyl carrier protein," *Mole Microbiol* (1992) 6(21):3237–3249.

Kuhstoss, S. et al., Gene (1996) 183:231–236.

Kunkel, T.A., Proc Natl Acad Sci USA (1985), 82:448.

Lambalot, R.H. et al., J. Antibiotics (1992), 45:1981–1982.

Lehrer, R. et al., J. Immunol Meth (1991), 137:167–173.

MacNeil, D.J. , J. Bacteriol (1988), 170:5607.

Malpartida et al., "Homology between Streptomyces genes coding for synthesis of different polyketides used to clone antibiotic biosynthetic genes," *Nature* (1987) 325(6107):818–821.

Malpartida et al., "Physical and genetic characterisation of the gene cluster for the antibiotic actinorhodin in *Streptomyces coelicolor* A3(2)," *Mol. Gen Genet* (1986) 205:66–73.

Martin, S.F. et al., J. Am. Chem. Soc. (1997), 119:3193.

Masamune et al., J. Am. Chem. Soc. (1975), 97:3512–3513.

Masumoto, T. et al., Tetrohedron Lett.(1988), 29:3575.

McDaniel et al., 1993 "Engineered biosynthesis of novel polyketides", *Science* 262:1546–1550 (1993).

Perun, T.J., Drug Action and Drug Resistance in Bacteria, vol. 1, S. Mitsuhashi (ed) Univ. Park Press, Baltimore, 1977.

Sherman et al., "Functional replacement of genes for individual polyketide synthase components in *Streptomyces coelicolor* A3(2) by heterogenous genes from a different polyketide pathway," *J Bacteriol* (1992) 174:6184–6190.

Sherman et al., "Structure and deduced function of the granaticin–producing polyketide synthase gene cluster of *Streptomyces violaceoruber* Tü22," *Embo J.* (1989) 8:2717–2725.

Toshima, K. et al., J. Am Chem. Soc. (1995), 117:3717.

Tuan et al., Gene (1990), 90:21.

Vedejs, E. et al., *J. Am Chem Soc* (1987), 109:5437–5446.

Vedejs, E. et al., *J. Am Chem Soc* (1989), 111:8430–8438.

Woodward, R.B. et al., J. Am. Chem. Soc. (1981), 103:3215.

Zoller, et al., Methods in Enzymology (1983), 100:468.

International Patent Search Report.

Netlach, M.C., et al., "Characterization of the Macrolide P–450 Hydroxylase from *Streptomyces venezuelae* which Converts Narbomycin t Picromycin," *Bichemistry* (1998) 37:14937–14942.

Cortes, J., et al., "An unusually large multifunctional polypeptide in the erythromycin–producing polyketide synthase of *Saccharopolyspora erythraea*," *Nature* (Nov. 8, 1990) 348:176–178.

Beck, J., et al., "the multifunctional 6–methylsalicylic acid synthase gene of *Penicillium patulum* its gene structure relative ot that of other polyketide synthases," *Eur J Biochem* (1990) 192:487–498.

MacNeil, D.J., et al., "Complex organization of the *Streptomyces avermitilis* genes encoding the avermectin polyketide synthase," *Gene* (1992) 115:119–125.

Donadio, S., et al., "Modular Organization of Genes Required for Complex Polyketide Biosynthesis," *Science* (May 3, 1991) 252:675–679.

Oliynyk, M., et al., "A hybrid modular polyketide synthase obtained by domain swapping," *Chemistry & Biology* (Oct. 1996) 3:833–839.

Xue, Y. et al., "Hydroxylation of macrolactones YC–17 and narbomycin is mediated by the pikc–encoded cytochrome P450 in *Streptomyces venezuelae*," *Chemistry & Biology* (1998), 5:661–667.

Xue, Y. et al., "A gene cluster for macrolide antibiotic biosynthesis in *Streptomyces venezuelae*: Architecture of metabolic diversity," *Proc. Natl. Acad. Sci. USA* (1998), 95:12111–12116.

Unpublished Manuscript, "The amino acid sequencing of the putative methymycin synthase from *Streptomyces venezuelae*." (Oct. 1997).

* cited by examiner

Scheme 1.

6: narbonolide (R=H)
7: 10-methylnarbonolide (R=Me)

8: narbomycin (R=H)
9: 10-methylnarbomycin (R=Me)

10: picromycin (R=H)
11: 10-methylpicromycin (R=Me)

Scheme 2.

Cosmid pKOS023-27, complete sequence of the insert, 38506 nucleotides

| From Nucleotide | To Nucleotide | Description |
|---|---|---|
| 70 | 13725 | picAI |
| 70 | 13725 | narbonilide synthase 1 (NARS1) |
| 148 | 1434 | KS start |
| 1780 | 2802 | AT start |
| 2869 | 3141 | ACP start |
| 3208 | 7593 | module 1 |
| 3208 | 4497 | KS1 |
| 4828 | 5847 | AT1 |
| 6499 | 7257 | KR1 |
| 7336 | 7593 | ACP1 |
| 7693 | 13332 | module 2 |
| 7693 | 8974 | KS2 |
| 9418 | 10554 | AT2 |
| 10594 | 11160 | DH2 |
| 12175 | 12960 | KR2 |
| 13063 | 13332 | ACP2 |
| 13830 | 25049 | picAII |
| 13830 | 25049 | narbonolide synthase 2 (NARS2) |
| 13935 | 18392 | module 3 |
| 13935 | 15224 | KS3 |
| 15540 | 16562 | AT3 |
| 17271 | 18071 | KR3 (inactive) |
| 18123 | 18392 | ACP3 |
| 18447 | 24767 | module 4 |
| 18447 | 19736 | KS4 |
| 20031 | 21050 | AT4 |
| 21093 | 21626 | DH4 |
| 22620 | 23588 | ER4 |
| 23652 | 24423 | KR4 |
| 24498 | 24765 | ACP4 |
| 25133 | 29821 | picAIII |
| 25133 | 29821 | narbonolide synthase 3 (NARS3) |
| 25235 | 29567 | module 5 |
| 25235 | 26530 | KS5 |
| 26822 | 27841 | AT5 |
| 28474 | 29227 | KR5 |
| 29302 | 29569 | ACP5 |
| 29924 | 33964 | picAIV |
| 29924 | 33964 | narbonolide synthase 4 (NARPS4) |
| 30026 | 31312 | KS6 |
| 30026 | 32986 | module 6 |
| 31604 | 32635 | AT6 |
| 32708 | 32986 | ACP6 |
| 33068 | 33961 | NARS thioesterase domain |
| 33961 | 34806 | picB |
| 33961 | 34806 | typeII thioesterase homolog |
| 34863 | 36011 | picCII |
| 34863 | 36011 | 4-keto-6-deoxyglucose isomerase |
| 36159 | 37439 | picCIII |
| 36159 | 37439 | desosaminyl transferase |
| 37529 | 38242 | picCVI |
| 37529 | 38242 | 3-amino dimethyltransferase |

*FIG. 5*
(CONTINUED)

KOS023-27 (SEQ ID NO:1)

```
   1 GATCATGCGG AGCACTCCTT CTCTCGTGCT CCTACCGGTG ATGTGCGCGC CGAATTGATT
  61 CGTGGAGAGA TGTCGACAGT GTCCAAGAGT GAGTCCGAGG AATTCGTGTC CGTGTCGAAC
 121 GACGCCGGTT CCGCGCACGG CACAGCGGAA CCCGTCGCCG TCGTCGGCAT CTCCTGCCGG
 181 GTGCCCGGCG CCCGGGACCC GAGAGAGTTC TGGGAACTCC TGGCGGCAGG CGGCCAGGCC
 241 GTCACCGACG TCCCCGCGGA CCGCTGGAAC GCCGGCGACT TCTACGACCC GGACCGCTCC
 301 GCCCCCGGCC GCTCGAACAG CCGGTGGGGC GGGTTCATCG AGGACGTCGA CCGGTTCGAC
 361 GCCGCCTTCT TCGGCATCTC GCCCCGCGAG GCCGCGGAGA TGGACCCGCA GCAGCGGCTC
 421 GCCCTGGAGC TGGGCTGGGA GGCCCTGGAG CGCGCCGGGA TCGACCCGTC CTCGCTCACC
 481 GGCACCCGCA CCGGCGTCTT CGCCGGCGCC ATCTGGGACG ACTACGCCAC CCTGAAGCAC
 541 CGCCAGGGCG CGCCGCGAT CACCCCGCAC ACCGTCACCG GCCTCCACCG CGGCATCATC
 601 GCGAACCGAC TCTCGTACAC GCTCGGGCTC CGCGGCCCCA GCATGGTCGT CGACTCCGGC
 661 CAGTCCTCGT CGCTCGTCGC CGTCCACCTC GCGTGCGAGA GCCTGCGGCG CGGCGAGTCC
 721 GAGCTCGCCC TCGCCGGCGG CGTCTCGCTC AACCTGGTGC CGGACAGCAT CATCGGGGCG
 781 AGCAAGTTCG GCGGCCTCTC CCCCGACGGC CGCGCCTACA CCTTCGACGC GCGCGCCAAC
 841 GGCTACGTAC GCGGCGAGGG CGGCGGTTTC GTCGTCCTGA AGCGCCTCTC CCGGGCCGTC
 901 GCCGACGGCG ACCCGGTGCT CGCCGTGATC CGGGGCAGCG CCGTCAACAA CGGCGGCGCC
 961 GCCCAGGGCA TGACGACCCC CGACGCGCAG GCGCAGGAGG CCGTGCTCCG CGAGGCCCAC
1021 GAGCGGGCCG GGACCGCGCC GGCCGACGTG CGGTACGTCG AGCTGCACGG CACCGGCACC
1081 CCCGTGGGCG ACCCGATCGA GGCCGCTGCG CTCGGCGCCG CCCTCGGCAC CGGCCGCCCG
1141 GCCGGACAGC CGCTCCTGGT CGGCTCGGTC AAGACGAACA TCGGCCACCT GGAGGGCGCG
1201 GCCGGCATCG CCGGCCTCAT CAAGGCCGTC CTGGCGGTCC GCGGTCGCGC GCTGCCCGCC
1261 AGCCTGAACT ACGAGACCCC GAACCCGGCG ATCCCGTTCG AGGAACTGAA CCTCCGGGTG
1321 AACACGGAGT ACCTGCCGTG GGAGCCGGAG CACGACGGGC AGCGGATGGT CGTCGGCGTG
1381 TCCTCGTTCG GCATGGGCGG CACGAACGCG CATGTCGTGC TCGAAGAGGC CCCGGGGGTT
1441 GTCGAGGGTG CTTCGGTCGT GGAGTCGACG GTCGGCGGGT CGGCGGTCGG CGGCGGTGTG
1501 GTGCCGTGGG TGGTGTCGGC GAAGTCCGCT GCCGCGCTGG ACGCGCAGAT CGAGCGGCTT
1561 GCCGCGTTCG CCTCGCGGGA TCGTACGGAT GGTGTCGACG CGGGCGCTGT CGATGCGGGT
1621 GCTGTCGATG CGGGTGCTGT CGCTCGCGTA CTGGCCGGCG GCGTGCTCA GTTCGAGCAC
1681 CGGGCCGTCG TCGTCGGCAG CGGGCCGGAC GATCTGGCGG CAGCGCTGGC CGCGCCTGAG
1741 GGTCTGGTCC GGGGCGTGGC TTCCGGTGTC GGGCGAGTGG CGTTCGTGTT CCCCGGGCAG
1801 GGCACGCAGT GGGCCGGCAT GGGTGCCGAA CTGCTGGACT CTTCCGCGGT GTTCGCGGCG
1861 GCCATGGCCG AATGCGAGGC CGCACTCTCC CCGTACGTCG ACTGGTCGCT GGAGGCCGTC
1921 GTACGGCAGG CCCCCGGTGC GCCCACGCTG GAGCGGGTCG ATGTCGTGCA GCCTGTGACG
1981 TTCGCCGTCA TGGTCTCGCT GGCTCGCGTG TGGCAGCACC ACGGGGTGAC GCCCCAGGCG
2041 GTCGTCGGCC ACTCGCAGGG CGAGATCGCC GCCGCGTACG TCGCCGGTGC CCTGAGCCTG
2101 GACGACGCCG CTCGTGTCGT GACCCTGCGC AGCAAGTCCA TCGCCGCCCA CCTCGCCGGC
2161 AAGGGCGGCA TGCTGTCCCT CGCGCTGAGC GAGGACGCCG TCCTGGAGCG ACTGGCCGGG
2221 TTCGACGGGC TGTCCGTCGC CGCTGTGAAC GGGCCCACCG CCACCGTGGT CTCCGGTGAC
2281 CCCGTACAGA TCGAAGAGCT TGCTCGGGCG TGTGAGGCCG ATGGGGTCCG TGCGCGGGTC
2341 ATTCCCGTCG ACTACGCGTC CCACAGCCGG CAGGTCGAGA TCATCGAGAG CGAGCTCGCC
2401 GAGGTCCTCG CCGGGCTCAG CCCGCAGGCT CCGCGCGTGC CGTTCTTCTC GACACTCGAA
2461 GGCGCCTGGA TCACCGAGCC CGTGCTCGAC GGCGGCTACT GGTACCGCAA CCTGCGCCAT
2521 CGTGTGGGCT TCGCCCCGGC CGTCGAGACC CTGGCCACCG ACGAGGGCTT CACCCACTTC
2581 GTCGAGGTCA GCGCCCACCC CGTCCTCACC ATGCCCTCC CCGGGACCGT CACCGGTCTG
2641 GCGACCCTGC GTCGCGACAA CGGCGGTCAG GACCGCCTCG TCGCCTCCCT CGCCGAAGCA
2701 TGGGCCAACG GACTCGCGGT CGACTGGAGC CCGCTCCTCC CCTCCGCGAC CGGCCACCAC
2761 TCCGACCTCC CCACCTACGC GTTCCAGACC GAGCGCCACT GGCTGGGCGA GATCGAGGCG
2821 CTCGCCCCGG CGGGCGAGCC GGCGGTGCAG CCCGCCGTCC TCCGCACGGA GGCGGCCGAG
2881 CCGGCGGAGC TCGACCGGGA CGAGCAGCTG CGCGTGATCC TGGACAAGGT CCGGGCGCAG
2941 ACGGCCCAGG TGCTGGGGTA CGCGACAGGC GGGCAGATCG AGGTCGACCG GACCTTCCGT
3001 GAGGCCGGTT GCACCTCCCT GACCGGCGTG GACCTGCGCA ACCGGATCAA CGCCGCCTTC
3061 GGCGTACGGA TGGCGCCGTC CATGATCTTC GACTTCCCCA CCCCCGAGGC TCTCGCGGAG
3121 CAGCTGCTCC TCGTCGTGCA CGGGGAGGCG GCGGCGAACC GGCCGGTGC GGAGCCGGCT
3181 CCGGTGGCGG CGGCCGGTGC CGTCGACGAG CCGGTGGCGA TCGTCGGCAT GGCCTGCCGC
3241 CTGCCCGGTG GGTCGCCTC GCCGGAGGAC CTGTGGCGGC TGGTGGCCGG CGGCGGGAC
3301 GCGATCTCGG AGTTCCCGCA GGACCGCGGC TGGGACGTGG AGGGGCTGTA CCACCCGGAT
3361 CCCGAGCACC CCGGCACGTC GTACGTCCGC CAGGGCGGTT TCATCGAGAA CGTCGCCGGC
```

*FIG. 5*
(CONTINUED)

```
3421 TTCGACGCGG CCTTCTTCGG GATCTCGCCG CGCGAGGCCC TCGCCATGGA CCCGCAGCAG
3481 CGGCTCCTCC TCGAAACCTC CTGGGAGGCC GTCGAGGACG CCGGGATCGA CCCGACCTCC
3541 CTGCGGGGAC GGCAGGTCGG CGTCTTCACT GGGGCGATGA CCCACGAGTA CGGGCCGAGC
3601 CTGCGGGACG GCGGGGAAGG CCTCGACGGC TACCTGCTGA CCGGCAACAC GGCCAGCGTG
3661 ATGTCGGGCC GCGTCTCGTA CACACTCGGC CTTGAGGGCC CCGCCCTGAC GGTGGACACG
3721 GCCTGCTCGT CGTCGCTGGT CGCCCTGCAC CTCGCCGTGC AGGCCCTGCG CAAGGGCGAG
3781 GTCGACATGG CGCTCGCCGG CGGCGTGGCC GTGATGCCCA CGCCCGGGAT GTTCGTCGAG
3841 TTCAGCCGGC AGCGCGGGCT GGCCGGGGAC GGCCGGTCGA AGGCGTTCGC CGCGTCGGCG
3901 GACGGCACCA GCTGGTCCGA GGGCGTCGGC GTCCTCCTCG TCGAGCGCCT GTCGGACGCC
3961 CGCCGCAACG GACACCAGGT CCTCGCGGTC GTCCGCGGCA GCGCCGTGAA CCAGGACGGC
4021 GCGAGCAACG GCCTCACGGC TCCGAACGGG CCCTCGCAGC AGCGCGTCAT CCGGCGCGCG
4081 CTGGCGGACG CCCGGCTGAC GACCTCCGAC GTGGACGTCG TCGAGGCACA CGGCACGGGC
4141 ACGCGACTCG GCGACCCGAT CGAGGCGCAG GCCCTGATCG CCACCTACGG CCAGGGCCGT
4201 GACGACGAAC AGCCGCTGCG CCTCGGGTCG TTGAAGTCCA ACATCGGGCA CACCCAGGCC
4261 GCGGCCGGCG TCTCCGGTGT CATCAAGATG GTCCAGGCGA TGCGCCACGG ACTGCTGCCA
4321 AAGACGCTGC ACGTCGACGA GCCCTCGGAC CAGATCGACT GGTCGGCTGG CGCCGTGGAA
4381 CTCCTCACCG AGGCCGTCGA CTGGCCGGAG AAGCAGGACG GCGGGCTGCG CCGGGCCGCC
4441 GTCTCCTCCT TCGGGATCAG CGGCACCAAT GCGCATGTGG TGCTCGAAGA GGCCCCGGTG
4501 GTTGTCGAGG GTGCTTCGGT CGTCGAGCCG TCGGTTGGCG GGTCGGCGGT CGGCGGCGGT
4561 GTGACGCCTT GGGTGGTGTC GGCGAAGTCC GCTGCCGCGC TCGACGCGCA GATCGAGCGG
4621 CTTGCCGCAT TCGCCTCGCG GGATCGTACG GATGACGCCG ACGCCGGTGC TGTCGACGCG
4681 GGCGCTGTCG CTCACGTACT GGCTGACGGG CGTGCTCAGT TCGAGCACCG GCCGTCGCG
4741 CTCGGCGCCG GGGCGGACGA CCTCGTACAG GCGCTGGCCG ATCCGGACGG GCTGATACGC
4801 GGAACGGCTT CCGGTGTCGG GCGAGTGGCG TTCGTGTTCC CCGGTCAGGG CACGCAGTGG
4861 GCTGGCATGG GTGCCGAACT GCTGGACTCT TCCGCGGTGT TCGCGGCGGC CATGGCCGAG
4921 TGTGAGGCCG CGCTGTCCCC GTACGTCGAC TGGTCGCTGG AGGCCGTCGT ACGGCAGGCC
4981 CCCGGTGCGC CCACGCTGGA GCGGGTCGAT GTCGTGCAGC CTGTGACGTT CGCCGTCATG
5041 GTCTCGCTGG CTCGCGTGTG GCAGCACCAC GGTGTGACGC CCCAGGCGGT CGTCGGCCAC
5101 TCGCAGGGCG AGATCGCCGC CGCGTACGTC GCCGGAGCCC TGCCCCTGGA CGACGCCGCC
5161 CGCGTCGTCA CCCTGCGCAG CAAGTCCATC GCCGCCCACC TCGCCGGCAA GGGCGGCATG
5221 CTGTCCCTCG CGCTGAACGA GGACGCCGTC CTGGAGCGAC TGAGTGACTT CGACGGGCTG
5281 TCCGTCGCCG CCGTCAACGG GCCCACCGCC ACTGTCGTGT CGGGTGACCC CGTACAGATC
5341 GAAGAGCTTG CTCAGGCGTG CAAGGCGGAC GGATTCCGCG CGCGGATCAT TCCCGTCGAC
5401 TACGCGTCCC ACAGCCGGCA GGTCGAGATC ATCGAGAGCG AGCTCGCCCA GGTCCTCGCC
5461 GGTCTCAGCC CGCAGGCCCC GCGCGTGCCG TTCTTCTCGA CGCTCGAAGG CACCTGGATC
5521 ACCGAGCCCG TCCTCGACGG CACCTACTGG TACCGCAACC TCCGTCACCG CGTCGGCTTC
5581 GCCCCCGCCA TCGAGACCCT GGCCGTCGAC GAGGGCTTCA CGCACTTCGT CGAGGTCAGC
5641 GCCCACCCCG TCCTCACCAT GACCCTCCCC GAGACCGTCA CCGGCCTCGG CACCCTCCGT
5701 CGCGAACAGG GAGGCCAAGA GCGTCTGGTC ACCTCGCTCG CCGAGGCGTG GTCAACGGG
5761 CTTCCCGTGG CATGGACTTC GCTCCTGCCC GCCACGGCCT CCCGCCCCGG TCTGCCCACC
5821 TACGCCTTCC AGGCCGAGCG CTACTGGCTC GAGAACACTC CCGCCGCCCT GGCCACCGGC
5881 GACGACTGGC GCTACCGCAT CGACTGGAGA CGCCTCCCGG CCGCCGAGGG GTCCGAGCGC
5941 ACCGGCCTGT CCGGCCGCTG GCTCGCCGTC ACGCCGGAGG ACCACTCCGC GCAGGCCGCC
6001 GCCGTGCTCA CCGCGCTGGT CGACGCCGGG GCGAAGGTCG AGGTGCTGAC GGCCGGGGCG
6061 GACGACGACC GTGAGGCCCT CGCCGCCCGG CTCACCGCAC TGACGACCGG TGACGGCTTC
6121 ACCGGCGTGG TCTCGCTCCT CGACGGACTC GTACCGCAGG TCGCCTGGGT CCAGGCGCTC
6181 GGCGACGCCG GAATCAAGGC GCCCCTGTGG TCCGTCACCC AGGGCGCGGT CTCCGTCGGA
6241 CGTCTCGACA CCCCCGCCGA CCCCGACCGG GCCATGCTCT GGGGCCTCGG CCGCGTCGTC
6301 GCCCTTGAGC ACCCCGAACG CTGGGCCGGC CTCGTCGACC TCCCCGCCCA GCCCGATGCC
6361 GCCGCCCTCG CCCACCTCGT CACCGCACTC TCCGGCGCCA CCGGCGAGGA CCAGATCGCC
6421 ATCCGCACCA CCGGACTCCA CGCCCGCCGC CTCGCCCGCG CACCCCTCCA CGGACGTCGG
6481 CCCACCCGCG ACTGGCAGCC CCACGGCACC GTCCTCATCA CCGGCGGCAC CGGAGCCCTC
6541 GGCAGCCACG CCGCACGCTG GATGGCCCAC CACGGAGCCG AACACCTCCT CCTCGTCAGC
6601 CGCAGCGGCG AACAAGCCCC GGAGCCACC CAACTCACCG CCGAACTCAC CGCATCGGGC
6661 GCCCGCGTCA CCATCGCCGC CTGCGACGTC GCCGACCCCC ACGCCATGCG CACCCTCCTC
6721 GACGCCATCC CCGCCGAGAC GCCCCTCACC GCCGTCGTCC ACACCGCCGG CGCGCTCGAC
6781 GACGGCATCG TGGACACGCT GACCGCCGAG CAGGTCCGGC GGGCCCACCG TGCGAAGGCC
6841 GTCGGCGCCT CGGTGCTCGA CGAGCTGACC CGGGACCTCG ACCTCGACGC GTTCGTGCTC
```

*FIG. 5*
(CONTINUED)

```
 6901 TTCTCGTCCG TGTCGAGCAC TCTGGGCATC CCCGGTCAGG GCAACTACGC CCCGCACAAC
 6961 GCCTACCTCG ACGCCCTCGC GGCTCGCCGC CGGGCCACCG GCCGGTCCGC CGTCTCGGTG
 7021 GCCTGGGGAC CGTGGGACGG TGGCGGCATG GCCGCCGGTG ACGGCGTGGC CGAGCGGCTG
 7081 CGCAACCACG GCGTGCCCGG CATGGACCCG GAACTCGCCC TGGCCGCACT GGAGTCCGCG
 7141 CTCGGCCGGG ACGAGACCGC GATCACCGTC GCGGACATCG ACTGGGACCG CTTCTACCTC
 7201 GCGTACTCCT CCGGTCGCCC GCAGCCCTC GTCGAGGAGC TGCCCGAGGT GCGGCGCATC
 7261 ATCGACGCAC GGGACAGCGC CACGTCCGGA CAGGGCGGGA GCTCCGCCCA GGGCGCCAAC
 7321 CCCCTGGCCG AGCGGCTGGC CGCCGCGGCT CCCGGCGAGC GTACGGAGAT CCTCCTCGGT
 7381 CTCGTACGGG CGCAGGCCGC CGCCGTGCTC CGGATGCGTT CGCCGGAGGA CGTCGCCGCC
 7441 GACCGCGCCT TCAAGGACAT CGGCTTCGAC TCGCTCGCCG GTGTCGAGCT GCGCAACAGG
 7501 CTGACCCGGG CGACCGGGCT CCAGCTGCCC GCGACGCTCG TCTTCGACCA CCCGACGCCG
 7561 CTGGCCCTCG TGTCGCTGCT CCGCAGCGAG TTCCTCGGTG ACGAGGAGAC GGCGGACGCC
 7621 CGGCGGTCCG CGGCGCTGCC CGCGACTGTC GGTGCCGGTG CCGGCGCCGG CGCCGGCACC
 7681 GATGCCGACG ACGATCCGAT CGCGATCGTC GCGATGAGCT GCCGCTACCC CGGTGACATC
 7741 CGCAGCCCGG AGGACCTGTG GCGGATGCTG TCCGAGGGCG CGAGGGCAT CACGCCGTTC
 7801 CCCACCGACC GCGGCTGGGA CCTCGACGGC CTGTACGACG CCGACCCGGA CGCGCTCGGC
 7861 AGGGCGTACG TCCGCGAGGG CGGGTTCCTG CACGACGCGG CCGAGTTCGA CGCGGAGTTC
 7921 TTCGGCGTCT CGCCGCGCGA GGCGCTGGCC ATGGACCCGC AGCAGCGGAT GCTCCTGACG
 7981 ACGTCCTGGG AGGCCTTCGA GCGGGCCGGC ATCGACCGCG CATCCTGCG CGGCAGCAGC
 8041 ACCGGTGTCT TCATCGGCCT CTCCTACCAG GACTACGCGG CCCGCGTCCC GAACGCCCCG
 8101 CGTGGCGTGG AGGGTTACCT GCTGACCGGC AGCACGCCGA GCGTCGCGTC GGGCCGTATC
 8161 GCGTACACCT TCGGTCTCGA AGGGCCCGCG ACGACCGTCG ACACCGCCTG CTCGTCGTCG
 8221 CTGACCGCCC TGCACCTGGC GGTGCGGGCG CTGCGCAGCG GCGAGTGCAC GATGGCGCTC
 8281 GCCGGTGGCG TGGCGATGAT GGCGACCCCG CACATGTTCG TGGAGTTCAG CCGTCAGCGG
 8341 GCGCTCGCCC CGGACGGCCG CAGCAAGGCC TTCTCGGCGG ACGCCGACGG GTTCGGCGCC
 8401 GCGGAGGGCG TCGGCCTGCT GCTCGTGGAG CGGCTCTCGG ACGCGCGGCG CAACGGTCAC
 8461 CCGGTGCTCG CCGTGGTCCG CGGTACCGCC GTCAACCAGG ACGGCGCCAG CAACGGGCTG
 8521 ACCGCGCCCA ACGGACCCTC GCAGCAGCGG GTGATCCGGC AGGCGCTCGC CGACGCCCGG
 8581 CTGGCACCCG GCGACATCGA CGCCGTCGAG ACGCACGGCA CGGGAACCTC GCTGGGCGAC
 8641 CCCATCGAGG CCCAGGGCCT CCAGGCCACG TACGGCAAGG AGCGGCCCGC GGAACGGCCG
 8701 CTCGCCATCG GCTCCGTGAA GTCCAACATC GGACACACCC AGGCCGCGGC CGGTGCGGCG
 8761 GGCATCATCA AGATGGTCCT CGCGATGCGC CACGGCACCC TGCCGAAGAC CCTCCACGCC
 8821 GACGAGCCGA GCCCGCACGT CGACTGGGCG AACAGCGGCC TGGCCCTCGT CACCGAGCCG
 8881 ATCGACTGGC CGGCCGGCAC CGGTCCGCGC CGCGCCGCCG TCTCCTCCTT CGGCATCAGC
 8941 GGGACGAACG CGCACGTCGT GCTGGAGCAG GCGCCGGATG CTGCTGGTGA GGTGCTTGGG
 9001 GCCGATGAGG TGCCTGAGGT GTCTGAGACG GTAGCGATGG CTGGGACGGC TGGGACCTCC
 9061 GAGGTCGCTG AGGGCTCTGA GGCCTCCGAG GCCCCGCGG CCCCGGCAG CCGTGAGGCG
 9121 TCCCTCCCCG GCACCTGCC CTGGGTGCTG TCCGCCAAGG ACGAGCAGTC GCTGCGCGGC
 9181 CAGGCCGCCG CCCTGCACGC GTGGCTGTCC GAGCCCGCCG CCGACCTGTC GGACGCGGAC
 9241 GGACCGGCCC GCCTGCGGGA CGTCGGGTAC ACGCTCGCCA CGAGCCGTAC CGCCTTCGCG
 9301 CACCGCGCCG CCGTGACCGC CGCCGACCGG GACGGGTTCC TGGACGGGCT GGCCACGCTG
 9361 GCCCAGGGCG GCACCTCGGC CCACGTCCAC CTGGACACCG CCCGGGACGG CACCACCGCG
 9421 TTCCTCTTCA CCGGCCAGGG CAGTCAGCGC CCCGGCGCCG GCCGTGAGCT GTACGACCGG
 9481 CACCCCGTCT TCGCCCGGGC GCTCGACGAG ATCTGCGCCC ACCTCGACGG TCACCTCGAA
 9541 CTGCCCCTGC TCGACGTGAT GTTCGCGGCC GAGGGCAGCG CGGAGGCCGC GCTGCTCGAC
 9601 GAGACGCGGT ACACGCAGTG CGCGCTGTTC GCCCTGGAGG TCGCGCTCTT CCGGCTCGTC
 9661 GAGAGCTGGG GCATGCGGCC GGCCGCACTG CTCGGTCACT CGGTCGGCGA GATCGCCGCC
 9721 GCGCACGTCG CCGGTGTGTT CTCGCTCGCC GACGCCGCCC GCCTGGTCGC CGCGCGCGGC
 9781 CGGCTCATGC AGGAGCTGCC CGCCGGTGGC GCGATGCTCG CCGTCCAGGC CGCGGAGGAC
 9841 GAGATCCGCG TGTGGCTGGA GACGGAGGAG CGGTACGCGG GACGTCTGGA CGTCGCCGCC
 9901 GTCAACGGCC CCGAGGCCGC CGTCCTGTCC GGCGACGCGG ACGCGGCGCG GGAGGCGGAG
 9961 GCGTACTGGT CCGGGCTCGG CCGCAGGACC CGCGCGCTGC GGGTCAGCCA CGCCTTCCAC
10021 TCCGCGCACA TGGACGGCAT GCTCGACGGG TTCCGCGCCG TCCTGGAGAC GGTGGAGTTC
10081 CGGCGCCCCT CCCTGACCGT GGTCTCGAAC GTCACCGGCC TGGCCGCCGG CCCGGACGAC
10141 CTGTGCGACC CCGAGTACTG GGTCCGGCAC GTCCGCGGCA CCGTCCGCTT CCTCGACGGC
10201 GTCCGTGTCC TGCCGACCT CGGCGTGCGG ACCTGCCTGG AGCTGGGCCC CGACGGGGTC
10261 CTCACCGCCA TGGCGGCCGA CGGCCTCGCG GACACCCCCG CGGATTCCGC TGCCGGCTCC
10321 CCCGTCGGCT CTCCCGCCGG CTCTCCCGCC GACTCCGCCG CCGGCGCGCT CCGGCCCCGG
```

FIG. 5
(CONTINUED)

```
10381 CCGCTGCTCG TGGCGCTGCT GCGCCGCAAG CGGTCGGAGA CCGAGACCGT CGCGGACGCC
10441 CTCGGCAGGG CGCACGCCCA CGGCACCGGA CCCGACTGGC ACGCCTGGTT CGCCGGCTCC
10501 GGGGCGCACC GCGTGGACCT GCCCACGTAC TCCTTCCGGC GCGACCGCTA CTGGCTGGAC
10561 GCCCCGGCGG CCGACACCGC GGTGGACACC GCCGGCCTCG GTCTCGGCAC CGCCGACCAC
10621 CCGCTGCTCG GCGCCGTGGT CAGCCTTCCG GACCGGGACG GCCTGCTGCT CACCGGCCGC
10681 CTCTCCCTGC GCACCCACCC GTGGCTCGCG GACCACGCCG TCCTGGGGAG CGTCCTGCTC
10741 CCCGGCGCCG CGATGGTCGA ACTCGCCGCG CACGCTGCGG AGTCCGCCGG TCTGCGTGAC
10801 GTGCGGGAGC TGACCCTCCT TGAACCGCTG GTACTGCCCG AGCACGGTGG CGTCGAGCTG
10861 CGCGTGACGG TCGGGGCGCC GGCCGGAGAG CCCGGTGGCG AGTCGGCCGG GGACGGCGCA
10921 CGGCCCGTCT CCCTCCACTC GCGGCTCGCC GACGCGCCCG CCGGTACCGC CTGGTCCTGC
10981 CACGCGACCG GTCTGCTGGC CACCGACCGG CCCGAGCTTC CCGTCGCGCC CGACCGTGCG
11041 GCCATGTGGC CGCCGCAGGG CGCCGAGGAG GTGCCGCTCG ACGGTCTCTA CGAGCGGCTC
11101 GACGGGAACG GCCTCGCCTT CGGTCCGCTG TTCCAGGGGC TGAACGCGGT GTGGCGGTAC
11161 GAGGGTGAGG TCTTCGCCGA CATCGCGCTC CCCGCCACCA CGAATGCGAC CGCGCCCGCG
11221 ACCGCGAACG GCGGCGGGAG TGCGGCGGCG GCCCCTACG GCATCCACCC CGCCCTGCTC
11281 GACGCTTCGC TGCACGCCAT CGCGGTCGGC GGTCTCGTCG ACGAGCCCGA GCTCGTCCGC
11341 GTCCCCTTCC ACTGGAGCGG TGTCACCGTG CACGCGGCCG GTGCCGCGGC GGCCCGGGTC
11401 CGTCTCGCCT CCGCGGGGAC GGACGCCGTC TCGCTGTCCC TGACGGACGG CGAGGGACGC
11461 CCGCTGGTCT CCGTGGAACG GCTCACGCTG CGCCCGGTCA CCGCCGATCA GGCGGCGGCG
11521 AGCCGCGTCG GCGGGCTGAT GCACCGGGTG GCCTGGCGTC CGTACGCCCT CGCCTCGTCC
11581 GGCGAACAGG ACCCGCACGC CACTTCGTAC GGGCCGACCG CCGTCCTCGG CAAGGACGAG
11641 CTGAAGGTCG CCGCCGCCCT GGAGTCCGCG GGCGTCGAAG TCGGGCTCTA CCCCGACCTG
11701 GCCGCGCTGT CCCAGGACGT GGCGGCCGGC GCCCCGGCGC CCGTACCGT CCTTGCGCCG
11761 CTGCCCGCGG GTCCGCCGA CGGCGGCGCG GAGGGTGTAC GGGGCACGGT GGCCCGGACG
11821 CTGGAGCTGC TCCAGGCCTG GCTGGCCGAC GAGCACCTCG CGGGCACCCG CCTGCTCCTG
11881 GTCACCCGCG GTGCGGTGCG GGACCCCGAG GGGTCCGGCG CCGACGATGG CGGCGAGGAC
11941 CTGTCGCACG CGGCCGCCTG GGGTCTCGTA CGGACCGCGC AGACCGAGAA CCCCGGCCGC
12001 TTCGGCCTTC TCGACCTGGC CGACGACGCC TCGTCGTACC GGACCCTGCC GTCGGTGCTC
12061 TCCGACGCGG GCCTGCGCGA CGAACCGCAG CTCGCCCTGC ACGACGGCAC CATCAGGCTG
12121 GCCCGCCTGG CCTCCGTCCG GCCCGAGACC GGCACCGCCG CACCGGCGCT CGCCCCGGAG
12181 GGCACGGTCC TGCTGACCGG CGGCACCGGC GGCCTGGGCG GACTGGTCGC CCGGCACGTG
12241 GTGGGCGAGT GGGGCGTACG ACGCCTGCTG CTGGTGAGCC GGCGGGGCAC GGACGCCCCG
12301 GGCGCCGACG AGCTCGTGCA CGAGCTGGAG GCCCTGGGAG CCGACGTCTC GGTGGCCGCG
12361 TGCGACGTCG CCGACCGCGA AGCCCTCACC GCCGTACTCG ACGCCATCCC CGCCGAACAC
12421 CCGCTCACCG CGGTCGTCCA CACGGCAGGC GTCCTCTCCG ACGGCACCCT CCCGTCCATG
12481 ACGACGGAGG ACGTGGAACA CGTACTGCGG CCCAAGGTCG ACGCCGCGTT CCTCCTCGAC
12541 GAACTCACCT CGACGCCCGC ATACGACCTG GCAGCGTTCG TCATGTTCTC CTCCGCCGCC
12601 GCCGTCTTCG GTGGCGCGGG GCAGGGCGCC TACGCCGCCG CCAACGCCAC CCTCGACGCC
12661 CTCGCCTGGC GCCGCCGGGC AGCCGGACTC CCCGCCCTCT CCCTCGGCTG GGGCCTCTGG
12721 GCCGAGACCA GCGGCATGAC CGGCGAGCTC GGCCAGGCGG ACCTGCGCCG GATGAGCCGC
12781 GCGGGCATCG GCGGGATCAG CGACGCCGAG GGCATCGCGC TCCTCGACGC CGCCCTCCGC
12841 GACGACCGCC ACCCGGTCCT GCTGCCCCTG CGGCTCGACG CCGCCGGGCT GCGGGACGCG
12901 GCCGGGAACG ACCCGGCCGG AATCCCGGCG CTCTTCCGGG ACGTCGTCGG CGCCAGGACC
12961 GTCCGGGCCC GGCCGTCCGC GGCCTCCGCC TCGACGACAG CCGGGACGGC CGGCACGCCG
13021 GGGACGGCGG ACGGCGCGGC GGAAACGGCG GCGGTCACGC TCGCCGACCG GGCCGCCACC
13081 GTGGACGGGC CCGCACGGCA GCGCCTGCTG CTCGAGTTCG TCGTCGGCGA GGTCGCCGAA
13141 GTACTCGGCC ACGCCCGCGG TCACCGGATC GACGCCGAAC GGGGCTTCCT CGACCTCGGC
13201 TTCGACTCCC TGACCGCCGT CGAACTCCGC AACCGGCTCA ACTCCGCCGG TGGCCTCGCC
13261 CTCCCGGCGA CCCTGGTCTT CGACCACCCA AGCCCGGCGG CACTCGCCTC CCACCTGGAC
13321 GCCGAGCTGC CGCGCGGCGC CTCGGACCAG GACGGAGCCG GAACCGGAA CGGGAACGAG
13381 AACGGGACGA CGGCGTCCCG GAGCACCGCC GAGACGGACG CGCTGCTGGC ACAACTGACC
13441 CGCCTGGAAG GCGCCTTGGT GCTGACGGGC CTCTCGGACG CCCCCGGGAG CGAAGAAGTC
13501 CTGGAGCACC TGCGGTCCCT GCGCTCGATG GTCACGGGCG AGACCGGGAC CGGGACCGCG
13561 TCCGGAGCCC CGGACGGCGC CGGGTCCGGC GCCGAGGACC GGCCCTGGGC GGCCGGGGAC
13621 GGAGCCGGGG GCGGGAGTGA GGACGGCGCG GGAGTGCCGG ACTTCATGAA CGCCTCGGCC
13681 GAGGAACTCT TCGGCCTCCT CGACCAGGAC CCAGCACGG ACTGATCCCT GCCGCACGGT
13741 CGCCTCCCGC CCCGGACCCC GTCCCGGGCA CCTCGACTCG AATCACTTCA TGCGCGCCTC
13801 GGGCGCCTCC AGGAACTCAA GGGGACAGCG TGTCCACGGT GAACGAAGAG AAGTACCTCG
```

FIG. 5
(CONTINUED)

```
13861 ACTACCTGCG TCGTGCCACG GCGGACCTCC ACGAGGCCCG TGGCCGCCTC CGCGAGCTGG
13921 AGGCGAAGGC GGGCGAGCCG GTGGCGATCG TCGGCATGGC CTGCCGCCTG CCCGGCGGCG
13981 TCGCCTCGCC CGAGGACCTG TGGCGGCTGG TGGCCGGCGG CGAGGACGCG ATCTCGGAGT
14041 TCCCCCAGGA CCGCGGCTGG GACGTGGAGG GCCTGTACGA CCCGAACCCG GAGGCCACGG
14101 GCAAGAGTTA CGCCCGCGAG GCCGGATTCC TGTACGAGGC GGGCGAGTTC GACGCCGACT
14161 TCTTCGGGAT CTCGCCGCGC GAGGCCCTCG CCATGGACCC GCAGCAGCGT CTCCTCCTGG
14221 AGGCCTCCTG GGAGGCGTTC GAGCACGCCG GGATCCCGGC GGCCACCGCG CGCGGCACCT
14281 CGGTCGGCGT CTTCACCGGC GTGATGTACC ACGACTACGC CACCCGTCTC ACCGATGTCC
14341 CGGAGGGCAT CGAGGGCTAC CTGGGCACCG GCAACTCCGG CAGTGTCGCC TCGGGCCGCG
14401 TCGCGTACAC GCTTGGCCTG GAGGGGCCGG CCGTCACGGT CGACACCGCC TGCTCGTCCT
14461 CGCTGGTCGC CCTGCACCTC GCCGTGCAGG CCCTGCGCAA GGGCGAGGTC GACATGGCGC
14521 TCGCCGGCGG CGTGACGGTC ATGTCGACGC CAGCACCTT CGTCGAGTTC AGCCGTCAGC
14581 GCGGGCTGGC GCCGGACGGC CGGTCGAAGT CCTTCTCGTC GACGGCCGAC GGCACCAGCT
14641 GGTCCGAGGG CGTCGGCGTC CTCCTCGTCG AGCGCCTGTC CGACGCGCGT CGCAAGGGCC
14701 ATCGGATCCT CGCCGTGGTC CGGGGCACCG CCGTCAACCA GGACGGCGCC AGCAGCGGCC
14761 TCACGGCTCC GAACGGGCCG TCGCAGCAGC GCGTCATCCG ACGTGCCCTG GCGGACGCCC
14821 GGCTCACGAC CTCCGACGTG GACGTCGTCG AGGCCCACGG CACGGGTACG CGACTCGGCG
14881 ACCCGATCGA GGCGCAGGCC GTCATCGCCA CGTACGGGCA GGGCCGTGAC GGCGAACAGC
14941 CGCTGCGCCT CGGGTCGTTG AAGTCCAACA TCGGACACAC CCAGGCCGCG GCCGGTGTCT
15001 CCGGCGTGAT CAAGATGGTC CAGGCCGATG GCCACGGCGT CCTGCCGAAG ACGCTCCACG
15061 TGGAGAAGCC GACGGACCAG GTGGACTGGT CCGCGGGCGC GGTCGAGCTG CTCACCGAGG
15121 CCATGGACTG GCCGGACAAG GGCGACGGCG GACTGCGCAG GGCCGCGGTC TCCTCCTTCG
15181 GCGTCAGCGG GACGAACGCG CACGTCGTGC TCAAGAGGC CCCGGCGGCC GAGGAGACCC
15241 CTGCCTCCGA GGCGACCCCG GCCGTCGAGC CGTCGGTCGG CGCCGGCCTG GTGCCGTGGC
15301 TGGTGTCGGC GAAGACTCCG GCCGCGCTGG ACGCCCAGAT CGGACGCCTC GCCGCGTTCG
15361 CCTCGCAGGG CCGTACGGAC GCCGCCGATC CGGGCGCGGT CGCTCGCGTA CTGGCCGGCG
15421 GGCGCGCCGA GTTCGAGCAC CGGGCCGTCG TGCTCGGCAC CGGACAGGAC GATTTCGCGC
15481 AGGCGCTGAC CGCTCCGGAA GGACTGATAC GCGGCACGCC CTCGGACGTG GGCCGGGTGG
15541 CGTTCGTGTT CCCCGGTCAG GGCACGCAGT GGGCCGGGAT GGGCGCCGAA CTCCTCGACG
15601 TGTCGAAGGA GTTCGCGGCG GCCATGGCCG AGTGCGAGAG CGCGCTCTCC CGCTATGTCG
15661 ACTGGTCGCT GGAGGCCGTC GTCCGGCAGG CGCCGGGCGC GCCCACGCTG AGCGGGTCG
15721 ACGTCGTCCA GCCCGTGACC TTCGCTGTCA TGGTTTCGCT GGCGAAGGTC TGGCAGCACC
15781 ACGGCGTGAC GCCGCAGGCC GTCGTCGGCC ACTCGCAGGG CGAGATCGCC GCCGCGTACG
15841 TCGCCGGTGC CCTCACCCTC GACGACGCCG CCCGCGTCGT CACCCTGCGC AGCAAGTCCA
15901 TCGCCGCCCA CCTCGCCGGC AAGGGCGGCA TGATCTCCCT CGCCCTCAGC GAGGAAGCCA
15961 CCCGGCAGCG CATCGAGAAC CTCCACGGAC TGTCGATCGC CGCCGTCAAC GGCCCCACCG
16021 CCACCGTGGT TTCGGGCGAC CCCACCCAGA TCCAAGAGCT CGCTCAGGCG TGTGAGGCCG
16081 ACGGGGTCCG CGCACGGATC ATCCCCGTCG ACTACGCCTC CCACAGCGCC CACGTCGAGA
16141 CCATCGAGAG CGAACTCGCC GAGGTCCTCG CCGGGCTCAG CCCGCGGACA CCTGAGGTGC
16201 CGTTCTTCTC GACACTCGAA GGCGCCTGGA TCACCGAGCC GGTGCTCGAC GGCACCTACT
16261 GGTACCGCAA CCTCCGCCAC CGCGTCGGCT TCGCCCCCGC CGTCGAGACC CTCGCCACCG
16321 ACGAAGGCTT CACCCACTTC ATCGAGGTCA GCGCCCACCC CGTCCTCACC ATGACCCTCC
16381 CCGAGACCGT CACCGGCCTC GGCACCCTCC GCCGCGAACA GGGAGGCCAG GAGCGTCTGG
16441 TCACCTCACT CGCCGAAGCC TGGACCAACG GCCTCACCAT CGACTGGGCG CCCGTCCTCC
16501 CCACCGCAAC CGGCCACCAC CCCGAGCTCC CCACCTACGC CTTCCAGCGC CGTCACTACT
16561 GGCTCCACGA CTCCCCCGCC GTCCAGGGCT CCGTGCAGGA CTCCTGGCGC TACCGCATCG
16621 ACTGGAAGCG CCTCGCGGTC GCCGACGCGT CCGAGCGCGC CGGGCTGTCC GGGCGCTGGC
16681 TCGTCGTCGT CCCCGAGGAC CGTTCCGCCG AGGCCGCCCC GGTGCTCGCC GCGCTGTCCG
16741 GCGCCGGCGC CGACCCCGTA CAGCTGGACG TGTCCCCGCT GGGCGACCGG CAGCGGCTCG
16801 CCGCGACGCT GGGCGAGGCC CTGGCGGCGG CCGGTGGAGC CGTCGACGGC GTCCTCTCGC
16861 TGCTCGCGTG GGACGAGAGC GCGCACCCCG GCCACCCCGC CCCCTTCACC CGGGGCACCG
16921 GCGCCACCCT CACCCTGGTG CAGGCGCTGG AGGACGCCGG CGTCGCCGCC CCGCTGTGGT
16981 GCGTGACCCA CGGCGCGGTG TCCGTCGGCC GGGCCGACCA CGTCACCTCC CCCGCCCAGG
17041 CCATGGTGTG GGGCATGGGC CGGGTCGCCG CCCTGGAGCA CCCCGAGCGG TGGGGCGGCC
17101 TGATCGACCT GCCCTCGGAC GCCGACCGGG CGGCCCTGGA CCGCATGACC ACGGTCCTCG
17161 CCGGCGGTAC GGGTGAGGAC CAGGTCGCGG TACGCGCCTC CGGGCTGCTC GCCCGCCGCC
17221 TCGTCCGCGC CTCCCTCCCG GCGCACGGCA CGGCTTCGCC GTGGTGGCAG GCCGACGGCA
17281 CGGTGCTCGT CACCGGTGCC GAGGAGCCTG CGGCCGCCGA GGCCGCACGC CGGCTGGCCC
```

FIG. 5
(CONTINUED)

```
17341 GCGACGGCGC CGGACACCTC CTCCTCCACA CCACCCCCTC CGGCAGCGAA GGCGCCGAAG
17401 GCACCTCCGG TGCCGCCGAG GACTCCGGCC TCGCCGGGCT CGTCGCCGAA CTCGCGGACC
17461 TGGGCGCGAC GGCCACCGTC GTGACCTGCG ACCTCACGGA CGCGGAGGCG GCCGCCCGGC
17521 TGCTCGCCGG CGTCTCCGAC GCGCACCCGC TCAGCGCCGT CCTCCACCTG CCGCCCACCG
17581 TCGACTCCGA GCCGCTCGCC GCGACCGACG CGGACGCGCT CGCCCGTGTC GTGACCGCGA
17641 AGGCCACCGC CGCGCTCCAC CTGGACCGCC TCCTGCGGGA GGCCGCGGCT GCCGGAGGCC
17701 GTCCGCCCGT CCTGGTCCTC TTCTCCTCGG TCGCCGCGAT CTGGGGCGGC GCCGGTCAGG
17761 GCGCGTACGC CGCCGGTACG GCCTTCCTCG ACGCCCTCGC CGGTCAGCAC CGGGCCGACG
17821 GCCCCACCGT GACCTCGGTG GCCTGGAGCC CCTGGGAGGG CAGCCGCGTC ACCGAGGGTG
17881 CGACCGGGGA GCGGCTGCGC CGCCTCGGCC TGCGCCCCCT CGCCCCGCG ACGGCGCTCA
17941 CCGCCCTGGA CACCGCGCTC GGCCACGGCG ACACCGCCGT CACGATCGCC GACGTCGACT
18001 GGTCGAGCTT CGCCCCCGGC TTCACCACGG CCCGGCCGGG CACCCTCCTC GCCGATCTGC
18061 CCGAGGCGCG CCGCGCGCTC GACGAGCAGC AGTCGACGAC GGCCGCCGAC GACACCGTCC
18121 TGAGCCGCGA GCTCGGTGCG CTCACCGGCG CCGAACAGCA GCGCCGTATG CAGGAGTTGG
18181 TCCGCGAGCA CCTCGCCGTG GTCCTCAACC ACCCCTCCCC CGAGGCCGTC GACACGGGGC
18241 GGGCCTTCCG TGACCTCGGA TTCGACTCGC TGACGGCGGT CGAGCTCCGC AACCGCCTCA
18301 AGAACGCCAC CGGCCTGGCC CTCCCGGCCA CTCTGGTCTT CGACTACCCG ACCCCCCGGA
18361 CGCTGGCGGA GTTCCTCCTC GCGGAGATCC TGGGCGAGCA GGCCGGTGCC GGCGAGCAGC
18421 TTCCGGTGGA CGGCGGGGTC GACGACGAGC CCGTCGCGAT CGTCGGCATG GCGTGCCGCC
18481 TGCCGGGCGG TGTCGCCTCG CCGGAGGACC TGTGGCGGCT GGTGGCCGGC GGCGAGGACG
18541 CGATCTCCGG CTTCCCGCAG GACCGCGGCT GGGACGTGGA GGGGCTGTAC GACCCGGACC
18601 CGGACGCGTC CGGGCGGACG TACTGCCGTG CCGGTGGCTT CCTCGACGAG GGGGCGAGT
18661 TCGACGCCGA CTTCTTCGGG ATCTCGCCGC GCGAGGCCCT CGCCATGGAC CCGCAGCAGC
18721 GGCTCCTCCT GGAGACCTCC TGGGAGGCCG TCGAGGACGC CGGGATCGAC CCGACCTCCC
18781 TTCAGGGGCA GCAGGTCGGC GTGTTCGCGG GCACCAACGG CCCCCACTAC GAGCCGCTGC
18841 TCCGCAACAC CGCCGAGGAT CTTGAGGGTT ACGTCGGGAC GGGCAACGCC GCCAGCATCA
18901 TGTCGGGCCG TGTCTCGTAC ACCCTCGGCC TGGAGGGCCC GGCCGTCACG GTCGACACCG
18961 CCTGCTCCTC CTCGCTGGTC GCCCTGCACC TCGCCGTGCA GGCCCTGCGC AAGGGCGAAT
19021 GCGGACTGGC GCTCGCGGGC GGTGTGACGG TCATGTCGAC GCCCACGACG TTCGTGGAGT
19081 TCAGCCGGCA GCGCGGGCTC GCGGAGGACG GCCGGTCGAA GGCGTTCGCC GCGTCGGCGG
19141 ACGGCTTCGG CCCGGCGGAG GGCGTCGGCA TGCTCCTCGT CGAGCGCCTG TCGGACGCCC
19201 GCCGCAACGG ACACCGTGTG CTGGCGGTCG TGCGCGGCAG CGCGGTCAAC CAGGACGGCG
19261 CGAGCAACGG CCTGACCGCC CCGAACGGGC CCTCGCAGCA GCGCGTCATC CGGCGCGCGC
19321 TCGCGGACGC CCGACTGACG ACCGCCGACG TGGACGTCGT CGAGGCCCAC GGCACGGGCA
19381 CGCGACTCGG CGACCCGATC GAGGCACAGG CCCTCATCGC CACCTACGGC CAGGGGCGCG
19441 ACACCGAACA GCCGCTGCGC CTGGGGTCGT TGAAGTCCAA CATCGGACAC ACCCAGGCCG
19501 CCGCCGGTGT CTCCGGCATC ATCAAGATGG TCCAGGCGAT GCGCCACGGC GTCCTGCCGA
19561 AGACGCTCCA CGTGGACCGG CCGTCGGACC AGATCGACTG GTCGGCGGGC ACGGTCGAGC
19621 TGCTCACCGA GGCCATGGAC TGGCCGAGGA AGCAGGAGGG CGGGCTGCGC CGCGCGGCCG
19681 TCTCCTCCTT CGGCATCAGC GGCACGAACG CGCACATCGT GCTCGAAGAA GCCCCGGTCG
19741 ACGAGGACGC CCCGGCGGAC GAGCCGTCGG TCGGCGGTGT GGTGCCGTGG CTCGTGTCCG
19801 CGAAGACTCC GGCCGCGCTG GACGCCCAGA TCGGACGCCT CGCCGCGTTC GCCTCGCAGG
19861 GCCGTACGGA CGCCGCCGAT CCGGGCGCGG TCGCTCGCGT ACTGGCCGGC GGGCGTGCGC
19921 AGTTCGAGCA CCGGGCCGTC GCGCTCGGCA CCGGACAGGA CGACCTGGCG GCCGCACTGG
19981 CCGCGCCTGA GGGTCTGGTC CGGGGTGTGG CCTCCGGTGT GGGTCGAGTG GCGTTCGTGT
20041 TCCCGGGACA GGGCACGCAG TGGGCCGGGA TGGGTGCCGA ACTCCTCGAC GTGTCGAAGG
20101 AGTTCGCGGC GGCCATGGCC GAGTGCGAGG CCGCGCTCGC TCCGTACGTG GACTGGTCGC
20161 TGGAGGCCGT CGTCCGACAG GCCCCGGCG CGCCCACGCT GGAGCGGGTC GATGTCGTCC
20221 AGCCCGTGAC GTTCGCCGTC ATGGTCTCGC TGGCGAAGGT CTGGCAGCAC ACGGGGTGA
20281 CCCCGCAAGC CGTCGTCGGC CACTCGCAGG GCGAGATCGC CGCCGCGTAC GTCGCCGGTG
20341 CCCTGAGCCT GGACGACGCC GCTCGTGTCG TGACCCTGCG CAGCAAGTCC ATCGGCGCCC
20401 ACCTCGCGGG CCAGGGCGGC ATGCTGCCC TCGCGCTGAG CGAGGCGGCC GTTGTGGAGC
20461 GACTGGCCGG GTTCGACGGG CTGTCCGTCG CCGCCGTCAA CGGGCCTACC GCCACCGTGG
20521 TTTCGGGCGA CCCGACCCAG ATCCAAGAGC TCGCTCAGGC GTGTGAGGCC GACGGGGTCC
20581 GCGCACGGAT CATCCCCGTC GACTACGCCT CCCACAGCGC CCACGTCGAG ACCATCGAGA
20641 GCGAACTCGC CGACGTCCTG GCGGGGTTGT CCCCCCAGAC ACCCCAGGTC CCCTTCTTCT
20701 CCACCCTCGA AGGCGCCTGG ATCACCGAAC CCGCCCTCGA CGGCGGCTAC TGGTACCGCA
20761 ACCTCCGCCA TCGTGTGGGC TTCGCCCCGG CCGTCGAAAC CCTGGCCACC GACGAAGGCT
```

FIG. 5
(CONTINUED)

```
20821 TCACCCACTT CGTCGAGGTC AGCGCCCACC CCGTCCTCAC CATGGCCCTG CCCGAGACCG
20881 TCACCGGCCT CGGCACCCTC CGCCGTGACA ACGGCGGACA GCACCGCCTC ACCACCTCCC
20941 TCGCCGAGGC CTGGGCCAAC GGCCTCACCG TCGACTGGGC CTCTCTCCTC CCCACCACGA
21001 CCACCCACCC CGATCTGCCC ACCTACGCCT TCCAGACCGA GCGCTACTGG CCGCAGCCCG
21061 ACCTCTCCGC CGCCGGTGAC ATCACCTCCG CCGGTCTCGG GGCGGCCGAG CACCCGCTGC
21121 TCGGCGCGGC CGTGGCGCTC GCGGACTCCG ACGGCTGCCT GCTCACGGGG AGCCTCTCCC
21181 TCCGTACGCA CCCCTGGCTG GCGGACCACG CGGTGGCCGG CACCGTGCTG CTGCCGGGAA
21241 CGGCGTTCGT GGAGCTGGCG TTCCGAGCCG GGGACCAGGT CGGTTGCGAT CTGGTCGAGG
21301 AGCTCACCCT CGACGCGCCG CTCGTGCTGC CCCGTCGTGG CGCGGTCCGT GTGCAGCTGT
21361 CCGTCGGCGC GAGCGACGAG TCCGGGCGTC GTACCTTCGG GCTCTACGCG CACCCGGAGG
21421 ACGCGCCGGG CGAGGCGGAG TGGACGCGGC ACGCCACCGG TGTGCTGGCC GCCCGTGCGG
21481 ACCGCACCGC CCCCGTCGCC GACCCGGAGG CCTGGCCGCC GCCGGGCGCC GAGCCGGTGG
21541 ACGTGGACGG TCTGTACGAG CGCTTCGCGG CGAACGGCTA CGGCTACGGC CCCCTCTTCC
21601 AGGGCGTCCG TGGTGTCTGG CGGCGTGGCG ACGAGGTGTT CGCCGACGTG GCCCTGCCGG
21661 CCGAGGTCGC CGGTGCCGAG GGCGCGCGGT TCGGCCTTCA CCCGGCGCTG CTCGACGCCG
21721 CCGTGCAGGC GGCCGGTGCG GGCGGGGCGT TCGGCGCGGG CACGCGGCTG CCGTTCGCCT
21781 GGAGCGGGAT CTCCCTGTAC GCGGTCGGCG CCACCGCCCT CCGCGTGCGG CTGGCCCCCG
21841 CCGGCCCGGA CACGGTGTCC GTGAGCGCCG CCGACTCCTC CGGGCAGCCG GTGTTCGCCG
21901 CGGACTCCCT CACGGTGCTG CCCGTCGACC CCGCGCAGCT GGCGGCCTTC AGCGACCCGA
21961 CTCTGGACGC GCTGCACCTG CTGGAGTGGA CCGGCTGGGA CGGTGCCGCG CAGGCCCTGC
22021 CCGGCGCGGT CGTGCTGGGC GGCGACGCCG ACGGTCTCGC CGCGGCGCTG CGCGCCGGTG
22081 GCACCGAGGT CCTGTCCTTC CCGGACCTTA CGGACCTGGT GGAGGCCGTC GACCGGGGCG
22141 AGACCCCGGC CCCGGCGACC GTCCTGGTGG CCTGCCCCGC CGCCGGCCCC GGTGGGCCGG
22201 AGCATGTCCG CGAGGCCCTG CACGGGTCGC TCGCGCTGAT GCAGGCCTGG CTGGCCGACG
22261 AGCGGTTCAC CGATGGGCGC CTGGTGCTCG TGACCCGCGA CGCGGTCGCC GCCCGTTCCG
22321 GCGACGGCCT GCGGTCCACG GGACAGGCCG CCGTCTGGGG CCTCGGCCGG TCCGCGCAGA
22381 CGGAGAGCCC GGGCCGGTTC GTCCTGCTCG ACCTCGCCGG GAAGCCCGG ACGGCCGGGG
22441 ACGCCACCGC CGGGGACGGC CTGACGACCG GGACGCCAC CGTCGGCGGC ACCTCTGGAG
22501 ACGCCGCCCT CGGCAGCGCC CTCGCGACCG CCCTCGGCTC GGGCGAGCCG CAGCTCGCCC
22561 TCCGGGACGG GGCGCTCCTC GTACCCCGCC TGGCGCGGGC CGCCGCGCCC GCCGCGGCCG
22621 ACGGCCTCGC CGCGGCCGAC GGCCTCGCCG CTCTGCCGCT GCCCGCCGCT CCGGCCCTCT
22681 GGCGTCTGGA GCCCGGTACG GACGGCAGCC TGGAGAGCCT CACGGCGGCG CCCGGCGACG
22741 CCGAGACCCT CGCCCCGGAG CCGCTCGATCC CGGGACAGGT CCGCATCGCG ATCCGGGCCA
22801 CCGGTCTCAA CTTCCGCGAC GTCCTGACCG CCCTCGGCAT GTACCCCGAT CCGGCGCTGA
22861 TGGGCACCGA GGGAGCCGGC GTGGTCACCG CGACCGGCCC CGGCGTCACG CACCTCGCCC
22921 CCGGCGACCG GGTCATGGGC CTGCTCTCCG GCGCGTACGC CCCGGTCGTC GTGGCGGACG
22981 CGCGGACCGT CGCGCGGATG CCCGAGGGGT GGACGTTCGC CCAGGGCGCC TCCGTGCCGG
23041 TGGTGTTCCT GACGGCCGTC TACGCCCTGC GCGACCTGGC GGACGTCAAG CCCGGCGAGC
23101 GCCTCCTGGT CCACTCCGCC GCCGGTGGCG TGGGCATGGC CGCCGTGCAG CTCGCCCGGC
23161 ACTGGGGCGT GGAGGTCCAC GGCACGGCGA GTCACGGGAA GTGGGACGCC CTGCGCGCGC
23221 TCGGCCTGGA CGACGCGCAC ATCGCCTCCT CCCGCACCCT GGACTTCGAG TCCGCGTTCC
23281 GTGCCGCTTC CGGCGGGGCG GGCATGGACG TCGTACTGAA CTCGCTCGCC CGCGAGTTCG
23341 TCGACGCCTC GCTGCGCCTG CTCGGGCCGG GCGGCCGGTT CGTGGAGATG GGGAAGACCG
23401 ACGTCCGCGA CGCGGAGCGG GTCGCCGCCG ACCACCCCGG TGTCGGCTAC CGCGCCTTCG
23461 ACCTGGGCGA GGCCGGGCCG GAGCGGATCG GCGAGATGCT CGCCGAGGTC ATCGCCCTCT
23521 TCGAGGACGG GGTGCTCCGG CACCTGCCCG TCACGACCTG GACGTGCGC CGGGCCCGCG
23581 ACGCCTTCCG GCACGTCAGC CAGGCCCGCC ACACGGGCAA GGTCGTCCTC ACGATGCCGT
23641 CGGGCCTCGA CCCGGAGGGT ACGGCCTCGC TGACCGGCGG CACCGGTGCG CTGGGGGGCA
23701 TCGTGGCCCG GCACGTGGTG GGCGAGTGGG GCGTACGACG CCTGCTGCTC GTGAGCCGGC
23761 GGGGCACGGA CGCCCCGGGC GCCGGCGAGC TCGTGCACGA GCTGGAGGCC CTGGGAGCCG
23821 ACGTCTCGGT GGCCGCGTGC GACGTCGCCG ACCGCGAAGC CCTCACCGCC GTACTCGACT
23881 CGATCCCCGC CGAACACCCG CTCACCGCGG TCGTCCACAC GGCAGGCGTC CTCTCCGACG
23941 GCACCCTCCC CTCGATGACA GCGGAGGATG TGGAACACGT ACTGCGTCCC AAGGTCGACG
24001 CCGCGTTCCT CCTCGACGAA CTCACCTCGA CGCCCGGCTA CGACCTGGCA GCGTTCGTCA
24061 TGTTCTCCTC CGCCGCCGCC GTCTTCGGTG GCGCGGGGCA GGGCGCCTAC GCCGCCGCCA
24121 ACGCCACCCT CGACGCCCTC GCCTGGCGCC GCCGGACAGC GGACTCCCC GCCCTCTCCC
24181 TCGGCTGGGG CCTCTGGGCC GAGACCAGCG GCATGACCGG CGGACTCAGC GACACCGACC
24241 GCTCGCGGCT GGCCCGTTCC GGGGCGACGC CCATGGACAG CGAGCTGACC CTGTCCCTCC
```

FIG. 5
(CONTINUED)

```
24301  TGGACGCGGC  CATGCGCCGC  GACGACCCGG  CGCTCGTCCC  GATCGCCCTG  GACGTCGCCG
24361  CGCTCCGCGC  CCAGCAGCGC  GACGGCATGC  TGGCGCCGCT  GCTCAGCGGG  CTCACCCGCG
24421  GATCGCGGGT  CGGCGGCGCG  CCGGTCAACC  AGCGCAGGGC  AGCCGCCGGA  GGCGCGGGCG
24481  AGGCGGACAC  GGACCTCGGC  GGGCGGCTCG  CCGCGATGAC  ACCGGACGAC  CGGGTCGCGC
24541  ACCTGCGGGA  CCTCGTCCGT  ACGCACGTGG  CGACCGTCCT  GGGACACGGC  ACCCCGAGCC
24601  GGGTGGACCT  GGAGCGGGCC  TTCCGCGACA  CCGGTTTCGA  CTCGCTCACC  GCCGTCGAAC
24661  TCCGCAACCG  TCTCAACGCC  GCGACCGGGC  TGCGGCTGCC  GGCCACGCTG  GTCTTCGACC
24721  ACCCCACCCC  GGGGGAGCTC  GCCGGGCACC  TGCTCGACGA  ACTCGCCACG  GCCGCGGGCG
24781  GGTCCTGGGC  GGAAGGCACC  GGGTCCGGAG  ACACGGCCTC  GGCGACCGAT  CGGCAGACCA
24841  CGGCGGCCCT  CGCCGAACTC  GACCGGCTGG  AAGGCGTGCT  CGCCTCCCTC  GCGCCCGCCG
24901  CCGGCGGCCG  TCCGGAGCTC  GCCGCCCGGC  TCAGGGCGCT  GGCCGCGGCC  CTGGGGGACG
24961  ACGGCGACGA  CGCCACCGAC  CTGGACGAGG  CGTCCGACGA  CGACCTCTTC  TCCTTCATCG
25021  ACAAGGAGCT  GGGCGACTCC  GACTTCTGAC  CTGCCCGACA  CCACCGGCAC  CACCGGCACC
25081  ACCAGCCCCC  CTCACACACG  GAACACGGAA  CGGACAGGCG  AGAACGGGAG  CCATGGCGAA
25141  CAACGAAGAC  AAGCTCCGCG  ACTACCTCAA  GCGCGTCACC  GCCGAGCTGC  AGCAGAACAC
25201  CAGGCGTCTG  CGCGAGATCG  AGGGACGCAC  GCACGAGCCG  GTGGCGATCG  TGGGCATGGC
25261  CTGCCGCCTG  CCGGGCGGTG  TCGCCTCGCC  CGAGGACCTG  TGGCAGCTGG  TGGCCGGGGA
25321  CGGGGACGCG  ATCTCCGAGT  TCCCGCAGGA  CCGCGGCTGG  GACGTGGAGG  GGCTCGTACGA
25381  CCCCGACCCG  GACGCGTCCG  GCAGGACGTA  CTGCCGGTCC  GGCGGATTCC  TGCACGACGC
25441  CGGCGAGTTC  GACGCCGACT  TCTTCGGGAT  CTCGCCGCGC  GAGGCCCTCG  CCATGGACCC
25501  GCAGCAGCGA  CTGTCCCTCA  CCACCGCGTG  GGAGGCGATC  GAGAGCGCGG  GCATCGACCC
25561  GACGGCCCTG  AAGGGCAGCG  GCCTCGGCGT  CTTCGTCGGC  GGCTGGCACA  CCGGCTACAC
25621  CTCGGGGCAG  ACCACCGCCG  TGCAGTCGCC  CGAGCTGGAG  GGCCACCTGG  TCAGCGGCGC
25681  GGCGCTGGGC  TTCCTGTCCG  GCCGTATCGC  GTACGTCCTC  GGTACGGACG  GACCGGCCCT
25741  GACCGTGGAC  ACGGCCTGCT  CGTCCTCGCT  GGTCGCCCTG  CACCTCGCCG  TGCAGGCCCT
25801  CCGCAAGGGC  GAGTGCGACA  TGGCCCTCGC  CGGTGGTGTC  ACGGTCATGC  CAACGCGGA
25861  CCTGTTCGTG  CAGTTCAGCC  GGCAGCGCGG  GCTGGCCGCG  GACGGCCGGT  CGAAGGCGTT
25921  CGCCACCTCG  GCGGACGGCT  TCGGCCCCGC  GGAGGGCGCC  GGAGTCCTGC  TGGTGGAGCG
25981  CCTGTCGGAC  GCCCGCCGCA  ACGGACACCG  GATCCTCGCG  GTCGTCCGCG  GCAGCGCGGT
26041  CAACCAGGAC  GGCGCCAGCA  ACGGCCTCAC  GGCTCCGCAC  GGGCCCTCCC  AGCAGCGCGT
26101  CATCCGACGG  GCCCTGGCGG  ACGCCCGGCT  CGCGCCGGGT  GACGTGGACG  TCGTCGAGGC
26161  GCACGGCACG  GGCACGCGGC  TCGGCGACCC  GATCGAGGCG  CAGGCCCTCA  TCGCCACCTA
26221  CGGCCAGGAG  AAGAGCAGCG  AACAGGCCGCT  GAGGCTGGGC  GCGTTGAAGT  CGAACATCGG
26281  GCACACGCAG  GCCGCGGCCG  GTGTCGCAGG  TGTCATCAAG  ATGGTCCAGG  CGATGCGCCA
26341  CGGACTGCTG  CCGAAGACGC  TGCACGTCGA  CGAGCCCTCG  GACCAGATCG  ACTGGTCGGC
26401  GGGCACGGTG  GAACTCCTCA  CCGAGGCCGT  CGACTGGCCG  GAGAAGCAGG  ACGGCGGGCT
26461  GCGCCGCGCG  GCTGTCTCCT  CCTTCGGCAT  CAGCGGGACG  AACGCGCACG  TCGTCCTGGA
26521  GGAGGCCCCG  GCGGTCGAGG  ACTCCCCGGC  CGTCGAGCCG  CCGGCCGGTG  GCGGTGTGGT
26581  GCCGTGGCCG  GTGTCCGCGA  AGACTCCGGC  CGCGCTGGAC  GCCAGATCG  GGCAGCTCGC
26641  CGCGTACGCG  GACGGTCGTA  CGGACGTGGA  TCCGGCGGTG  GCCGCCCGCG  CCCTGGTCGA
26701  CAGCCGTACG  GCGATGGAGC  ACCGCGCGGT  CGCGGTCGGC  GACAGCCGGG  AGGCACTGCG
26761  GGACGCCCTG  CGGATGCCGG  AAGGACTGGT  ACGCGGCACG  TCCTCGGACG  TGGGCCGGGT
26821  GGCGTTCGTC  TTCCCCGGCC  AGGGCACGCA  GTGGGCCGGC  ATGGGCGCCG  AACTCCTTGA
26881  CAGCTCACCG  GAGTTCGCTG  CCTCGATGGC  CGAATGCGAG  ACCGCGCTCT  CCCGCTACGT
26941  CGACTGGTCT  CTTGAAGCCG  TCGTCCGACA  GGAACCCGGC  GCACCCACGC  TCGACCGCGT
27001  CGACGTCGTC  CAGCCCGTGA  CCTTCGCTGT  CATGGTCTCG  CTGGCGAAGG  TCTGGCAGCA
27061  CCACGGCATC  ACCCCCAGG  CCGTCGTCGG  CCACTCGCAG  GGCGAGATCG  CCGCCGCGTA
27121  CGTCGCCGGT  GCACTCACCC  TCGACGACGC  CGCCCGCGTC  GTCACCCGTGC  GCAGCAAGTC
27181  CATCGCCGCC  CACCTCGCCG  GCAAGGGCGG  CATGATCTCC  CTCGCCCTCG  ACGAGGCGGC
27241  CGTCCTGAAG  CGACTGAGCG  ACTTCGACGG  ACTCTCCGTC  GCCGCCGTCA  ACGGCCCCAC
27301  CGCCACCGTC  GTCTCCGGCG  ACCCGACCCA  GATCGAGGAA  CTCGCCCGCA  CCTGCGAGGC
27361  CGACGGCGTC  CGTGCGCGGA  TCATCCCGGT  CGACTACGCC  TCCCACAGCC  GGCAGGTCGA
27421  GATCATCGAG  AAGGAGCTGG  CCGAGGTCCT  CGCCGGACTC  GCCCCGCAGG  CTCCGCACGT
27481  GCCGTTCTTC  TCCACCCTCG  AAGGCACCTG  GATCACCGAG  CCGGTGCTCG  ACGGCACCTA
27541  CTGGTACCGC  AACCTGCGCC  ATCGCGTGGG  CTTCGCCCCC  GCCGTGGAGA  CCTTGGCGGT
27601  TGACGGCTTC  ACCCACTTCA  TCGAGGTCAG  CGCCCACCCC  GTCCTCACCA  TGACCCTCCC
27661  CGAGACCGTC  ACCGGCCTCG  GCACCCTCCG  CCGCGAACAG  GGAGGCCAGG  AGCGTCTGGT
27721  CACCTCACTC  GCCGAAGCCT  GGGCCAACGG  CCTCACCATC  GACTGGGCGC  CCATCCTCCC
```

FIG. 5
(CONTINUED)

```
27781 CACCGCAACC GGCCACCACC CCGAGCTCCC CACCTACGCC TTCCAGACCG AGCGCTTCTG
27841 GCTGCAGAGC TCCGCGCCCA CCAGCGCCGC CGACGACTGG CGTTACCGCG TCGAGTGGAA
27901 GCCGCTGACG GCCTCCGGCC AGGCGGACCT GTCCGGGCGG TGGATCGTCG CCGTCGGGAG
27961 CGAGCCAGAA GCCGAGCTGC TGGGCGCGCT GAAGGCCGCG GGAGCGGAGG TCGACGTACT
28021 GGAAGCCGGG GCGGACGACG ACCGTGAGGC CCTCGCCGCC CGGCTCACCG CACTGACGAC
28081 CGGCGACGGC TTCACCGGCG TGGTCTCGCT CCTCGACGAC CTCGTGCCAC AGGTCGCCTG
28141 GGTGCAGGCA CTCGGCGACG CCGGAATCAA GGCGCCCCTG TGGTCCGTCA CCCAGGGCGC
28201 GGTCTCCGTC GGACGTCTCG ACACCCCCGC CGACCCCGAC CGGGCCATGC TCTGGGGCCT
28261 CGGCCGCGTC GTCGCCCTTG AGCACCCCGA ACGCTGGGCC GGCCTCGTCG ACCTCCCCGC
28321 CCAGCCCGAT GCCGCCGCCC TCGCCCACCT CGTCACCGCA CTCTCCGGCG CCACCGGCGA
28381 GGACCAGATC GCCATCCGCA CCACCGGACT CCACGCCCGC CGCCTCGCCC GCGCACCCCT
28441 CCACGGACGT CGGCCCACCC GCGACTGGCA GCCCCACGGC ACCGTCCTCA TCACCGGCGG
28501 CACCGGAGCC CTCGGCAGCC ACGCCGCACG CTGGATGGCC CACCACGGAG CCGAACACCT
28561 CCTCCTCGTC AGCCGCAGCG GCGAACAAGC CCCCGGAGCC ACCCAACTCA CCGCCGAACT
28621 CACCGCATCG GGCGCCCGCG TCACCATCGC CGCCTGCGAC GTCGCCGACC CCACGCCAT
28681 GCGCACCCTC CTCGACGCCA TCCCCGCCGA GACGCCCCTC ACCGCCGTCG TCCACACCGC
28741 CGGCGCACCG GGCGGCGATC CGCTGGACGT CACCGGCCCG GAGGACATCG CCCGCATCCT
28801 GGGCGCGAAG ACGAGCGGCG CCGAGGTCCT CGACGACCTG CTCCGCGGCA CTCCGCTGGA
28861 CGCCTTCGTC CTCTACTCCT CGAACGCCGG GGTCTGGGGC AGCGGCAGCC AGGGCGTCTA
28921 CGCGGCGGCC AACGCCCACC TCGACGCGCT CGCCGCCCGG CGCCGCGCCC GGGGCGAGAC
28981 GGCGACCTCG GTCGCCTGGG GCCTCTGGGC CGGCGACGGC ATGGGCCGGG GCGCCGACGA
29041 CGCGTACTGG CAGCGTCGCG GCATCCGTCC GATGAGCCCC GACCGCGCCC TGGACGAACT
29101 GGCCAAGGCC CTGAGCCACG ACGAGACCTT CGTCGCCGTG GCCGATGTCG ACTGGGAGCG
29161 GTTCGCGCCC GCGTTCACGG TGTCCCGTCC CAGCCTTCTG CTCGACGGCG TCCCGGAGGC
29221 CCGGCAGGCG CTCGCCGCAC CCGTCGGTGC CCCGGCTCCC GGCGACGCCG CCGTGGCGCC
29281 GACCGGGCAG TCGTCGGCGC TGGCCGCGAT CACCGCGCTC CCCGAGCCCG AGCGCCGGCC
29341 GGCGCTCCTC ACCCTCGTCC GTACCCACGC GGCGGCCGTA CTCGGCCATT CCTCCCCCGA
29401 CCGGGTGGCC CCCGGCCGTG CCTTCACCGA GCTCGGCTTC GACTCGCTGA CGGCCGTGCA
29461 GCTCCGCAAC CAGCTCTCCA CGGTGGTCGG CAACAGGCTC CCCGCCACCA CGGTCTTCGA
29521 CCACCCGACG CCCGCCCGAC TCGCCGCGCA CCTCCACGAG GCGTACCTCG CACCGGCCGA
29581 GCCGGCCCCG ACGGACTGGG AGGGGCGGGT GCGCCGGGCC CTGGCCGAAC TGCCCCTCGA
29641 CCGGCTGCGG GACGCGGGGG TCCTCGACAC CGTCCTGCGC CTCACCGGCA TCGAGCCCGA
29701 GCCGGGTTCC GGCGGTTCGG ACGGCGGCGC CGCCGACCCT GGTGCGGAGC CGGAGGCGTC
29761 GATCGACGAC CTGGACGCCG AGGCCCTGAT CCGGATGGCT CTCGGCCCCC GTAACACCTG
29821 ACCCGACCGC GGTCCTGCCC CACGCGCCGC ACCCCGCGCA TCCCGCGCAC CACCCGCCCC
29881 CACACGCCCA CAACCCCATC CACGAGCGGA AGACCACACC CAGATGACGA GTTCCAACGA
29941 ACAGTTGGTG GACGCTCTGC GCGCCTCTCT CAAGGAGAAC GAAGAACTCC GGAAAGAGAG
30001 CCGTCGCCGG GCCGACCGTC GGCAGGAGCC CATGGCGATC GTCGGCATGA GCTGCCGGTT
30061 CGCGGGCGGA ATCCGGTCCC CCGAGGACCT CTGGGACGCC GTCGCCGCGG GCAAGGACCT
30121 GGTCTCCGAG GTACCGGAGG AGCGCGGCTG GACATCGAC TCCCTCTACG ACCCGGTGCC
30181 CGGGCGCAAG GGCACGACGT ACGTCCGCAA CGCCGCGTTC CTCGACGACG CCGCCGGATT
30241 CGACGCGGCC TTCTTCGGGA TCTCGCCGCG CGAGGCCCTC GCCATGGACC CGCAGCAGCG
30301 GCAGCTCCTC GAAGCCTCCT GGGAGGTCTT CGAGCGGGCC GGCATCGACC CCGCGTCGGT
30361 CCGCGGCACC GACGTCGGCG TGTACGTGGG CTGTGGCTAC CAGGACTACG CGCCGGACAT
30421 CCGGGTCGCC CCCGAAGGCA CCGGCGGTTA CGTCGTCACC GGCAACTCCT CCGCCGTGGC
30481 CTCCGGGCGC ATCGCGTACT CCCTCGGCCT GGAGGGACCC GCCGTGACCG TGGACACGGC
30541 GTGCTCCTCT TCGCTCGTCG CCCTGCACCT CGCCCTGAAG GGCCTGCGGA ACGGCGACTG
30601 CTCGACGGCA CTCGTGGGCG GCGTGGCCGT CCTCGCGACG CCGGGCGCGT TCATCGAGTT
30661 CAGCAGCCAG CAGGCCATGG CCGCCGACGG CCGGACCAAG GCTTCGCCT CGGCGGCGGA
30721 CGGCCTCGCC TGGGGCGAGG GCGTCGCCGT ACTCCTCCTC GAACGGCTCT CCGACGCGCG
30781 GCGCAAGGGC CACCGGGTCC TGGCCGTCGT GCGCGGCAGC GCCATCAACC AGGACGGCGC
30841 GAGCAACGGC CTCACGGCTC CGCACGGGCC CTCCCAGCAG CGCCTGATCC GCCAGGCCCT
30901 GGCCGACGCG CGGCTCACGT CGAGCGACGT GGACGTCGTG GAGGGCCACG GCACGGGGAC
30961 CCCTCTCGGC GACCCGATCG AGGCGCAGGC GCTGCTCGCC ACGTACGGGC AGGGGCGCGC
31021 CCCGGGGCAG CCGCTGCGGC TGGGGACGCT GAAGTCGAAC ATCGGGCACA CGCAGGCCGC
31081 TTCGGGTGTC GCCGGTGTCA TCAAGATGGT GCAGGCGCTG CGCCACGGGG TGCTGCCGAA
31141 GACCCTGCAC GTGGACGAGC CGACGGACCA GGTCGACTGG TCGGCCGGTT CGGTCGAGCT
31201 CCTCACCGAG GCCGTGGACT GGCCGGAGCG GCCGGGCCGG CTCCGCCGGG CGGGCGTCTC
```

FIG. 5
(CONTINUED)

```
31261 CGCGTTCGGC GTGGGCGGGA CGAACGCGCA CGTCGTCCTG GAGGAGGCCC CGGCGGTCGA
31321 GGAGTCCCCT GCCGTCGAGC CGCCGGCCGG TGGCGGCGTG GTGCCGTGGC CGGTGTCCGC
31381 GAAGACCTCG GCCGCACTGG ACGCCCAGAT CGGGCAGCTC GCCGCATACG CGGAAGACCG
31441 CACGGACGTG GATCCGGCGG TGGCCGCCCG CGCCCTGGTC GACAGCCGTA CGGCGATGGA
31501 GCACCGCGCG GTCGCGGTCG GCGACAGCCG GGAGGCACTG CGGGACGCCC TGCGGATGCC
31561 GGAAGGACTG GTACGGGGCA CGGTCACCGA TCCGGGCCGG GTGGCGTTCG TCTTCCCCGG
31621 CCAGGGCACG CAGTGGGCCG GCATGGGCGC CGAACTCCTC GACAGCTCAC CCGAATTCGC
31681 CGCCGCCATG GCCGAATGCG AGACCGCACT CTCCCCGTAC GTCGACTGGT CTCTCGAAGC
31741 CGTCGTCCGA CAGGCTCCCA GCGCACCGAC ACTCGACCGC GTCGACGTCG TCCAGCCCGT
31801 CACCTTCGCC GTCATGGTCT CCCTCGCCAA GGTCTGGCAG CACCACGGCA TCACCCCCGA
31861 GGCCGTCATC GGCCACTCCC AGGGCGAGAT CGCCGCCGCG TACGTCGCCG GTGCCCTCAC
31921 CCTCGACGAC GCCGCTCGTG TCGTGACCCT CCGCAGCAAG TCCATCGCCG CCCACCTCGC
31981 CGGCAAGGGC GGCATGATCT CCCTCGCCCT CAGCGAGGAA GCCACCCGGC AGCGCATCGA
32041 GAACCTCCAC GGACTGTCGA TCGCCGCCGT CAACGGGCCT ACCGCCACCG TGGTTTCGGG
32101 CGACCCCACC CAGATCCAAG AACTTGCTCA GGCGTGTGAG GCCGACGGCA TCCGCGCACG
32161 GATCATCCCC GTCGACTACG CCTCCCACAG CGCCCACGTC GAGACCATCG AGAACGAACT
32221 CGCCGACGTC CTGGCGGGGT TGTCCCCCCA GACACCCCAG GTCCCCTTCT CTCCACCCT
32281 CGAAGGCACC TGGATCACCG AACCCGCCCT CGACGGCGGC TACTGGTACC GCAACCTCCG
32341 CCATCGTGTG GGCTTCGCCC CGGCCGTCGA GACCCTCGCC ACCGACGAAG GCTTCACCCA
32401 CTTCATCGAG GTCAGCGCCC ACCCCGTCCT CACCATGACC CTCCCCGACA AGGTCACCGG
32461 CCTGGCCACC CTCCGACGCG AGGACGGCGG ACAGCACCGC CTCACCACCT CCCTTGCCGA
32521 GGCCTGGGCC AACGGCCTCG CCCTCGACTG GCCTCCCTC CTGCCCGCCA CGGGCGCCCT
32581 CAGCCCCGCC GTCCCCGACC TCCGACGTA CGCCTTCCAG CACCGCTCGT ACTGGATCAG
32641 CCCCGCGGGT CCCGGCGAGG CGCCCGCGCA CACCGCTTCC GGGCGCGAGG CCGTCGCCGA
32701 GACGGGGCTC GCGTGGGGCC CGGGTGCCGA GGACCTCGAC GAGGAGGGCC GGCGCAGCGC
32761 CGTACTCCG ATGGGATGC GGCAGGCGGC CTCCGTGCTC CGGTGCGACT CGCCCGAAGA
32821 GGTCCCCGTC GACCGCCCGC TGCGGGAGAT CGGCTTCGAC TCGCTGACCG CCGTCGACTT
32881 CCGCAACCGC GTCAACCGGC TGACCGGTCT CCAGCTGCCG CCCACCGTCG TGTTCGAGCA
32941 CCCCGACGCC GTCGCGCTCG CCGAGCGCAT CAGCGACGAG CTGGCCGAGC GGAACTGGGC
33001 CGTCGCCGAG CCGTCGGATC ACGAGCAGGC GGAGGAGGAG AAGGCCGCCG CTCCGGCGGG
33061 GGCCCGCTCC GGGGCCGACA CCGGCGCCGG CGCCGGGATG TTCCGCGCCC TGTTCCGGCA
33121 GGCCGTGGAG GACGACCGGT ACGGCGAGTT CCTCGACGTC CTCGCCGAAG CCTCCGCGTT
33181 CCGCCCGCAG TTCGCCTCGC CCGAGGCCTG CTCGGAGCGG CTCGACCCGG TGCTGCTCGC
33241 CGGCGGTCCG ACGGACCGGG CGGAAGGCCG TGCCGTTCTC GTCGGCTGCA CCGGCACCGC
33301 GGCGAACGGC GGCCCGCACG AGTTCCTGCG GCTCAGCACC TCCTTCCAGG AGGAGCGGGA
33361 CTTCCTCGCC GTACCTCTCC CCGGCTACGG CACGGGTACG GGCACCGGCA CGGCCCTCCT
33421 CCCGGCCGAT CTCGACACCG CGCTCGACGC CCAGGCCCGG GCGATCCTCC GGGCCGCCGG
33481 GGACGCCCCG GTCGTCCTGC TCGGGCACTC CGGCGGCGCC CTGCTCGCGC ACGAGCTGGC
33541 CTTCCGCCTG GAGCGGGCGC ACGGCGCGCC GCCGGCCGGG ATCGTCCTGG TCGACCCCTA
33601 TCCGCCGGGC CATCAGGAGC CCATCGAGGT GTGGAGCAGG CAGCTGGGCG AGGGCCTGTT
33661 CGCGGGCGAG CTGGAGCCGA TGTCCGATGC GCGGCTGCTG GCCATGGGCC GGTACGCGCG
33721 GTTCCTCGCC GGCCCGCGGC CGGGCCGCAG CAGCGCGCCC GTGCTTCTGG TCCGTGCCTC
33781 CGAACCGCTG GGCGACTGGC AGGAGGAGCG GGGCGACTGG CGTGCCCACT GGGACCTTCC
33841 GCACACCGTC GCGGACGTGC CGGGCGACCA CTTCACGATG ATGCGGGACC ACGCGCCGGC
33901 CGTCGCCGAG GCCGTCCTCT CCTGGCTCGA CGCCATCGAG GGCATCGAGG GGCGGGCAA
33961 GTGACCGACA GACCTCTGAA CGTGGACAGC GGACTGTGGA TCCGGCGCTT CCACCCCGCG
34021 CCGAACAGCG CGGTGCGGCT GGTCTGCCTG CCGCACGCCG GCGGCTCCGC CAGCTACTTC
34081 TTCCGCTTCT CGGAGGAGCT GCACCCCTCC GTCGAGGCCC TGTCGGTGCA GTATCCGGGC
34141 CGCCAGGACC GGCGTGCCGA GCCGTGTCTG GAGAGCGTCG AGGAGCTCGC CGAGCATGTG
34201 GTCGCGGCCA CCGAACCCTG GTGGCAGGAG GGCCGCTGG CCTTCTTCGG GCACAGCCTC
34261 GGCGCCTCCG TCGCCTTCGA GACGGCCCGC ATCCTGGAAC AGCGGCACGG GGTACGGCCC
34321 GAGGGCCTGT ACGTCTCCGG TCGGCGCGCC CCGTCGCTGG CGCCGGACCG GCTCGTCCAC
34381 CAGCTGGACG ACCGGGCGTT CCTGGCCGAG ATCCGGCGGC TCAGCGGCAC CGACGAGCGG
34441 TTCCTCCAGG ACGACGAGCT GCTGCGGCTG GTGCTGCCCG CGCTGCGCAG CGACTACAAG
34501 GCGGCGGAGA CGTACCTGCA CCGGCCGTCC GCCAAGCTCA CCTGCCCGGT GATGGCCCTG
34561 GCCGGCGACC GTGACCCGAA GGCGCCGCTG AACGAGGTGG CCGAGTGGCG TCGGCACACC
34621 AGCGGGCCGT TCTGCCTCCG GGCGTACTCC GGCGGCCACT TCTACCTCAA CGACCAGTGG
34681 CACGAGATCT GCAACGACAT CTCCGACCAC CTGCTCGTCA CCCGCGGCGC GCCCGATGCC
```

FIG. 5
(CONTINUED)

```
34741 CGCGTCGTGC AGCCCCCGAC CAGCCTTATC GAAGGAGCGG CGAAGAGATG GCAGAACCCA
34801 CGGTGACCGA CGACCTGACG GGGGCCCTCA CGCAGCCCCC GCTGGGCCGC ACCGTCCGCG
34861 CGGTGGCCGA CCGTGAACTC GGCACCCACC TCCTGGAGAC CCGCGGCATC CACTGGATCC
34921 ACGCCGCGAA CGGCGACCCG TACGCCACCG TGCTGCGCGG CCAGGCGGAC GACCCGTATC
34981 CCGCGTACGA GCGGGTGCGT GCCCGCGGCG CGCTCTCCTT CAGCCCGACG GGCAGCTGGG
35041 TCACCGCCGA TCACGCCCTG GCGGCGAGCA TCCTCTGCTC GACGGACTTC GGGGTCTCCG
35101 GCGCCGACGG CGTCCCGGTG CCGCAGCAGG TCCTCTCGTA CGGGGAGGGC TGTCCGCTGG
35161 AGCGCGAGCA GGTGCTGCCG GCGGCCGGTG ACGTGCCGGA GGGCGGGCAG CGTGCCGTGG
35221 TCGAGGGGAT CCACCGGGAG ACGCTGGAGG GTCTCGCGCC GGACCCGTCG GCGTCGTACG
35281 CCTTCGAGCT GCTGGGCGGT TTCGTCCGCC CGGCGGTGAC GGCCGCTGCC GCCGCCGTGC
35341 TGGGTGTTCC CGCGGACCGG CGCGCGGACT TCGCGGATCT GCTGGAGCGG CTCCGGCCGC
35401 TGTCCGACAG CCTGCTGGCC CCGCAGTCCC TGCGGACGGT ACGGCGGCG GACGGCGCGC
35461 TGGCCGAGCT CACGGCGCTG CTCGCCGATT CGGACGACTC CCCCGGGGCC CTGCTGTCGG
35521 CGCTCGGGGT CACCGCAGCC GTCCAGCTCA CCGGGAACGC GGTGCTCGCG CTCCTCGCGC
35581 ATCCCGAGCA GTGGCGGGAG CTGTGCGACC GGCCCGGGCT CGCGGCGGCC GCGGTGGAGG
35641 AGACCCTCCG CTACGACCCG CCGGTGCAGC TCGACGCCCG GGTGGTCCGC GGGGAGACGG
35701 AGCTGGCGGG CCGGCGGCTG CCGGCCGGGG CGCATGTCGT CGTCCTGACC GCCGCGACCG
35761 GCCGGGACCC GGAGGTCTTC ACGGACCCGG AGCGCTTCGA CCTCGCGCGC CCCGACGCCG
35821 CCGCGCACCT CGCGCTGCAC CCCGCCGGTC CGTACGGCCC GGTGGCGTCC CTGGTCCGGC
35881 TTCAGGCGGA GGTCGCGCTG CGGACCCTGG CCGGGCGTTT CCCCGGGCTG CGGCAGGCGG
35941 GGGACGTGCT CCGCCCCCGC CGCGCGCCTG TCGGCCGCGG GCCGCTGAGC GTCCCGGTCA
36001 GCAGCTCCTG AGACACCGGG GCCCCGGTCC GCCCGGCCCC CCTTCGGACG GACCGGACGG
36061 CTCGGACCAC GGGGACGGCT CAGACCGTCC CGTGTGTCCC CGTCCGGCTC CCGTCCGCCC
36121 CATCCCGCCC CTCCACCGGC AAGGAAGGAC ACGACGCCAT GCGCGTCCTG CTGACCTCGT
36181 TCGCACATCA CACGCACTAC TACGGCCTGG TGCCCCTGGC CTGGGCGCTG CTCGCCGCCG
36241 GGCACGAGGT GCGGGTCGCC AGCCAGCCCG CGCTCACGGA CACCATCACC GGGTCCGGGC
36301 TCGCCGCGGT GCCGGTCGGC ACCGACCACC TCATCCACGA GTACCGGGTG CGGATGGCGG
36361 GCGAGCCGCG CCCGAACCAT CCGGCGATCG CCTTCGACGA GGCCCGTCCC GAGCCGCTGG
36421 ACTGGGACCA CGCCCTCGGC ATCGAGGCGA TCCTCGCCCC GTACTTCTAT CTGCTCGCCA
36481 ACAACGACTC GATGGTCGAC GACCTCGTCG ACTTCGCCCG GTCCTGGCAG CCGGACCTGG
36541 TGCTGTGGGA GCCGACGACC TACGCGGGCG CCGTCGCCGC CCAGGTCACC GGTGCCGCGC
36601 ACGCCCGGGT CCTGTGGGGG CCCGACGTGA TGGGCAGCGC CCGCCGCAAG TTCGTCGCGC
36661 TGCGGGACCG GCAGCCGCCC GAGCACCGCG AGGACCCCAC CGCGGAGTGG CTGACGTGGA
36721 CGCTCGACCG GTACGGCGCC TCCTTCGAAG AGGAGCTGCT CACCGGCCAG TTCACGATCG
36781 ACCCGACCCC GCCGAGCCTG CGCCTCGACA CGGGCCTGCC GACCGTCGGG ATGCGTTATG
36841 TTCCGTACAA CGGCACGTCG GTCGTGCCGG ACTGGCTGAG TGAGCCGCCC GCGCGGCCCC
36901 GGGTCTGCCT GACCCTCGGC GTCTCCGCGC GTGAGGTCCT CGGCGGCGAC GGCGTCTCGC
36961 AGGGCGACAT CCTGGAGGCG CTCGCCGACC TCGACATCGA GCTCGTCGCC ACGCTCGACG
37021 CGAGTCAGCG CGCCGAGATC CGCAACTACC CGAAGCACAC CCGGTTCACG GACTTCGTGC
37081 CGATGCACGC GCTCCTGCCG AGCTGCTCGG CGATCATCCA CCACGGCGGG GCGGGCACCT
37141 ACGCGACCGC CGTGATCAAC GCGGTGCCGG AGGTCATGCT CGCCGAGCTG TGGGACGCGC
37201 CGGTCAAGGC GCGGGCCGTC GCCGAGCAGG GGGCGGGGTT CTTCCTGCCG CCGGCCGAGC
37261 TCACGCCGCA GGCCGTGGCG GACGCCGTCG TCCGCATCCT CGACGACCCC TCGGTCGCCA
37321 CCGCCGCGCA CCGGCTGCGC GAGGAGACCT TCGGCGACCC CACCCCGGCC GGGATCGTCC
37381 CCGAGCTGGA GCGGCTCGCC GCGCAGCACC GCCGCCCGCC GGCCGACGCC CGGCACTGAG
37441 CCGCACCCCT CGCCCCAGGC CTCACCCCTG TATCTGCGCC GGGGGACGCC CCCGGCCCAC
37501 CCTCCGAAAG ACCGAAAGCA GGAGCACCGT GTACGAAGTC GACCACGCCG ACGTCTACGA
37561 CCTCTTCTAC CTGGGTCGCG GCAAGGACTA CGCCGCCGAG GCCTCGACA TCGCCGACCT
37621 GGTGCGCTCC CGTACCCCCG AGGCCTCCTC GCTCCTGGAC GTGGCCTGCG GTACGGGCAC
37681 GCATCTGGAG CACTTCACCA AGGAGTTCGG CGACACCGCC GGCCTGGAGC TGTCCGAGGA
37741 CATGCTCACC CACGCCCGCA AGCGGCTGCC CGACGCCACG CTCCACCAGG CCGACATGCG
37801 GGACTTCCGG CTCGGCCGGA AGTTCTCCGC CGTGGTCAGC ATGTTCAGCT CCGTCGGCTA
37861 CCTGAAGACG ACCGAGGAAC TCGGCGCGGC CGTCGCCTCG TTCGCGGAGC ACCTGGAGCC
37921 CGGTGGCGTC GTCGTCGTCG AGCCGTGGTG GTTCCCGGAG ACCTTCGCCG ACGGCTGGGT
37981 CAGCGCCGAC GTCGTCCGCC GTGACGGGCG CACCGTGGCC CGTGTCTCGC ACTCGGTGCG
38041 GGAGGGGAAC GCGACGCGCA TGGAGGTCCA CTTCACCGTG GCCGACCCGG GCAAGGGCGT
38101 GCGGCACTTC TCCGACGTCC ATCTCATCAC CCTGTTCCAC CAGGCCGAGT ACGAGGCCGC
38161 GTTCACGGCC GCCGGGCTGC GCGTCGAGTA CCTGGAGGGC GGCCCGTCGG GCCGTGGCCT
```

FIG. 5
(CONTINUED)

```
38221 CTTCGTCGGC GTCCCCGCCT GAGCACCGCC CAAGACCCCC CGGGGCGGGA CGTCCCGGGT
38281 GCACCAAGCA AAGAGAGAGA AACGAACCGT GACAGGTAAG ACCCGAATAC CGCGTGTCCG
38341 CCGCGGCCGC ACCACGCCCA GGGCCTTCAC CCTGGCCGTC GTCGGCACCC TGCTGGCGGG
38401 CACCACCGTG GCGGCCGCCG CTCCCGGCGC CGCCGACACG GCCAATGTTC AGTACACGAG
38461 CCGGGCGGCG GAGCTCGTCG CCCAGATGAC GCTCGACGAG AAGATC
```

Amino acid sequence of narbonolide synthase subunit 1, PICAI, 4552 AA (SEQ ID NO:2)

```
   1 MSTVSKSESE EFVSVSNDAG SAHGTAEPVA VVGISCRVPG ARDPREFWEL LAAGGQAVTD
  61 VPADRWNAGD FYDPDRSAPG RSNSRWGGFI EDVDRFDAAF FGISPREAAE MDPQQRLALE
 121 LGWEALERAG IDPSSLTGTR TGVFAGAIWD DYATLKHRQG GAAITPHTVT GLHRGIIANR
 181 LSYTLGLRGP SMVVDSGQSS SLVAVHLACE SLRRGESELA LAGGVSLNLV PDSIIGASKF
 241 GGLSPDGRAY TFDARANGYV RGEGGGFVVL KRLSRAVADG DPVLAVIRGS AVNNGGAAQG
 301 MTTPDAQAQE AVLREAHERA GTAPADVRYV ELHGTGTPVG DPIEAAALGA ALGTGRPAGQ
 361 PLLVGSVKTN IGHLEGAAGI AGLIKAVLAV RGRALPASLN YETPNPAIPF EELNLRVNTE
 421 YLPWEPEHDG QRMVVGVSSF GMGGTNAHVV LEEAPGVVEG ASVVESTVGG SAVGGGVVPW
 481 VVSAKSAAAL DAQIERLAAF ASRDRTDGVD AGAVDAGAVD AGAVARVLAG GRAQFEHRAV
 541 VVGSGPDDLA AALAAPEGLV RGVASGVGRV AFVFPGQGTQ WAGMGAELLD SSAVFAAAMA
 601 ECEAALSPYV DWSLEAVVRQ APGAPTLERV DVVQPVTFAV MVSLARVWQH HGVTPQAVVG
 661 HSQGEIAAAY VAGALSLDDA ARVVTLRSKS IAAHLAGKGG MLSLALSEDA VLERLAGFDG
 721 LSVAAVNGPT ATVVSGDPVQ IEELARACEA DGVRARVIPV DYASHSRQVE IIESELAEVL
 781 AGLSPQAPRV PFFSTLEGAW ITEPVLDGGY WYRNLRHRVG FAPAVETLAT DEGFTHFVEV
 841 SAHPVLTMAL PGTVTGLATL RRDNGGQDRL VASLAEAWAN GLAVDWSPLL PSATGHHSDL
 901 PTYAFQTERH WLGEIEALAP AGEPAVQPAV LRTEAAEPAE LDRDEQLRVI LDKVRAQTAQ
 961 VLGYATGGQI EVDRTFREAG CTSLTGVDLR NRINAAFGVR MAPSMIFDFP TPEALAEQLL
1021 LVVHGEAAAN PAGAEPAPVA AAGAVDEPVA IVGMACRLPG GVASPEDLWR LVAGGGDAIS
1081 EFPQDRGWDV EGLYHPDPEH PGTSYVRQGG FIENVAGFDA AFFGISPREA LAMDPQQRLL
1141 LETSWEAVED AGIDPTSLRG RQVGVFTGAM THEYGPSLRD GGEGLDGYLL TGNTASVMSG
1201 RVSYTLGLEG PALTVDTACS SSLVALHLAV QALRKGEVDM ALAGGVAMP  TPGMFVEFSR
1261 QRGLAGDGRS KAFAASADGT SWSEGVGVLL VERLSDARRN GHQVLAVVRG SAVNQDGASN
1321 GLTAPNGPSQ QRVIRRALAD ARLTTSDVDV VEAHGTGTRL GDPIEAQALI ATYGQGRDDE
1381 QPLRLGSLKS NIGHTQAAAG VSGVIKMVQA MRHGLLPKTL HVDEPSDQID WSAGAVELLT
1441 EAVDWPEKQD GGLRRAAVSS FGISGTNAHV VLEEAPVVVE GASVVEPSVG GSAVGGGVTP
1501 WVVSAKSAAA LDAQIERLAA FASRDRTDDA DAGAVDAGAV AHVLADGRAQ FEHRAVALGA
1561 GADDLVQALA DPDGLIRGTA SGVGRVAFVF PGQGTQWAGM GAELLDSSAV FAAAMAECEA
1621 ALSPYVDWSL EAVVRQAPGA PTLERVDVVQ PVTFAVMVSL ARVWQHHGVT PQAVVGHSQG
1681 EIAAAYVAGA LPLDDAARVV TLRSKSIAAH LAGKGGMLSL ALNEDAVLER LSDFDGLSVA
1741 AVNGPTATVV SGDPVQIEEL AQACKADGFR ARIIPVDYAS HSRQVEIIES ELAQVLAGLS
1801 PQAPRVPFFS TLEGTWITEP VLDGTYWYRN LRHRVGFAPA IETLAVDEGF THFVEVSAHP
1861 VLTMTLPETV TGLGTLRREQ GGQERLVTSL AEAWVNGLPV AWTSLLPATA SRPGLPTYAF
1921 QAERYWLENT PAALATGDDW RYRIDWKRLP AAEGSERTGL SGRWLAVTPE DHSAQAAAVL
1981 TALVDAGAKV EVLTAGADDD REALAARLTA LTTGDGFTGV VSLLDGLVPQ VAWVQALGDA
2041 GIKAPLWSVT QGAVSVGRLD TPADPDRAML WGLGRVVALE HPERWAGLVD LPAQPDAAAL
2101 AHLVTALSGA TGEDQIAIRT TGLHARRLAR APLHGRRPTR DWQPHGTVLI TGGTGALGSH
2161 AARWMAHHGA EHLLLVSRSG EQAPGATQLT AELTASGARV TIAACDVADP HAMRTLLDAI
2221 PAETPLTAVV HTAGALDDGI VDTLTAEQVR RAHRAKAVGA SVLDELTRDL DLDAFVLFSS
2281 VSSTLGIPGQ GNYAPHNAYL DALAARRRAT GRSAVSVAWG PWDGGGMAAG DGVAERLRNH
2341 GVPGMDPELA LAALESALGR DETAITVADI DWDRFYLAYS SGRPQPLVEE LPEVRRIIDA
2401 RDSATSGQGG SSAQGANPLA ERLAAAAPGE RTEILLGLVR AQAAAVLRMR SPEDVAADRA
2461 FKDIGFDSLA GVELRNRLTR ATGLQLPATL VFDHPTPLAL VSLLRSEFLG DEETADARRS
2521 AALPATVGAG AGAGAGTDAD DDPIAIVAMS CRYPGDIRSP EDLWRMLSEG GEGITPFPTD
2581 RGWDLDGLYD ADPDALGRAY VREGGFLHDA AEFDAEFFGV SPREALAMDP QQRMLLTTSW
2641 EAFERAGIEP ASLRGSSTGV FIGLSYQDYA ARVPNAPRGV EGYLLTGSTP SVASGRIAYT
2701 FGLEGPATTV DTACSSSLTA LHLAVRALRS GECTMALAGG VAMMATPHMF VEFSRQRALA
2761 PDGRSKAFSA DADGFGAAEG VGLLLVERLS DARRNGHPVL AVVRGTAVNQ DGASNGLTAP
2821 NGPSQQRVIR QALADARLAP GDIDAVETHG TGTSLGDPIE AQGLQATYGK ERPAERPLAI
```

*FIG. 5*
(CONTINUED)

```
2881 GSVKSNIGHT QAAAGAAGII KMVLAMRHGT LPKTLHADEP SPHVDWANSG LALVTEPIDW
2941 PAGTGPRRAA VSSFGISGTN AHVVLEQAPD AAGEVLGADE VPEVSETVAM AGTAGTSEVA
3001 EGSEASEAPA APGSREASLP GHLPWVLSAK DEQSLRGQAA ALHAWLSEPA ADLSDADGPA
3061 RLRDVGYTLA TSRTAFAHRA AVTAADRDGF LDGLATLAQG GTSAHVHLDT ARDGTTAFLF
3121 TGQGSQRPGA GRELYDRHPV FARALDEICA HLDGHLELPL LDVMFAAEGS AEAALLDETR
3181 YTQCALFALE VALFRLVESW GMRPAALLGH SVGEIAAAHV AGVFSLADAA RLVAARGRLM
3241 QELPAGGAML AVQAAEDEIR VWLETEERYA GRLDVAAVNG PEAAVLSGDA DAAREAEAYW
3301 SGLGRRTRAL RVSHAFHSAH MDGMLDGFRA VLETVEFRRP SLTVVSNVTG LAAGPDDLCD
3361 PEYWVRHVRG TVRFLDGVRV LRDLGVRTCL ELGPDGVLTA MAADGLADTP ADSAAGSPVG
3421 SPAGSPADSA AGALRPRPLL VALLRRKRSE TETVADALGR AHAHGTGPDW HAWFAGSGAH
3481 RVDLPTYSFR RDRYWLDAPA ADTAVDTAGL GLGTADHPLL GAVVSLPDRD GLLLTGRLSL
3541 RTHPWLADHA VLGSVLLPGA AMVELAAHAA ESAGLRDVRE LTLLEPLVLP EHGGVELRVT
3601 VGAPAGEPGG ESAGDGARPV SLHSRLADAP AGTAWSCHAT GLLATDRPEL PVAPDRAAMW
3661 PPQGAEEVPL DGLYERLDGN GLAFGPLFQG LNAVWRYEGE VFADIALPAT TNATAPATAN
3721 GGGSAAAAPY GIHPALLDAS LHAIAVGGLV DEPELVRVPF HWSGVTVHAA GAAAARVRLA
3781 SAGTDAVSLS LTDGEGRPLV SVERLTLRPV TADQAAASRV GGLMHRVAWR PYALASSGEQ
3841 DPHATSYGPT AVLGKDELKV AAALESAGVE VGLYPDLAAL SQDVAAGAPA PRTVLAPLPA
3901 GPADGGAEGV RGTVARTLEL LQAWLADEHL AGTRLLLVTR GAVRDPEGSG ADDGGEDLSH
3961 AAAWGLVRTA QTENPGRFGL LDLADDASSY RTLPSVLSDA GLRDEPQLAL HDGTIRLARL
4021 ASVRPETGTA APALAPEGTV LLTGGTGGLG GLVARHVVGE WGVRRLLLVS RRGTDAPGAD
4081 ELVHELEALG ADVSVAACDV ADREALTAVL DAIPAEHPLT AVVHTAGVLS DGTLPSMTTE
4141 DVEHVLRPKV DAAFLLDELT STPAYDLAAF VMFSSAAAVF GGAGQGAYAA ANATLDALAW
4201 RRRAAGLPAL SLGWGLWAET SGMTGELGQA DLRRMSRAGI GGISDAEGIA LLDAALRDDR
4261 HPVLLPLRLD AAGLRDAAGN DPAGIPALFR DVVGARTVRA RPSAASASTT AGTAGTPGTA
4321 DGAAETAAVT LADRAATVDG PARQRLLLEF VVGEVAEVLG HARGHRIDAE RGFLDLGFDS
4381 LTAVELRNRL NSAGGLALPA TLVFDHPSPA ALASHLDAEL PRGASDQDGA GNRNGNENGT
4441 TASRSTAETD ALLAQLTRLE GALVLTGLSD APGSEEVLEH LRSLRSMVTG ETGTGTASGA
4501 PDGAGSGAED RPWAAGDGAG GGSEDGAGVP DFMNASAEEL FGLLDQDPST D
```

Amino acid sequence of narbonolide synthase subunit 2, PICAII, 3740 AA (SEQ ID NO:3)

```
   1 VSTVNEEKYL DYLRRATADL HEARGRLREL EAKAGEPVAI VGMACRLPGG VASPEDLWRL
  61 VAGGEDAISE FPQDRGWDVE GLYDPNPEAT GKSYAREAGF LYEAGEFDAD FFGISPREAL
 121 AMDPQQRLLL EASWEAFEHA GIPAATARGT SVGVFTGVMY HDYATRLTDV PEGIEGYLGT
 181 GNSGSVASGR VAYTLGLEGP AVTVDTACSS SLVALHLAVQ ALRKGEVDMA LAGGVTVMST
 241 PSTFVEFSRQ RGLAPDGRSK SFSSTADGTS WSEGVGVLLV ERLSDARRKG HRILAVVRGT
 301 AVNQDGASSG LTAPNGPSQQ RVIRRALADA RLTTSDVDVV EAHGTGTRLG DPIEAQAVIA
 361 TYGQGRDGEQ PLRLGSLKSN IGHTQAAAGV SGVIKMVQAM RHGVLPKTLH VEKPTDQVDW
 421 SAGAVELLTE AMDWPDKGDG GLRRAAVSSF GVSGTNAHVV LEEAPAAEET PASEATPAVE
 481 PSVGAGLVPW LVSAKTPAAL DAQIGRLAAF ASQGRTDAAD PGAVARVLAG GRAEFEHRAV
 541 VLGTGQDDFA QALTAPEGLI RGTPSDVGRV AFVFPGQGTQ WAGMGAELLD VSKEFAAAMA
 601 ECESALSRYV DWSLEAVVRQ APGAPTLERV DVVQPVTFAV MVSLAKVWQH HGVTPQAVVG
 661 HSQGEIAAAY VAGALTLDDA ARVVTLRSKS IAAHLAGKGG MISLALSEEA TRQRIENLHG
 721 LSIAAVNGPT ATVVSGDPTQ IQELAQACEA DGVRARIIPV DYASHSAHVE TIESELAEVL
 781 AGLSPRTPEV PFFSTLEGAW ITEPVLDGTY WYRNLRHRVG FAPAVETLAT DEGFTHFIEV
 841 SAHPVLTMTL PETVTGLGTL RREQGGQERL VTSLAEAWTN GLTIDWAPVL PTATGHHPEL
 901 PTYAFQRRHY WLHDSPAVQG SVQDSWRYRI DWKRLAVADA SERAGLSGRW LVVVPEDRSA
 961 EAAPVLAALS GAGADPVQLD VSPLGDRQRL AATLGEALAA AGGAVDGVLS LLAWDESAHP
1021 GHPAPFTRGT GATLTLVQAL EDAGVAAPLW CVTHGAVSVG RADHVTSPAQ AMVWGMGRVA
1081 ALEHPERWGG LIDLPSDADR AALDRMTTVL AGGTGEDQVA VRASGLLARR LVRASLPAHG
1141 TASPWWQADG TVLVTGAEEP AAAEAARRLA RDGAGHLLLH TTPSGSECAE GTSGAAEDSG
1201 LAGLVAELAD LGATATVVTC DLTDAEAAAR LLAGVSDAHP LSAVLHLPPT VDSEPLAATD
1261 ADALARVVTA KATAALHLDR LLREAAAGG RPPVLVLFSS VAAIWGGAGQ GAYAAGTAFL
1321 DALAGQHRAD GPTVTSVAWS PWEGSRVTEG ATGERLRRLG LRPLAPATAL TALDTALGHG
1381 DTAVTIADVD WSSFAPGFTT ARPGTLLADL PFARRALDEQ QSTTAADDTV LSRELGALTG
1441 AEQQRRMQEL VREHLAVVLN HPSPEAVDTG RAFRDLGFDS LTAVELRNRL KNATGLALPA
1501 TLVFDYPTPR TLAEFLLAEI LGEQAGAGEQ LPVDGGVDDE PVAIVGMACR LPGGVASPED
1561 LWRLVAGGED AISGFPQDRG WDVEGLYDPD PDASGRTYCR AGGFLDEAGF FDADFFGISP
```

FIG. 5
(CONTINUED)

```
1621 REALAMDPQQ RLLLETSWEA VEDAGIDPTS LQGQQVGVFA GTNGPHYEPL LRNTAEDLEG
1681 YVGTGNAASI MSGRVSYTLG LEGPAVTVDT ACSSSLVALH LAVQALRKGE CGLALAGGVT
1741 VMSTPTTFVE FSRQRGLAED GRSKAFAASA DGFGPAEGVG MLLVERLSDA RRNGHRVLAV
1801 VRGSAVNQDG ASNGLTAPNG PSQQRVIRRA LADARLTTAD VDVVEAHGTG TRLGDPIEAQ
1861 ALIATYGQGR DTEQPLRLGS LKSNIGHTQA AAGVSGIIKM VQAMRHGVLP KTLHVDRPSD
1921 QIDWSAGTVE LLTEAMDWPR KQEGGLRRAA VSSFGISGTN AHIVLEEAPV DEDAPADEPS
1981 VGGVVPWLVS AKTPAALDAQ IGRLAAFASQ GRTDAADPGA VARVLAGGRA QFEHRAVALG
2041 TGQDDLAAAL AAPEGLVRGV ASGVGRVAFV FPGQGTQWAG MGAELLDVSK EFAAAMAECE
2101 AALAPYVDWS LEAVVRQAPG APTLERVDVV QPVTFAVMVS LAKVWQHHGV TPQAVVGHSQ
2161 GEIAAAYVAG ALSLDDAARV VTLRSKSIGA HLAGQGGMLS LALSEAAVVE RLAGFDGLSV
2221 AAVNGPTATV VSGDPTQIQE LAQACEADGV RARIIPVDYA SHSAHVETIE SELADVLAGL
2281 SPQTPQVPFF STLEGAWITE PALDGGYWYR NLRHRVGFAP AVETLATDEG FTHFVEVSAH
2341 PVLTMALPET VTGLGTLRRD NGGQHRLTTS LAEAWANGLT VDWASLLPTT TTHPDLPTYA
2401 FQTERYWPQP DLSAAGDITS AGLGAAEHPL LGAAVALADS DGCLLTGSLS LRTHPWLADH
2461 AVAGTVLLPG TAFVELAFRA GDQVGCDLVE ELTLDAPLVL PRRGAVRVQL SVGASDESGR
2521 RTFGLYAHPE DAPGEAEWTR HATGVLAARA DRTAPVADPE AWPPPGAEPV DVDGLYERFA
2581 ANGYGYGPLF QGVRGVWRRG DEVFADVALP AEVAGAEGAR FGLHPALLDA AVQAAGAGGA
2641 FGAGTRLPFA WSGISLYAVG ATALRVRLAP AGPDTVSVSA ADSSGQPVFA ADSLTVLPVD
2701 PAQLAAFSDP TLDALHLLEW TAWDGAAQAL PGAVVLGGDA DGLAAALRAG GTEVLSFPDL
2761 TDLVEAVDRG ETPAPATVLV ACPAAGPGGP EHVREALHGS LALMQAWLAD ERFTDGRLVL
2821 VTRDAVAARS GDGLRSTGQA AVWGLGRSAQ TESPGRFVLL DLAGEARTAG DATAGDGLTT
2881 GDATVGGTSG DAALGSALAT ALGSGEPQLA LRDGALLVPR LARAAAPAAA DGLAAADGLA
2941 ALPLPAAPAL WRLEPGTDGS LESLTAAPGD AETLAPEPLG PGQVRIAIRA TGLNFRDVLI
3001 ALGMYPDPAL MGTEGAGVVT ATGPGVTHLA PGDRVMGLLS GAYAPVVVAD ARTVARMPEG
3061 WTFAQGASVP VVFLTAVYAL RDLADVKPGE RLLVHSAAGG VGMAAVQLAR HWGVEVHGTA
3121 SHGKWDALRA LGLDDAHIAS SRTLDFESAF RAASGGAGMD VVLNSLAREF VDASLRLLGP
3181 GGRFVEMGKT DVRDAERVAA DHPGVGYRAF DLGEAGPERI GEMLAEVIAL FEDGVLRHLP
3241 VTTWDVRRAR DAFRHVSQAR HTGKVVLTMP SGLDPEGTVL LTGGTGALGG IVARHVVGEW
3301 GVRRLLLVSR RGTDAPGAGE LVHELEALGA DVSVAACDVA DREALTAVLD SIPAEHPLTA
3361 VVHTAGVLSD GTLPSMTAED VEHVLRPKVD AAFLLDELTS TPGYDLAAFV MFSSAAAVFG
3421 GAGQGAYAAA NATLDALAWR RRTAGLPALS LGWGLWAETS GMTGGLSDTD RSRLARSGAT
3481 PMDSELTLSL LDAAMRRDDP ALVPIALDVA ALRAQQRDGM LAPLLSGLTR GSRVGGAPVN
3541 QRRAAAGGAG EADTDLGGRL AAMTPDDRVA HLRDLVRTHV ATVLGHGTPS RVDLERAFRD
3601 TGFDSLTAVE LRNRLNAATG LRLPATLVFD HPTPGELAGH LLDELATAAG GSWAEGTGSG
3661 DTASATDRQT TAALAELDRL EGVLASLAPA AGGRPELAAR LRALAAALGD DGDDATDLDE
3721 ASDDDLFSFI DKELGDSDF
```

Amino acid sequence of narbonilide synthase subunit 3, PICAIII, 1563 AA (SEQ ID NO:4)

```
   1 MANNEDKLRD YLKRVTAELQ QNTRRLREIE GRTHEPVAIV GMACRLPGGV ASPEDLWQLV
  61 AGDGDAISEF PQDRGWDVEG LYDPDPDASG RTYCRSGGFL HDAGEFDADF FGISPREALA
 121 MDPQQRLSLT TAWEAIESAG IDPTALKGSG LGVFVGGWHT GYTSGQTTAV QSPELEGHLV
 181 SGAALGFLSG RIAYVLGTDG PALTVDTACS SSLVALHLAV QALRKGECDM ALAGGVTVMP
 241 NADLFVQFSR QRGLAADGRS KAFATSADGF GPAEGAGVLL VERLSDARRN GHRILAVVRG
 301 SAVNQDGASN GLTAPHGPSQ QRVIRRALAD ARLAPGDVDV VEAHGTGTRL GDPIEAQALI
 361 ATYGQEKSSE QPLRLGALKS NIGHTQAAAG VAGVIKMVQA MRHGLLPKTL HVDEPSDQID
 421 WSAGTVELLT EAVDWPEKQD GGLRRAAVSS FGISGTNAHV VLEEAPAVED SPAVEPPAGG
 481 GVVPWPVSAK TPAALDAQIG QLAAYADGRT DVDPAVAARA LVDSRTAMEH RAVAVGDSRE
 541 ALRDALRMPE GLVRGTSSDV GRVAFVFPGQ GTQWAGMGAE LLDSSPEFAA SMAECETALS
 601 RYVDWSLEAV VRQEPGAPTL DRVDVVQPVT FAVMVSLAKV WQHHGITPQA VVGHSQGEIA
 661 AAYVAGALTL DDAARVVTLR SKSIAAHLAG KGGMISLALD EAAVLKRLSD FDGLSVAAVN
 721 GPTATVVSGD PTQIEELART CEADGVRARI IPVDYASHSR QVEIIEKELA EVLAGLAPQA
 781 PHVPFFSTLE GTWITEPVLD GTYWYRNLRH RVGFAPAVET LAVDGFTHFI EVSAHPVLTM
 841 TLPETVTGLG TLRREQGGQE RLVTSLAEAW ANGLTIDWAP ILPTATGHHP ELPTYAFQTE
 901 RFWLQSSAPT SAADDWRYRV EWKPLTASGQ ADLSGRWIVA VGSEPEAELL GALKAAGAEV
 961 DVLEAGADDD REALAARLTA LTTGDGFTGV VSLLDDLVPQ VAWVQALGDA GIKAPLWSVT
1021 QGAVSVGRLD TPADPDRAML WGLGRVVALE HPERWAGLVD LPAQPDAAAL AHLVTALSGA
1081 TGEDQIAIRT TGLHARRLAR APLHGRRPTR DWQPHGTVLI TGGTGALGSH AARWMAHHGA
```

FIG. 5
(CONTINUED)

```
1141 EHLLLVSRSG EQAPGATQLT AELTASGARV TIAACDVADP HAMRTLLDAI PAETPLTAVV
1201 HTAGAPGGDP LDVTGPEDIA RILGAKTSGA EVLDDLLRGT PLDAFVLYSS NAGVWGSGSQ
1261 GVYAAANAHL DALAARRRAR GETATSVAWG LWAGDGMGRG ADDAYWQRRG IRPMSPDRAL
1321 DELAKALSHD ETFVAVADVD WERFAPAFTV SRPSLLLDGV PEARQALAAP VGAPAPGDAA
1381 VAPTGQSSAL AAITALPEPE RRPALLTLVR THAAAVLGHS SPDRVAPGRA FTELGFDSLT
1441 AVQLRNQLST VVGNRLPATT VFDHPTPAAL AAHLHEAYLA PAEPAPTDWE GRVRRALAEL
1501 PLDRLRDAGV LDTVLRLTGI EPEPGSGGSD GGAADPGAEP EASIDDLDAE ALIRMALGPR
1561 NT
```

Amino acid sequence of narbonolide synthase subunit 4, PICAIV, 1347 AA (SEQ ID NO:5)

```
   1 MTSSNEQLVD ALRASLKENE ELRKESRRRA DRRQEPMAIV GMSCRFAGGI RSPEDLWDAV
  61 AAGKDLVSEV PEERGWDIDS LYDPVGRKG TTYVRNAAFL DDAAGFDAAF FGISPREALA
 121 MDPQQRQLLE ASWEVFERAG IDPASVRGTD VGVYVGCGYQ DYAPDIRVAP EGTGGYVVTG
 181 NSSAVASGRI AYSLGLEGPA VTVDTACSSS LVALHLALKG LRNGDCSTAL VGGVAVLATP
 241 GAFIEFSSQQ AMAADGRTKG FASAADGLAW GEGVAVLLLE RLSDARRKGH RVLAVVRGSA
 301 INQDGASNGL TAPHGPSQQR LIRQALADAR LTSSDVDVVE GHGTGTRLGD PIEAQALLAT
 361 YGQGRAPGQP LRLGTLKSNI GHTQAASGVA GVIKMVQALR HGVLPKTLHV DEPTDQVDWS
 421 AGSVELLTEA VDWPERPGRL RRAGVSAFGV GGTNAHVVLE EAPAVEESPA VEPPAGGGVV
 481 PWPVSAKTSA ALDAQIGQLA AYAEDRTDVD PAVAARALVD SRTAMEHRAV AVGDSREALR
 541 DALRMPEGLV RGTVTDPGRV AFVFPGQGTQ WAGMGAELLD SSPEFAAAMA ECETALSPYV
 601 DWSLEAVVRQ APSAPTLDRV DVVQPVTFAV MVSLAKVWQH HGITPEAVIG HSQGEIAAAY
 661 VAGALTLDDA ARVVTLRSKS IAAHLAGKGG MISLALSEEA TRQRIENLHG LSIAAVNGPT
 721 ATVVSGDPTQ IQELAQACEA DGIRARIIPV DYASHSAHVE TIENELADVL AGLSPQTPQV
 781 PFFSTLEGTW ITEPALDGGY WYRNLRHRVG FAPAVETLAT DEGFTHFIEV SAHPVLTMTL
 841 PDKVTGLATL RREDGGQHRL TTSLAEAWAN GLALDWASLL PATGALSPAV PDLPTYAFQH
 901 RSYWISPAGP GEAPAHTASG REAVAETGLA WGPGAEDLDE EGRRSAVLAM VMRQAASVLR
 961 CDSPEEVPVD RPLREIGFDS LTAVDFRNRV NRLTGLQLPP TVVFEHPTPV ALAERISDEL
1021 AERNWAVAEP SDHEQAEEEK AAAPAGARSG ADTGAGAGMF RALFRQAVED DRYGEFLDVL
1081 AEASAFRPQF ASPEACSERL DPVLLAGGPT DRAEGRAVLV GCTGTAANGG PHEFLRLSTS
1141 FQEERDFLAV PLPGYGTGTG TGTALLPADL DTALDAQARA ILRAAGDAPV VLLGHSGGAL
1201 LAHELAFRLE RAHGAPPAGI VLVDPYPPGH QEPIEVWSRQ LGEGLFAGEL EPMSDARLLA
1261 MGRYARFLAG PRPGRSSAPV LLVRASEPLG DWQEERGDWR AHWDLPHTVA DVPGDHFTMM
1321 RDHAPAVAEA VLSWLDAIEG IEGAGK
```

Amino acid sequence of typeII thioesterase, PICB, 282 AA (SEQ ID NO:6)

```
   1 VTDRPLNVDS GLWIRRFHPA PNSAVRLVCL PHAGGSASYF FRFSEELHPS VEALSVQYPG
  61 RQDRRAEPCL ESVEELAEHV VAATEPWWQE GRLAFFGHSL GASVAFETAR ILEQRHGVRP
 121 EGLYVSGRRA PSLAPDRLVH QLDDRAFLAE IRRLSGTDER FLQDDELLRL VLPALRSDYK
 181 AAETYLHRPS AKLTCPVMAL AGDRDPKAPL NEVAEWRRHT SGPFCLRAYS GGHFYLNDQW
 241 HEICNDISDH LLVTRGAPDA RVVQPPTSLI EGAAKRWQNP R
```

Amino acid sequence of 3-keto-6-deoxyglucose isomerase, PICCII, 383 AA (SEQ ID NO:7)

```
   1 VADRELGTHL LETRGIHWIH AANGDPYATV LRGQADDPYP AYERVRARGA LSFSPTGSWV
  61 TADHALAASI LCSTDFGVSG ADGVPVPQQV LSYGEGCPLE REQVLPAAGD VPEGGQRAVV
 121 EGIHRETLEG LAPDPSASYA FELLGGFVRP AVTAAAAAVL GVPADRRADF ADLLERLRPL
 181 SDSLLAPQSL RTVRAADGAL AELTALLADS DDSPGALLSA LGVTAAVQLT GNAVLALLAH
 241 PEQWRELCDR PGLAAAAVEE TLRYDPPVQL DARVVRGETE LAGRRLPAGA HVVVLTAATG
 301 RDPEVFTDPE RFDLARPDAA AHLALHPAGP YGPVASLVRL QAEVALRTLA GRFPGLRQAG
 361 DVLRPRRAPV GRGPLSVPVS SS
```

FIG. 5
(CONTINUED)

Amino acid sequence of desosaminyl transferase, PICCIII, 427 AA (SEQ ID NO:8)

```
  1 MRVLLTSFAH HTHYYGLVPL AWALLAAGHE VRVASQPALT DTITGSGLAA VPVGTDHLIH
 61 EYRVRMAGEP RPNHPAIAFD EARPEPLDWD HALGIEAILA PYFYLLANND SMVDDLVDFA
121 RSWQPDLVLW EPTTYAGAVA AQVTGAAHAR VLWGPDVMGS ARRKFVALRD RQPPEHREDP
181 TAEWLTWTLD RYGASFEEEL LTGQFTIDPT PPSLRLDTGL PTVGMRYVPY NGTSVVPDWL
241 SEPPARPRVC LTLGVSAREV LGGDGVSQGD ILEALADLDI ELVATLDASQ RAEIRNYPKH
301 TRFTDFVPMH ALLPSCSAII HHGGAGTYAT AVINAVPQVM LAELWDAPVK ARAVAEQGAG
361 FFLPPAELTP QAVRDAVVRI LDDPSVATAA HRLREETFGD PTPAGIVPEL ERLAAQHRRP
421 PADARH
```

FIG. 5
(CONTINUED)

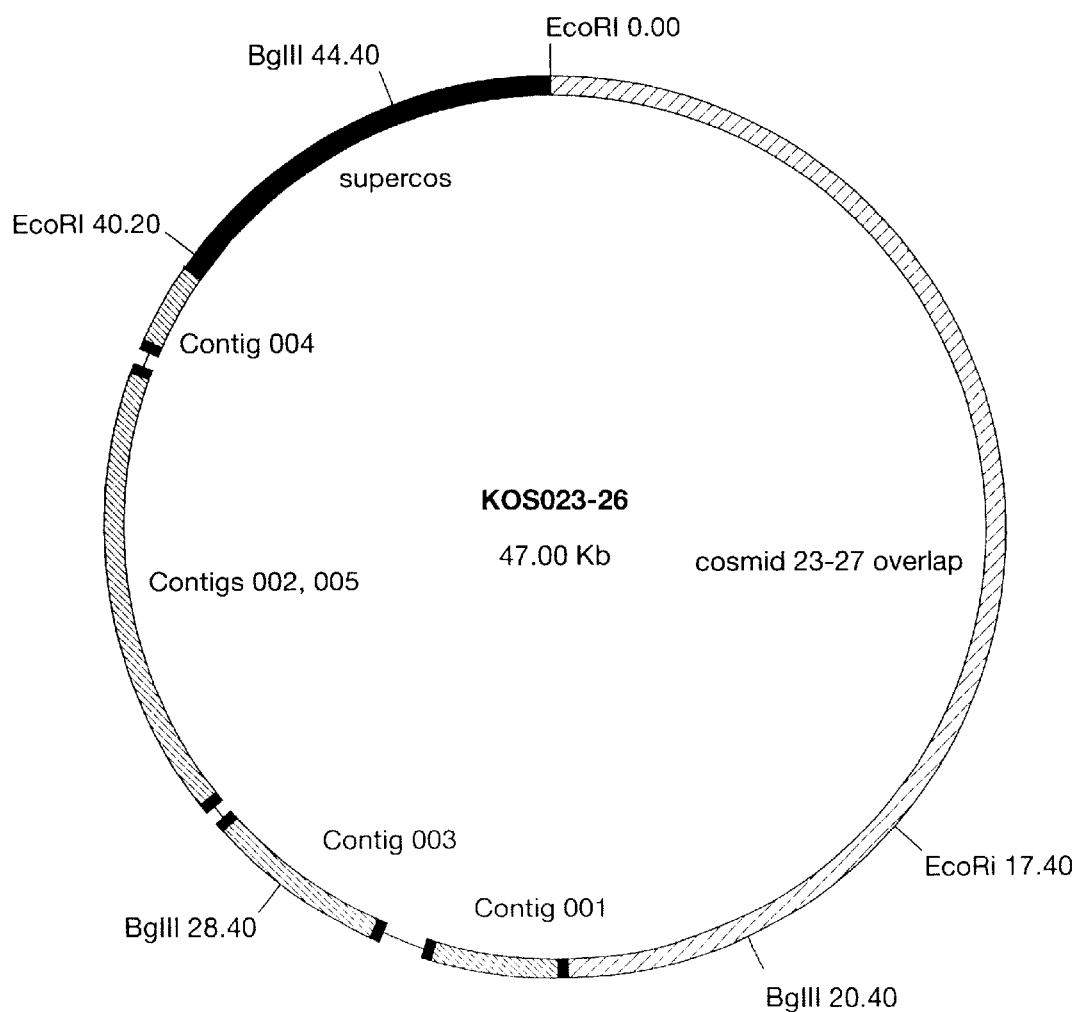

FIG. 6

Contig 001 from cosmid pKOS023-26, 2401 nucleotides (SEQ ID NO:9)

```
   1 CGTGGCGGCC GCCGCTCCCG GCGCCGCCGA CACGGCCAAT GTTCAGTACA CGAGCCGGGC
  61 GGCGGAGCTC GTCGCCCAGA TGACGCTCGA CGAGAAGATC AGCTTCGTCC ACTGGGCGCT
 121 GGACCCCGAC CGGCAGAACG TCGGCTACCT TCCCGGCGTG CCGCGTCTGG GCATCCCGGA
 181 GCTGCGTGCC GCCGACGGCC CGAACGGCAT CCGCCTGGTG GGGCAGACCG CCACCGCGCT
 241 GCCCGCGCCG GTCGCCCTGG CCAGCACCTT CGACGACACC ATGGCCGACA GCTACGGCAA
 301 GGTCATGGGC CGCGACGGTC GCGCGCTCAA CCAGGACATG GTCCTGGGCC CGATGATGAA
 361 CAACATCCGG GTGCCGCACG GCGGCCGGAA CTACGAGACC TTCAGCGAGG ACCCCCTGGT
 421 CTCCTCGCGC ACCGCGGTCG CCCAGATCAA GGGCATCCAG GGTGCGGGTC TGATGACCAC
 481 GGCCAAGCAC TTCGCGGCCA ACAACCAGGA GAACAACCGC TTCTCCGTGA ACGCCAATGT
 541 CGACGAGCAG ACGCTCCGCG AGATCGAGTT CCCGGCGTTC GAGGCGTCCT CCAAGGCCGG
 601 CGCGGGCTCC TTCATGTGTG CCTACAACGG CCTCAACGGG AAGCCGTCCT GCGGCAACGA
 661 CGAGCTCCTC AACAACGTGC TGCGCACGCA GTGGGGCTTC AGGGCTGGG TGATGTCCGA
 721 CTGGCTCGCC ACCCCGGGCA CCGACGCCAT CACCAAGGGC CTCGACCAGG AGATGGGCGT
 781 CGAGCTCCCC GGCGACGTCC CGAAGGGCGA GCCCTCGCCG CCGGCCAAGT TCTTCGGCGA
 841 GGCGCTGAAG ACGGCCGTCC TGAACGGCAC GGTCCCCGAG GCGGCCGTGA CGCGGTCGGC
 901 GGAGCGGATC GTCGGCCAGA TGGAGAAGTT CGGTCTGCTC CTCGCCACTC CGGCGCCGCG
 961 GCCCGAGCGC GACAAGGCGG GTGCCCAGGC GGTGTCCCGC AAGGTCGCCG AGAACGGCGC
1021 GGTGCTCCTG CGCAACGAGG GCCAGGCCCT GCCGCTCGCC GGTGACGCCG GCAAGAGCAT
1081 CGCGGTCATC GGCCCGACGG CCGTCGACCC CAAGGTCACC GGCCTGGGCA GCGCCCACGT
1141 CGTCCCGGAC TCGGCGGCGG CGCCACTCGA CACCATCAAG GCCGCGCGG GTGCGGGTGC
1201 GACGGTGACG TACGAGACGG GTGAGGAGAC CTTCGGGACG CAGATCCCGG CGGGGAACCT
1261 CAGCCCGGCG TTCAACCAGG GCCACCAGCT CGAGCCGGGC AAGGCGGGGG CGCTGTACGA
1321 CGGCACGCTG ACCGTGCCCG CCGACGGCGA GTACCGCATC GCGGTCCGTG CCACCGGTGG
1381 TTACGCCACG GTGCAGCTCG GCAGCCACAC CATCGAGGCC GGTCAGGTCT ACGGCAAGGT
1441 GAGCAGCCCG CTCCTCAAGC TGACCAAGGG CACGCACAAG CTCACGATCT CGGGCTTCGC
1501 GATGAGTGCC ACCCCGCTCT CCCTGGAGCT GGGCTGGGTN ACGCCGGCGG CGGCCGACGC
1561 GACGATCGCG AAGGCCGTGG AGTCGGCGCG GAAGGCCCGT ACGGCGGTCG TCTTCGCCTA
1621 CGACGACGGC ACCGAGGGCG TCGACCGTCC GAACCTGTCG CTGCCGGGTA CGCAGGACAA
1681 GCTGATCTCG GCTGTCGCGG ACGCCAACCC GAACACGATC GTGGTCCTCA ACACCGGTTC
1741 GTCGGTGCTG ATGCCGTGGC TGTCCAAGAC CCGCGCGGTC CTGGACATGT GGTACCCGGG
1801 CCAGGCGGGC GCCGAGGCCA CCGCCGCGCT GCTCTACGGT GACGTCAACC CGAGCGGCAA
1861 GCTCACGCAG AGCTTCCCGG CCGCCGAGAA CCAGCACGCG GTCGCCGGCG ACCCGACCAG
1921 CTACCCGGGC GTCGACAACC AGCAGACGTA CCGCGAGGGC ATCCACGTCG GGTACCGCTG
1981 GTTCGACAAG GAGAACGTCA AGCCGCTGTT CCCGTTCGGG CACGGCCTGT CGTACACCTC
2041 GTTCACGCAG AGCGCCCCGA CCGTCGTGCG TACGTCCACG GGTGGTCTGA AGGTCACGGT
2101 CACGGTCCGC AACAGCGGGA AGCGGCCCGG CCAGGAGGTC GTCCAGGCGT ACCTCGGTGC
2161 CAGCCCGAAC GTGACGGCTC CGCAGGCGAA GAAGAAGCTC GTGGGCTACA CGAAGGTCTC
2221 GCTCGCCGCG GGCGAGGCGA AGACGGTGAC GGTGAACGTC GACCGCCGTC AGCTGCAGTT
2281 CTGGGATGCC GCCACGGACA ACTGGAAGAC GGGAACGGGC AACCGCCTCC TGCAGACCGG
2341 TTCGTCCTCC GCCGACCTGC GGGGCAGCGC CACGGTCAAC GTCTGGTGAC GTGACGCCGT
2401 G
```

Amino acid sequence of beta glucosidase, ORF11, 770 AA (SEQ ID NO:10)

```
  1 MTLDEKISFV HWALDPDRQN VGYLPGVPRL GIPELRAADG PNGIRLVGQT ATALPAPVAL
 61 ASTFDDTMAD SYGKVMGRDG RALNQDMVLG PMMNNIRVPH GGRNYETFSE DPLVSSRTAV
121 AQIKGIQGAG LMTTAKHFAA NNQENNRFSV NANVDEQTLR EIEFPAFEAS SKAGAGSFMC
181 AYNGLNGKPS CGNDELLNNV LRTQWGFQGW VMSDWLATPG TDAITKGLDQ EMGVELPGDV
241 PKGEPSPPAK FFGEALKTAV LNGTVPEAAV TRSAERIVGQ MEKFGLLLAT PAPRPERDKA
301 GAQAVSRKVA ENGAVLLRNE GQALPLAGDA GKSIAVIGPT AVDPKVTGLG SAHVVPDSAA
361 APLDTIKARA GAGATVTYET GEETFGTQIP AGNLSPAFNQ GHQLEPGKAG ALYDGTLTVP
421 ADGEYRIAVR ATGGYATVQL GSHTIEAGQV YGKVSSPLLK LTKGTHKLTI SGFAMSATPL
481 SLELGWVTPA AADATIAKAV ESARKARTAV VFAYDDGTEG VDRPNLSLPG TQDKLISAVA
541 DANPNTIVVL NTGSSVLMPW LSKTRAVLDM WYPGQAGAEA TAALLYGDVN PSGKLTQSFP
601 AAENQHAVAG DPTSYPGVDN QQTYREGIHV GYRWFDKENV KPLFPFGHGL SYTSFTQSAP
661 TVVRTSTGGL KVTVTVRNSG KRAGQEVVQA YLGASPNVTA PQAKKKLVGY TKVSLAAGEA
721 KTVTVNVDRR QLQFWDAATD NWKTGTGNRL LQTGSSSADL RGSATVNVW
```

FIG. 6
(CONTINUED)

Contig 002 from cosmid pKOS023-26, 5970 nucleotides (SEQ ID NO:11)

```
   1 GGCGAGAAGT AGGCGCGGGT GTGCACGCCT TCGGCCTTCA GGACCTCCAT GACGAGGTCG
  61 CGGTGGATGC CGGTGGTGGC CTCGTCGATC TCGACGATCA CGTACTGGTG GTTGTTGAGG
 121 CCGTGGCGGT CGTGGTCGGC GACGAGGACG CCGGGGAGGT CCGCGAGGTG CTCGCGGTAG
 181 SCGGCGTGGT TGCGCCGGTT CCGGTCGATG ACCTCGGGAA ACGCGTCGAG GGAGGTGAGG
 241 CCCATGGCGG CGGCGGCCTC GCTCATCTTG GCGTTGGTCC CGCCGGCGGG GCTGCCGCCG
 301 GGCAGGTCGA AGCCGAAGTT GTGGAGGGCG CGGATCCGGG CGGCGAGGTC GGCGTCGTCG
 361 GTGACGACGG CGCCGCCCTC GAAGGCGTTG ACGGCCTTGG TGGCGTGGAA GCTGAAGACC
 421 TCGGCGTCGC CGAGGCTGCC GGCGGGCCGG CCGTCGACCG CGCAGCCGAG GGCGTGCGCG
 481 GCGTCGAAGT ACAGCCGCAG GCCGTGCTCG TCGGCGACCT TCCGCAGCTG GTCGGCGGCG
 541 CAGGGGCGGC CCCAGAGGTG GACGCCGACG ACGGCCGAGG TGCGGGGTGT GACCGCGGCG
 601 GCCACCTGGT CCGGGTCGAG GTTGCCGGTG TCCGGGTCGA TGTCGGCGAA GACCGGGGTG
 661 AGGCCGATCC AGCGCAGTGC GTGCGGGGTG GCGGCGAACG TCATCGACGG CATGATCACT
 721 TCGCCGGTGA GGCCGGCGGC GTGCGCGAGG AGCTGGAGCC CGGCCGTGGC GTTGCAGGTG
 781 GCCACGGCAT GCCGGACCCC GGCGAGCCCG GCGACGCGCT CCTCGAACTC GCGGACGAGC
 841 GGGCCGCCGT TGGACAGCCA CTGGCTGTCG AGGGCCCGGT CGAGCCGCTC GTACAGCCTG
 901 GCGCGGTCGA TGCGGTTGGG CCGCCCCACG AGGAGCGGCT GGTCGAAAGC GGCGGGGCCG
 961 CCGAAGAATG CGAGGTCGGA TAAGGCGCTT TTCACGGATG TTCCCTCCGG GCCACCGTCA
1021 CGAAATGATT CGCCGATCCG GGAATCCCGA ACGAGGTCGC CGCGCTCCAC CGTGACGTAC
1081 GACGAGATGG TCGATTGTGG TGGTCGATTT CGGGGGGACT CTAATCCGCG CGGAACGGGA
1141 CCGACAAGAG CACGCTATGC GCTCTCGATG TGCTTCGGAT CACATCCGCC TCCGGGGTAT
1201 TCCATCGGCG GCCCGAATGT GATGATCCTT GACAGGATCC GGGAATCAGC CGAGCCGCCG
1261 GGAGGGCCGG GGCGCGCTCC GCGGAAGAGT ACGTGTGAGA AGTCCCGTTC CTCTTCCCGT
1321 TTCCGTTCCG CTTCCGGCCC GGTCTGGAGT TCTCCGTGCG CCGTACCCAG CAGGGAACGA
1381 CCGCTTCTCC CCCGGTACTC GACCTCGGGG CCCTGGGGCA GGATTTCGCG GCCGATCCGT
1441 ATCCGACGTA CGCGAGACTG CGTGCCGAGG GTCCGGCCCA CCGGGTGCGC ACCCCCGAGG
1501 GGGACGAGGT GTGGCTGGTC GTCGGCTACG ACCGGGCGCG GCGGTCCTC GCCGATCCCC
1561 GGTTCAGCAA GGACTGGCGC AACTCCACGA CTCCCCTGAC CGAGGCCGAG GCCGCGCTCA
1621 ACCACAACAT GCTGGAGTCC GACCCGCCGC GGCACACCCG GCTGCGCAAG CTGGTGGCCC
1681 GTGAGTTCAC CATGCGCCGG GTCGAGTTGC TGCGGCCCCG GGTCCAGGAG ATCGTCGACG
1741 GGCTCGTGGA CGCCATGCTG GCGGCGCCCG ACGGCCGCGC CGATCTGATG GAGTCCCTGG
1801 CCTGGCCGCT GCCGATCACC GTGATCTCCG AACTCCTCGG CGTGCCCGAG CCGGACCGCG
1861 CCGCCTTCCG CGTCTGGACC GACGCCTTCG TCTTCCCGGA CGATCCCGCC CAGGCCCAGA
1921 CCGCCATGGC CGAGATGAGC GGCTATCTCT CCCGGCTCAT CGACTCCAAG CGCGGGCAGG
1981 ACGGCGAGGA CCTGCTCAGC GCGCTCGTGC GGACCAGCGA CGAGGACGGC TCCCGGCTGA
2041 CCTCCGAGGA GCTGCTCGGT ATGGCCCACA TCCTGCTCGT CGCGGGGCAC GAGACCACGG
2101 TCAATCTGAT CGCCAACGGC ATGTACGCGC TGCTCTCGCA CCCCGACCAG CTGGCCGCCC
2161 TGCGGGCCGA CATGACGCTC TTGGACGGCG CGGTGGAGGA GATGTTGCGC TACGAGGGCC
2221 CGGTGGAATC CGCGACCTAC CGCTTCCCGG TCGAGCCCGT CGACCTGGAC GGCACGGTCA
2281 TCCCGGCCGG TGACACGGTC CTCGTCGTCC TGGCCGACGC CCACCGCACC CCCGAGCGCT
2341 TCCCGGACCC GCACCGCTTC GACATCGCC GGGACACCGC CGGCCATCTC GCCTTCGGCC
2401 ACGGCATCCA CTTCTGCATC GGCGCCCCCT TGGCCCGGTT GGAGGCCCGG ATCCGGTCC
2461 GCGCCCTTCT CGAACGCTGC CCGGACCTCG CCCTGGACGT CTCCCCCGGC GAACTCGTGT
2521 GGTATCCGAA CCCGATGATC CGCGGCTCA AGGCCCTGCC GATCCGCTGG CGGCGAGGAC
2581 GGGAGGCGGG CCGCCGTACC GGTTGAACCC GCACGTCACC CATTACGACT CCTTGTCACG
2641 GAAGCCCCGG ATCGGTCCCC CCTCGCCGTA ACAAGACCTG GTTAGAGTGA TGGAGGACGA
2701 CGAAGGGTTC GGCGCCCGGA CGAGGGGGA CTTCCGCGAT GAATCTGGTG GAACGCGACG
2761 GGGAGATAGC CCATCTCAGG GCCGTTCTTG ACGCATCCGC CGCAGGTGAC GGGACGCTCT
2821 TACTCGTCTC CGGACCGGCC GGCAGCGGGA AGACGGAGCT GCTGCGGTCG CTCCGCCGGC
2881 TGGCCGCCGA GCGGGAGACC CCGTCTGGT CGGTCCGGGC GCTGCCGGGT GACGCGACA
2941 TCCCCCTGGG CGTCCTCTGC CAGTTACTCC GCAGCGCCGA CAACACGGT GCCGACACCT
3001 CCGCCGTCCG CGACCTGCTG GACGCCGCCT CGCGGCGGGC CGGAACCTCA CCTCCCCCGC
3061 CGACGCGCCG CTCCGCGTCG ACGAGACACA CCGCCTGCAC GACTGGCTGC TCTCCGTCTC
3121 CCGCCGGCAC CCCGTTCCTC GTCGCCGTCG ACGACCTGAC CCACGCCGAC ACCGCGTCCC
3181 TGAGGTTCCT CCTGTACTGC GCCGCCACC ACGACCAGGG CGGCATCGGC TTCGTCATGA
3241 CCGAGCGGGC CTCGCAGCGC GCCGGATACC GGGTGTTCCG CGCCGAGCTG CTCCGCCAGC
3301 CGCACTGCCG CAACATGTGG CTCTCCGGGC TTCCCCCCAG CGGGGTACGC CAGTTACTCG
```

FIG. 6
(CONTINUED)

```
3361 CCCACTACTA CGGCCCCGAG GCCGCCGAGC GGCGGGCCCC CGCGTACCAC GCGACGACCG
3421 GCGGGAACCC GCTGCTCCTG CGGGCCGCTGA CCCAGGACCG GCAGGCCTCC CACACCACCC
3481 TCGGCGCGGC CGGCGGCGAC GAGCCCGTCC ACGGCGACGC CTTCGCCCAG GCCGTCCTCG
3541 ACTGCCTGCA CCGCAGCGCC GAGGGCACAC TGGAGACCGC CCGCTGGCTC GCGGTCCTCG
3601 AACAGTCCGA CCCGCTCCTG GTGGAGCGGC TCACGGGAAC GACCGCCGCC GCCGTCGAGC
3661 GCCACATCCA GGAGCTCGCC GCCATCGGCC TCCTGGACGA GGACGGCACC CTGGGACAGC
3721 CCGCGATCCG CGAGGCCGCC CTCCAGGACC TGCCGGCCGG CGAGCGCACC GAACTGCACC
3781 GGCGCGCCGC GGAGCAGCTG CACCGGGACG GCGCCGACGA GGACACCGTG GCCCGCCACC
3841 TGCTGGTCGG CGGCGCCCCC GACGCTCCCT GGGCGCTGCC CCTGCTCGAA CGGGGCGCGC
3901 AGCAGGCCCT GTTCGACGAC CGACTCGACG ACGCCTTCCG GATCCTCGAG TTCGCCGTGC
3961 GGTCGAGCAC CGACAACACC CAGCTGGCCC GCCTCGCCCC ACACCTGGTC GCGGCCTCCT
4021 GGCGGATGAA CCCGCACATG ACGACCCGGG CCCTCGCACT CTTCGACCGG CTCCTGAGCG
4081 GTGAACTGCC GCCCAGCCAC CCGGTCATGG CCCTGATCCG CTGCCTCGTC TGGTACGGNC
4141 GGCTGCCCGA GGCCGCCGAC GCGCTGTCCC GGCTGCGGCC CAGCTCCGAC AACGATGCCT
4201 TGGAGCTGTC GCTCACCCGG ATGTGGCTCG CGGCGCTGTG CCCGCCGCTC CTGGAGTCCC
4261 TGCCGGCCAC GCCGGAGCCG GAGCGGGGTC CCGTCCCCGT ACGGCTCGCG CCGCGGACGA
4321 CCGCGCTCCA GGCCCAGGCC GGCGTCTTCC AGCGGGGCCC GGACAACGCC TCGGTCGCGC
4381 AGGCCGAACA GATCCTGCAG GGCTGCCGGC TGTCGGAGGA GACGTACGAG GCCCTGGAGA
4441 CGGCCCTCTT GGTCCTCGTC CACGCCGACC GGCTCGACCG GGCGCTGTTC TGGTCGGACG
4501 CCCTGCTCGC CGAGGCCGTG GAGCGGCGGT CGCTCGGCTG GGAGGCGGTC TTCGCCGCGA
4561 CCCGGGCGAT GATCGCGATC CGCTGCGGCG ACCTCCCGAC GGCGCGGGAG CGGGCCGAGC
4621 TGGCGCTCTC CCACGCGGCG CCGGAGAGCT GGGGCCTCGC CGTGGGCATG CCCCTCTCCG
4681 CGCTGCTGCT CGCCTGCACG GAGGCCGGCG AGTACGAACA GGCGGAGCGG GTCCTGCGGC
4741 AGCCGGTGCC GGACGGATG TTCGACTCGC GGCACGGCAT GGAGTACATG CACGCCCGGG
4801 GCCGCTACTG GCTGGCGANC GGCCGGCTGC ACGCGGCGCT GGGCGAGTTC ATGCTCTGCG
4861 GGGAGATCCT GGGCAGCTGG AACCTCGACC AGCCCTCGAT CGTGCCCTGG CGGACCTCCG
4921 CCGCCGAGGT GTACCTGCGG CTCGGCAACC GCCAGAAGGC CAGGGCGCTG GCCGAGGCCC
4981 AGCTCGCCCT GGTGCGGCCC GGGCGCTCCC GCACCCGGGG TCTCACCCTG CGGGTCCTGG
5041 CGGCGGCGGT GGACGGCCAG CAGGCGGAGC GGCTGCACGC CGAGGCGGTC GACATGCTGC
5101 ACGACAGCGG CGACCGGCTC GAACACGCCC GCGCGCTCGC CGGGATGAGC CGCCACCAGC
5161 AGGCCCAGGG GGACAACTAC CGGGCGAGGA TGACGGCGCG GCTCGCCGGC GACATGGCGT
5221 GGGCCTGCGG CGCGTACCCG CTGGCCGAGG AGATCGTGCC GGGCCGCGGC GGCCGCCGGG
5281 CGAAGGCGGT GAGCACGGAG CTGGAACTGC CGGGCGGCCC GGACGTCGGC CTGCTCTCGG
5341 AGGCCGAACG CCGGGTGGCG GCCCTGGCAG CCCGAGGATT GACGAACCGC CAGATAGCGC
5401 GCCGGCTCTG CGTCACCGCG AGCACGGTCG AACAGCACCT GACGCGCGTC TACCGCAAAC
5461 TGAACGTGAC CCGCCGAGCA GACCTCCCGA TCAGCCTCGC CCAGGACAAG TCCGTCACGG
5521 CCTGAGCCAC CCCCGGTGTC CCCGTGCGAC GACCCGCCGC ACGGGCCACC GGGCCCGCCG
5581 GGACACGCCG GTGCGACACG GGGGCGCGCC AGGTGCCATG GGGACCTCCG TGACCGCCCG
5641 AGGCGCCCGA GGCGCCCGGT GCGGCACCCG GAGACGCCAG GACCGCCGGG ACCACCGGAG
5701 ACGCCAGGGA CCGCTGGGGA CACCGGGACC TCAGGGACCG CCGGGACCGC CCGAGTTGCA
5761 CCCGGTGCGC CCGGGGACAC CAGACCGCCG GGACCACCCG AGGGTGCCCG GTGTGGCCCC
5821 GGCGGCCGGG GTGTCCTTCA TCGGTGGGCC TTCATCGGCA GGAGGAAGCG ACCGTGAGAC
5881 CCGTCGTGCC GTCGGCGATC AGCCGCCTGT ACGGGCGTCG GACTCCCTGG CGGTCCCGGA
5941 CCCGTCGTAC GGGCTCGCGG GACCCGGTGC
```

Partial amino acid sequence of aminotransferase-dehydrase, PICCIV, 331 AA (SEQ ID NO:12)

```
  1 VKSALSDLAF FGGPAAFDQP LLVGRPNRID RARLYERLDR ALDSQWLSNG GPLVREFEER
 61 VAGLAGVRHA VATCNATAGL QLLAHAAGLT GEVIMPSMTF AATPHALRWI GLTPVFADID
121 PDTGNLDPDQ VAAAVTPRTS AVVGVHLWGR PCAADQLRKV ADEHGLRLYF DAAHALGCAV
181 DGRPAGSLGD AEVFSFHATK AVNAFEGGAV VTDDADLAAR IRALHNFGFD LPGGSPAGGT
241 NAKMSFAAAA MGLTSLDAFP EVIDRNRRNH AXYREHLADL PGVLVADHDR HGLNNHQYVI
301 VEIDEATTGI HRDLVMEVLK AEGVHTRAYF S
```

FIG. 6
(CONTINUED)

Amino acid sequence of picromycin/methymycin cytochrome P450 hydroxylase,
PICK, 417 AA (SEQ ID NO:13)

```
  1 VRRTQQGTTA SPPVLDLGAL GQDFAADPYP TYARLRAEGP AHRVRTPEGD EVWLVVGYDR
 61 ARAVLADPRF SKDWRNSTTP LTEAEAALNH NMLESDPPRH TRLRKLVARE FTMRRVELLR
121 PRVQEIVDGL VDAMLAAPDG RADLMESLAW PLPITVISEL LGVPEPDRAA FRVWTDAFVF
181 PDDPAQAQTA MAEMSGYLSR LIDSKRGQDG EDLLSALVRT SDEDGSRLTS EELLGMAHIL
241 LVAGHETTVN LIANGMYALL SHPDQLAALR ADMTLLDGAV EEMLRYEGPV ESATYRFPVE
301 PVDLDGTVIP AGDTVLVVLA DAHRTPERFP DPHRFDIRRD TAGHLAFGHG IHFCIGAPLA
361 RLEARIAVRA LLERCPDLAL DVSPGELVWY PNPMIRGLKA LPIRWRRGRE AGRRTG
```

Amino acid sequence of putative transcriptional activator, ORF12, 929 AA (SEQ ID NO:14)

```
  1 MNLVERDGEI AHLRAVLDAS AAGDGTLLLV SGPAGSGKTE LLRSLRRLAA ERETPVWSVR
 61 ALPGDRDIPL GVLCQLLRSA EQHGADTSAV RDLLDAASRR AGTSPPPPTR RSASTRHTAC
121 TTGCSPSPAG TPFLVAVDDL THADTASLRF LLYCAAHHDQ GGIGFVMTER ASQRAGYRVF
181 RAELLRQPHC RNMWLSGLPP SGVRQLLAHY YGPEAAERRA PAYHATTGGN PLLLRALTQD
241 RQASHTTLGA AGGDEPVHGD AFAQAVLDCL HRSAEGTLET ARWLAVLEQS DPLLVERLTG
301 TTAAAVERHI QELAAIGLLD EDGTLGQPAI REAALQDLPA GERTELHRRA AEQLHRDGAD
361 EDTVARHLLV GGAPDAPWAL PLLERGAQQA LFDDRLDDAF RILEFAVRSS TDNTQLARLA
421 PHLVAASWRM NPHMTTRALA LFDRLLSGEL PPSHPVMALI RCLVWYGRLP EAADALSRLR
481 PSSDNDALEL SLTRMWLAAL CPPLLESLPA TPEPERGPVP VRLAPRTTAL QAQAGVFQRG
541 PDNASVAQAE QILQGCRLSE ETYEALETAL LVLVHADRLD RALFWSDALL AEAVERRSLG
601 WEAVFAATRA MIAIRCGDLP TARERAELAL SHAAPESWGL AVGMPLSALL LACTEAGEYE
661 QAERVLRQPV PDAMFDSRHG MEYMHARGRY WLAXGRLHAA LGEFMLCGEI LGSWNLDQPS
721 IVPWRTSAAE VYLRLGNRQK ARALAEAQLA LVRPGRSRTR GLTLRVLAAA VDGQQAERLH
781 AEAVDMLHDS GDRLEHARAL AGMSRHQQAQ GDNYRARMTA RLAGDMAWAC GAYPLAEEIV
841 PGRGGRRAKA VSTELELPGG PDVGLLSEAE RRVAALAARG LTNRQIARRL CVTASTVEQH
901 LTRVYRKLNV TRRADLPISL AQDKSVTA
```

Contig 003 from cosmid pKOS023-26, 3292 nucleotides (SEQ ID NO:15)

```
   1 ACCCCCCAAA GGGGTGGTGA CACTCCCCCT GCGCAGCCCC TAGCGCCCCC CTAACTCGCC
  61 ACGCCGACCG TTATCACCGG CGCCCTGCTG CTAGTTTCCG AGAATGAAGG GAATAGTCCT
 121 GGCCGGCGGG AGCGGAACTC GGCTGCATCC GGCGACCTCG GTCATTTCGA AGCAGATTCT
 181 TCCGGTCTAC AACAAACCGA TGATCTACTA TCCGCTGTCG GTTCTCATGC TCGGCGGTAT
 241 TCGCGAGATT CAAATCATCT CGACCCCCCA GCACATCGAA CTCTTCCAGT CGCTTCTCGG
 301 AAACGGCAGG CACCTGGGAA TAGAACTCGA CTATGCGGTC CAGAAAGAGC CCGCAGGAAT
 361 CGCGGACGCA CTTCTCGTCG GAGCCGAGCA CATCGGCGAC GACACCTGCG CCCTGATCCT
 421 GGGCGACAAC ATCTTCCACG GCCCGGCCT CTACACGCTC CTGCGGGACA GCATCGCGCG
 481 CCTCGACGGC TGCGTGCTCT TCGGCTACCC GGTCAAGGAC CCCGAGCGGT ACGGCGTCGC
 541 CGAGGTGGAC GCGACGGGCC GGCTGACCGA CCTCGTCGAG AAGCCCGTCA GCCGCGCTC
 601 CAACCTCGCC GTCACCGGCC TCTACCTCTA CGACAACGAC GTCGTCGACA TCGCCAAGAA
 661 CATCCGGCCC TCGCCGCGCG GCGAGCTGGA GATCACCGAC GTCAACCGCG TCTACCTGGA
 721 GCGGGGCCGG GCCGAACTCG TCAACCTGGG CCGCGGCTTC GCCTGGCTGG ACACCGGCAC
 781 CCACGACTCG CTCCTGCGGG CCGCCAGTA CGTCCAGGTC CTGGAGGAGC GGCAGGGCGT
 841 CTGGATCGCG GGCCTTGAGG AGATCGCCTT CCGCATGGGC TTCATCGACG CCGAGGCCTG
 901 TCACGGCCTG GGAGAAGGCC TCTCCCGCAC CGAGTACGGC AGCTATCTGA TGGAGATCGC
 961 CGGCCGCGAG GGAGCCCCGT GAGGGCACCT CGCGGCCGAC GCGTTCCCAC GACCGACAGC
1021 GCCACCGACA GTGCGACCCA CACCGCGACC CGCACCGCCA CCGACAGTGC GACCCACACC
1081 GCGACCTACA GCGCGACCGA AAGGAAGACG GCAGTGCGGC TTCTGGTGAC CGGAGGTGCG
1141 GGCTTCATCG GCTCGCACTT CGTGCGGCAG CTCCTCGCCG GGGCGTACCC CGACGTGCCC
1201 GCCGATGAGG TGATCGTCCT GGACAGCCTC ACCTACGCGG CAACCGCGC CAACCTCGCC
1261 CCGGTGGACG CGGACCCGCG ACTGCGCTTC GTCCACGGCG ACATCCGCGA CGCCGGCCTC
1321 CTCGCCCGGG AACTGCGCGG CGTGGACGCC ATCGTCCACT CGCGGCCGA GAGCCACGTG
1381 GACCGCTCCA TCGCGGGCGC GTCCTGTTC ACCGAGACCA ACGTGCAGGG CACGCAGACG
1441 CTGCTCCAGT GCGCCGTCGA CGCCGGCGTC GGCCGGGTCG TGCACGTCTC CACCGACGAG
1501 GTGTACGGGT CGATCGACTC CGGCTCCTGG ACCGAGAGCA GCCCGCTGGA GCCCAACTCG
1561 CCCTACGCGG CGTCCAAGGC CGGCTCCGAC CTCGTTGCCC GCGCCTACCA CCGGACGTAC
```

FIG. 6
(CONTINUED)

```
1621 GGCCTCGACG TACGGATCAC CCGCTGCTGC AACAACTACG GGCCGTACCA GCACCCCGAG
1681 AAGCTCATCC CCCTCTTCGT GACGAACCTC CTCGACGGCG GGACGCTCCC GCTGTACGGC
1741 GACGGCGCGA ACGTCCGCGA GTGGGTGCAC ACCGACGACC ACTGCCGGGG CATCGCGCTC
1801 GTCCTCGCGG GCGGCCGGGC CGGCGAGATC TACCACATCG GCGGCGGCCT GGAGCTGACC
1861 AACCGCGAAC TCACCGGCAT CCTCCTGGAC TCGCTCGGCG CCGACTGGTC CTCGGTCCGG
1921 AAGGTCGCCG ACCGCAAGGG CCACGACCTG CGCTACTCCC TCGACGGCGG CAAGATCGAG
1981 CGCGAGCTCG GCTACCGCCC GCAGGTCTCC TTCGCGGACG GCCTCGCGCG GACCGTCCGC
2041 TGGTACCGGG AGAACCGCGG CTGGTGGGAA CCGCTCAAGG CGACCGCCCC GCAGCTGCCC
2101 GCCACCGCCG TGGAGGTGTC CGCCGAGCA GCCGCGCCGA GACCCCGCG GTCCCCTTCC
2161 TCGACCTCAA GGCCGCCTAC GAGGAGCTCC GCGCGGAGAC CGACGCCGCG ATCGCCCGCG
2221 TCCTCGACTC GGGGCGCTAC CTCCTCGGAC CCGAACTCGA AGGATTCGAG GCGGAGTTCG
2281 CCGCGTACTG CGAGACGGAC CACGCCGTCG GCGTGAACAG CGGGATGGAC GCCCTCCAGC
2341 TCGCCCTCCG CGGCCTCGGC ATCGGACCCG GGACGAGGT GATCGTCCCC TCGCACACGT
2401 ACATCGCCAG CTGGCTCGCG GTGTCCGCCA CCGGCGCGAC CCCCGTGCCC GTCGAGCCGC
2461 ACGAGGACCA CCCCACCCTG GACCCGCTGC TCGTCGAGAA GGCGATCACC CCCCGCACCC
2521 GGGCGCTCCT CCCCGTCCAC CTCTACGGGC ACCCCGCCGA CATGGACGCC CTCCGCGAGC
2581 TCGCGGACCG GCACGGCCTG CACATCGTCG AGGACGCCGC GCAGGCCCAC GGCGCCCGCT
2641 ACCGGGGCCG GCGGATCGGC GCCGGGTCGT CGGTGGCCGC GTTCAGCTTC TACCCGGGCA
2701 AGAACCTCGG CTGCTTCGGC GACGGCGGCG CCGTCGTCAC CGGCGACCCC GAGCTCGCCG
2761 AACGGCTCCG GATGCTCCGC AACTACGGCT CGCGGCAGAA GTACAGCCAC GAGACGAAGG
2821 GCACCAACTC CCGCCTGGAC GAGATGCAGG CCGCCGTGCT GCGGATCCGG CTCGNCCACC
2881 TGGACAGCTG GAACGGCCGC AGGTCGGCGC TGGCCGCGGA GTACCTCTCC GGGCTCGCCG
2941 GACTGCCCGG CATCGGCCTG CCGGTGACCG CGCCCGACAC CGACCCGGTC TGGCACCTCT
3001 TCACCGTGCG CACCGAGCGC CGCGACGAGC TGCGCAGCCA CCTCGACGCC CGCGGCATCG
3061 ACACCCTCAC GCACTACCCG GTACCCGTGC ACCTCTCGCC CGCCTACGCG GGCGAGGCAC
3121 CGCCGGAAGG CTCGCTCCCG CGGGCCGAGA GCTTCGCGCG GCAGGTCCTC AGCCTGCCGA
3181 TCGGCCCGCA CCTGGAGCGC CGCAGGCGC TGCGGGTGAT CGACGCCGTG CGCGAATGGG
3241 CCGAGCGGGT CGACCAGGCC TAGTCAGGTG GTCCGGTAGA CCCAGCAGGC CG
```

Amino acid sequence of dNDP-glucose synthase (glucose-1-phosphate thymidyl transferase),
ORF13, 293 AA (SEQ ID NO:16)

```
  1 MKGIVLAGGS GTRLHPATSV ISKQILPVYN KPMIYYPLSV LMLGGIREIQ IISTPQHIEL
 61 FQSLLGNGRH LGIELDYAVQ KEPAGIADAL LVGAEHIGDD TCALILGDNI FHGPGLYTLL
121 RDSIARLDGC VLFGYPVKDP ERYGVAEVDA TGRLTDLVEK PVKPRSNLAV TGLYLYDNDV
181 VDIAKNIRPS PRGELEITDV NRVYLERGRA ELVNLGRGFA WLDTGTHDSL LRAAQYVQVL
241 EERQGVWIAG LEEIAFRMGF IDAEACHGLG EGLSRTEYGS YLMEIAGREG AP
```

Amino acid sequence of dNDP-glucose 4,6-dehydratase, ORF14, 338 AA (SEQ ID NO:17)

```
  1 VRLLVTGGAG FIGSHFVRQL LAGAYPDVPA DEVIVLDSLT YAGNRANLAP VDADPRLRFV
 61 HGDIRDAGLL ARELRGVDAI VHFAAESHVD RSIAGASVFT ETNVQGTQTL LQCAVDAGVG
121 RVVHVSTDEV YGSIDSGSWT ESSPLEPNSP YAASKAGSDL VARAYHRTYG LDVRITRCCN
181 NYGPYQHPEK LIPLFVTNLL DGGTLPLYGD GANVREWVHT DDHCRGIALV LAGGRAGEIY
241 HIGGGLELTN RELTGILLDS LGADWSSVRK VADRKGHDLR YSLDGGKIER ELGYRPQVSF
301 ADGLARTVRW YRENRGWWEP LKATAPQLPA TAVEVSA
```

Amino acid sequence of PICCI, 380 AA (SEQ ID NO:18)

```
  1 VSSRAETPRV PFLDLKAAYE ELRAETDAAI ARVLDSGRYL LGPELEGFEA EFAAYCETDH
 61 AVGVNSGMDA LQLALRGLGI GPGDEVIVPS HTYIASWLAV SATGATPVPV EPHEDHPTLD
121 PLLVEKAITP RTRALLPVHL YGHPADMDAL RELADRHGLH IVEDAAQAHG ARYRGRRIGA
181 GSSVAAFSFY PGKNLGCFGD GGAVVTGDPE LAERLRMLRN YGSRQKYSHE TKGTNSRLDE
241 MQAAVLRIRL XHLDSWNGRR SALAAEYLSG LAGLPGIGLP VTAPDTDPVW HLFTVRTERR
301 DELRSHLDAR GIDTLTHYPV PVHLSPAYAG EAPPEGSLPR AESFARQVLS LPIGPHLERP
361 QALRVIDAVR EWAERVDQA
```

FIG. 6
(CONTINUED)

Contig 004 from cosmid pKOS023-26, 1693 nucleotides (SEQ ID NO:19)

```
   1 ATGCGGCACC CCTTGGCGCC GAGCGTGGTG ATCCAGGTGC CGACCCGGGC GAGCACCTCC
  61 TGCTCGGTCC AGCCCGTCTT GCTGAGCAGC AGCGCCCGCT CGTAGGCGTT CGTGAACAGC
 121 AGCTCGGCTC CGTCGACGAG CTCCCGGACG CTGTCGCCCT CCAGCCGGGC GAGCTGCTGC
 181 GAGGGGTCCG CGGCCCGGCG GAGGCCCAGC TCGCGGCAGA CCCGCGTGTG CCGCACCATC
 241 GCCTCGGGGT CGTCCGCGCC GACGAGGACG AGGTCGATCC CGCCGGGCCG GCCGGCCGTC
 301 TCGCCCAGGT CGATGTCGCG CGCCTCGGCC ATCGCGCCCG CGTAGAACGA GGCGAGCTGA
 361 TTGCCGTCCT CGTCGGTGGT GCACATGAAG CGGGCGGTGT GCTGACGGTC CGACACCCGC
 421 ACGGAGTCGG TGTCGACGCC CGCGGCGCGG AGCAGCTGCC CGTACCCGTC GAAGTCCTTG
 481 CCGACGGCGC CGACGAGGAC GGGGCGGCGA CCGAGCAGGC CGAGGCCGTA CGCGATGTTG
 541 GCGGCGACGC CGCCGTGCCG GATGTCCAGG GTGTCGACGA GGAACGACAG GGACACGTGG
 601 GCGAGCTGGT CCGGCAGGAT CTGCTCGGCG AAGCGGCCCG GGAAGGTCAT CAGGTGGTCG
 661 GTGGCGATCG ACCCGGTGAC GGCTATACGC ATGTCAGAGC CCCGCGGCCT TCTTCAGGGC
 721 GTCCACGCGG TCGGTGCGCT CCCAGGTGAA GTCCGGCAGC TCGCGGCCGA AGTGGCCGTA
 781 GGCGGCGGTC TGGGAGTAGA TCGGGCGGAG CAGGTCGAGG TCGCGGATGA TCGCGGCCGG
 841 GCGGAGGTCG AAGACCTCGC CGATGGCGTT CTCGATCTTC TCGGTCTCGA TCTTGTGGGT
 901 GCCGAAGGTC TCGACGAAGA GGCCGACGGG CTCGGCCTTG CCGATCGCGT ACGCGACCTG
 961 GACCTCGCAG CGCGAGGCGA GACCGGCGGC GACGACGTTC TTCGCCACCC AGCGCATCGC
1021 GTACGCGGCG GAGCGGTCGA CCTTCGACGG GTCCTTGCCG GAGAAGGCGC CGCCACCGTG
1081 GCGGGCCATG CCGCCGTAGG TGTCGATGAT GATCTTGCGG CCGGTGAGGC CGGCGTCGCC
1141 CATCGGGCCG CCGATCTCGA AGCGACCGGT CGGGTTCACG AGCAGGCGGT AGCCGTCGGT
1201 GTCGAGCTTG ATGCCGTCCT CGACGAGCTG CGCAAGCACG TGCTCGACGA CGAACTTCCG
1261 CACGTCGGGG GCGAGCAGCG ACTCCAGGTC GATGTCCGAG GCGTGCTGCG AGGAGACGAC
1321 GACCGTGTCG AGACGGACCG CCCTGTCGCC GTCGTACTCG ATGGTGACCT GGGTCTTGCC
1381 GTCGGGACGC AGGTACGGGA TGGTCCCGTT CTTCGGGACC TCGGTCAGGC GGCGCGAGAG
1441 ACGGTGCGCG AGGTGGATCG GCAGCGGCAT CAGCTCGGGC GTCTCGTCCG AGGCATAGCC
1501 GAACATCAGG CCCTGGTCAC CGGCGCCCTG CTTGTCGAGC TCGTCCCCCT CGTCCCGCTG
1561 GGAGGCACCC TCGACCCGCT TCTCGTACGC GGTGTCGACA CCCTGGGCGA TGTCCGGGGA
1621 CTGCGACCCG ATGGACACCG ACACGCCGCA GGAGGCGCCG TCGAAGCCCT TCTTCGAGGA
1681 GTCGTACCCG ATC
```

Partial amino acid sequence of S-adenosylmethionine synthase, ORF15, 333 AA (SEQ ID NO:20)

```
   1 IGYDSSKKGF DGASCGVSVS IGSQSPDIAQ GVDTAYEKRV EGASQRDEGD ELDKQGAGDQ
  61 GLMFGYASDE TPELMPLPIH LAHRLSRRLT EVRKNGTIPY LRPDGKTQVT IEYDGDRAVR
 121 LDTVVVSSQH ASDIDLESLL APDVRKFVVE HVLAQLVEDG IKLDTDGYRL LVNPTGRFEI
 181 GGPMGDAGLT GRKIIIDTYG GMARHGGGAF SGKDPSKVDR SAAYAMRWVA KNVVAAGLAS
 241 RCEVQVAYAI GKAEPVGLFV ETFGTHKIET EKIENAIGEV FDLRPAAIIR DLDLLRPIYS
 301 QTAAYGHFGR ELPDFTWERT DRVDALKKAA GL
```

Amino acid sequence of ORF16 (homologous to M. tuberculosis cbhK), 230 AA (SEQ ID NO:21)

```
   1 MRIAVTGSIA TDHLMTFPGR FAEQILPDQL AHVSLSFLVD TLDIRHGGVA ANIAYGLGLL
  61 GRRPVLVGAV GKDFDGYGQL LRAAGVDTDS VRVSDRQHTA RFMCTTDEDG NQLASFYAGA
 121 MAEARDIDLG ETAGRPGGID LVLVGADDPE AMVRHTRVCR ELGLRRAADP SQQLARLEGD
 181 SVRELVDGAE LLFTNAYERA LLLSKTGWTE QEVLARVGTW ITTLGAKGCR
```

Contig 005 from cosmid pKOS023-26, 1565 nucleotides (SEQ ID NO:22)

```
   1 CCCCGCTCGC GGCCCCCCAG ACATCCACGC CCACGATTGG ACGCTCCCGA TGACCGCCCC
  61 CGCCCTCTCC GCCACCGCCC CGGCCGAACG CTGCGCGCAC CCCGGAGCCG ATCTGGGGGC
 121 GGCGGTCCAC GCCGTCGGCC AGACCCTCGC CGCCGGCGGC CTCGTGCCGC CCGACGAGGC
 181 CGGAACGACC GCCCGCCACC TCGTCCGGCT CGCCGTGCGC TACGGCAACA GCCCCTTCAC
 241 CCCGCTGGAG GAGGCCCGCC ACGACCTGGG CGTCGACCGG GACGCCTTCC GGCGCCTCCT
 301 CGCCCTGTTC GGGCAGGTCC GGAGCTCCG CACCGCGGTC GAGACCGGCC CCGCCGGGC
 361 GTACTGGAAG AACACCCTGC TCCCGCTCGA CAGCGCGGC GTCTTCGACG CGGCGCTCGC
 421 CAGGAAGCCC GTCTTCCCGT ACAGCGTCGG CCTCTACCCC GGCCCGACCT GCATGTTCCG
```

FIG. 6
(CONTINUED)

```
 481 CTGCCACTTC TGCGTCCGTG TGACCGGCGC CCGCTACGAC CCGTCCGCCC TCGACGCCGG
 541 CAACGCCATG TTCCGGTCGG TCATCGACGA GATACCCGCG GGCAACCCCT CGGCGATGTA
 601 CTTCTCCGGC GGCCTGGAGC CGCTCACCAA CCCCGGCCTC GGGAGCCTGG CCGCGCACGC
 661 CACCGACCAC GGCCTGCGGC CCACCGTCTA CACGAACTCC TTCGCGCTCA CCGAGCGCAC
 721 CCTGGAGCGC CAGCCCGGCC TCTGGGGCCT GCACGCCATC CGCACCTCGC TCTACGGCCT
 781 CAACGACGAG GAGTACGAGC AGACCACCGG CAAGAAGGCC GCCTTCCGCC GCGTCCGCGA
 841 GAACCTGCGC CGCTTCCAGC AGCTGCGCGC CGAGCGCGAG TCGCCGATCA ACCTCGGCTT
 901 CGCCTACATC GTGCTCCCGG GCCGTGCCTC CCGCCTGCTC GACCTGGTCG ACTTCATCGC
 961 CGACCTCAAC GACGCCGGGC AGGGCAGGAC GATCGACTTC GTCAACATTC GCGAGGACTA
1021 CAGCGGCCGT GACGACGGCA AGCTGCCGCA GGAGGAGCGG GCCGAGCTCC AGGAGGCCCT
1081 CAACGCCTTC GAGGAGCGGG TCCGCGAGCG CACCCCCGGA CTCCACATCG ACTACGGCTA
1141 CGCCCTGAAC AGCCTGCGCA CCGGGGCCGA CGCCGAACTG CTGCGGATCA AGCCCGCCAC
1201 CATGCGGCCC ACCGCGCACC CGCAGGTCGC GGTGCAGGTC GATCTCCTCG GCGACGTGTA
1261 CCTGTACCGC GAGGCCGGCT TCCCCGACCT GGACGGCGCG ACCCGCTACA TCGCGGGCCG
1321 CGTGACCCCC GACACCTCCC TCACCGAGGT CGTCAGGGAC TTCGTCGAGC GCGGCGGCGA
1381 GGTGGCGGCC GTCGACGGCG ACGAGTACTT CATGGACGGC TTCGATCAGG TCGTCACCGC
1441 CCGCCTGAAC CAGCTGGAGC GCGACGCCGC GGACGGCTGG GAGGAGGCCC GCGGCTTCCT
1501 GCGCTGACCC GCACCCGCCC CGATCCCCCC GATCCCCCCC CCACGATCCC CCCACCTGAG
1561 GGCCC
```

Amino acid sequence of PICCV, 486 AA (SEQ ID NO:23)

```
  1 MTAPALSATA PAERCAHPGA DLGAAVHAVG QTLAAGGLVP PDEAGTTARH LVRLAVRYGN
 61 SPFTPLEEAR HDLGVDRDAF RRLLALFGQV PELRTAVETG PAGAYWKNTL LPLEQRGVFD
121 AALARKPVFP YSVGLYPGPT CMFRCHFCVR VTGARYDPSA LDAGNAMFRS VIDEIPAGNP
181 SAMYFSGGLE PLTNPGLGSL AAHATDHGLR PTVYTNSFAL TERTLERQPG LWGLHAIRTS
241 LYGLNDEEYE QTTGKKAAFR RVRENLRRFQ QLRAERESPI NLGFAYIVLP GRASRLLDLV
301 DFIADLNDAG QGRTIDFVNI REDYSGRDDG KLPQEERAEL QEALNAFEER VRERTPGLHI
361 DYGYALNSLR TGADAELLRI KPATMRPTAH PQVAVQVDLL GDVYLYREAG FPDLDGATRY
421 IAGRVTPDTS LTEVVRDFVE RGGEVAAVDG DEYFMDGFDQ VVTARLNQLE RDAADGWEEA
481 RGFLR
```

FIG. 6
(CONTINUED)

SEQUENCE LISTING

<160> NUMBER OF SEQ ID NOS: 31

<210> SEQ ID NO 1
<211> LENGTH: 38506
<212> TYPE: DNA
<213> ORGANISM: Streptomyces venezuelae

<400> SEQUENCE: 1

| | | | | | |
|---|---|---|---|---|---|
| gatcatgcgg | agcactcctt | ctctcgtgct | cctaccggtg | atgtgcgcgc | cgaattgatt | 60 |
| cgtggagaga | tgtcgacagt | gtccaagagt | gagtccgagg | aattcgtgtc | cgtgtcgaac | 120 |
| gacgccggtt | ccgcgcacgg | cacagcggaa | cccgtcgccg | tcgtcggcat | ctcctgccgg | 180 |
| gtgcccggcg | cccgggaccc | gagagagttc | tgggaactcc | tggcggcagg | cggccaggcc | 240 |
| gtcaccgacg | tccccgcgga | ccgctggaac | gccggcgact | tctacgaccc | ggaccgctcc | 300 |
| gcccccggcc | gctcgaacag | ccggtggggc | gggttcatcg | aggacgtcga | ccggttcgac | 360 |
| gccgccttct | tcggcatctc | gcccgcgag | ccgcgcgaga | tggacccgca | gcagcggctc | 420 |
| gccctggagc | tgggctggga | ggccctggag | cgcgccggga | tcgaccgtc | ctcgctcacc | 480 |
| ggcacccgca | ccggcgtctt | cgccggcgcc | atctgggacg | actacgccac | cctgaagcac | 540 |
| cgccagggcg | gcgccgcgat | caccccgcac | accgtcaccg | gcctccaccg | cggcatcatc | 600 |
| gcgaaccgac | tctcgtacac | gctcgggctc | cgcggcccca | gcatggtcgt | cgactccggc | 660 |
| cagtcctcgt | cgctcgtcgc | cgtccacctc | gcgtgcgaga | gcctgcggcg | cggcgagtcc | 720 |
| gagctcgccc | tcgccggcgg | cgtctcgctc | aacctggtgc | cggacagcat | catcggggcg | 780 |
| agcaagttcg | gcggcctctc | ccccgacggc | cgcgcctaca | ccttcgacgc | gcgcgccaac | 840 |
| ggctacgtac | gcggcgaggg | cggcggttc | gtcgtcctga | gcgcctctc | ccgggccgtc | 900 |
| gccgacggcc | acccggtgct | cgccgtgatc | cggggcagcg | ccgtcaacaa | cggcggcgcc | 960 |
| gcccagggca | tgacgacccc | cgacgcgcag | gcgcaggagg | ccgtgctccg | cgaggcccac | 1020 |
| gagcgggcc | ggaccgcgcc | ggccgacgtg | cggtacgtcg | agctgcacgg | caccggcacc | 1080 |
| cccgtgggcg | acccgatcga | ggccgctgcg | ctcggcgccg | ccctcggcac | cggccgcccg | 1140 |
| gccggacagc | cgctcctggt | cggctcggtc | aagacgaaca | tcggccacct | ggagggcgcg | 1200 |
| gccggcatcg | ccggcctcat | caaggccgtc | ctggcggtcc | gcggtcgcgc | gctgccgcc | 1260 |
| agcctgaact | acgagacccc | gaacccggcg | atcccgttcg | aggaactgaa | cctccgggtg | 1320 |
| aacacggagt | acctgccgtg | ggagccggag | cacgacgggc | agcggatggt | cgtcgcgtg | 1380 |
| tcctcgttcg | gcatgggcgg | cacgaacgcg | catgtcgtgc | tcgaagaggc | cccggggtt | 1440 |
| gtcgagggtg | cttcggtcgt | ggagtcgacg | gtcggcgggt | cggcggtcgg | cggcggtgtg | 1500 |
| gtgccgtggg | tggtgtcggc | gaagtccgct | gccgcgctgg | acgcgcagat | cgagcggctt | 1560 |
| gccgcgttcg | cctcgcggga | tcgtacggat | ggtgtcgacg | cgggcgctgt | cgatgcgggt | 1620 |
| gctgtcgatg | cgggtgctgt | cgctcgcgta | ctggccggcg | ggcgtgctca | gttcgagcac | 1680 |
| cgggccgtcg | tcgtcggcag | cgggccggac | gatctggcgg | cagcgctggc | cgcgcctgag | 1740 |
| ggtctggtcc | ggggcgtggc | ttccggtgtc | gggcgagtgg | cgttcgtgtt | ccccgggcag | 1800 |
| ggcacgcagt | gggccggcat | gggtgccgaa | ctgctggact | cttccgcggt | gttcgcggcg | 1860 |
| gccatggccg | aatgcgaggc | cgcactctcc | ccgtacgtcg | actggtcgct | ggaggccgtc | 1920 |
| gtacggcagg | ccccggtgc | gcccacgctg | gagcgggtcg | atgtcgtgca | gcctgtgacg | 1980 |
| ttcgccgtca | tggtctcgct | ggctcgcgtg | tggcagcacc | acggggtgac | gccccaggcg | 2040 |

```
gtcgtcggcc actcgcaggg cgagatcgcc gccgcgtacg tcgccggtgc cctgagcctg    2100
gacgacgccg ctcgtgtcgt gaccctgcgc agcaagtcca tcgccgccca cctcgccggc    2160
aagggcggca tgctgtccct cgcgctgagc gaggacgccg tcctggagcg actggccggg    2220
ttcgacgggc tgtccgtcgc cgctgtgaac gggcccaccg ccaccgtggt ctccggtgac    2280
cccgtacaga tcgaagagct tgctcgggcg tgtgaggcca tggggtccg tgcgcgggtc     2340 attcccgtcg actacgcgtc ccacagccgg caggtcgaga tcatcgagag cgagctcgcc    2400
gaggtcctcg ccgggctcag cccgcaggct ccgcgcgtgc cgttcttctc gacactcgaa    2460
ggcgcctgga tcaccgagcc cgtgctcgac ggcggctact ggtaccgcaa cctgcgccat    2520
cgtgtgggct tcgccccggc cgtcgagacc ctggccaccg acgagggctt cacccacttc    2580
gtcgaggtca gcgcccaccc cgtcctcacc atggccctcc ccgggaccgt caccggtctg    2640
gcgaccctgc gtcgcgacaa cggcggtcag gaccgcctcg tcgcctccct cgccgaagca    2700
tgggccaacg gactcgcggt cgactggagc ccgctcctcc cctccgcgac cggccaccac    2760
tccgacctcc ccacctacgc gttccagacc gagcgccact ggctgggcga gatcgaggcg    2820
ctcgccccgg cgggcgagcc ggcggtgcag cccgccgtcc tccgcacgga ggcggccgag    2880
ccggcggagc tcgaccggga cgagcagctg cgcgtgatcc tggacaaggt ccgggcgcag    2940
acggcccagg tgctggggta cgcgacaggc gggcagatcg aggtcgaccg gaccttccgt    3000
gaggccggtt gcacctccct gaccggcgtg gacctgcgca accggatcaa cgccgccttc    3060
ggcgtacgga tggcgccgtc catgatcttc gacttcccca cccccgaggc tctcgcggag    3120
cagctgctcc tcgtcgtgca cggggaggcg gcggcgaacc cggccggtgc ggagccggct    3180
ccggtggcgg cggccggtgc cgtcgacgag ccggtggcga tcgtcggcat ggcctgccgc    3240
ctgcccggtg gggtcgcctc gccggaggac ctgtggcggc tggtggccgg cggcggggac    3300
gcgatctcgg agttcccgca ggaccgcggc tgggacgtgg aggggctgta ccacccggat    3360
cccgagcacc ccggcacgtc gtacgtccgc caggcggtt tcatcgagaa cgtcgccggc    3420
ttcgacgcgg ccttcttcgg gatctcgccg cgcgaggccc tcgccatgga cccgcagcag    3480
cggctcctcc tcgaaacctc ctgggaggcc gtcgaggacg ccgggatcga cccgacctcc    3540
ctgcggggac ggcaggtcgg cgtcttcact ggggcgatga cccacgagta cgggccgagc    3600
ctgcgggacg gcggggaagg cctcgacggc tacctgctga ccggcaacac ggccagcgtg    3660
atgtcgggcc gcgtctcgta cacactcggc cttgagggcc ccgccctgac ggtggacacg    3720
gcctgctcgt cgtcgctggt cgccctgcac ctcgccgtgc aggccctgcg caagggcgag    3780
gtcgacatgg cgctcgccgg cggcgtggcc gtgatgccca cgcccgggat gttcgtcgag    3840
ttcagccggc agcgcgggct ggccggggac ggccggtcga aggcgttcgc cgcgtcggcg    3900
gacggcacca gctggtccga gggcgtcggc gtcctcctcg tcgagcgcct gtcggacgcc    3960
cgccgcaacg gacaccaggt cctcgcggtc gtccgcggca gcgccgtgaa ccaggacggc    4020
gcgagcaacg gcctcacggc tccgaacggg ccctcgcagc agcgcgtcat ccggcgcgcg    4080
ctggcggacg cccggctgac gacctccgac gtggacgtcg tcgaggcaca cggcacgggc    4140
acgcgactcg gcgacccgat cgaggcgcag gccctgatcg ccacctacgg ccagggccgt    4200
gacgacgaac agccgctgcg cctcgggtcg ttgaagtcca acatcgggca cacccaggcc    4260
gcggccggcc tctccggtgt catcaagatg gtccaggcga tgcgccacgg actgctgccg    4320
aagacgctgc acgtcgacga gccctcggac cagatcgact ggtcggctgg cgccgtggaa    4380
```

-continued

```
ctcctcaccg aggccgtcga ctggccggag aagcaggacg gcgggctgcg ccgggccgcc    4440
gtctcctcct tcgggatcag cggcaccaat gcgcatgtgg tgctcgaaga ggccccggtg    4500
gttgtcgagg gtgcttcggt cgtcgagccg tcggttggcg gtcggcggt cggcggcggt    4560 gtgacgcctt gggtggtgtc ggcgaagtcc gctgccgcgc tcgacgcgca gatcgagcgg    4620
cttgccgcat tcgcctcgcg ggatcgtacg gatgacgccg acgccggtgc tgtcgacgcg    4680
ggcgctgtcg ctcacgtact ggctgacggg cgtgctcagt tcgagcaccg ggccgtcgcg    4740
ctcggcgccg gggcggacga cctcgtacag gcgctggccg atccggacgg gctgatacgc    4800
ggaacggctt ccggtgtcgg gcgagtggcg ttcgtgttcc ccggtcaggg cacgcagtgg    4860
gctggcatgg gtgccgaact gctggactct tccgcggtgt tcgcggcggc catggccgag    4920
tgtgaggccg cgctgtcccc gtacgtcgac tggtcgctgg aggccgtcgt acggcaggcc    4980
cccggtgcgc ccacgctgga gcgggtcgat gtcgtgcagc ctgtgacgtt cgccgtcatg    5040
gtctcgctgg ctcgcgtgtg gcagcaccac ggtgtgacgc cccaggcggt cgtcggccac    5100
tcgcagggcg agatcgccgc cgcgtacgtc gccggagccc tgccctgga cgacgccgcc    5160 cgcgtcgtca ccctgcgcag caagtccatc gccgcccacc tcgccggcaa gggcggcatg    5220
ctgtccctcg cgctgaacga ggacgccgtc ctggagcgac tgagtgactt cgacgggctg    5280
tccgtcgccc ccgtcaacgg gcccaccgcc actgtcgtgt cgggtgaccc cgtacagatc    5340
gaagagcttg ctcaggcgtg caaggcggac ggattccgcg cgcggatcat tcccgtcgac    5400
tacgcgtccc acagccggca ggtcgagatc atcgagagcg agctcgccca ggtcctcgcc    5460
ggtctcagcc cgcaggcccc gcgcgtgccg ttcttctcga cgctcgaagg cacctggatc    5520
accgagcccg tcctcgacgg cacctactgg taccgcaacc tccgtcaccg cgtcggcttc    5580
gcccccgcca tcgagaccct ggccgtcgac gagggcttca cgcacttcgt cgaggtcagc    5640
gcccaccccg tcctcaccat gacctctccc gagaccgtca ccggcctcgg caccctccgt    5700
cgcgaacagg gaggccaaga gcgtctggtc acctcgctcg ccgaggcgtg ggtcaacggg    5760
cttcccgtgg catggacttc gctcctgccc gccacgcct cccgcccgg tctgcccacc    5820 tacgccttcc aggccgagcg ctactggctc gagaacactc ccgccgccct ggccaccggc    5880
gacgactggc gctaccgcat cgactggaag cgcctcccgg ccgccgaggg gtccgagcgc    5940
accggcctgt ccggccgctg gctcgccgtc acgccggagg accactccgc gcaggccgcc    6000
gccgtgctca ccgcgctggt cgacgccggg gcgaaggtcg aggtgctgac ggccggggcg    6060
gacgacgacc gtgaggccct cgccgcccgg ctcaccgcac tgacgaccgg tgacggcttc    6120
accggcgtgg tctcgctcct cgacggactc gtaccgcagg tcgcctgggt ccaggcgctc    6180
ggcgacgccg gaatcaaggc gcccctgtgg tccgtcaccc agggcgcggt ctccgtcgga    6240
cgtctcgaca ccccgccga ccccgaccgg gccatgctct ggggcctcgg ccgcgtcgtc    6300
gcccttgagc acccgaacg ctgggccggc ctcgtcgacc tccccgccca gcccgatgcc    6360
gccgccctcg cccacctcgt caccgcactc tccggcgcca ccggcgagga ccagatcgcc    6420
atccgcacca ccggactcca cgcccgccgc ctcgcccgcg caccctcca cggacgtcgg    6480 cccaccccgg actggcagcc ccacggcacc gtcctcatca ccggcggcac cggagccctc    6540
ggcagccacg ccgcacgctg gatggcccac acggagccg aacacctcct cctcgtcagc    6600
cgcagcggcc aacaagcccc cggagccacc caactcaccg ccgaactcac cgcatcgggc    6660
gcccgcgtca ccatcgccgc ctgcgacgtc ccgaccccc acgccatgcg caccctcctc    6720
gacgccatcc ccgccgagac gcccctcacc gccgtcgtcc acaccgccgg cgcgctcgac    6780
```

```
gacggcatcg tggacacgct gaccgccgag caggtccggc gggcccaccg tgcgaaggcc    6840
gtcggcgcct cggtgctcga cgagctgacc cgggacctcg acctcgacgc gttcgtgctc    6900
ttctcgtccg tgtcgagcac tctgggcatc cccggtcagg caactacgc cccgcacaac     6960 gcctacctcg acgccctcgc ggctcgccgc cgggccaccg gccggtccgc cgtctcggtg    7020
gcctggggac cgtgggacgg tggcggcatg gccgccggtg acggcgtggc cgagcggctg    7080
cgcaaccacg gcgtgcccgg catggacccg gaactcgccc tggccgcact ggagtccgcg    7140
ctcggccggg acgagaccgc gatcaccgtc gcggacatcg actgggaccg cttctacctc    7200
gcgtactcct ccggtcgccc gcagcccctc gtcgaggagc tgcccgaggt gcggcgcatc    7260
atcgacgcac gggacagcgc cacgtccgga cagggcggga gctccgccca gggcgccaac    7320
cccctggccg agcggctggc cgccgcggct cccggcgagc gtacggagat cctcctcggt    7380
ctcgtacggg cgcaggccgc cgccgtgctc cggatgcgtt cgccggagga cgtcgccgcc    7440
gaccgcgcct tcaaggacat cggcttcgac tcgctcgccg tgtcgagct gcgcaacagg     7500 ctgacccggg cgaccgggct ccagctgccc gcgacgctcg tcttcgacca cccgacgccg    7560
ctggccctcg tgtcgctgct ccgcagcgag ttcctcggtg acgaggagac ggcggacgcc    7620
cggcggtccg cggcgctgcc cgcgactgtc ggtgccggtg ccggcgccgg cgccggcacc    7680
gatgccgacg acgatccgat cgcgatcgtc gcgatgagct gccgctaccc cggtgacatc    7740
cgcagcccgg aggacctgtg gcggatgctg tccgagggcg gcgagggcat cacgccgttc    7800
cccaccgacc gcggctggga cctcgacggc ctgtacgacg ccgacccgga cgcgctcggc    7860
agggcgtacg tccgcgaggg cggggttcctg cacgacgcgg ccgagttcga cgcggagttc    7920
ttcggcgtct cgccgcgcga ggcgctggcc atggacccgc agcagcggat gctcctgacg    7980
acgtcctggg aggccttcga gcgggccggc atcgagccgg catcgctgcg cggcagcagc    8040
accggtgtct tcatcggcct ctcctaccag gactacgcgg cccgcgtccc gaacgccccg    8100
cgtggcgtgg agggttacct gctgaccggc agcacgccga gcgtcgcgtc gggccgtatc    8160
gcgtacacct tcggtctcga agggcccgcg acgaccgtcg acaccgcctg ctcgtcgtcg    8220
ctgaccgccc tgcacctggc ggtgcgggcg ctgcgcagcg gcgagtgcac gatgcgctc     8280 gccggtggcg tggcgatgat ggcgaccccg cacatgttcg tggagttcag ccgtcagcgg    8340
gcgctcgccc cggacggccg cagcaaggcc ttctcggcgg acgccgacgg gttcggcgcc    8400
gcggagggcg tcggcctgct gctcgtggag cggctctcgg acgcgcggcg caacggtcac    8460
ccggtgctcg ccgtggtccg cggtaccgcc gtcaaccagg acggcgccag caacgggctg    8520
accgcgccca acgaccctc gcagcagcgg gtgatccggc aggcgctcgc cgacgcccgg    8580
ctggcacccg cgacatcga cgccgtcgag acgcacggca cgggaacctc gctgggcgac    8640
cccatcgagg cccagggcct ccaggccacg tacggcaagg agcggcccgc ggaacggccg    8700
ctcgccatcg gctccgtgaa gtccaacatc ggacacaccc aggccgcggc cggtgcggcg    8760
ggcatcatca agatggtcct cgcgatgcgc cacggcaccc tgccgaagac cctccacgcc    8820
gacgagccga gcccgcacgt cgactgggcg aacagcggcc tggccctcgt caccgagccg    8880
atcgactggc cggccggcac cggtccgcgc cgcgccgccg tctcctcctt cggcatcagc    8940
gggacgaacg cgcacgtcgt gctggagcag gcgccggatg ctgctggtga ggtgcttggg    9000
gccgatgagg tgcctgaggt gtctgagacg gtagcgatgg ctgggacggc tgggacctcc    9060
gaggtcgctg agggctctga ggcctccgag gccccgcgg ccccggcag ccgtgaggcg       9120
```

```
tccctccccg ggcacctgcc ctgggtgctg tccgccaagg acgagcagtc gctgcgcggc    9180
caggccgccg ccctgcacgc gtggctgtcc gagcccgccg ccgacctgtc ggacgcggac    9240
ggaccggccc gcctgcggga cgtcgggtac acgctcgcca cgagccgtac cgccttcgcg    9300
caccgcgccg ccgtgaccgc cgccgaccgg gacgggttcc tggacgggct ggccacgctg    9360
gcccagggcg gcacctcggc ccacgtccac ctggacaccg cccgggacgg caccaccgcg    9420
ttcctcttca ccggccaggg cagtcagcgc cccggcgccg gccgtgagct gtacgaccgg    9480
cacccgtct tcgcccgggc gctcgacgag atctgcgccc acctcgacgg tcacctcgaa    9540
ctgcccctgc tcgacgtgat gttcgcggcc gagggcagcg cggaggccgc gctgctcgac    9600
gagacgcggt acacgcagtg cgcgctgttc gccctggagg tcgcgctctt ccggctcgtc    9660
gagagctggg gcatgcggcc ggccgcactg ctcggtcact cggtcggcga gatcgccgcc    9720
gcgcacgtcg ccggtgtgtt ctcgctcgcc gacgccgccc gcctggtcgc cgcgcgcggc    9780
cggctcatgc aggagctgcc cgccggtggc gcgatgctcg ccgtccaggc cgcggaggac    9840
gagatccgcg tgtggctgga gacggaggag cggtacgcgg gacgtctgga cgtcgccgcc    9900
gtcaacggcc ccgaggccgc cgtcctgtcc ggcgacgcgg acgcggcgcg ggaggcggag    9960
gcgtactggt ccgggctcgg ccgcaggacc cgcgcgctgc gggtcagcca cgccttccac   10020
tccgcgcaca tggacggcat gctcgacggg ttccgcgccg tcctggagac ggtggagttc   10080
cggcgcccct ccctgaccgt ggtctcgaac gtcaccggcc tggccgccgg cccggacgac   10140
ctgtgcgacc ccgagtactg ggtccggcac gtccgcggca ccgtccgctt cctcgacggc   10200
gtccgtgtcc tgcgcgacct cggcgtgcgg acctgcctgg agctgggccc cgacggggtc   10260
ctcaccgcca tggcggccga cggcctcgcg gacacccccg cggattccgc tgccggctcc   10320
cccgtcggct ctcccgccgg ctctcccgcc gactccgccg ccggcgcgct ccggccccgg   10380
ccgctgctcg tggcgctgct cgccgcaag cggtcggaga ccgagaccgt cgcggacgcc   10440
ctcggcaggg cgcacgccca cggcaccgga cccgactggc acgcctggtt cgccggctcc   10500
ggggcgcacc gcgtggacct gcccacgtac tccttccggc gcgaccgcta ctggctggac   10560
gccccggcgg ccgacaccgc ggtggacacc gccggcctcg gtctcggcac cgccgaccac   10620
ccgctgctcg gcgccgtggt cagccttccg gaccgggacg gctgctgct caccggccgc   10680
ctctccctgc gcacccaccc gtggctcgcg gaccacgccg tcctggggag cgtcctgctc   10740
cccggcgccg cgatggtcga actcgccgcg cacgctgcgg agtccgccgg tctgcgtgac   10800
gtgcgggagc tgaccctcct tgaaccgctg gtactgcccg agcacggtgg cgtcgagctg   10860
cgcgtgacgg tcggggcgcc ggccggagag cccggtggcg agtcggccgg ggacggcgca   10920
cggcccgtct ccctccactc gcggctcgcc gacgcgcccg ccggtaccgc ctggtcctgc   10980
cacgcgaccg tctgctggc caccgaccgg cccgagcttc ccgtcgcgcc cgaccgtgcg   11040
gccatgtggc cgccgcaggg cgccgaggag gtgccgctcg acggtctcta cgagcggctc   11100
gacgggaacg gcctcgcctt cggtccgctg ttccaggggc tgaacgcggt gtggcggtac   11160
gagggtgagg tcttcgccga catcgcgctc cccgccacca cgaatgcgac cgcgcccgcg   11220
accgcgaacg gcgcgggag tgcggcggcg gcccccacg gcatccaccc cgccctgctc   11280
gacgcttcgc tgcacgccat cgcggtcggc ggtctcgtcg acgagcccga gctcgtccgc   11340
gtcccccttcc actggagcgg tgtcaccgtg cacgcggccg gtgccgcggc ggcccgggtc   11400
cgtctcgcct ccgcggggac ggacgccgtc tcgctgtccc tgacgacgg cgaggacgc    11460
ccgctggtct ccgtggaacg gctcacgctg cgcccggtca ccgccgatca ggcggcggcg   11520
```

```
agccgcgtcg gcgggctgat gcaccggtg gcctggcgtc cgtacgccct cgcctcgtcc      11580
ggcgaacagg acccgcacgc cacttcgtac gggccgaccg ccgtcctcgg caaggacgag      11640
ctgaaggtcg ccgccgccct ggagtccgcg ggcgtcgaag tcgggctcta ccccgacctg      11700
gccgcgctgt cccaggacgt ggcggccggc gccccggcgc cccgtaccgt ccttgcgccg      11760
ctgcccgcgg gtcccgccga cggcggcgcg gagggtgtac ggggcacggt ggcccggacg      11820
ctggagctgc tccaggcctg gctggccgac gagcacctcg cgggcacccg cctgctcctg      11880
gtcacccgcg gtgcggtgcg ggaccccgag gggtccggcg ccgacgatgg cggcgaggac      11940
ctgtcgcacg cggccgcctg gggtctcgta cggaccgcgc agaccgagaa ccccggccgc      12000
ttcggccttc tcgacctggc cgacgacgcc tcgtcgtacc ggaccctgcc gtcggtgctc      12060
tccgacgcgg gcctgcgcga cgaaccgcag ctcgccctgc acgacggcac catcaggctg      12120
gcccgcctgg cctccgtccg gcccgagacc ggcaccgccg caccggcgct cgccccggag      12180
ggcacggtcc tgctgaccgg cggcaccggc ggcctgggcg gactggtcgc ccggcacgtg      12240
gtgggcgagt ggggcgtacg acgcctgctg ctggtgagcc ggcggggcac ggacgccccg      12300
ggcgccgacg agctcgtgca cgagctggag gccctgggag ccgacgtctc ggtggccgcg      12360
tgcgacgtcc ccgaccgcga agccctcacc gccgtactcg acgccatccc cgccgaacac      12420
ccgctcaccg cggtcgtcca cacggcaggc gtcctctccg acggcaccct cccgtccatg      12480 acgacgagg acgtggaaca cgtactgcgg cccaaggtcg acgccgcgtt cctcctcgac      12540
gaactcacct cgacgcccgc atacgacctg gcagcgttcg tcatgttctc ctccgccgcc      12600
gccgtcttcg gtggcgcggg gcagggcgcc tacgccgccg ccaacgccac cctcgacgcc      12660
ctcgcctggc gccgccgggc agccggactc cccgccctct ccctcggctg ggcctctgg      12720 gccgagacca gcggcatgac cggcgagctc ggccaggcgg acctgcgccg gatgagccgc      12780
gcgggcatcg gcgggatcag cgacgccgag ggcatcgcgc tcctcgacgc cgccctccgc      12840
gacgaccgcc acccggtcct gctgcccctg cggctcgacg ccgccgggct gcgggacgcg      12900
gccgggaacg acccggccgg aatcccggcg ctcttccggg acgtcgtcgg cgccaggacc      12960
gtccgggccc ggccgtccgc ggcctccgcc tcgacgacag ccgggacggc cggcacgccg      13020
gggacggcgg acggcgcggc ggaaacggcg gcggtcacgc tcgccgaccg gccgccacc       13080 gtggacgggc ccgcacggca gcgcctgctg ctcgagttcg tcgtcggcga ggtcgccgaa      13140
gtactcggcc acgcccgcgg tcaccggatc gacgccgaac ggggcttcct cgacctcggc      13200
ttcgactccc tgaccgccgt cgaactccgc aaccggctca actccgccgg tggcctcgcc      13260
ctcccggcga ccctggtctt cgaccaccca agccggcgg cactcgcctc ccacctggac       13320
gccgagctgc cgcgcggcgc ctcggaccag gacggagccg ggaaccggaa cgggaacgag      13380
aacgggacga cggcgtcccg gagcaccgcc gagacgacg cgctgctggc acaactgacc       13440
cgcctggaag gcgccttggt gctgacgggc ctctcggacg ccccgggag cgaagaagtc      13500 ctggagcacc tgcggtccct cgcgctcgatg gtcacgggcg agaccgggac cgggaccgcg      13560
tccggagccc cggacggcgc cgggtccggc gccgaggacc ggccctgggc ggccggggac      13620
ggagccgggg gcgggagtga ggacggcgcg ggagtgccgg acttcatgaa cgcctcggcc      13680
gaggaactct tcggcctcct cgaccaggac cccagcacgg actgatccct gccgcacggt      13740
cgcctcccgc cccggacccc gtcccgggca cctcgactcg aatcacttca tgcgcgcctc      13800
gggcgcctcc aggaactcaa ggggacagcg tgtccacggt gaacgaagag aagtacctcg      13860
```

-continued

```
actacctgcg tcgtgccacg gcggacctcc acgaggcccg tggccgcctc cgcgagctgg    13920
aggcgaaggc gggcgagccg gtggcgatcg tcggcatggc ctgccgcctg cccggcggcg    13980
tcgcctcgcc cgaggacctg tggcggctgg tggccggcgg cgaggacgcg atctcggagt    14040
tcccccagga ccgcggctgg gacgtggagg gcctgtacga cccgaacccg gaggccacgg    14100
gcaagagtta cgcccgcgag gccggattcc tgtacgaggc gggcgagttc gacgccgact    14160
tcttcgggat ctcgccgcgc gaggccctcg ccatggaccc gcagcagcgt ctcctcctgg    14220
aggcctcctg ggaggcgttc gagcacgccg ggatcccggc ggccaccgcg cgcggcacct    14280
cggtcggcgt cttcaccggc gtgatgtacc acgactacgc cacccgtctc accgatgtcc    14340
cggagggcat cgagggctac ctgggcaccg gcaactccgg cagtgtcgcc tcgggccgcg    14400
tcgcgtacac gcttggcctg gaggggccgg ccgtcacggt cgacaccgcc tgctcgtcct    14460
cgctggtcgc cctgcacctc gccgtgcagg ccctgcgcaa gggcgaggtc gacatggcgc    14520
tcgccggcgg cgtgacggtc atgtcgacgc ccagcacctt cgtcgagttc agccgtcagc    14580
gcgggctggc gccggacggc cggtcgaagt ccttctcgtc gacggccgac ggcaccagct    14640
ggtccgaggg cgtcggcgtc ctcctcgtcg agcgcctgtc cgacgcgcgt cgcaagggcc    14700
atcggatcct cgccgtggtc cggggcaccg ccgtcaacca ggacggcgcc agcagcggcc    14760
tcacggctcc gaacgggccg tcgcagcagc gcgtcatccg acgtgccctg gcggacgccc    14820
ggctcacgac ctccgacgtg gacgtcgtcg aggcccacgg cacgggtacg cgactcggcg    14880
acccgatcga ggcgcaggcc gtcatcgcca cgtacgggca gggccgtgac ggcgaacagc    14940
cgctgcgcct cgggtcgttg aagtccaaca tcggacacac ccaggccgcc gccggtgtct    15000
ccggcgtgat caagatggtc caggcgatgc gccacggcgt cctgccgaag acgctccacg    15060
tggagaagcc gacggaccag gtggactggt ccgcgggcgc ggtcgagctg ctcaccgagg    15120
ccatggactg gccggacaag ggcgacgcg gactgcgcag ggccgcggtc tcctccttcg    15180
gcgtcagcgg gacgaacgcg cacgtcgtgc tcgaagaggc cccggcggcc gaggagaccc    15240
ctgcctccga ggcgaccccg gccgtcgagc cgtcggtcgg cgccgcctg gtgccgtggc    15300
tggtgtcggc gaagactccg gccgcgctgg acgcccagat cggacgcctc gccgcgttcg    15360
cctcgcaggg ccgtacggac gccgccgatc cgggcgcggt cgctcgcgta ctggccggcg    15420
ggcgcgccga gttcgagcac cgggccgtcg tgctcggcac cggacaggac gatttcgcgc    15480
aggcgctgac cgctccggaa ggactgatac gcggcacgcc ctcggacgtg gccgggtgg    15540
cgttcgtgtt ccccggtcag ggcacgcagt gggccgggat gggcgccgaa ctcctcgacg    15600
tgtcgaagga gttcgcggcg gccatggccg agtgcgagag cgcgctctcc cgctatgtcg    15660
actggtcgct ggaggccgtc gtccggcagg cgccgggcgc gcccacgctg gagcgggtcg    15720
acgtcgtcca gcccgtgacc ttcgctgtca tggtttcgct ggcgaaggtc tggcagcacc    15780
acggcgtgac gccgcaggcc gtcgtcggcc actcgcaggg cgagatcgcc gccgcgtacg    15840
tcgccggtgc cctcacctc gacgacgccg cccgcgtcgt caccctgcgc agcaagtcca    15900
tcgccgccca cctcgccggc aagggcggca tgatctccct cgccctcagc gaggaagcca    15960
cccggcagcg catcgagaac ctccacggac tgtcgatcgc cgccgtcaac ggccccaccg    16020
ccaccgtggt ttcgggcgac cccacccaga tccaagagct cgctcaggcg tgtgaggccg    16080
acggggtccg cgcacggatc atcccgtcg actacgcctc ccacagcgcc cacgtcgaga    16140
ccatcgagag cgaactcgcc gaggtcctcg ccgggctcag cccgcggaca cctgaggtgc    16200
cgttcttctc gacactcgaa ggcgcctgga tcaccgagcc ggtgctcgac ggcacctact    16260
```

-continued

```
ggtaccgcaa cctccgccac cgcgtcggct tcgccccgc cgtcgagacc ctcgccaccg    16320
acgaaggctt cacccacttc atcgaggtca gcgcccaccc cgtcctcacc atgaccctcc    16380
ccgagaccgt caccggcctc ggcaccctcc gccgcgaaca gggaggccag gagcgtctgg    16440
tcacctcact cgccgaagcc tggaccaacg gcctcaccat cgactgggcg cccgtcctcc    16500
ccaccgcaac cggccaccac cccgagctcc ccacctacgc cttccagcgc cgtcactact    16560
ggctccacga ctccccgcc gtccagggct ccgtgcagga ctcctggcgc taccgcatcg    16620
actggaagcg cctcgcggtc gccgacgcgt ccgagcgcg cgggctgtcc gggcgctggc    16680
tcgtcgtcgt ccccgaggac cgttccgccg aggccgcccc ggtgctcgcc gcgctgtccg    16740
gcgccggcgc cgaccccgta cagctggacg tgtccccgct gggcgaccgg cagcggctcg    16800
ccgcgacgct gggcgaggcc ctggcggcgg ccggtggagc cgtcgacggc gtcctctcgc    16860
tgctcgcgtg ggacgagagc gcgcaccccg gccaccccgc cccttcacc cggggcaccg    16920 gcgccaccct caccctggtg caggcgctgg aggacgccgg cgtcgccgcc ccgctgtggt    16980
gcgtgaccca cggcgcggtg tccgtcggcc gggccgacca cgtcacctcc cccgcccagg    17040
ccatggtgtg gggcatgggc cgggtcgccg ccctggagca ccccgagcgg tggggcggcc    17100
tgatcgacct gccctcggac gccgaccggg cggccctgga ccgcatgacc acggtcctcg    17160
ccggcggtac gggtgaggac caggtcgcgg tacgcgcctc cgggctgctc gcccgccgcc    17220
tcgtccgcgc ctccctcccg gcgcacggca cggcttcgcc gtggtggcag gccgacggca    17280
cggtgctcgt caccggtgcc gaggagcctg cggccgccga ggccgcacgc cggctggccc    17340 gcgacgcgc cggacacctc ctcctccaca ccacccctc cggcagcgaa ggcgccgaag    17400
gcacctccgg tgccgccgag gactccggcc tcgccgggct cgtcgccgaa ctcgcggacc    17460
tgggcgcgac ggccaccgtc gtgacctgcg acctcacgga cgcggaggcg gccgcccggc    17520
tgctcgccgg cgtctccgac gcgcacccgc tcagcgccgt cctccacctg ccgcccaccg    17580
tcgactccga gccgctcgcc gcgaccgacg cggacgcgct cgcccgtgtc gtgaccgcga    17640
aggccaccgc cgcgctccac ctggaccgcc tcctgcggga ggccgcggct gccggaggcc    17700
gtccgcccgt cctggtcctc ttctcctcgg tcgccgcgat ctgggcggc gccggtcagg    17760 gcgcgtacgc cgccggtacg gccttcctcg acgccctcgc cggtcagcac cgggccgacg    17820
gccccaccgt gacctcggtg gcctggagcc cctgggaggg cagccgcgtc accgagggtg    17880
cgaccgggga gcggctgcgc cgcctcggcc tgcgcccct cgccccgcg acggcgctca    17940 ccgccctgga caccgcgctc ggccacggcg acaccgccgt cacgatcgcc gacgtcgact    18000
ggtcgagctt cgccccggc ttcaccacgg cccggccggg caccctcctc gccgatctgc    18060
ccgaggcgcg ccgcgcgctc gacgagcagc agtcgacgac ggccgccgac gacaccgtcc    18120
tgagccgcga gctcggtgcg ctcaccggcg ccgaacagca gcgccgtatg caggagttgg    18180
tccgcgagca cctcgccgtg gtcctcaacc cccctcccc cgaggccgtc gacacggggc    18240
gggccttccg tgacctcgga ttcgactcgc tgacggcggt cgagctccgc aaccgcctca    18300
agaacgccac cggcctggcc ctccggccca tctggtctt cgactacccg accccccgga    18360
cgctggcgga gttcctcctc gcggagatcc tgggcgagca ggccggtgcc ggcgagcagc    18420
ttccggtgga cggcggggtc gacgacgagc ccgtcgcgat cgtcggcatg cgtgccgcc    18480 tgccgggcg tgtcgcctcg ccggaggacc tgtggcggct ggtggccggc ggcgaggacg    18540
cgatctccgg cttcccgcag gaccgcggct gggacgtgga ggggctgtac gacccggacc    18600
```

-continued

```
cggacgcgtc cgggcggacg tactgccgtg ccggtggctt cctcgacgag gcgggcgagt    18660
tcgacgccga cttcttcggg atctcgccgc gcgaggccct cgccatggac ccgcagcagc    18720
ggctcctcct ggagacctcc tgggaggccg tcgaggacgc cgggatcgac ccgacctccc    18780
ttcaggggca gcaggtcggc gtgttcgcgg gcaccaacgg cccccactac gagccgctgc    18840
tccgcaacac cgccgaggat cttgagggtt acgtcgggac gggcaacgcc gccagcatca    18900
tgtcgggccg tgtctcgtac accctcggcc tggagggccc ggccgtcacg gtcgacaccg    18960
cctgctcctc ctcgctggtc gccctgcacc tcgccgtgca ggcctgcgc aagggcgaat    19020
gcggactggc gctcgcgggc ggtgtgacgg tcatgtcgac gcccacgacg ttcgtggagt    19080
tcagccggca gcgcgggctc gcggaggacg gccggtcgaa ggcgttcgcc gcgtcggcgg    19140
acggcttcgg cccggcggag ggcgtcggca tgctcctcgt cgagcgcctg tcggacgccc    19200
gccgcaacgg acaccgtgtg ctggcggtcg tgcgcggcag cgcggtcaac caggacggcg    19260
cgagcaacgg cctgaccgcc ccgaacgggc cctcgcagca gcgcgtcatc cggcgcgcgc    19320
tcgcggacgc ccgactgacg accgccgacg tggacgtcgt cgaggcccac ggcacgggca    19380
cgcgactcgg cgacccgatc gaggcacagg ccctcatcgc cacctacggc cagggcgcg    19440
acaccgaaca gccgctgcgc ctgggggtcgt tgaagtccaa catcggacac acccaggccg    19500
ccgccggtgt ctccggcatc atcaagatgg tccaggcgat gcgccacggc gtcctgccga    19560
agacgctcca cgtggaccgg ccgtcggacc agatcgactg gtcggcgggc acggtcgagc    19620
tgctcaccga ggccatggac tggccgagga agcaggaggg cgggctgcgc cgcgcggccg    19680
tctcctcctt cggcatcagc ggcacgaacg cgcacatcgt gctcgaagaa gccccggtcg    19740
acgaggacgc cccggcggac gagccgtcgg tcggcggtgt ggtgccgtgg ctcgtgtccg    19800
cgaagactcc ggccgcgctg gacgcccaga tcggacgcct cgccgcgttc gcctcgcagg    19860
gccgtacgga cgccgccgat ccgggcgcgg tcgctcgcgt actggccggc gggcgtgcgc    19920
agttcgagca ccgggccgtc gcgctcggca ccggacagga cgacctggcg gccgcactgg    19980
ccgcgcctga gggtctggtc cggggtgtgg cctccggtgt gggtcgagtg gcgttcgtgt    20040
tcccgggaca gggcacgcag tgggccggga tgggtgccga actcctcgac gtgtcgaagg    20100
agttcgcggc ggccatggcc gagtgcgagg ccgcgctcgc tccgtacgtg gactggtcgc    20160
tggaggccgt cgtccgacag gcccccggcg cgcccacgct ggagcgggtc gatgtcgtcc    20220
agcccgtgac gttcgccgtc atggtctcgc tggcgaaggt ctggcagcac cacgggtga    20280
ccccgcaagc cgtcgtcggc cactcgcagg gcgagatcgc cgccgcgtac gtcgccggtg    20340
ccctgagcct ggacgacgcc gctcgtgtcg tgaccctgcg cagcaagtcc atcgcgcccc    20400
acctcgcggg ccagggcggc atgctgtccc tcgcgctgag cgaggcggcc gttgtggagc    20460
gactggccgg gttcgacggg ctgtccgtcg ccgccgtcaa cgggcctacc gccaccgtgg    20520
tttcgggcga cccgacccag atccaagagc tcgctcaggc gtgtgaggcc gacggggtcc    20580
gcgcacggat catcccgtc gactacgcct cccacagcgc ccacgtcgag accatcgaga    20640
gcgaactcgc cgacgtcctg gcggggttgt cccccagac acccaggtc cccttcttct    20700
ccaccctcga aggcgcctgg atcaccgaac ccgcctcga cggcggctac tggtaccgca    20760
acctccgcca tcgtgtgggc ttcgcccgg ccgtcgaaac cctggccacc gacgaaggct    20820
tcacccactt cgtcgaggtc agcgcccacc ccgtcctcac catggccctg cccgagaccg    20880
tcaccggcct cggcaccctc cgccgtgaca acggcggaca gcaccgcctc accacctccc    20940
tcgccgaggc ctgggccaac ggcctcaccg tcgactgggc ctctctcctc cccaccacga    21000
```

```
ccacccaccc cgatctgccc acctacgcct tccagaccga gcgctactgg ccgcagcccg   21060
acctctccgc cgccggtgac atcacctccg ccggtctcgg ggcggccgag cacccgctgc   21120
tcggcgcggc cgtggcgctc gcggactccg acggctgcct gctcacgggg agcctctccc   21180
tccgtacgca ccccctggctg gcggaccacg cggtggccgg caccgtgctg ctgccgggaa   21240
cggcgttcgt ggagctggcg ttccgagccg ggaccaggtc cggttgcgat ctggtcgagg   21300
agctcaccct cgacgcgccg ctcgtgctgc ccgtcgtgg cgcggtccgt gtgcagctgt   21360
ccgtcggcgc gagcgacgag tccgggcgtc gtaccttcgg gctctacgcg cacccggagg   21420
acgcgccggg cgaggcggag tggacgcggc acgccaccgg tgtgctggcc gcccgtgcgg   21480
accgcaccgc ccccgtcgcc gacccggagg cctggccgcc gccgggcgcc gagccggtgg   21540
acgtggacgg tctgtacgag cgcttcgcgg cgaacggcta cggctacggc cccctcttcc   21600
agggcgtccg tggtgtctgg cggcgtggcg acgaggtgtt cgccgacgtg gccctgccgg   21660
ccgaggtcgc cggtgccgag ggcgcgcggt tcggccttca cccggcgctg ctcgacgccg   21720
ccgtgcaggc ggccggtgcg ggcggggcgt tcggcgcggg cacgcggctg ccgttcgcct   21780
ggagcgggat ctccctgtac gcggtcggcg ccaccgccct ccgcgtgcgg ctggccccg   21840
ccggcccgga cacggtgtcc gtgagcgccg ccgactcctc cgggcagccg gtgttcgccg   21900
cggactccct cacggtgctg ccgtcgacc ccgcgcagct ggcggccttc agcgacccga   21960
ctctggacgc gctgcacctg ctggagtgga ccgcctggga cggtgccgcg caggccctgc   22020
ccggcgcggt cgtgctgggc ggcgacgccg acggtctcgc cgcggcgctg cgcgccggtg   22080
gcaccgaggt cctgtccttc ccggaccta cggacctggt ggaggccgtc gaccggggcg   22140
agaccccggc cccggcgacc gtcctggtgg cctgccccgc cgccggcccc ggtgggccgg   22200
agcatgtccg cgaggccctg cacggtcgc tcgcgctgat gcaggcctgg ctggccgacg   22260
agcggttcac cgatgggcgc ctggtgctcg tgacccgcga cgcggtcgcc gcccgttccg   22320
gcgacgcct gcggtccacg ggacaggccg ccgtctgggg cctcggccgg tccgcgcaga   22380
cggagagccc gggccggttc gtcctgctcg acctcgccgg ggaagcccgg acggccgggg   22440
acgccaccgc cggggacggc ctgacgaccg gggacgccac cgtcggcggc acctctggag   22500
acgccgccct cggcagcgcc ctcgcgaccg ccctcggctc gggcgagccg cagctcgccc   22560
tccgggacgg ggcgctcctc gtaccccgcc tggcgcgggc cgccgcgccc gccgcggccg   22620
acggcctcgc cgcggccgac ggcctcgccg ctctgccgct gccgccgct ccggccctct   22680
ggcgtctgga gcccggtacg gacggcagcc tggagagcct cacggcggcg cccggcgacg   22740
ccgagaccct cgccccggag ccgctcggcc cgggacaggt ccgcatcgcg atccgggcca   22800
ccgtctcaa cttccgcgac gtcctgatcg ccctcggcat gtaccccgat ccggcgctga   22860
tgggcaccga gggagccggc gtggtcaccg cgaccggccc cggcgtcacg cacctcgccc   22920
ccggcgaccg ggtcatgggc ctgctctccg gcgcgtacgc cccggtcgtc gtggcggacg   22980
cgcggaccgt cgcgcggatg cccgaggggt ggacgttcgc ccaggcgcc tcgtgccgg   23040
tggtgttcct gacggccgtc tacgccctgc gcgacctggc ggacgtcaag cccggcgagc   23100
gcctcctggt ccactccgcc gccggtgggc tgggcatggc cgccgtgcag ctcgcccggc   23160
actggggcgt ggaggtccac ggcacggcga gtcacgggaa gtgggacgcc ctgcgcgcgc   23220
tcggcctgga cgacgcgcac atcgcctcct cccgcacct ggacttcgag tccgcgttcc   23280
gtgccgcttc cggcggggcg ggcatggacg tcgtactgaa ctcgctcgcc cgcgagttcg   23340
```

```
tcgacgcctc gctgcgcctg ctcgggccgg gcggccggtt cgtggagatg gggaagaccg    23400
acgtccgcga cgcggagcgg gtcgccgccg accaccccgg tgtcggctac cgcgccttcg    23460
acctgggcga ggccgggccg gagcggatcg gcgagatgct cgccgaggtc atcgccctct    23520
tcgaggacgg ggtgctccgg cacctgcccg tcacgacctg ggacgtgcgc cgggcccgcg    23580
acgccttccg gcacgtcagc caggcccgcc acacgggcaa ggtcgtcctc acgatgccgt    23640
cgggcctcga cccggagggt acggtcctgc tgaccggcgg caccggtgcg ctgggggggca    23700 tcgtggcccg gcacgtggtg ggcgagtggg gcgtacgacg cctgctgctc gtgagccggc    23760
ggggcacgga cgcccgggc gccggcgagc tcgtgcacga gctggaggcc ctgggagccg    23820
acgtctcggt ggccgcgtgc gacgtcgccg accgcgaagc cctcaccgcc gtactcgact    23880
cgatccccgc cgaacacccg ctcaccgcgg tcgtccacac ggcaggcgtc ctctccgacg    23940
gcaccctccc ctcgatgaca gcggaggatg tggaacacgt actgcgtccc aaggtcgacg    24000
ccgcgttcct cctcgacgaa ctcacctcga cgcccggcta cgacctggca gcgttcgtca    24060
tgttctcctc cgccgccgcc gtcttcggtg gcgcggggca gggcgcctac gccgccgcca    24120
acgccaccct cgacgccctc gcctggcgcc gccggacagc cggactcccc gccctctccc    24180
tcggctgggg cctctgggcc gagaccagcg gcatgaccgg cggactcagc gacaccgacc    24240
gctcgcggct ggcccgttcc ggggcgacgc ccatggacag cgagctgacc ctgtccctcc    24300
tggacgcggc catgcgccgc gacgacccgg cgctcgtccc gatcgccctg gacgtcgccg    24360
cgctccgcgc ccagcagcgc gacggcatgc tggcgccgct gctcagcggg ctcacccgcg    24420
gatcgcgggt cggcggcgcg ccggtcaacc agcgcaggc agccgccgga ggcgcgggcg    24480
aggcggacac ggacctcggc gggcggctcg ccgcgatgac accggacgac cggtcgcgc    24540 acctgcggga cctcgtccgt acgcacgtgg cgaccgtcct gggacacggc accccgagcc    24600
gggtggacct ggagcgggcc ttccgcgaca ccggtttcga ctcgctcacc gccgtcgaac    24660
tccgcaaccg tctcaacgcc gcgaccgggc tgcggctgcc ggccacgctg gtcttcgacc    24720
accccacccc gggggagctc gccgggcacc tgctcgacga actcgccacg gccgcgggc    24780 ggtcctgggc ggaaggcacc gggtccggag acacggcctc ggcgaccgat cggcagacca    24840
cggcggcccc cgccgaactc gaccggctgg aaggcgtgct cgcctccctc gcgcccgccg    24900
ccggcggccg tccggagctc gccgcccggc tcagggcgct ggccgcggcc ctggggacg    24960 acggcgacga cgccaccgac ctggacgagg cgtccgacga cgacctcttc tccttcatcg    25020
acaaggagct gggcgactcc gacttctgac ctgcccgaca ccaccggcac caccggcacc    25080
accagccccc ctcacacacg gaacacgaaa cggacaggcg agaacgggag ccatggcgaa    25140
caacgaagac aagctccgcg actacctcaa gcgcgtcacc gccgagctgc agcagaacac    25200
caggcgtctg cgcgagatcg agggacgcac gcacgagccg gtggcgatcg tgggcatggc    25260
ctgccgcctg ccgggcggtg tcgcctcgcc cgaggacctg tggcagctgg tggccgggga    25320
cggggacgcg atctcggagt tcccgcagga ccgcggctgg gacgtggagg ggctgtacga    25380
ccccgacccg gacgcgtccg gcaggacgta ctgccggtcc ggcggattcc tgcacgacgc    25440
cggcgagttc gacgccgact tcttcgggat ctcgccgcgc gaggccctcg ccatggaccc    25500
gcagcagcga ctgtccctca ccaccgcgtg ggaggcgatc gagagcgcgg gcatcgaccc    25560
gacggccctg aagggcagcg gcctcggcgt cttcgtcggc ggctggcaca ccggctacac    25620
ctcggggcag accaccgccg tgcagtcgcc cgagctggag ggccacctgg tcagcggcgc    25680
ggcgctgggc ttcctgtccg gccgtatcgc gtacgtcctc ggtacggacg gaccggccct    25740
```

```
gaccgtggac acggcctgct cgtcctcgct ggtcgccctg cacctcgccg tgcaggccct   25800
ccgcaagggc gagtgcgaca tggccctcgc cggtggtgtc acggtcatgc ccaacgcgga   25860
cctgttcgtg cagttcagcc ggcagcgcgg gctggccgcg gacggccggt cgaaggcgtt   25920
cgccacctcg gcggacggct tcggccccgc ggagggcgcc ggagtcctgc tggtggagcg   25980
cctgtcggac gcccgccgca acggacaccg gatcctcgcg gtcgtccgcg gcagcgcggt   26040
caaccaggac ggcgccagca acggcctcac ggctccgcac gggccctccc agcagcgcgt   26100
catccgacgg gccctggcgg acgcccggct cgcgccgggt gacgtggacg tcgtcgaggc   26160
gcacggcacg ggcacgcggc tcggcgaccc gatcgaggcg caggccctca tcgccaccta   26220
cggccaggag aagagcagcg aacagccgct gaggctgggc gcgttgaagt cgaacatcgg   26280
gcacacgcag gccgcggccg gtgtcgcagg tgtcatcaag atggtccagg cgatgcgcca   26340
cggactgctg ccgaagacgc tgcacgtcga cgagccctcg gaccagatcg actggtcggc   26400
gggcacggtg gaactcctca ccgaggccgt cgactggccg gagaagcagg acggcgggct   26460
gcgccgcgcg gctgtctcct ccttcggcat cagcgggacg aacgcgcacg tcgtcctgga   26520
ggaggccccg gcggtcgagg actccccggc cgtcgagccg ccggccggtg gcggtgtggt   26580
gccgtggccg gtgtccgcga agactccggc cgcgctggac gcccagatcg ggcagctcgc   26640
cgcgtacgcg gacggtcgta cggacgtgga tccggcggtg gccgcccgcg ccctggtcga   26700
cagccgtacg gcgatggagc accgcgcggt gcggtcggc gacagccggg aggcactgcg   26760
ggacgccctg cggatgccgg aaggactggt acgcggcacg tcctcggacg tgggccgggt   26820
ggcgttcgtc ttccccggcc agggcacgca gtgggccggc atgggcgccg aactccttga   26880
cagctcaccg gagttcgctg cctcgatggc cgaatgcgag accgcgctct cccgctacgt   26940
cgactggtct cttgaagccg tcgtccgaca ggaacccggc gcacccacgc tcgaccgcgt   27000
cgacgtcgtc cagcccgtga ccttcgctgt catggtctcg ctggcgaagg tctggcagca   27060
ccacggcatc acccccagg ccgtcgtcgg ccactcgcag ggcgagatcg ccgccgcgta   27120
cgtcgccggt gcactcaccc tcgacgacgc cgcccgcgtc gtcaccctgc gcagcaagtc   27180
catcgccgcc cacctcgccg gcaagggcgg catgatctcc ctcgcccctcg acgaggcggc   27240 cgtcctgaag cgactgagcg acttcgacgg actctccgtc gccgccgtca acggcccac   27300 cgccaccgtc gtctccggcg acccgaccca gatcgaggaa ctcgcccgca cctgcgaggc   27360
cgacggcgtc cgtgcgcgga tcatcccggt cgactacgcg tcccacagcc ggcaggtcga   27420
gatcatcgag aaggagctgg ccgaggtcct cgccggactc gccccgcagg ctccgcacgt   27480
gccgttcttc tccaccctcg aaggcacctg gatcaccgag ccggtgctcg acggcaccta   27540
ctggtaccgc aacctgcgcc atcgcgtggg cttcgccccc gccgtggaga ccttggcgt   27600 tgacggcttc acccacttca tcgaggtcag cgcccacccc gtcctcacca tgaccctccc   27660
cgagaccgtc accggcctcg gcaccctccg ccgcgaacag ggaggccagg agcgtctggt   27720
cacctcactc gccgaagcct gggccaacgg cctcaccatc gactgggcgc ccatcctccc   27780
caccgcaacc ggccaccacc ccgagctccc cacctacgcc ttccagaccg agcgcttctg   27840
gctgcagagc tccgcgccca ccagcgccgc cgacgactgg cgttaccgcg tcgagtggaa   27900
gccgctgacg gcctccggcc aggcggacct gtccgggcgg tggatcgtcg ccgtcgggag   27960
cgagccagaa gccgagctgc tgggcgcgct gaaggccgcg ggagcggagg tcgacgtact   28020
ggaagccggg gcggacgacg accgtgaggc cctcgccgcc cggctcaccg cactgacgac   28080
```

```
cggcgacggc ttcaccggcg tggtctcgct cctcgacgac ctcgtgccac aggtcgcctg    28140
ggtgcaggca ctcggcgacg ccggaatcaa ggcgcccctg tggtccgtca cccagggcgc    28200
ggtctccgtc ggacgtctcg acaccccgc cgaccccgac cgggccatgc tctgggcct     28260 cggccgcgtc gtcgcccttg agcaccccga acgctgggcc ggcctcgtcg acctccccgc    28320
ccagcccgat gccgccgccc tcgcccacct cgtcaccgca ctctccggcg ccaccggcga    28380
ggaccagatc gccatccgca ccaccggact ccacgcccgc cgcctcgccc gcgcacccct    28440
ccacggacgt cggcccaccc gcgactggca gccccacggc accgtcctca tcaccggcgg    28500
caccggagcc ctcggcagcc acgccgcacg ctggatggcc caccacggag ccgaacacct    28560
cctcctcgtc agccgcagcg gcgaacaagc ccccggagcc acccaactca ccgccgaact    28620
caccgcatcg ggcgcccgcg tcaccatcgc cgcctgcgac gtcgccgacc ccacgccat    28680 gcgcaccctc ctcgacgcca tccccgccga gacgccctc accgccgtcg tccacaccgc    28740
cggcgcaccg ggcggcgatc cgctggacgt caccggcccg gaggacatcg cccgcatcct    28800
gggcgcgaag acgagcggcg ccgaggtcct cgacgacctg ctccgcgcca ctccgctgga    28860
cgccttcgtc ctctactcct cgaacgccgg ggtctggggc agcggcagcc agggcgtcta    28920 cgcggcgggcc aacgcccacc tcgacgcgct cgccgcccgg cgccgcgccc ggggcgagac    28980
ggcgacctcg gtcgcctggg gcctctggcc ggcgacggca atgggccggg gcgccgacga    29040
cgcgtactgg cagcgtcgcg gcatccgtcc gatgagcccc gaccgcgccc tggacgaact    29100
ggccaaggcc ctgagccacg acgagacctt cgtcgccgtg gccgatgtcg actgggagcg    29160
gttcgcgccc gcgttcacgg tgtcccgtcc cagccttctg ctcgacggcg tcccggaggc    29220
ccggcaggcg ctcgccgcac ccgtcggtgc cccggctccc ggcgacgccg ccgtggcgcc    29280
gaccgggcag tcgtcggcgc tggccgcgat caccgcgctc cccgagcccg agcgccggcc    29340
ggcgctcctc acccctcgtcc gtacccacgc ggcggccgta ctcggccatt cctcccccga    29400
ccgggtggcc cccggccgtg ccttcaccga gctcggcttc gactcgctga cggccgtgca    29460
gctccgcaac cagctctcca cggtggtcgg caacaggctc cccgccacca cggtcttcga    29520
ccacccgacg cccgccgcac tcgccgcgca cctccacgag gcgtacctcg caccggccga    29580
gccggccccg acggactggg aggggcgggt gcgccgggcc ctggccgaac tgcccctcga    29640
ccggctgcgg gacgcgggg tcctcgacac cgtcctgcgc ctcaccggca tcgagcccga    29700
gccgggttcc ggcggttcgg acggcggcgc cgccgaccct ggtgcggagc cggaggcgtc    29760
gatcgacgac ctggacgccg aggccctgat ccggatggct ctcggccccc gtaacacctg    29820
acccgaccgc ggtcctgccc cacgcgccgc acccgcgca tcccgcgcac cacccgcccc    29880
cacacgccca caaccccatc cacgagcgga agaccacacc cagatgacga gttccaacga    29940
acagttggtg gacgctctgc gcgcctctct caaggagaac gaagaactcc ggaaagagag    30000
ccgtcgccgg gccgaccgtc ggcaggagcc catggcgatc gtcggcatga gctgccggtt    30060
cgcgggcgga atccggtccc ccgaggacct ctgggacgcc gtcgccgcgg gcaaggacct    30120
ggtctccgag gtaccggagg agcgcggctg ggacatcgac tccctctacg acccggtgcc    30180
cgggcgcaag ggcacgacgt acgtccgcaa cgccgcgttc ctcgacgacg ccgccggatt    30240
cgacgcggcc ttcttcggga tctcgccgcg cgaggccctc gccatggacc cgcagcagcg    30300
gcagctcctc gaagcctcct gggaggtctt cgagcgggcc ggcatcgacc ccgcgtcggt    30360
ccgcggcacc gacgtcggcg tgtacgtggg ctgtggctac caggactacg cgccggacat    30420
ccgggtcgcc cccgaaggca ccggcggtta cgtcgtcacc ggcaactcct ccgccgtggc    30480
```

-continued

```
ctccgggcgc atcgcgtact ccctcggcct ggagggaccc gccgtgaccg tggacacggc    30540
gtgctcctct tcgctcgtcg ccctgcacct cgccctgaag ggcctgcgga acggcgactg    30600
ctcgacggca ctcgtgggcg gcgtggccgt cctcgcgacg ccgggcgcgt tcatcgagtt    30660
cagcagccag caggccatgg ccgccgacgg ccggaccaag ggcttcgcct cggcggcgga    30720
cggcctcgcc tggggcgagg gcgtcgccgt actcctcctc gaacggctct ccgacgcgcg    30780
gcgcaagggc caccgggtcc tggccgtcgt gcgcggcagc gccatcaacc aggacggcgc    30840
gagcaacggc ctcacggctc cgcacgggcc ctcccagcag cgcctgatcc gccaggccct    30900
ggccgacgcg cggctcacgt cgagcgacgt ggacgtcgtg gagggccacg gcacggggac    30960
ccgtctcggc gacccgatcg aggcgcaggc gctgctcgcc acgtacgggc aggggcgcgc    31020
cccggggcag ccgctgcggc tggggacgct gaagtcgaac atcgggcaca cgcaggccgc    31080
ttcgggtgtc gccggtgtca tcaagatggt gcaggcgctg cgccacgggg tgctgccgaa    31140
gaccctgcac gtggacgagc cgacggacca ggtcgactgg tcggccggtt cggtcgagct    31200
gctcaccgag gccgtggact ggccggagcg gccgggccgg ctccgccggg cgggcgtctc    31260
cgcgttcggc gtgggcggga cgaacgcgca cgtcgtcctg gaggaggccc ggcggtcga    31320 ggagtccccct gccgtcgagc cgccggccgg tggcggcgtg gtgccgtggc cggtgtccgc    31380
gaagacctcg gccgcactgg acgcccagat cgggcagctc ccgcatacg cggaagaccg    31440 cacggacgtg gatccggcgg tggccgcccg cgccctggtc gacagccgta cggcgatgga    31500
gcaccgcgcg gtcgcggtcg gcgacagccg ggaggcactg cgggacgccc tgcggatgcc    31560
ggaaggactg gtacggggca cggtcaccga tccgggccgg gtggcgttcg tcttccccgg    31620
ccagggcacg cagtgggccg gcatgggcgc cgaactcctc gacagctcac ccgaattcgc    31680
cgccgccatg gccgaatgcg agaccgcact ctccccgtac gtcgactggt ctctcgaagc    31740
cgtcgtccga caggctccca gcgcaccgac actcgaccgc gtcgacgtcg tccagcccgt    31800
caccttcgcc gtcatggtct ccctcgccaa ggtctggcag caccacgca tcaccccga    31860 ggccgtcatc ggccactccc agggcgagat cgccgccgcg tacgtcgccg gtgccctcac    31920
cctcgacgac gccgctcgtg tcgtgaccct ccgcagcaag tccatcgccg cccacctcgc    31980
cggcaagggc ggcatgatct ccctcgccct cagcgaggaa gccacccggc agcgcatcga    32040
gaacctccac ggactgtcga tcgccgccgt caacgggcct accgccaccg tggtttcggg    32100
cgaccccacc cagatccaag aacttgctca ggcgtgtgag gccgacggca tccgcgcacg    32160
gatcatcccc gtcgactacg cctcccacag cgcccacgtc gagaccatcg agaacgaact    32220
cgccgacgtc ctggcggggt tgtcccccca gacaccccag gtccccttct tctccaccct    32280
cgaaggcacc tggatcaccg aacccgccct cgacggcggc tactggtacc gcaacctccg    32340
ccatcgtgtg gcttcgccc cggccgtcga gaccctcgcc accgacgaag gcttcaccca    32400
cttcatcgag gtcagcgccc accccgtcct caccatgacc ctccccgaca aggtcaccgg    32460
cctggccacc ctccgacgcg aggacggcgg acagcaccgc ctcaccacct cccttgccga    32520
ggcctgggcc aacggcctcg ccctcgactg gcctccctc ctgcccgcca gggcgccct    32580 cagccccgcc gtccccgacc tcccgacgta cgccttccag caccgctcgt actggatcag    32640
ccccgcgggt ccggcgagg cgcccgcgca caccgcttcc gggcgcgagg ccgtcgccga    32700
gacggggctc gcgtggggcc cggtgccga ggacctcgac gaggagggcc ggcgcagcgc    32760
cgtactcgcg atggtgatgc ggcaggcggc ctccgtgctc cggtgcgact cgcccgaaga    32820
```

```
ggtccccgtc gaccgcccgc tgcgggagat cggcttcgac tcgctgaccg ccgtcgactt   32880
ccgcaaccgc gtcaaccggc tgaccggtct ccagctgccg cccaccgtcg tgttcgagca   32940
cccgacgccc gtcgcgctcg ccgagcgcat cagcgacgcg ctggccgagc ggaactgggc   33000
cgtcgccgag ccgtcggatc acgagcaggc ggaggaggag aaggccgccg ctccggcggg   33060
ggcccgctcc ggggccgaca ccggcgccgg cgccgggatg ttccgcgccc tgttccggca   33120
ggccgtggag gacgaccggt acggcgagtt cctcgacgtc ctcgccgaag cctccgcgtt   33180
ccgcccgcag ttcgcctcgc ccgaggcctg ctcggagcgg ctcgaccggg tgctgctcgc   33240
cggcggtccg acggaccggg cggaaggccg tgccgttctc gtcggctgca ccggcaccgc   33300
ggcgaacggc ggcccgcacg agttcctgcg gctcagcacc tccttccagg aggagcggga   33360
cttcctcgcc gtacctctcc ccggctacgg cacgggtacg ggcaccggca cggccctcct   33420
cccggccgat ctcgacaccg cgctcgacgc ccaggcccgg gcgatcctcc gggccgccgg   33480
ggacgccccg gtcgtcctgc tcgggcactc cggcggcgcc ctgctcgcgc acgagctggc   33540
cttccgcctg gagcgggcgc acggcgcgcc gccggccggg atcgtcctgg tcgaccccta   33600
tccgccgggc catcaggagc ccatcgaggt gtggagcagg cagctgggcg agggcctgtt   33660
cgcgggcgag ctggagccga tgtccgatgc gcggctgctg gccatgggcc ggtacgcgcg   33720
gttcctcgcc ggcccgcggc cgggccgcag cagcgcgccc gtgcttctgg tccgtgcctc   33780
cgaaccgctg ggcgactggc aggaggagcg gggcgactgg cgtgcccact gggaccttcc   33840
gcacaccgtc gcggacgtgc cgggcgacca cttcacgatg atgcgggacc acgcgccggc   33900
cgtcgccgag gccgtcctct cctggctcga cgccatcgag ggcatcgagg gggcgggcaa   33960
gtgaccgaca gacctctgaa cgtggacagc ggactgtgga tccggcgctt ccaccccgcg   34020
ccgaacagcg cggtgcggct ggtctgcctg ccgcacgccg gcggctccgc cagctacttc   34080
ttccgcttct cggaggagct gcaccccctcc gtcgaggccc tgtcggtgca gtatccgggc   34140
cgccaggacc ggcgtgccga ccgtgtctg gagagcgtcg aggagctcgc cgagcatgtg   34200
gtcgcggcca ccgaaccctg gtggcaggag ggccggctgg ccttcttcgg gcacagcctc   34260
ggcgcctccg tcgccttcga gacggcccgc atcctggaac agcggcacgg ggtacggccc   34320
gagggcctgt acgtctccgg tcggcgcgcc cgtcgctgg cgccgaccg gctcgtccac   34380 cagctggacg accgggcgtt cctggccgag atccggcggc tcagcggcac cgacgagcgg   34440
ttcctccagg acgacgagct gctgcggctg gtgctgcccg cgctgcgcag cgactacaag   34500
gcggcggaga cgtacctgca ccggccgtcc gccaagctca cctgcccggt gatggccctg   34560
gccggcgacc gtgaccccgaa ggcgccgctg aacgaggtgg ccgagtggcg tcggcacacc   34620
agcgggccgt tctgcctccg ggcgtactcc ggcggccact tctacctcaa cgaccagtgg   34680
cacgagatct gcaacgacat ctccgaccac ctgctcgtca cccgcggcgc gcccgatgcc   34740
cgcgtcgtgc agcccccgac cagccttatc gaaggagcgg cgaagagatg gcagaaccca   34800
cggtgaccga cgacctgacg ggggccctca cgcagccccc gctgggccgc accgtccgcg   34860
cggtggccga ccgtgaactc ggcacccacc tcctggagac ccgcggcatc cactggatcc   34920
acgccgcgaa cggcgacccg tacgccaccg tgctgcgcgg ccaggcggac gacccgtatc   34980
ccgcgtacga gcgggtgcgt gcccgcggcg cgctctcctt cagcccgacg ggcagctggg   35040
tcaccgccga tcacgccctg gcggcagca tcctctgctc gacggacttc ggggtctccg   35100
gcgccgacgg cgtcccggtg ccgcagcagg tcctctcgta cggggagggc tgtccgctgg   35160
agcgcgagca ggtgctgccg gcggccggtg acgtgccgga gggcgggcag cgtgccgtgg   35220
```

-continued

```
tcgagggat ccaccgggag acgctggagg gtctcgcgcc ggacccgtcg gcgtcgtacg    35280
ccttcgagct gctgggcggt ttcgtccgcc cggcggtgac ggccgctgcc gccgccgtgc    35340
tgggtgttcc cgcggaccgg cgcgcggact tcgcggatct gctggagcgg ctccggccgc    35400
tgtccgacag cctgctggcc ccgcagtccc tgcggacggt acgggcggcg gacggcgcgc    35460
tggccgagct cacggcgctg ctcgccgatt cggacgactc ccccgggcc ctgctgtcgg     35520 cgctcgggt caccgcagcc gtccagctca ccgggaacgc ggtgctcgcg ctcctcgcgc     35580
atcccgagca gtggcgggag ctgtgcgacc ggcccgggct cgcggcggcc gcggtggagg    35640
agaccctccg ctacgacccg ccggtgcagc tcgacgcccg ggtggtccgc ggggagacgg    35700
agctggcggg ccggcggctg ccggccgggg cgcatgtcgt cgtcctgacc gccgcgaccg    35760
gccgggaccc ggaggtcttc acggacccgg agcgcttcga cctcgcgcgc cccgacgccg    35820
ccgcgcacct cgccgctgcac cccgccggtc cgtacggccc ggtggcgtcc ctggtccggc    35880
ttcaggcgga ggtcgcgctg cggaccctgg ccgggcgttt ccccgggctg cggcaggcgg    35940
gggacgtgct ccgcccccgc cgcgcgcctg tcggccgcgg gccgctgagc gtcccggtca    36000
gcagctcctg agacaccggg gccccggtcc gcccggcccc ccttcggacg gaccggacgg    36060
ctcggaccac ggggacggct cagaccgtcc cgtgtgtccc cgtccggctc ccgtccgccc    36120
catcccgccc ctccaccggc aaggaaggac acgacgccat gcgcgtcctg ctgacctcgt    36180
tcgcacatca cacgcactac tacggcctgg tgcccctggc ctgggcgctg ctcgccgccg    36240
ggcacgaggt gcgggtcgcc agccagcccg cgctcacgga caccatcacc gggtccgggc    36300
tcgccgcggt gccggtcggc accgaccacc tcatccacga gtaccgggtg cggatggcgg    36360
gcgagccgcg cccgaaccat ccggcgatcg ccttcgacga ggcccgtccc gagccgctgg    36420
actgggacca cgcccctcggc atcgaggcga tcctcgcccc gtacttctat ctgctcgcca    36480
acaacgactc gatggtcgac gacctcgtcg acttcgcccg gtcctggcag ccggacctgg    36540
tgctgtggga ccgacgacc tacgcggcg ccgtcgccgc ccaggtcacc ggtgccgcgc     36600
acgcccgggt cctgtggggg cccgacgtga tgggcagcgc ccgccgcaag ttcgtcgcgc    36660
tgcgggaccg gcagccgccc gagcaccgcg aggacccac cgcggagtgg ctgacgtgga    36720
cgctcgaccg gtacggcgcc tccttcgaag aggagctgct caccggccag ttcacgatcg    36780
acccgacccc gccgagcctg cgcctcgaca cgggcctgcc gaccgtcggg atgcgttatg    36840
ttccgtacaa cggcacgtcg gtcgtgccgg actggctgag tgagccgccc gcgcggcccc    36900
gggtctgcct gaccctcggc gtctccgcgc gtgaggtcct cggcggcgac ggcgtctcgc    36960
agggcgacat cctggaggcg ctcgccgacc tcgacatcga gctcgtcgcc acgctcgacg    37020
cgagtcagcg cgccgagatc cgcaactacc cgaagcacac ccggttcacg gacttcgtgc    37080
cgatgcacgc gctcctgccg agctgctcgg cgatcatcca ccacgcgggg cgggcacct    37140 acgcgaccgc cgtgatcaac gcggtgccgc aggtcatgct cgccgagctg tgggacgcgc    37200
cggtcaaggc gcgggccgtc gccgagcagg gggcggggtt cttcctgccg ccggccgagc    37260
tcacgccgca ggccgtgcgg gacgccgtcg tccgcatcct cgacgacccc tcggtcgcca    37320
ccgccgcgca ccggctgcgc gaggagacct tcggcgaccc caccccggcc gggatcgtcc    37380
ccgagctgga gcggctcgcc gcgcagcacc gccgcccgcc ggccgacgcc cggcactgag    37440
ccgcacccct cgcccaggc ctcacccctg tatctgcgcc gggggacgcc cccggcccac     37500
cctccgaaag accgaaagca ggagcaccgt gtacgaagtc gaccacgccg acgtctacga    37560
```

-continued

```
cctcttctac ctgggtcgcg gcaaggacta cgccgccgag gcctccgaca tcgccgacct   37620
ggtgcgctcc cgtaccccg aggcctcctc gctcctggac gtggcctgcg gtacgggcac    37680
gcatctggag cacttcacca aggagttcgg cgacaccgcc ggcctggagc tgtccgagga   37740
catgctcacc cacgcccgca agcggctgcc cgacgccacg ctccaccagg gcgacatgcg   37800
ggacttccgg ctcggccgga agttctccgc cgtggtcagc atgttcagct ccgtcggcta   37860
cctgaagacg accgaggaac tcggcgcggc cgtcgcctcg ttcgcggagc acctggagcc   37920
cggtggcgtc gtcgtcgtcg agccgtggtg gttcccggag accttcgccg acggctgggt   37980
cagcgccgac gtcgtccgcc gtgacgggcg caccgtggcc cgtgtctcgc actcggtgcg   38040 ggagggaac gcgacgcgca tggaggtcca cttcaccgtg gccgacccgg caagggcgt    38100 gcggcacttc tccgacgtcc atctcatcac cctgttccac caggccgagt acgaggccgc   38160
gttcacggcc gccgggctgc gcgtcgagta cctggagggc ggcccgtcgg gccgtggcct   38220
cttcgtcggc gtccccgcct gagcaccgcc caagaccccc cggggcggga cgtcccgggt   38280
gcaccaagca aagagagaga aacgaaccgt gacaggtaag acccgaatac cgcgtgtccg   38340
ccgcggccgc accacgccca gggccttcac cctggccgtc gtcggcaccc tgctggcggg   38400
caccaccgtg gcggccgccg ctcccggcgc cgccgacacg gccaatgttc agtacacgag   38460
ccgggcggcg gagctcgtcg cccagatgac gctcgacgag aagatc                 38506
```

<210> SEQ ID NO 2
<211> LENGTH: 4551
<212> TYPE: PRT
<213> ORGANISM: Streptomyces venezuelae

<400> SEQUENCE: 2

```
Met Ser Thr Val Ser Lys Ser Glu Ser Glu Glu Phe Val Ser Val Ser
  1               5                  10                  15

Asn Asp Ala Gly Ser Ala His Gly Thr Ala Glu Pro Val Ala Val Val
             20                  25                  30

Gly Ile Ser Cys Arg Val Pro Gly Ala Arg Asp Pro Arg Glu Phe Trp
         35                  40                  45

Glu Leu Leu Ala Ala Gly Gly Gln Ala Val Thr Asp Val Pro Ala Asp
     50                  55                  60

Arg Trp Asn Ala Gly Asp Phe Tyr Asp Pro Asp Arg Ser Ala Pro Gly
 65                  70                  75                  80

Arg Ser Asn Ser Arg Trp Gly Gly Phe Ile Glu Asp Val Asp Arg Phe
                 85                  90                  95

Asp Ala Ala Phe Phe Gly Ile Ser Pro Arg Glu Ala Ala Glu Met Asp
            100                 105                 110

Pro Gln Gln Arg Leu Ala Leu Glu Leu Gly Trp Glu Ala Leu Glu Arg
        115                 120                 125

Ala Gly Ile Asp Pro Ser Ser Leu Thr Gly Thr Arg Thr Gly Val Phe
    130                 135                 140

Ala Gly Ala Ile Trp Asp Asp Tyr Ala Thr Leu Lys His Arg Gln Gly
145                 150                 155                 160

Gly Ala Ala Ile Thr Pro His Thr Val Thr Gly Leu His Arg Gly Ile
                165                 170                 175

Ile Ala Asn Arg Leu Ser Tyr Thr Leu Gly Leu Arg Gly Pro Ser Met
            180                 185                 190

Val Val Asp Ser Gly Gln Ser Ser Leu Val Ala Val His Leu Ala
        195                 200                 205
```

-continued

```
Cys Glu Ser Leu Arg Arg Gly Glu Ser Glu Leu Ala Leu Ala Gly Gly
    210                 215                 220

Val Ser Leu Asn Leu Val Pro Asp Ser Ile Ile Gly Ala Ser Lys Phe
225                 230                 235                 240

Gly Gly Leu Ser Pro Asp Gly Arg Ala Tyr Thr Phe Asp Ala Arg Ala
                245                 250                 255

Asn Gly Tyr Val Arg Gly Glu Gly Gly Phe Val Val Leu Lys Arg
            260                 265                 270

Leu Ser Arg Ala Val Ala Asp Gly Asp Pro Val Leu Ala Val Ile Arg
        275                 280                 285

Gly Ser Ala Val Asn Asn Gly Ala Ala Gln Gly Met Thr Thr Pro
    290                 295                 300

Asp Ala Gln Ala Gln Glu Ala Val Leu Arg Glu Ala His Glu Arg Ala
305                 310                 315                 320

Gly Thr Ala Pro Ala Asp Val Arg Tyr Val Glu Leu His Gly Thr Gly
                325                 330                 335

Thr Pro Val Gly Asp Pro Ile Glu Ala Ala Leu Gly Ala Ala Leu
                340                 345                 350

Gly Thr Gly Arg Pro Ala Gly Gln Pro Leu Leu Val Gly Ser Val Lys
        355                 360                 365

Thr Asn Ile Gly His Leu Glu Gly Ala Ala Gly Ile Ala Gly Leu Ile
    370                 375                 380

Lys Ala Val Leu Ala Val Arg Gly Arg Ala Leu Pro Ala Ser Leu Asn
385                 390                 395                 400

Tyr Glu Thr Pro Asn Pro Ala Ile Pro Phe Glu Glu Leu Asn Leu Arg
                405                 410                 415

Val Asn Thr Glu Tyr Leu Pro Trp Glu Pro Glu His Asp Gly Gln Arg
            420                 425                 430

Met Val Val Gly Val Ser Ser Phe Gly Met Gly Thr Asn Ala His
        435                 440                 445

Val Val Leu Glu Glu Ala Pro Gly Val Val Glu Gly Ala Ser Val Val
450                 455                 460

Glu Ser Thr Val Gly Gly Ser Ala Val Gly Gly Val Val Pro Trp
465                 470                 475                 480

Val Val Ser Ala Lys Ser Ala Ala Leu Asp Ala Gln Ile Glu Arg
                485                 490                 495

Leu Ala Ala Phe Ala Ser Arg Asp Arg Thr Asp Gly Val Asp Ala Gly
                500                 505                 510

Ala Val Asp Ala Gly Ala Val Asp Ala Gly Ala Val Ala Arg Val Leu
        515                 520                 525

Ala Gly Gly Arg Ala Gln Phe Glu His Arg Ala Val Val Gly Ser
    530                 535                 540

Gly Pro Asp Asp Leu Ala Ala Leu Ala Ala Pro Glu Gly Leu Val
545                 550                 555                 560

Arg Gly Val Ala Ser Gly Val Gly Arg Val Ala Phe Val Phe Pro Gly
                565                 570                 575

Gln Gly Thr Gln Trp Ala Gly Met Gly Ala Glu Leu Leu Asp Ser Ser
            580                 585                 590

Ala Val Phe Ala Ala Ala Met Ala Glu Cys Glu Ala Ala Leu Ser Pro
        595                 600                 605

Tyr Val Asp Trp Ser Leu Glu Ala Val Val Arg Gln Ala Pro Gly Ala
    610                 615                 620

Pro Thr Leu Glu Arg Val Asp Val Val Gln Pro Val Thr Phe Ala Val
```

-continued

```
                625                 630                 635                 640
Met Val Ser Leu Ala Arg Val Trp Gln His His Gly Val Thr Pro Gln
                645                 650                 655
Ala Val Val Gly His Ser Gln Gly Glu Ile Ala Ala Tyr Val Ala
                660                 665                 670
Gly Ala Leu Ser Leu Asp Asp Ala Arg Val Val Thr Leu Arg Ser
                675                 680                 685
Lys Ser Ile Ala Ala His Leu Ala Gly Lys Gly Met Leu Ser Leu
    690                 695                 700
Ala Leu Ser Glu Asp Ala Val Leu Glu Arg Leu Ala Gly Phe Asp Gly
705                 710                 715                 720
Leu Ser Val Ala Ala Val Asn Gly Pro Thr Ala Thr Val Val Ser Gly
                725                 730                 735
Asp Pro Val Gln Ile Glu Glu Leu Ala Arg Ala Cys Glu Ala Asp Gly
                740                 745                 750
Val Arg Ala Arg Val Ile Pro Val Asp Tyr Ala Ser His Ser Arg Gln
                755                 760                 765
Val Glu Ile Ile Glu Ser Glu Leu Ala Glu Val Leu Ala Gly Leu Ser
    770                 775                 780
Pro Gln Ala Pro Arg Val Pro Phe Phe Ser Thr Leu Glu Gly Ala Trp
785                 790                 795                 800
Ile Thr Glu Pro Val Leu Asp Gly Gly Tyr Trp Tyr Arg Asn Leu Arg
                805                 810                 815
His Arg Val Gly Phe Ala Pro Ala Val Glu Thr Leu Ala Thr Asp Glu
                820                 825                 830
Gly Phe Thr His Phe Val Glu Val Ser Ala His Pro Val Leu Thr Met
    835                 840                 845
Ala Leu Pro Gly Thr Val Thr Gly Leu Ala Thr Leu Arg Arg Asp Asn
    850                 855                 860
Gly Gly Gln Asp Arg Leu Val Ala Ser Leu Ala Glu Ala Trp Ala Asn
865                 870                 875                 880
Gly Leu Ala Val Asp Trp Ser Pro Leu Leu Pro Ser Ala Thr Gly His
                885                 890                 895
His Ser Asp Leu Pro Thr Tyr Ala Phe Gln Thr Glu Arg His Trp Leu
                900                 905                 910
Gly Glu Ile Glu Ala Leu Ala Pro Ala Gly Glu Pro Ala Val Gln Pro
            915                 920                 925
Ala Val Leu Arg Thr Glu Ala Ala Glu Pro Ala Glu Leu Asp Arg Asp
    930                 935                 940
Glu Gln Leu Arg Val Ile Leu Asp Lys Val Arg Ala Gln Thr Ala Gln
945                 950                 955                 960
Val Leu Gly Tyr Ala Thr Gly Gly Gln Ile Glu Val Asp Arg Thr Phe
                965                 970                 975
Arg Glu Ala Gly Cys Thr Ser Leu Thr Gly Val Asp Leu Arg Asn Arg
                980                 985                 990
Ile Asn Ala Ala Phe Gly Val Arg Met Ala Pro Ser Met Ile Phe Asp
            995                 1000                1005
Phe Pro Thr Pro Glu Ala Leu Ala Glu Gln Leu Leu Leu Val Val His
    1010                1015                1020
Gly Glu Ala Ala Ala Asn Pro Ala Gly Ala Glu Pro Ala Pro Val Ala
1025                1030                1035                1040
Ala Ala Gly Ala Val Asp Glu Pro Val Ala Ile Val Gly Met Ala Cys
                1045                1050                1055
```

-continued

Arg Leu Pro Gly Gly Val Ala Ser Pro Glu Asp Leu Trp Arg Leu Val
        1060                1065                1070

Ala Gly Gly Gly Asp Ala Ile Ser Glu Phe Pro Gln Asp Arg Gly Trp
    1075                1080                1085

Asp Val Glu Gly Leu Tyr His Pro Asp Pro Glu His Pro Gly Thr Ser
    1090                1095                1100

Tyr Val Arg Gln Gly Gly Phe Ile Glu Asn Val Ala Gly Phe Asp Ala
1105                1110                1115                1120

Ala Phe Phe Gly Ile Ser Pro Arg Glu Ala Leu Ala Met Asp Pro Gln
        1125                1130                1135

Gln Arg Leu Leu Leu Glu Thr Ser Trp Glu Ala Val Glu Asp Ala Gly
        1140                1145                1150

Ile Asp Pro Thr Ser Leu Arg Gly Arg Gln Val Gly Val Phe Thr Gly
        1155                1160                1165

Ala Met Thr His Glu Tyr Gly Pro Ser Leu Arg Asp Gly Gly Glu Gly
        1170                1175                1180

Leu Asp Gly Tyr Leu Leu Thr Gly Asn Thr Ala Ser Val Met Ser Gly
1185                1190                1195                1200

Arg Val Ser Tyr Thr Leu Gly Leu Glu Gly Pro Ala Leu Thr Val Asp
        1205                1210                1215

Thr Ala Cys Ser Ser Leu Val Ala Leu His Leu Ala Val Gln Ala
        1220                1225                1230

Leu Arg Lys Gly Glu Val Asp Met Ala Leu Ala Gly Gly Val Ala Val
        1235                1240                1245

Met Pro Thr Pro Gly Met Phe Val Glu Phe Ser Arg Gln Arg Gly Leu
        1250                1255                1260

Ala Gly Asp Gly Arg Ser Lys Ala Phe Ala Ala Ser Ala Asp Gly Thr
1265                1270                1275                1280

Ser Trp Ser Glu Gly Val Gly Val Leu Leu Val Glu Arg Leu Ser Asp
            1285                1290                1295

Ala Arg Arg Asn Gly His Gln Val Leu Ala Val Val Arg Gly Ser Ala
        1300                1305                1310

Val Asn Gln Asp Gly Ala Ser Asn Gly Leu Thr Ala Pro Asn Gly Pro
        1315                1320                1325

Ser Gln Gln Arg Val Ile Arg Arg Ala Leu Ala Asp Ala Arg Leu Thr
        1330                1335                1340

Thr Ser Asp Val Asp Val Val Glu Ala His Gly Thr Gly Thr Arg Leu
1345                1350                1355                1360

Gly Asp Pro Ile Glu Ala Gln Ala Leu Ile Ala Thr Tyr Gly Gln Gly
        1365                1370                1375

Arg Asp Asp Glu Gln Pro Leu Arg Leu Gly Ser Leu Lys Ser Asn Ile
        1380                1385                1390

Gly His Thr Gln Ala Ala Ala Gly Val Ser Gly Val Ile Lys Met Val
        1395                1400                1405

Gln Ala Met Arg His Gly Leu Leu Pro Lys Thr Leu His Val Asp Glu
        1410                1415                1420

Pro Ser Asp Gln Ile Asp Trp Ser Ala Gly Ala Val Glu Leu Leu Thr
1425                1430                1435                1440

Glu Ala Val Asp Trp Pro Glu Lys Gln Asp Gly Gly Leu Arg Arg Ala
            1445                1450                1455

Ala Val Ser Ser Phe Gly Ile Ser Gly Thr Asn Ala His Val Val Leu
        1460                1465                1470

-continued

```
Glu Glu Ala Pro Val Val Glu Gly Ala Ser Val Val Glu Pro Ser
    1475                1480                1485

Val Gly Gly Ser Ala Val Gly Gly Val Thr Pro Trp Val Val Ser
    1490                1495                1500

Ala Lys Ser Ala Ala Ala Leu Asp Ala Gln Ile Glu Arg Leu Ala Ala
1505                1510                1515                1520

Phe Ala Ser Arg Asp Arg Thr Asp Asp Ala Asp Ala Gly Ala Val Asp
        1525                1530                1535

Ala Gly Ala Val Ala His Val Leu Ala Asp Gly Arg Ala Gln Phe Glu
        1540                1545                1550

His Arg Ala Val Ala Leu Gly Ala Gly Ala Asp Asp Leu Val Gln Ala
    1555                1560                1565

Leu Ala Asp Pro Asp Gly Leu Ile Arg Gly Thr Ala Ser Gly Val Gly
    1570                1575                1580

Arg Val Ala Phe Val Phe Pro Gly Gln Gly Thr Gln Trp Ala Gly Met
1585                1590                1595                1600

Gly Ala Glu Leu Leu Asp Ser Ser Ala Val Phe Ala Ala Ala Met Ala
        1605                1610                1615

Glu Cys Glu Ala Ala Leu Ser Pro Tyr Val Asp Trp Ser Leu Glu Ala
        1620                1625                1630

Val Val Arg Gln Ala Pro Gly Ala Pro Thr Leu Glu Arg Val Asp Val
    1635                1640                1645

Val Gln Pro Val Thr Phe Ala Val Met Val Ser Leu Ala Arg Val Trp
    1650                1655                1660

Gln His His Gly Val Thr Pro Gln Ala Val Val Gly His Ser Gln Gly
1665                1670                1675                1680

Glu Ile Ala Ala Ala Tyr Val Ala Gly Ala Leu Pro Leu Asp Asp Ala
        1685                1690                1695

Ala Arg Val Val Thr Leu Arg Ser Lys Ser Ile Ala Ala His Leu Ala
        1700                1705                1710

Gly Lys Gly Gly Met Leu Ser Leu Ala Leu Asn Glu Asp Ala Val Leu
    1715                1720                1725

Glu Arg Leu Ser Asp Phe Asp Gly Leu Ser Val Ala Ala Val Asn Gly
    1730                1735                1740

Pro Thr Ala Thr Val Val Ser Gly Asp Pro Val Gln Ile Glu Glu Leu
1745                1750                1755                1760

Ala Gln Ala Cys Lys Ala Asp Gly Phe Arg Ala Arg Ile Ile Pro Val
        1765                1770                1775

Asp Tyr Ala Ser His Ser Arg Gln Val Glu Ile Ile Glu Ser Glu Leu
        1780                1785                1790

Ala Gln Val Leu Ala Gly Leu Ser Pro Gln Ala Pro Arg Val Pro Phe
    1795                1800                1805

Phe Ser Thr Leu Glu Gly Thr Trp Ile Thr Glu Pro Val Leu Asp Gly
    1810                1815                1820

Thr Tyr Trp Tyr Arg Asn Leu Arg His Arg Val Gly Phe Ala Pro Ala
1825                1830                1835                1840

Ile Glu Thr Leu Ala Val Asp Glu Gly Phe Thr His Phe Val Glu Val
        1845                1850                1855

Ser Ala His Pro Val Leu Thr Met Thr Leu Pro Glu Thr Val Thr Gly
        1860                1865                1870

Leu Gly Thr Leu Arg Arg Glu Gln Gly Gly Gln Glu Arg Leu Val Thr
    1875                1880                1885

Ser Leu Ala Glu Ala Trp Val Asn Gly Leu Pro Val Ala Trp Thr Ser
```

-continued

```
               1890                1895                1900
Leu Leu Pro Ala Thr Ala Ser Arg Pro Gly Leu Pro Thr Tyr Ala Phe
1905                1910                1915                1920

Gln Ala Glu Arg Tyr Trp Leu Glu Asn Thr Pro Ala Ala Leu Ala Thr
               1925                1930                1935

Gly Asp Asp Trp Arg Tyr Arg Ile Asp Trp Lys Arg Leu Pro Ala Ala
               1940                1945                1950

Glu Gly Ser Glu Arg Thr Gly Leu Ser Gly Arg Trp Leu Ala Val Thr
1955                1960                1965

Pro Glu Asp His Ser Ala Gln Ala Ala Ala Val Leu Thr Ala Leu Val
1970                1975                1980

Asp Ala Gly Ala Lys Val Glu Val Leu Thr Ala Gly Ala Asp Asp Asp
1985                1990                1995                2000

Arg Glu Ala Leu Ala Ala Arg Leu Thr Ala Leu Thr Thr Gly Asp Gly
               2005                2010                2015

Phe Thr Gly Val Val Ser Leu Leu Asp Gly Leu Val Pro Gln Val Ala
               2020                2025                2030

Trp Val Gln Ala Leu Gly Asp Ala Gly Ile Lys Ala Pro Leu Trp Ser
               2035                2040                2045

Val Thr Gln Gly Ala Val Ser Val Gly Arg Leu Asp Thr Pro Ala Asp
               2050                2055                2060

Pro Asp Arg Ala Met Leu Trp Gly Leu Gly Arg Val Val Ala Leu Glu
2065                2070                2075                2080

His Pro Glu Arg Trp Ala Gly Leu Val Asp Leu Pro Ala Gln Pro Asp
               2085                2090                2095

Ala Ala Ala Leu Ala His Leu Val Thr Ala Leu Ser Gly Ala Thr Gly
               2100                2105                2110

Glu Asp Gln Ile Ala Ile Arg Thr Thr Gly Leu His Ala Arg Arg Leu
               2115                2120                2125

Ala Arg Ala Pro Leu His Gly Arg Arg Pro Thr Arg Asp Trp Gln Pro
               2130                2135                2140

His Gly Thr Val Leu Ile Thr Gly Gly Thr Gly Ala Leu Gly Ser His
2145                2150                2155                2160

Ala Ala Arg Trp Met Ala His His Gly Ala Glu His Leu Leu Leu Val
               2165                2170                2175

Ser Arg Ser Gly Glu Gln Ala Pro Gly Ala Thr Gln Leu Thr Ala Glu
               2180                2185                2190

Leu Thr Ala Ser Gly Ala Arg Val Thr Ile Ala Ala Cys Asp Val Ala
               2195                2200                2205

Asp Pro His Ala Met Arg Thr Leu Leu Asp Ala Ile Pro Ala Glu Thr
               2210                2215                2220

Pro Leu Thr Ala Val Val His Thr Ala Gly Ala Leu Asp Asp Gly Ile
2225                2230                2235                2240

Val Asp Thr Leu Thr Ala Glu Gln Val Arg Arg Ala His Arg Ala Lys
               2245                2250                2255

Ala Val Gly Ala Ser Val Leu Asp Glu Leu Thr Arg Asp Leu Asp Leu
               2260                2265                2270

Asp Ala Phe Val Leu Phe Ser Ser Val Ser Ser Thr Leu Gly Ile Pro
               2275                2280                2285

Gly Gln Gly Asn Tyr Ala Pro His Asn Ala Tyr Leu Asp Ala Leu Ala
               2290                2295                2300

Ala Arg Arg Arg Ala Thr Gly Arg Ser Ala Val Ser Val Ala Trp Gly
2305                2310                2315                2320
```

```
Pro Trp Asp Gly Gly Met Ala Ala Gly Asp Gly Val Ala Glu Arg
            2325                2330                2335

Leu Arg Asn His Gly Val Pro Gly Met Asp Pro Glu Leu Ala Leu Ala
        2340                2345                2350

Ala Leu Glu Ser Ala Leu Gly Arg Asp Glu Thr Ala Ile Thr Val Ala
            2355                2360                2365

Asp Ile Asp Trp Asp Arg Phe Tyr Leu Ala Tyr Ser Ser Gly Arg Pro
    2370                2375                2380

Gln Pro Leu Val Glu Glu Leu Pro Glu Val Arg Arg Ile Ile Asp Ala
2385                2390                2395                2400

Arg Asp Ser Ala Thr Ser Gly Gln Gly Gly Ser Ser Ala Gln Gly Ala
            2405                2410                2415

Asn Pro Leu Ala Glu Arg Leu Ala Ala Ala Pro Gly Glu Arg Thr
        2420                2425                2430

Glu Ile Leu Leu Gly Leu Val Arg Ala Gln Ala Ala Ala Val Leu Arg
    2435                2440                2445

Met Arg Ser Pro Glu Asp Val Ala Ala Asp Arg Ala Phe Lys Asp Ile
        2450                2455                2460

Gly Phe Asp Ser Leu Ala Gly Val Glu Leu Arg Asn Arg Leu Thr Arg
2465                2470                2475                2480

Ala Thr Gly Leu Gln Leu Pro Ala Thr Leu Val Phe Asp His Pro Thr
            2485                2490                2495

Pro Leu Ala Leu Val Ser Leu Leu Arg Ser Glu Phe Leu Gly Asp Glu
            2500                2505                2510

Glu Thr Ala Asp Ala Arg Arg Ser Ala Ala Leu Pro Ala Thr Val Gly
        2515                2520                2525

Ala Gly Ala Gly Ala Gly Ala Gly Thr Asp Ala Asp Asp Pro Ile
        2530                2535                2540

Ala Ile Val Ala Met Ser Cys Arg Tyr Pro Gly Asp Ile Arg Ser Pro
2545                2550                2555                2560

Glu Asp Leu Trp Arg Met Leu Ser Glu Gly Gly Glu Gly Ile Thr Pro
            2565                2570                2575

Phe Pro Thr Asp Arg Gly Trp Asp Leu Asp Gly Leu Tyr Asp Ala Asp
            2580                2585                2590

Pro Asp Ala Leu Gly Arg Ala Tyr Val Arg Glu Gly Gly Phe Leu His
        2595                2600                2605

Asp Ala Ala Glu Phe Asp Ala Glu Phe Phe Gly Val Ser Pro Arg Glu
    2610                2615                2620

Ala Leu Ala Met Asp Pro Gln Gln Arg Met Leu Leu Thr Thr Ser Trp
2625                2630                2635                2640

Glu Ala Phe Glu Arg Ala Gly Ile Glu Pro Ala Ser Leu Arg Gly Ser
            2645                2650                2655

Ser Thr Gly Val Phe Ile Gly Leu Ser Tyr Gln Asp Tyr Ala Ala Arg
        2660                2665                2670

Val Pro Asn Ala Pro Arg Gly Val Glu Gly Tyr Leu Leu Thr Gly Ser
        2675                2680                2685

Thr Pro Ser Val Ala Ser Gly Arg Ile Ala Tyr Thr Phe Gly Leu Glu
    2690                2695                2700

Gly Pro Ala Thr Thr Val Asp Thr Ala Cys Ser Ser Ser Leu Thr Ala
2705                2710                2715                2720

Leu His Leu Ala Val Arg Ala Leu Arg Ser Gly Glu Cys Thr Met Ala
            2725                2730                2735
```

-continued

```
Leu Ala Gly Gly Val Ala Met Met Ala Thr Pro His Met Phe Val Glu
        2740                2745                2750
Phe Ser Arg Gln Arg Ala Leu Ala Pro Asp Gly Arg Ser Lys Ala Phe
        2755                2760                2765
Ser Ala Asp Ala Asp Gly Phe Gly Ala Ala Glu Gly Val Gly Leu Leu
2770                2775                2780
Leu Val Glu Arg Leu Ser Asp Ala Arg Arg Asn Gly His Pro Val Leu
2785                2790                2795                2800
Ala Val Val Arg Gly Thr Ala Val Asn Gln Asp Gly Ala Ser Asn Gly
        2805                2810                2815
Leu Thr Ala Pro Asn Gly Pro Ser Gln Gln Arg Val Ile Arg Gln Ala
        2820                2825                2830
Leu Ala Asp Ala Arg Leu Ala Pro Gly Asp Ile Asp Ala Val Glu Thr
        2835                2840                2845
His Gly Thr Gly Thr Ser Leu Gly Asp Pro Ile Glu Ala Gln Gly Leu
        2850                2855                2860
Gln Ala Thr Tyr Gly Lys Glu Arg Pro Ala Glu Arg Pro Leu Ala Ile
2865                2870                2875                2880
Gly Ser Val Lys Ser Asn Ile Gly His Thr Gln Ala Ala Gly Ala
        2885                2890                2895
Ala Gly Ile Ile Lys Met Val Leu Ala Met Arg His Gly Thr Leu Pro
        2900                2905                2910
Lys Thr Leu His Ala Asp Glu Pro Ser Pro His Val Asp Trp Ala Asn
        2915                2920                2925
Ser Gly Leu Ala Leu Val Thr Glu Pro Ile Asp Trp Pro Ala Gly Thr
        2930                2935                2940
Gly Pro Arg Arg Ala Ala Val Ser Ser Phe Gly Ile Ser Gly Thr Asn
2945                2950                2955                2960
Ala His Val Val Leu Glu Gln Ala Pro Asp Ala Ala Gly Glu Val Leu
        2965                2970                2975
Gly Ala Asp Glu Val Pro Glu Val Ser Glu Thr Val Ala Met Ala Gly
        2980                2985                2990
Thr Ala Gly Thr Ser Glu Val Ala Glu Gly Ser Glu Ala Ser Glu Ala
        2995                3000                3005
Pro Ala Ala Pro Gly Ser Arg Glu Ala Ser Leu Pro Gly His Leu Pro
        3010                3015                3020
Trp Val Leu Ser Ala Lys Asp Glu Gln Ser Leu Arg Gly Gln Ala Ala
3025                3030                3035                3040
Ala Leu His Ala Trp Leu Ser Glu Pro Ala Ala Asp Leu Ser Asp Ala
        3045                3050                3055
Asp Gly Pro Ala Arg Leu Arg Asp Val Gly Tyr Thr Leu Ala Thr Ser
        3060                3065                3070
Arg Thr Ala Phe Ala His Arg Ala Ala Val Thr Ala Ala Asp Arg Asp
        3075                3080                3085
Gly Phe Leu Asp Gly Leu Ala Thr Leu Ala Gln Gly Gly Thr Ser Ala
        3090                3095                3100
His Val His Leu Asp Thr Ala Arg Asp Gly Thr Thr Ala Phe Leu Phe
3105                3110                3115                3120
Thr Gly Gln Gly Ser Gln Arg Pro Gly Ala Gly Arg Glu Leu Tyr Asp
        3125                3130                3135
Arg His Pro Val Phe Ala Arg Ala Leu Asp Glu Ile Cys Ala His Leu
        3140                3145                3150
Asp Gly His Leu Glu Leu Pro Leu Leu Asp Val Met Phe Ala Ala Glu
```

```
                3155                3160                3165

Gly Ser Ala Glu Ala Ala Leu Leu Asp Glu Thr Arg Tyr Thr Gln Cys
    3170            3175            3180

Ala Leu Phe Ala Leu Glu Val Ala Leu Phe Arg Leu Val Glu Ser Trp
3185            3190            3195            3200

Gly Met Arg Pro Ala Ala Leu Leu Gly His Ser Val Gly Glu Ile Ala
        3205            3210            3215

Ala Ala His Val Ala Gly Val Phe Ser Leu Ala Asp Ala Ala Arg Leu
        3220            3225            3230

Val Ala Ala Arg Gly Arg Leu Met Gln Glu Leu Pro Ala Gly Gly Ala
        3235            3240            3245

Met Leu Ala Val Gln Ala Ala Glu Asp Glu Ile Arg Val Trp Leu Glu
    3250            3255            3260

Thr Glu Glu Arg Tyr Ala Gly Arg Leu Asp Val Ala Ala Val Asn Gly
3265            3270            3275            3280

Pro Glu Ala Ala Val Leu Ser Gly Asp Ala Asp Ala Ala Arg Glu Ala
        3285            3290            3295

Glu Ala Tyr Trp Ser Gly Leu Gly Arg Arg Thr Arg Ala Leu Arg Val
        3300            3305            3310

Ser His Ala Phe His Ser Ala His Met Asp Gly Met Leu Asp Gly Phe
    3315            3320            3325

Arg Ala Val Leu Glu Thr Val Glu Phe Arg Arg Pro Ser Leu Thr Val
        3330            3335            3340

Val Ser Asn Val Thr Gly Leu Ala Ala Gly Pro Asp Asp Leu Cys Asp
3345            3350            3355            3360

Pro Glu Tyr Trp Val Arg His Val Arg Gly Thr Val Arg Phe Leu Asp
        3365            3370            3375

Gly Val Arg Val Leu Arg Asp Leu Gly Val Arg Thr Cys Leu Glu Leu
        3380            3385            3390

Gly Pro Asp Gly Val Leu Thr Ala Met Ala Ala Asp Gly Leu Ala Asp
        3395            3400            3405

Thr Pro Ala Asp Ser Ala Ala Gly Ser Pro Val Gly Ser Pro Ala Gly
    3410            3415            3420

Ser Pro Ala Asp Ser Ala Ala Gly Ala Leu Arg Pro Arg Pro Leu Leu
3425            3430            3435            3440

Val Ala Leu Leu Arg Arg Lys Arg Ser Glu Thr Glu Thr Val Ala Asp
            3445            3450            3455

Ala Leu Gly Arg Ala His Ala His Gly Thr Gly Pro Asp Trp His Ala
        3460            3465            3470

Trp Phe Ala Gly Ser Gly Ala His Arg Val Asp Leu Pro Thr Tyr Ser
        3475            3480            3485

Phe Arg Arg Asp Arg Tyr Trp Leu Asp Ala Pro Ala Ala Asp Thr Ala
    3490            3495            3500

Val Asp Thr Ala Gly Leu Gly Leu Gly Thr Ala Asp His Pro Leu Leu
3505            3510            3515            3520

Gly Ala Val Val Ser Leu Pro Asp Arg Asp Gly Leu Leu Leu Thr Gly
        3525            3530            3535

Arg Leu Ser Leu Arg Thr His Pro Trp Leu Ala Asp His Ala Val Leu
    3540            3545            3550

Gly Ser Val Leu Leu Pro Gly Ala Ala Met Val Glu Leu Ala Ala His
        3555            3560            3565

Ala Ala Glu Ser Ala Gly Leu Arg Asp Val Arg Glu Leu Thr Leu Leu
    3570            3575            3580
```

-continued

```
Glu Pro Leu Val Leu Pro Glu His Gly Gly Val Glu Leu Arg Val Thr
3585                3590                3595                3600

Val Gly Ala Pro Ala Gly Glu Pro Gly Gly Glu Ser Ala Gly Asp Gly
                3605                3610                3615

Ala Arg Pro Val Ser Leu His Ser Arg Leu Ala Asp Ala Pro Ala Gly
            3620                3625                3630

Thr Ala Trp Ser Cys His Ala Thr Gly Leu Leu Ala Thr Asp Arg Pro
            3635                3640                3645

Glu Leu Pro Val Ala Pro Asp Arg Ala Ala Met Trp Pro Pro Gln Gly
        3650                3655                3660

Ala Glu Glu Val Pro Leu Asp Gly Leu Tyr Glu Arg Leu Asp Gly Asn
3665                3670                3675                3680

Gly Leu Ala Phe Gly Pro Leu Phe Gln Gly Leu Asn Ala Val Trp Arg
            3685                3690                3695

Tyr Glu Gly Glu Val Phe Ala Asp Ile Ala Leu Pro Ala Thr Thr Asn
                3700                3705                3710

Ala Thr Ala Pro Ala Thr Ala Asn Gly Gly Ser Ala Ala Ala Ala
            3715                3720                3725

Pro Tyr Gly Ile His Pro Ala Leu Leu Asp Ala Ser Leu His Ala Ile
    3730                3735                3740

Ala Val Gly Gly Leu Val Asp Glu Pro Glu Leu Val Arg Val Pro Phe
3745                3750                3755                3760

His Trp Ser Gly Val Thr Val His Ala Ala Gly Ala Ala Ala Ala Arg
            3765                3770                3775

Val Arg Leu Ala Ser Ala Gly Thr Asp Ala Val Ser Leu Ser Leu Thr
        3780                3785                3790

Asp Gly Glu Gly Arg Pro Leu Val Ser Val Glu Arg Leu Thr Leu Arg
        3795                3800                3805

Pro Val Thr Ala Asp Gln Ala Ala Ser Arg Val Gly Gly Leu Met
    3810                3815                3820

His Arg Val Ala Trp Arg Pro Tyr Ala Leu Ala Ser Ser Gly Glu Gln
3825                3830                3835                3840

Asp Pro His Ala Thr Ser Tyr Gly Pro Thr Ala Val Leu Gly Lys Asp
            3845                3850                3855

Glu Leu Lys Val Ala Ala Ala Leu Glu Ser Ala Gly Val Glu Val Gly
        3860                3865                3870

Leu Tyr Pro Asp Leu Ala Ala Leu Ser Gln Asp Val Ala Ala Gly Ala
            3875                3880                3885

Pro Ala Pro Arg Thr Val Leu Ala Pro Leu Pro Ala Gly Pro Ala Asp
        3890                3895                3900

Gly Gly Ala Glu Gly Val Arg Gly Thr Val Ala Arg Thr Leu Glu Leu
3905                3910                3915                3920

Leu Gln Ala Trp Leu Ala Asp Glu His Leu Ala Gly Thr Arg Leu Leu
            3925                3930                3935

Leu Val Thr Arg Gly Ala Val Arg Asp Pro Glu Gly Ser Gly Ala Asp
                3940                3945                3950

Asp Gly Gly Glu Asp Leu Ser His Ala Ala Ala Trp Gly Leu Val Arg
        3955                3960                3965

Thr Ala Gln Thr Glu Asn Pro Gly Arg Phe Gly Leu Leu Asp Leu Ala
    3970                3975                3980

Asp Asp Ala Ser Ser Tyr Arg Thr Leu Pro Ser Val Leu Ser Asp Ala
3985                3990                3995                4000
```

-continued

```
Gly Leu Arg Asp Glu Pro Gln Leu Ala Leu His Asp Gly Thr Ile Arg
            4005                4010                4015

Leu Ala Arg Leu Ala Ser Val Arg Pro Glu Thr Gly Thr Ala Ala Pro
        4020                4025                4030

Ala Leu Ala Pro Glu Gly Thr Val Leu Thr Gly Gly Thr Gly Gly
        4035                4040                4045

Leu Gly Gly Leu Val Ala Arg His Val Val Gly Glu Trp Gly Val Arg
    4050                4055                4060

Arg Leu Leu Leu Val Ser Arg Gly Thr Asp Ala Pro Gly Ala Asp
4065                4070                4075                4080

Glu Leu Val His Glu Leu Glu Ala Leu Gly Ala Asp Val Ser Val Ala
            4085                4090                4095

Ala Cys Asp Val Ala Asp Arg Glu Ala Leu Thr Ala Val Leu Asp Ala
            4100                4105                4110

Ile Pro Ala Glu His Pro Leu Thr Ala Val Val His Thr Ala Gly Val
        4115                4120                4125

Leu Ser Asp Gly Thr Leu Pro Ser Met Thr Thr Glu Asp Val Glu His
    4130                4135                4140

Val Leu Arg Pro Lys Val Asp Ala Ala Phe Leu Leu Asp Glu Leu Thr
4145                4150                4155                4160

Ser Thr Pro Ala Tyr Asp Leu Ala Ala Phe Val Met Phe Ser Ser Ala
            4165                4170                4175

Ala Ala Val Phe Gly Gly Ala Gly Gln Gly Ala Tyr Ala Ala Ala Asn
            4180                4185                4190

Ala Thr Leu Asp Ala Leu Ala Trp Arg Arg Arg Ala Ala Gly Leu Pro
        4195                4200                4205

Ala Leu Ser Leu Gly Trp Gly Leu Trp Ala Glu Thr Ser Gly Met Thr
4210                4215                4220

Gly Glu Leu Gly Gln Ala Asp Leu Arg Arg Met Ser Arg Ala Gly Ile
4225                4230                4235                4240

Gly Gly Ile Ser Asp Ala Glu Gly Ile Ala Leu Leu Asp Ala Ala Leu
        4245                4250                4255

Arg Asp Asp Arg His Pro Val Leu Leu Pro Leu Arg Leu Asp Ala Ala
            4260                4265                4270

Gly Leu Arg Asp Ala Ala Gly Asn Asp Pro Ala Gly Ile Pro Ala Leu
        4275                4280                4285

Phe Arg Asp Val Val Gly Ala Arg Thr Val Arg Ala Arg Pro Ser Ala
    4290                4295                4300

Ala Ser Ala Ser Thr Thr Ala Gly Thr Ala Gly Thr Pro Gly Thr Ala
4305                4310                4315                4320

Asp Gly Ala Ala Glu Thr Ala Ala Val Thr Leu Ala Asp Arg Ala Ala
            4325                4330                4335

Thr Val Asp Gly Pro Ala Arg Gln Arg Leu Leu Leu Glu Phe Val Val
        4340                4345                4350

Gly Glu Val Ala Glu Val Leu Gly His Ala Arg Gly His Arg Ile Asp
        4355                4360                4365

Ala Glu Arg Gly Phe Leu Asp Leu Gly Phe Asp Ser Leu Thr Ala Val
    4370                4375                4380

Glu Leu Arg Asn Arg Leu Asn Ser Ala Gly Gly Leu Ala Leu Pro Ala
4385                4390                4395                4400

Thr Leu Val Phe Asp His Pro Ser Pro Ala Ala Leu Ala Ser His Leu
            4405                4410                4415

Asp Ala Glu Leu Pro Arg Gly Ala Ser Asp Gln Asp Gly Ala Gly Asn
```

```
                    4420                4425                4430
     Arg Asn Gly Asn Glu Asn Gly Thr Thr Ala Ser Arg Ser Thr Ala Glu
             4435                4440                4445

Thr Asp Ala Leu Leu Ala Gln Leu Thr Arg Leu Glu Gly Ala Leu Val
         4450                4455                4460

Leu Thr Gly Leu Ser Asp Ala Pro Gly Ser Glu Glu Val Leu Glu His
 4465                4470                4475                4480

Leu Arg Ser Leu Arg Ser Met Val Thr Gly Glu Thr Gly Thr Gly Thr
                 4485                4490                4495

Ala Ser Gly Ala Pro Asp Gly Ala Gly Ser Gly Ala Glu Asp Arg Pro
             4500                4505                4510

Trp Ala Ala Gly Asp Gly Ala Gly Gly Gly Ser Glu Asp Gly Ala Gly
             4515                4520                4525

Val Pro Asp Phe Met Asn Ala Ser Ala Glu Glu Leu Phe Gly Leu Leu
         4530                4535                4540

Asp Gln Asp Pro Ser Thr Asp
 4545                4550

<210> SEQ ID NO 3
<211> LENGTH: 3739
<212> TYPE: PRT
<213> ORGANISM: Streptomyces venezuelae

<400> SEQUENCE: 3

Val Ser Thr Val Asn Glu Glu Lys Tyr Leu Asp Tyr Leu Arg Arg Ala
  1                   5                  10                  15

Thr Ala Asp Leu His Glu Ala Arg Gly Arg Leu Arg Glu Leu Glu Ala
                 20                  25                  30

Lys Ala Gly Glu Pro Val Ala Ile Val Gly Met Ala Cys Arg Leu Pro
             35                  40                  45

Gly Gly Val Ala Ser Pro Glu Asp Leu Trp Arg Leu Val Ala Gly Gly
         50                  55                  60

Glu Asp Ala Ile Ser Glu Phe Pro Gln Asp Arg Gly Trp Asp Val Glu
  65                  70                  75                  80

Gly Leu Tyr Asp Pro Asn Pro Glu Ala Thr Gly Lys Ser Tyr Ala Arg
                 85                  90                  95

Glu Ala Gly Phe Leu Tyr Glu Ala Gly Glu Phe Asp Ala Asp Phe Phe
             100                 105                 110

Gly Ile Ser Pro Arg Glu Ala Leu Ala Met Asp Pro Gln Gln Arg Leu
         115                 120                 125

Leu Leu Glu Ala Ser Trp Glu Ala Phe Glu His Ala Gly Ile Pro Ala
     130                 135                 140

Ala Thr Ala Arg Gly Thr Ser Val Gly Val Phe Thr Gly Val Met Tyr
 145                 150                 155                 160

His Asp Tyr Ala Thr Arg Leu Thr Asp Val Pro Glu Gly Ile Glu Gly
                 165                 170                 175

Tyr Leu Gly Thr Gly Asn Ser Gly Ser Val Ala Ser Gly Arg Val Ala
             180                 185                 190

Tyr Thr Leu Gly Leu Glu Gly Pro Ala Val Thr Val Asp Thr Ala Cys
         195                 200                 205

Ser Ser Ser Leu Val Ala Leu His Leu Ala Val Gln Ala Leu Arg Lys
     210                 215                 220

Gly Glu Val Asp Met Ala Leu Ala Gly Gly Val Thr Val Met Ser Thr
 225                 230                 235                 240
```

-continued

```
Pro Ser Thr Phe Val Glu Phe Ser Arg Gln Arg Gly Leu Ala Pro Asp
            245                 250                 255

Gly Arg Ser Lys Ser Phe Ser Ser Thr Ala Asp Gly Thr Ser Trp Ser
            260                 265                 270

Glu Gly Val Gly Val Leu Leu Val Glu Arg Leu Ser Asp Ala Arg Arg
            275                 280                 285

Lys Gly His Arg Ile Leu Ala Val Val Arg Gly Thr Ala Val Asn Gln
290                 295                 300

Asp Gly Ala Ser Ser Gly Leu Thr Ala Pro Asn Gly Pro Ser Gln Gln
305                 310                 315                 320

Arg Val Ile Arg Arg Ala Leu Ala Asp Ala Arg Leu Thr Thr Ser Asp
                325                 330                 335

Val Asp Val Val Glu Ala His Gly Thr Gly Thr Arg Leu Gly Asp Pro
                340                 345                 350

Ile Glu Ala Gln Ala Val Ile Ala Thr Tyr Gly Gln Gly Arg Asp Gly
            355                 360                 365

Glu Gln Pro Leu Arg Leu Gly Ser Leu Lys Ser Asn Ile Gly His Thr
370                 375                 380

Gln Ala Ala Ala Gly Val Ser Gly Val Ile Lys Met Val Gln Ala Met
385                 390                 395                 400

Arg His Gly Val Leu Pro Lys Thr Leu His Val Glu Lys Pro Thr Asp
                405                 410                 415

Gln Val Asp Trp Ser Ala Gly Ala Val Glu Leu Leu Thr Glu Ala Met
                420                 425                 430

Asp Trp Pro Asp Lys Gly Asp Gly Gly Leu Arg Arg Ala Ala Val Ser
            435                 440                 445

Ser Phe Gly Val Ser Gly Thr Asn Ala His Val Val Leu Glu Glu Ala
            450                 455                 460

Pro Ala Glu Glu Thr Pro Ala Ser Glu Ala Thr Pro Ala Val Glu
465                 470                 475                 480

Pro Ser Val Gly Ala Gly Leu Val Pro Trp Leu Val Ser Ala Lys Thr
                485                 490                 495

Pro Ala Ala Leu Asp Ala Gln Ile Gly Arg Leu Ala Ala Phe Ala Ser
                500                 505                 510

Gln Gly Arg Thr Asp Ala Ala Asp Pro Gly Ala Val Ala Arg Val Leu
            515                 520                 525

Ala Gly Gly Arg Ala Glu Phe Glu His Arg Ala Val Val Leu Gly Thr
530                 535                 540

Gly Gln Asp Asp Phe Ala Gln Ala Leu Thr Ala Pro Glu Gly Leu Ile
545                 550                 555                 560

Arg Gly Thr Pro Ser Asp Val Gly Arg Val Ala Phe Val Phe Pro Gly
                565                 570                 575

Gln Gly Thr Gln Trp Ala Gly Met Gly Ala Glu Leu Leu Asp Val Ser
                580                 585                 590

Lys Glu Phe Ala Ala Ala Met Ala Glu Cys Glu Ser Ala Leu Ser Arg
            595                 600                 605

Tyr Val Asp Trp Ser Leu Glu Ala Val Val Arg Gln Ala Pro Gly Ala
            610                 615                 620

Pro Thr Leu Glu Arg Val Asp Val Val Gln Pro Val Thr Phe Ala Val
625                 630                 635                 640

Met Val Ser Leu Ala Lys Val Trp Gln His His Gly Val Thr Pro Gln
                645                 650                 655

Ala Val Val Gly His Ser Gln Gly Glu Ile Ala Ala Ala Tyr Val Ala
```

-continued

```
              660                 665                 670
Gly Ala Leu Thr Leu Asp Asp Ala Ala Arg Val Val Thr Leu Arg Ser
                675                 680                 685
Lys Ser Ile Ala Ala His Leu Ala Gly Lys Gly Met Ile Ser Leu
    690                 695                 700
Ala Leu Ser Glu Glu Ala Thr Arg Gln Arg Ile Glu Asn Leu His Gly
705                 710                 715                 720
Leu Ser Ile Ala Ala Val Asn Gly Pro Thr Ala Thr Val Ser Gly
                725                 730                 735
Asp Pro Thr Gln Ile Gln Glu Leu Ala Gln Ala Cys Glu Ala Asp Gly
                740                 745                 750
Val Arg Ala Arg Ile Ile Pro Val Asp Tyr Ala Ser His Ser Ala His
                755                 760                 765
Val Glu Thr Ile Glu Ser Glu Leu Ala Glu Val Leu Ala Gly Leu Ser
    770                 775                 780
Pro Arg Thr Pro Glu Val Pro Phe Phe Ser Thr Leu Glu Gly Ala Trp
785                 790                 795                 800
Ile Thr Glu Pro Val Leu Asp Gly Thr Tyr Trp Tyr Arg Asn Leu Arg
                805                 810                 815
His Arg Val Gly Phe Ala Pro Ala Val Glu Thr Leu Ala Thr Asp Glu
                820                 825                 830
Gly Phe Thr His Phe Ile Glu Val Ser Ala His Pro Val Leu Thr Met
                835                 840                 845
Thr Leu Pro Glu Thr Val Thr Gly Leu Gly Thr Leu Arg Arg Glu Gln
    850                 855                 860
Gly Gly Gln Glu Arg Leu Val Thr Ser Leu Ala Glu Ala Trp Thr Asn
865                 870                 875                 880
Gly Leu Thr Ile Asp Trp Ala Pro Val Leu Pro Thr Ala Thr Gly His
                885                 890                 895
His Pro Glu Leu Pro Thr Tyr Ala Phe Gln Arg Arg His Tyr Trp Leu
                900                 905                 910
His Asp Ser Pro Ala Val Gln Gly Ser Val Gln Asp Ser Trp Arg Tyr
    915                 920                 925
Arg Ile Asp Trp Lys Arg Leu Ala Val Ala Asp Ala Ser Glu Arg Ala
    930                 935                 940
Gly Leu Ser Gly Arg Trp Leu Val Val Pro Glu Asp Arg Ser Ala
945                 950                 955                 960
Glu Ala Ala Pro Val Leu Ala Ala Leu Ser Gly Ala Gly Ala Asp Pro
                965                 970                 975
Val Gln Leu Asp Val Ser Pro Leu Gly Asp Arg Gln Arg Leu Ala Ala
                980                 985                 990
Thr Leu Gly Glu Ala Leu Ala Ala Gly Gly Ala Val Asp Gly Val
    995                 1000                1005
Leu Ser Leu Leu Ala Trp Asp Glu Ser Ala His Pro Gly His Pro Ala
    1010                1015                1020
Pro Phe Thr Arg Gly Thr Gly Ala Thr Leu Thr Leu Val Gln Ala Leu
1025                1030                1035                1040
Glu Asp Ala Gly Val Ala Ala Pro Leu Trp Cys Val Thr His Gly Ala
                1045                1050                1055
Val Ser Val Gly Arg Ala Asp His Val Thr Ser Pro Ala Gln Ala Met
            1060                1065                1070
Val Trp Gly Met Gly Arg Val Ala Ala Leu Glu His Pro Glu Arg Trp
        1075                1080                1085
```

-continued

```
Gly Gly Leu Ile Asp Leu Pro Ser Asp Ala Asp Arg Ala Ala Leu Asp
    1090                1095                1100

Arg Met Thr Thr Val Leu Ala Gly Gly Thr Gly Glu Asp Gln Val Ala
1105                1110                1115                1120

Val Arg Ala Ser Gly Leu Leu Ala Arg Arg Leu Val Arg Ala Ser Leu
            1125                1130                1135

Pro Ala His Gly Thr Ala Ser Pro Trp Trp Gln Ala Asp Gly Thr Val
                1140                1145                1150

Leu Val Thr Gly Ala Glu Glu Pro Ala Ala Glu Ala Ala Arg Arg
        1155                1160                1165

Leu Ala Arg Asp Gly Ala Gly His Leu Leu His Thr Thr Pro Ser
    1170                1175                1180

Gly Ser Glu Gly Ala Glu Gly Thr Ser Gly Ala Ala Glu Asp Ser Gly
1185                1190                1195                1200

Leu Ala Gly Leu Val Ala Glu Leu Ala Asp Leu Gly Ala Thr Ala Thr
            1205                1210                1215

Val Val Thr Cys Asp Leu Thr Asp Ala Glu Ala Ala Ala Arg Leu Leu
            1220                1225                1230

Ala Gly Val Ser Asp Ala His Pro Leu Ser Ala Val Leu His Leu Pro
        1235                1240                1245

Pro Thr Val Asp Ser Glu Pro Leu Ala Ala Thr Asp Ala Asp Ala Leu
1250                1255                1260

Ala Arg Val Val Thr Ala Lys Ala Thr Ala Ala Leu His Leu Asp Arg
1265                1270                1275                1280

Leu Leu Arg Glu Ala Ala Ala Ala Gly Gly Arg Pro Pro Val Leu Val
            1285                1290                1295

Leu Phe Ser Ser Val Ala Ala Ile Trp Gly Gly Ala Gly Gln Gly Ala
            1300                1305                1310

Tyr Ala Ala Gly Thr Ala Phe Leu Asp Ala Leu Ala Gly Gln His Arg
        1315                1320                1325

Ala Asp Gly Pro Thr Val Thr Ser Val Ala Trp Ser Pro Trp Glu Gly
    1330                1335                1340

Ser Arg Val Thr Glu Gly Ala Thr Gly Glu Arg Leu Arg Arg Leu Gly
1345                1350                1355                1360

Leu Arg Pro Leu Ala Pro Ala Thr Ala Leu Thr Ala Leu Asp Thr Ala
            1365                1370                1375

Leu Gly His Gly Asp Thr Ala Val Thr Ile Ala Asp Val Asp Trp Ser
            1380                1385                1390

Ser Phe Ala Pro Gly Phe Thr Thr Ala Arg Pro Gly Thr Leu Leu Ala
        1395                1400                1405

Asp Leu Pro Glu Ala Arg Arg Ala Leu Asp Glu Gln Gln Ser Thr Thr
    1410                1415                1420

Ala Ala Asp Asp Thr Val Leu Ser Arg Glu Leu Gly Ala Leu Thr Gly
1425                1430                1435                1440

Ala Glu Gln Gln Arg Arg Met Gln Glu Leu Val Arg Glu His Leu Ala
            1445                1450                1455

Val Val Leu Asn His Pro Ser Pro Glu Ala Val Asp Thr Gly Arg Ala
            1460                1465                1470

Phe Arg Asp Leu Gly Phe Asp Ser Leu Thr Ala Val Glu Leu Arg Asn
        1475                1480                1485

Arg Leu Lys Asn Ala Thr Gly Leu Ala Leu Pro Ala Thr Leu Val Phe
    1490                1495                1500
```

-continued

```
Asp Tyr Pro Thr Pro Arg Thr Leu Ala Glu Phe Leu Ala Glu Ile
1505                1510                1515                1520

Leu Gly Glu Gln Ala Gly Ala Gly Glu Gln Leu Pro Val Asp Gly Gly
            1525                1530                1535

Val Asp Asp Glu Pro Val Ala Ile Val Gly Met Ala Cys Arg Leu Pro
        1540                1545                1550

Gly Gly Val Ala Ser Pro Glu Asp Leu Trp Arg Leu Val Ala Gly Gly
    1555                1560                1565

Glu Asp Ala Ile Ser Gly Phe Pro Gln Asp Arg Gly Trp Asp Val Glu
1570                1575                1580

Gly Leu Tyr Asp Pro Asp Pro Asp Ala Ser Gly Arg Thr Tyr Cys Arg
1585                1590                1595                1600

Ala Gly Gly Phe Leu Asp Glu Ala Gly Glu Phe Asp Ala Asp Phe Phe
            1605                1610                1615

Gly Ile Ser Pro Arg Glu Ala Leu Ala Met Asp Pro Gln Gln Arg Leu
        1620                1625                1630

Leu Leu Glu Thr Ser Trp Glu Ala Val Glu Asp Ala Gly Ile Asp Pro
    1635                1640                1645

Thr Ser Leu Gln Gly Gln Gln Val Gly Val Phe Ala Gly Thr Asn Gly
1650                1655                1660

Pro His Tyr Glu Pro Leu Leu Arg Asn Thr Ala Glu Asp Leu Glu Gly
1665                1670                1675                1680

Tyr Val Gly Thr Gly Asn Ala Ala Ser Ile Met Ser Gly Arg Val Ser
            1685                1690                1695

Tyr Thr Leu Gly Leu Glu Gly Pro Ala Val Thr Val Asp Thr Ala Cys
        1700                1705                1710

Ser Ser Ser Leu Val Ala Leu His Leu Ala Val Gln Ala Leu Arg Lys
    1715                1720                1725

Gly Glu Cys Gly Leu Ala Leu Ala Gly Gly Val Thr Val Met Ser Thr
1730                1735                1740

Pro Thr Thr Phe Val Glu Phe Ser Arg Gln Arg Gly Leu Ala Glu Asp
1745                1750                1755                1760

Gly Arg Ser Lys Ala Phe Ala Ala Ser Ala Asp Gly Phe Gly Pro Ala
            1765                1770                1775

Glu Gly Val Gly Met Leu Leu Val Glu Arg Leu Ser Asp Ala Arg Arg
        1780                1785                1790

Asn Gly His Arg Val Leu Ala Val Val Arg Gly Ser Ala Val Asn Gln
    1795                1800                1805

Asp Gly Ala Ser Asn Gly Leu Thr Ala Pro Asn Gly Pro Ser Gln Gln
1810                1815                1820

Arg Val Ile Arg Arg Ala Leu Ala Asp Ala Arg Leu Thr Thr Ala Asp
1825                1830                1835                1840

Val Asp Val Val Glu Ala His Gly Thr Gly Thr Arg Leu Gly Asp Pro
            1845                1850                1855

Ile Glu Ala Gln Ala Leu Ile Ala Thr Tyr Gly Gln Gly Arg Asp Thr
        1860                1865                1870

Glu Gln Pro Leu Arg Leu Gly Ser Leu Lys Ser Asn Ile Gly His Thr
    1875                1880                1885

Gln Ala Ala Ala Gly Val Ser Gly Ile Ile Lys Met Val Gln Ala Met
1890                1895                1900

Arg His Gly Val Leu Pro Lys Thr Leu His Val Asp Arg Pro Ser Asp
1905                1910                1915                1920

Gln Ile Asp Trp Ser Ala Gly Thr Val Glu Leu Leu Thr Glu Ala Met
```

-continued

```
                1925                1930                1935
Asp Trp Pro Arg Lys Gln Glu Gly Gly Leu Arg Arg Ala Ala Val Ser
            1940                1945                1950

Ser Phe Gly Ile Ser Gly Thr Asn Ala His Ile Val Leu Glu Glu Ala
            1955                1960                1965

Pro Val Asp Glu Asp Ala Pro Ala Asp Glu Pro Ser Val Gly Gly Val
            1970                1975                1980

Val Pro Trp Leu Val Ser Ala Lys Thr Pro Ala Ala Leu Asp Ala Gln
1985                1990                1995                2000

Ile Gly Arg Leu Ala Ala Phe Ala Ser Gln Gly Arg Thr Asp Ala Ala
            2005                2010                2015

Asp Pro Gly Ala Val Ala Arg Val Leu Ala Gly Arg Ala Gln Phe
            2020                2025                2030

Glu His Arg Ala Val Ala Leu Gly Thr Gly Gln Asp Asp Leu Ala Ala
            2035                2040                2045

Ala Leu Ala Ala Pro Glu Gly Leu Val Arg Gly Val Ala Ser Gly Val
            2050                2055                2060

Gly Arg Val Ala Phe Val Phe Pro Gly Gln Gly Thr Gln Trp Ala Gly
2065                2070                2075                2080

Met Gly Ala Glu Leu Leu Asp Val Ser Lys Glu Phe Ala Ala Ala Met
            2085                2090                2095

Ala Glu Cys Glu Ala Ala Leu Ala Pro Tyr Val Asp Trp Ser Leu Glu
            2100                2105                2110

Ala Val Val Arg Gln Ala Pro Gly Ala Pro Thr Leu Glu Arg Val Asp
            2115                2120                2125

Val Val Gln Pro Val Thr Phe Ala Val Met Val Ser Leu Ala Lys Val
            2130                2135                2140

Trp Gln His His Gly Val Thr Pro Gln Ala Val Val Gly His Ser Gln
2145                2150                2155                2160

Gly Glu Ile Ala Ala Ala Tyr Val Ala Gly Ala Leu Ser Leu Asp Asp
            2165                2170                2175

Ala Ala Arg Val Val Thr Leu Arg Ser Lys Ser Ile Gly Ala His Leu
            2180                2185                2190

Ala Gly Gln Gly Gly Met Leu Ser Leu Ala Leu Ser Glu Ala Ala Val
            2195                2200                2205

Val Glu Arg Leu Ala Gly Phe Asp Gly Leu Ser Val Ala Ala Val Asn
            2210                2215                2220

Gly Pro Thr Ala Thr Val Val Ser Gly Asp Pro Thr Gln Ile Gln Glu
2225                2230                2235                2240

Leu Ala Gln Ala Cys Glu Ala Asp Gly Val Arg Ala Arg Ile Ile Pro
            2245                2250                2255

Val Asp Tyr Ala Ser His Ser Ala His Val Glu Thr Ile Glu Ser Glu
            2260                2265                2270

Leu Ala Asp Val Leu Ala Gly Leu Ser Pro Gln Thr Pro Gln Val Pro
            2275                2280                2285

Phe Phe Ser Thr Leu Glu Gly Ala Trp Ile Thr Glu Pro Ala Leu Asp
            2290                2295                2300

Gly Gly Tyr Trp Tyr Arg Asn Leu Arg His Arg Val Gly Phe Ala Pro
2305                2310                2315                2320

Ala Val Glu Thr Leu Ala Thr Asp Glu Gly Phe Thr His Phe Val Glu
            2325                2330                2335

Val Ser Ala His Pro Val Leu Thr Met Ala Leu Pro Glu Thr Val Thr
            2340                2345                2350
```

-continued

```
Gly Leu Gly Thr Leu Arg Arg Asp Asn Gly Gly Gln His Arg Leu Thr
        2355                2360                2365
Thr Ser Leu Ala Glu Ala Trp Ala Asn Gly Leu Thr Val Asp Trp Ala
    2370                2375                2380
Ser Leu Leu Pro Thr Thr Thr Thr His Pro Asp Leu Pro Thr Tyr Ala
2385                2390                2395                2400
Phe Gln Thr Glu Arg Tyr Trp Pro Gln Pro Asp Leu Ser Ala Ala Gly
            2405                2410                2415
Asp Ile Thr Ser Ala Gly Leu Gly Ala Ala Glu His Pro Leu Leu Gly
        2420                2425                2430
Ala Ala Val Ala Leu Ala Asp Ser Asp Gly Cys Leu Leu Thr Gly Ser
        2435                2440                2445
Leu Ser Leu Arg Thr His Pro Trp Leu Ala Asp His Ala Val Ala Gly
        2450                2455                2460
Thr Val Leu Leu Pro Gly Thr Ala Phe Val Glu Leu Ala Phe Arg Ala
2465                2470                2475                2480
Gly Asp Gln Val Gly Cys Asp Leu Val Glu Glu Leu Thr Leu Asp Ala
            2485                2490                2495
Pro Leu Val Leu Pro Arg Arg Gly Ala Val Arg Val Gln Leu Ser Val
            2500                2505                2510
Gly Ala Ser Asp Glu Ser Gly Arg Arg Thr Phe Gly Leu Tyr Ala His
        2515                2520                2525
Pro Glu Asp Ala Pro Gly Glu Ala Glu Trp Thr Arg His Ala Thr Gly
        2530                2535                2540
Val Leu Ala Ala Arg Ala Asp Arg Thr Ala Pro Val Ala Asp Pro Glu
2545                2550                2555                2560
Ala Trp Pro Pro Pro Gly Ala Glu Pro Val Asp Val Asp Gly Leu Tyr
            2565                2570                2575
Glu Arg Phe Ala Ala Asn Gly Tyr Gly Tyr Gly Pro Leu Phe Gln Gly
        2580                2585                2590
Val Arg Gly Val Trp Arg Arg Gly Asp Glu Val Phe Ala Asp Val Ala
        2595                2600                2605
Leu Pro Ala Glu Val Ala Gly Ala Glu Gly Ala Arg Phe Gly Leu His
    2610                2615                2620
Pro Ala Leu Leu Asp Ala Ala Val Gln Ala Ala Gly Ala Gly Gly Ala
2625                2630                2635                2640
Phe Gly Ala Gly Thr Arg Leu Pro Phe Ala Trp Ser Gly Ile Ser Leu
            2645                2650                2655
Tyr Ala Val Gly Ala Thr Ala Leu Arg Val Arg Leu Ala Pro Ala Gly
        2660                2665                2670
Pro Asp Thr Val Ser Val Ser Ala Ala Asp Ser Ser Gly Gln Pro Val
        2675                2680                2685
Phe Ala Ala Asp Ser Leu Thr Val Leu Pro Val Asp Pro Ala Gln Leu
    2690                2695                2700
Ala Ala Phe Ser Asp Pro Thr Leu Asp Ala Leu His Leu Leu Glu Trp
2705                2710                2715                2720
Thr Ala Trp Asp Gly Ala Ala Gln Ala Leu Pro Gly Ala Val Val Leu
            2725                2730                2735
Gly Gly Asp Ala Asp Gly Leu Ala Ala Ala Leu Arg Ala Gly Gly Thr
        2740                2745                2750
Glu Val Leu Ser Phe Pro Asp Leu Thr Asp Leu Val Glu Ala Val Asp
        2755                2760                2765
```

-continued

```
Arg Gly Glu Thr Pro Ala Pro Ala Thr Val Leu Val Ala Cys Pro Ala
    2770            2775            2780

Ala Gly Pro Gly Gly Pro Glu His Val Arg Glu Ala Leu His Gly Ser
2785            2790            2795            2800

Leu Ala Leu Met Gln Ala Trp Leu Ala Asp Glu Arg Phe Thr Asp Gly
        2805            2810            2815

Arg Leu Val Leu Val Thr Arg Asp Ala Val Ala Ala Arg Ser Gly Asp
        2820            2825            2830

Gly Leu Arg Ser Thr Gly Gln Ala Ala Val Trp Gly Leu Gly Arg Ser
    2835            2840            2845

Ala Gln Thr Glu Ser Pro Gly Arg Phe Val Leu Leu Asp Leu Ala Gly
    2850            2855            2860

Glu Ala Arg Thr Ala Gly Asp Ala Thr Ala Gly Asp Gly Leu Thr Thr
2865            2870            2875            2880

Gly Asp Ala Thr Val Gly Gly Thr Ser Gly Asp Ala Ala Leu Gly Ser
        2885            2890            2895

Ala Leu Ala Thr Ala Leu Gly Ser Gly Glu Pro Gln Leu Ala Leu Arg
        2900            2905            2910

Asp Gly Ala Leu Leu Val Pro Arg Leu Ala Arg Ala Ala Ala Pro Ala
        2915            2920            2925

Ala Ala Asp Gly Leu Ala Ala Ala Asp Gly Leu Ala Ala Leu Pro Leu
    2930            2935            2940

Pro Ala Ala Pro Ala Leu Trp Arg Leu Glu Pro Gly Thr Asp Gly Ser
2945            2950            2955            2960

Leu Glu Ser Leu Thr Ala Ala Pro Gly Asp Ala Glu Thr Leu Ala Pro
        2965            2970            2975

Glu Pro Leu Gly Pro Gly Gln Val Arg Ile Ala Ile Arg Ala Thr Gly
        2980            2985            2990

Leu Asn Phe Arg Asp Val Leu Ile Ala Leu Gly Met Tyr Pro Asp Pro
        2995            3000            3005

Ala Leu Met Gly Thr Glu Gly Ala Gly Val Val Thr Ala Thr Gly Pro
    3010            3015            3020

Gly Val Thr His Leu Ala Pro Gly Asp Arg Val Met Gly Leu Leu Ser
3025            3030            3035            3040

Gly Ala Tyr Ala Pro Val Val Ala Asp Ala Arg Thr Val Ala Arg
        3045            3050            3055

Met Pro Glu Gly Trp Thr Phe Ala Gln Gly Ala Ser Val Pro Val Val
        3060            3065            3070

Phe Leu Thr Ala Val Tyr Ala Leu Arg Asp Leu Ala Asp Val Lys Pro
        3075            3080            3085

Gly Glu Arg Leu Leu Val His Ser Ala Ala Gly Gly Val Gly Met Ala
    3090            3095            3100

Ala Val Gln Leu Ala Arg His Trp Gly Val Glu Val His Gly Thr Ala
3105            3110            3115            3120

Ser His Gly Lys Trp Asp Ala Leu Arg Ala Leu Gly Leu Asp Asp Ala
        3125            3130            3135

His Ile Ala Ser Ser Arg Thr Leu Asp Phe Glu Ser Ala Phe Arg Ala
        3140            3145            3150

Ala Ser Gly Gly Ala Gly Met Asp Val Val Leu Asn Ser Leu Ala Arg
        3155            3160            3165

Glu Phe Val Asp Ala Ser Leu Arg Leu Leu Gly Pro Gly Gly Arg Phe
    3170            3175            3180

Val Glu Met Gly Lys Thr Asp Val Arg Asp Ala Glu Arg Val Ala Ala
```

-continued

```
      3185             3190             3195             3200

Asp His Pro Gly Val Gly Tyr Arg Ala Phe Asp Leu Gly Glu Ala Gly
             3205             3210             3215

Pro Glu Arg Ile Gly Glu Met Leu Ala Glu Val Ile Ala Leu Phe Glu
             3220             3225             3230

Asp Gly Val Leu Arg His Leu Pro Val Thr Thr Trp Asp Val Arg Arg
             3235             3240             3245

Ala Arg Asp Ala Phe Arg His Val Ser Gln Ala Arg His Thr Gly Lys
             3250             3255             3260

Val Val Leu Thr Met Pro Ser Gly Leu Asp Pro Glu Gly Thr Val Leu
3265             3270             3275             3280

Leu Thr Gly Gly Thr Gly Ala Leu Gly Gly Ile Val Ala Arg His Val
             3285             3290             3295

Val Gly Glu Trp Gly Val Arg Arg Leu Leu Val Ser Arg Arg Gly
             3300             3305             3310

Thr Asp Ala Pro Gly Ala Gly Glu Leu Val His Glu Leu Glu Ala Leu
             3315             3320             3325

Gly Ala Asp Val Ser Val Ala Ala Cys Asp Val Ala Asp Arg Glu Ala
             3330             3335             3340

Leu Thr Ala Val Leu Asp Ser Ile Pro Ala Glu His Pro Leu Thr Ala
3345             3350             3355             3360

Val Val His Thr Ala Gly Val Leu Ser Asp Gly Thr Leu Pro Ser Met
             3365             3370             3375

Thr Ala Glu Asp Val Glu His Val Leu Arg Pro Lys Val Asp Ala Ala
             3380             3385             3390

Phe Leu Leu Asp Glu Leu Thr Ser Thr Pro Gly Tyr Asp Leu Ala Ala
             3395             3400             3405

Phe Val Met Phe Ser Ser Ala Ala Ala Val Phe Gly Gly Ala Gly Gln
             3410             3415             3420

Gly Ala Tyr Ala Ala Ala Asn Ala Thr Leu Asp Ala Leu Ala Trp Arg
3425             3430             3435             3440

Arg Arg Thr Ala Gly Leu Pro Ala Leu Ser Leu Gly Trp Gly Leu Trp
             3445             3450             3455

Ala Glu Thr Ser Gly Met Thr Gly Gly Leu Ser Asp Thr Asp Arg Ser
             3460             3465             3470

Arg Leu Ala Arg Ser Gly Ala Thr Pro Met Asp Ser Glu Leu Thr Leu
             3475             3480             3485

Ser Leu Leu Asp Ala Ala Met Arg Arg Asp Asp Pro Ala Leu Val Pro
             3490             3495             3500

Ile Ala Leu Asp Val Ala Ala Leu Arg Ala Gln Gln Arg Asp Gly Met
3505             3510             3515             3520

Leu Ala Pro Leu Leu Ser Gly Leu Thr Arg Gly Ser Arg Val Gly Gly
             3525             3530             3535

Ala Pro Val Asn Gln Arg Arg Ala Ala Ala Gly Gly Ala Gly Glu Ala
             3540             3545             3550

Asp Thr Asp Leu Gly Gly Arg Leu Ala Ala Met Thr Pro Asp Asp Arg
             3555             3560             3565

Val Ala His Leu Arg Asp Leu Val Arg Thr His Val Ala Thr Val Leu
             3570             3575             3580

Gly His Gly Thr Pro Ser Arg Val Asp Leu Glu Arg Ala Phe Arg Asp
3585             3590             3595             3600

Thr Gly Phe Asp Ser Leu Thr Ala Val Glu Leu Arg Asn Arg Leu Asn
             3605             3610             3615
```

```
Ala Ala Thr Gly Leu Arg Leu Pro Ala Thr Leu Val Phe Asp His Pro
        3620                3625                3630

Thr Pro Gly Glu Leu Ala Gly His Leu Leu Asp Glu Leu Ala Thr Ala
    3635                3640                3645

Ala Gly Gly Ser Trp Ala Glu Gly Thr Gly Ser Gly Asp Thr Ala Ser
    3650                3655                3660

Ala Thr Asp Arg Gln Thr Thr Ala Ala Leu Ala Glu Leu Asp Arg Leu
3665                3670                3675                3680

Glu Gly Val Leu Ala Ser Leu Ala Pro Ala Ala Gly Gly Arg Pro Glu
            3685                3690                3695

Leu Ala Ala Arg Leu Arg Ala Leu Ala Ala Leu Gly Asp Asp Gly
        3700                3705                3710

Asp Asp Ala Thr Asp Leu Asp Glu Ala Ser Asp Asp Leu Phe Ser
        3715                3720                3725

Phe Ile Asp Lys Glu Leu Gly Asp Ser Asp Phe
        3730                3735

<210> SEQ ID NO 4
<211> LENGTH: 1562
<212> TYPE: PRT
<213> ORGANISM: Streptomyces venezuelae

<400> SEQUENCE: 4

Met Ala Asn Asn Glu Asp Lys Leu Arg Asp Tyr Leu Lys Arg Val Thr
1               5                   10                  15

Ala Glu Leu Gln Gln Asn Thr Arg Arg Leu Arg Glu Ile Glu Gly Arg
            20                  25                  30

Thr His Glu Pro Val Ala Ile Val Gly Met Ala Cys Arg Leu Pro Gly
        35                  40                  45

Gly Val Ala Ser Pro Glu Asp Leu Trp Gln Leu Val Ala Gly Asp Gly
    50                  55                  60

Asp Ala Ile Ser Glu Phe Pro Gln Asp Arg Gly Trp Asp Val Glu Gly
65                  70                  75                  80

Leu Tyr Asp Pro Asp Pro Asp Ala Ser Gly Arg Thr Tyr Cys Arg Ser
                85                  90                  95

Gly Gly Phe Leu His Asp Ala Gly Glu Phe Asp Ala Asp Phe Phe Gly
            100                 105                 110

Ile Ser Pro Arg Glu Ala Leu Ala Met Asp Pro Gln Gln Arg Leu Ser
        115                 120                 125

Leu Thr Thr Ala Trp Glu Ala Ile Glu Ser Ala Gly Ile Asp Pro Thr
    130                 135                 140

Ala Leu Lys Gly Ser Gly Leu Gly Val Phe Val Gly Gly Trp His Thr
145                 150                 155                 160

Gly Tyr Thr Ser Gly Gln Thr Thr Ala Val Gln Ser Pro Glu Leu Glu
                165                 170                 175

Gly His Leu Val Ser Gly Ala Ala Leu Gly Phe Leu Ser Gly Arg Ile
            180                 185                 190

Ala Tyr Val Leu Gly Thr Asp Gly Pro Ala Leu Thr Val Asp Thr Ala
        195                 200                 205

Cys Ser Ser Ser Leu Val Ala Leu His Leu Ala Val Gln Ala Leu Arg
    210                 215                 220

Lys Gly Glu Cys Asp Met Ala Leu Ala Gly Gly Val Thr Val Met Pro
225                 230                 235                 240

Asn Ala Asp Leu Phe Val Gln Phe Ser Arg Gln Arg Gly Leu Ala Ala
```

```
                        245                 250                 255
Asp Gly Arg Ser Lys Ala Phe Ala Thr Ser Ala Asp Gly Phe Gly Pro
                260                 265                 270
Ala Glu Gly Ala Gly Val Leu Leu Val Glu Arg Leu Ser Asp Ala Arg
            275                 280                 285
Arg Asn Gly His Arg Ile Leu Ala Val Arg Gly Ser Ala Val Asn
        290                 295                 300
Gln Asp Gly Ala Ser Asn Gly Leu Thr Ala Pro His Gly Pro Ser Gln
305                 310                 315                 320
Gln Arg Val Ile Arg Arg Ala Leu Ala Asp Ala Arg Leu Ala Pro Gly
                325                 330                 335
Asp Val Asp Val Val Glu Ala His Gly Thr Gly Thr Arg Leu Gly Asp
                340                 345                 350
Pro Ile Glu Ala Gln Ala Leu Ile Ala Thr Tyr Gly Gln Glu Lys Ser
                355                 360                 365
Ser Glu Gln Pro Leu Arg Leu Gly Ala Leu Lys Ser Asn Ile Gly His
    370                 375                 380
Thr Gln Ala Ala Ala Gly Val Ala Gly Val Ile Lys Met Val Gln Ala
385                 390                 395                 400
Met Arg His Gly Leu Leu Pro Lys Thr Leu His Val Asp Glu Pro Ser
                405                 410                 415
Asp Gln Ile Asp Trp Ser Ala Gly Thr Val Glu Leu Leu Thr Glu Ala
                420                 425                 430
Val Asp Trp Pro Glu Lys Gln Asp Gly Gly Leu Arg Arg Ala Ala Val
                435                 440                 445
Ser Ser Phe Gly Ile Ser Gly Thr Asn Ala His Val Val Leu Glu Glu
    450                 455                 460
Ala Pro Ala Val Glu Asp Ser Pro Ala Val Glu Pro Pro Ala Gly Gly
465                 470                 475                 480
Gly Val Val Pro Trp Pro Val Ser Ala Lys Thr Pro Ala Ala Leu Asp
                485                 490                 495
Ala Gln Ile Gly Gln Leu Ala Ala Tyr Ala Asp Gly Arg Thr Asp Val
                500                 505                 510
Asp Pro Ala Val Ala Ala Arg Ala Leu Val Asp Ser Arg Thr Ala Met
                515                 520                 525
Glu His Arg Ala Val Ala Val Gly Asp Ser Arg Glu Ala Leu Arg Asp
    530                 535                 540
Ala Leu Arg Met Pro Glu Gly Leu Val Arg Gly Thr Ser Ser Asp Val
545                 550                 555                 560
Gly Arg Val Ala Phe Val Phe Pro Gly Gln Gly Thr Gln Trp Ala Gly
                565                 570                 575
Met Gly Ala Glu Leu Leu Asp Ser Ser Pro Glu Phe Ala Ala Ser Met
                580                 585                 590
Ala Glu Cys Glu Thr Ala Leu Ser Arg Tyr Val Asp Trp Ser Leu Glu
            595                 600                 605
Ala Val Val Arg Gln Glu Pro Gly Ala Pro Thr Leu Asp Arg Val Asp
        610                 615                 620
Val Val Gln Pro Val Thr Phe Ala Val Met Val Ser Leu Ala Lys Val
625                 630                 635                 640
Trp Gln His His Gly Ile Thr Pro Gln Ala Val Val Gly His Ser Gln
                645                 650                 655
Gly Glu Ile Ala Ala Ala Tyr Val Ala Gly Ala Leu Thr Leu Asp Asp
                660                 665                 670
```

-continued

```
Ala Ala Arg Val Val Thr Leu Arg Ser Lys Ser Ile Ala Ala His Leu
            675                 680                 685
Ala Gly Lys Gly Gly Met Ile Ser Leu Ala Leu Asp Glu Ala Ala Val
        690                 695                 700
Leu Lys Arg Leu Ser Asp Phe Asp Gly Leu Ser Val Ala Ala Val Asn
705                 710                 715                 720
Gly Pro Thr Ala Thr Val Ser Gly Asp Pro Thr Gln Ile Glu Glu
                725                 730                 735
Leu Ala Arg Thr Cys Glu Ala Asp Gly Val Arg Ala Arg Ile Ile Pro
                740                 745                 750
Val Asp Tyr Ala Ser His Ser Arg Gln Val Glu Ile Ile Glu Lys Glu
                755                 760                 765
Leu Ala Glu Val Leu Ala Gly Leu Ala Pro Gln Ala Pro His Val Pro
770                 775                 780
Phe Phe Ser Thr Leu Glu Gly Thr Trp Ile Thr Glu Pro Val Leu Asp
785                 790                 795                 800
Gly Thr Tyr Trp Tyr Arg Asn Leu Arg His Arg Val Gly Phe Ala Pro
                805                 810                 815
Ala Val Glu Thr Leu Ala Val Asp Gly Phe Thr His Phe Ile Glu Val
                820                 825                 830
Ser Ala His Pro Val Leu Thr Met Thr Leu Pro Glu Thr Val Thr Gly
        835                 840                 845
Leu Gly Thr Leu Arg Arg Glu Gln Gly Gln Glu Arg Leu Val Thr
        850                 855                 860
Ser Leu Ala Glu Ala Trp Ala Asn Gly Leu Thr Ile Asp Trp Ala Pro
865                 870                 875                 880
Ile Leu Pro Thr Ala Thr Gly His His Pro Glu Leu Pro Thr Tyr Ala
                885                 890                 895
Phe Gln Thr Glu Arg Phe Trp Leu Gln Ser Ser Ala Pro Thr Ser Ala
                900                 905                 910
Ala Asp Asp Trp Arg Tyr Arg Val Glu Trp Lys Pro Leu Thr Ala Ser
        915                 920                 925
Gly Gln Ala Asp Leu Ser Gly Arg Trp Ile Val Ala Val Gly Ser Glu
    930                 935                 940
Pro Glu Ala Glu Leu Leu Gly Ala Leu Lys Ala Ala Gly Ala Glu Val
945                 950                 955                 960
Asp Val Leu Glu Ala Gly Ala Asp Asp Arg Glu Ala Leu Ala Ala
                965                 970                 975
Arg Leu Thr Ala Leu Thr Thr Gly Asp Gly Phe Thr Gly Val Val Ser
            980                 985                 990
Leu Leu Asp Asp Leu Val Pro Gln Val Ala Trp Val Gln Ala Leu Gly
            995                 1000                1005
Asp Ala Gly Ile Lys Ala Pro Leu Trp Ser Val Thr Gln Gly Ala Val
    1010                1015                1020
Ser Val Gly Arg Leu Asp Thr Pro Ala Asp Pro Asp Arg Ala Met Leu
1025                1030                1035                1040
Trp Gly Leu Gly Arg Val Val Ala Leu Glu His Pro Glu Arg Trp Ala
                1045                1050                1055
Gly Leu Val Asp Leu Pro Ala Gln Pro Asp Ala Ala Ala Leu Ala His
            1060                1065                1070
Leu Val Thr Ala Leu Ser Gly Ala Thr Gly Glu Asp Gln Ile Ala Ile
        1075                1080                1085
```

-continued

```
Arg Thr Thr Gly Leu His Ala Arg Arg Leu Ala Arg Ala Pro Leu His
    1090                1095                1100
Gly Arg Arg Pro Thr Arg Asp Trp Gln Pro His Gly Thr Val Leu Ile
1105                1110                1115                1120
Thr Gly Gly Thr Gly Ala Leu Gly Ser His Ala Ala Arg Trp Met Ala
                1125                1130                1135
His His Gly Ala Glu His Leu Leu Val Ser Arg Ser Gly Glu Gln
         1140                1145                1150
Ala Pro Gly Ala Thr Gln Leu Thr Ala Glu Leu Thr Ala Ser Gly Ala
         1155                1160                1165
Arg Val Thr Ile Ala Ala Cys Asp Val Ala Asp Pro His Ala Met Arg
    1170                1175                1180
Thr Leu Leu Asp Ala Ile Pro Ala Glu Thr Pro Leu Thr Ala Val Val
1185                1190                1195                1200
His Thr Ala Gly Ala Pro Gly Gly Asp Pro Leu Asp Val Thr Gly Pro
                1205                1210                1215
Glu Asp Ile Ala Arg Ile Leu Gly Ala Lys Thr Ser Gly Ala Glu Val
         1220                1225                1230
Leu Asp Asp Leu Leu Arg Gly Thr Pro Leu Asp Ala Phe Val Leu Tyr
         1235                1240                1245
Ser Ser Asn Ala Gly Val Trp Gly Ser Gly Ser Gln Gly Val Tyr Ala
         1250                1255                1260
Ala Ala Asn Ala His Leu Asp Ala Leu Ala Ala Arg Arg Ala Arg
1265                1270                1275                1280
Gly Glu Thr Ala Thr Ser Val Ala Trp Gly Leu Trp Ala Gly Asp Gly
                1285                1290                1295
Met Gly Arg Gly Ala Asp Asp Ala Tyr Trp Gln Arg Arg Gly Ile Arg
         1300                1305                1310
Pro Met Ser Pro Asp Arg Ala Leu Asp Glu Leu Ala Lys Ala Leu Ser
         1315                1320                1325
His Asp Glu Thr Phe Val Ala Val Ala Asp Val Asp Trp Glu Arg Phe
         1330                1335                1340
Ala Pro Ala Phe Thr Val Ser Arg Pro Ser Leu Leu Leu Asp Gly Val
1345                1350                1355                1360
Pro Glu Ala Arg Gln Ala Leu Ala Ala Pro Val Gly Ala Pro Ala Pro
         1365                1370                1375
Gly Asp Ala Ala Val Ala Pro Thr Gly Gln Ser Ser Ala Leu Ala Ala
         1380                1385                1390
Ile Thr Ala Leu Pro Glu Pro Glu Arg Arg Pro Ala Leu Leu Thr Leu
         1395                1400                1405
Val Arg Thr His Ala Ala Ala Val Leu Gly His Ser Ser Pro Asp Arg
    1410                1415                1420
Val Ala Pro Gly Arg Ala Phe Thr Glu Leu Gly Phe Asp Ser Leu Thr
1425                1430                1435                1440
Ala Val Gln Leu Arg Asn Gln Leu Ser Thr Val Val Gly Asn Arg Leu
                1445                1450                1455
Pro Ala Thr Thr Val Phe Asp His Pro Thr Pro Ala Ala Leu Ala Ala
                1460                1465                1470
His Leu His Glu Ala Tyr Leu Ala Pro Ala Glu Pro Ala Pro Thr Asp
         1475                1480                1485
Trp Glu Gly Arg Val Arg Arg Ala Leu Ala Glu Leu Pro Leu Asp Arg
    1490                1495                1500
Leu Arg Asp Ala Gly Val Leu Asp Thr Val Leu Arg Leu Thr Gly Ile
```

-continued

```
                1505                1510                1515                1520
            Glu Pro Glu Pro Gly Ser Gly Gly Ser Asp Gly Gly Ala Ala Asp Pro
                            1525                1530                1535
            Gly Ala Glu Pro Glu Ala Ser Ile Asp Asp Leu Asp Ala Glu Ala Leu
                        1540                1545                1550
            Ile Arg Met Ala Leu Gly Pro Arg Asn Thr
                    1555                1560

<210> SEQ ID NO 5
<211> LENGTH: 1346
<212> TYPE: PRT
<213> ORGANISM: Streptomyces venezuelae

<400> SEQUENCE: 5

Met Thr Ser Ser Asn Glu Gln Leu Val Asp Ala Leu Arg Ala Ser Leu
  1               5                  10                  15

Lys Glu Asn Glu Glu Leu Arg Lys Glu Ser Arg Arg Ala Asp Arg
                 20                  25                  30

Arg Gln Glu Pro Met Ala Ile Val Gly Met Ser Cys Arg Phe Ala Gly
             35                  40                  45

Gly Ile Arg Ser Pro Glu Asp Leu Trp Asp Ala Val Ala Ala Gly Lys
         50                  55                  60

Asp Leu Val Ser Glu Val Pro Glu Arg Gly Trp Asp Ile Asp Ser
 65                  70                  75                  80

Leu Tyr Asp Pro Val Pro Gly Arg Lys Gly Thr Thr Tyr Val Arg Asn
                 85                  90                  95

Ala Ala Phe Leu Asp Asp Ala Ala Gly Phe Asp Ala Ala Phe Phe Gly
                100                 105                 110

Ile Ser Pro Arg Glu Ala Leu Ala Met Asp Pro Gln Gln Arg Gln Leu
            115                 120                 125

Leu Glu Ala Ser Trp Glu Val Phe Glu Arg Ala Gly Ile Asp Pro Ala
        130                 135                 140

Ser Val Arg Gly Thr Asp Val Gly Val Tyr Val Gly Cys Gly Tyr Gln
145                 150                 155                 160

Asp Tyr Ala Pro Asp Ile Arg Val Ala Pro Glu Gly Thr Gly Tyr
                165                 170                 175

Val Val Thr Gly Asn Ser Ser Ala Val Ala Ser Gly Arg Ile Ala Tyr
            180                 185                 190

Ser Leu Gly Leu Glu Gly Pro Ala Val Thr Val Asp Thr Ala Cys Ser
        195                 200                 205

Ser Ser Leu Val Ala Leu His Leu Ala Leu Lys Gly Leu Arg Asn Gly
210                 215                 220

Asp Cys Ser Thr Ala Leu Val Gly Gly Val Ala Val Leu Ala Thr Pro
225                 230                 235                 240

Gly Ala Phe Ile Glu Phe Ser Gln Gln Ala Met Ala Ala Asp Gly
                245                 250                 255

Arg Thr Lys Gly Phe Ala Ser Ala Asp Gly Leu Ala Trp Gly Glu
            260                 265                 270

Gly Val Ala Val Leu Leu Leu Glu Arg Leu Ser Asp Ala Arg Arg Lys
        275                 280                 285

Gly His Arg Val Leu Ala Val Val Arg Gly Ser Ala Ile Asn Gln Asp
    290                 295                 300

Gly Ala Ser Asn Gly Leu Thr Ala Pro His Gly Pro Ser Gln Gln Arg
305                 310                 315                 320
```

-continued

```
Leu Ile Arg Gln Ala Leu Ala Asp Ala Arg Leu Thr Ser Ser Asp Val
                325                 330                 335

Asp Val Val Glu Gly His Gly Thr Gly Thr Arg Leu Gly Asp Pro Ile
            340                 345                 350

Glu Ala Gln Ala Leu Leu Ala Thr Tyr Gly Gln Gly Arg Ala Pro Gly
            355                 360                 365

Gln Pro Leu Arg Leu Gly Thr Leu Lys Ser Asn Ile Gly His Thr Gln
    370                 375                 380

Ala Ala Ser Gly Val Ala Gly Val Ile Lys Met Val Gln Ala Leu Arg
385                 390                 395                 400

His Gly Val Leu Pro Lys Thr Leu His Val Asp Glu Pro Thr Asp Gln
                405                 410                 415

Val Asp Trp Ser Ala Gly Ser Val Glu Leu Leu Thr Glu Ala Val Asp
                420                 425                 430

Trp Pro Glu Arg Pro Gly Arg Leu Arg Arg Ala Gly Val Ser Ala Phe
            435                 440                 445

Gly Val Gly Gly Thr Asn Ala His Val Val Leu Glu Glu Ala Pro Ala
            450                 455                 460

Val Glu Glu Ser Pro Ala Val Glu Pro Pro Ala Gly Gly Val Val
465                 470                 475                 480

Pro Trp Pro Val Ser Ala Lys Thr Ser Ala Ala Leu Asp Ala Gln Ile
                485                 490                 495

Gly Gln Leu Ala Ala Tyr Ala Glu Asp Arg Thr Asp Val Asp Pro Ala
            500                 505                 510

Val Ala Ala Arg Ala Leu Val Asp Ser Arg Thr Ala Met Glu His Arg
            515                 520                 525

Ala Val Ala Val Gly Asp Ser Arg Glu Ala Leu Arg Asp Ala Leu Arg
            530                 535                 540

Met Pro Glu Gly Leu Val Arg Gly Thr Val Thr Asp Pro Gly Arg Val
545                 550                 555                 560

Ala Phe Val Phe Pro Gly Gln Gly Thr Gln Trp Ala Gly Met Gly Ala
                565                 570                 575

Glu Leu Leu Asp Ser Ser Pro Glu Phe Ala Ala Ala Met Ala Glu Cys
            580                 585                 590

Glu Thr Ala Leu Ser Pro Tyr Val Asp Trp Ser Leu Glu Ala Val Val
            595                 600                 605

Arg Gln Ala Pro Ser Ala Pro Thr Leu Asp Arg Val Asp Val Val Gln
            610                 615                 620

Pro Val Thr Phe Ala Val Met Val Ser Leu Ala Lys Val Trp Gln His
625                 630                 635                 640

His Gly Ile Thr Pro Glu Ala Val Ile Gly His Ser Gln Gly Glu Ile
                645                 650                 655

Ala Ala Ala Tyr Val Ala Gly Ala Leu Thr Leu Asp Asp Ala Ala Arg
                660                 665                 670

Val Val Thr Leu Arg Ser Lys Ser Ile Ala Ala His Leu Ala Gly Lys
            675                 680                 685

Gly Gly Met Ile Ser Leu Ala Leu Ser Glu Glu Ala Thr Arg Gln Arg
    690                 695                 700

Ile Glu Asn Leu His Gly Leu Ser Ile Ala Ala Val Asn Gly Pro Thr
705                 710                 715                 720

Ala Thr Val Val Ser Gly Asp Pro Thr Gln Ile Gln Glu Leu Ala Gln
                725                 730                 735

Ala Cys Glu Ala Asp Gly Ile Arg Ala Arg Ile Ile Pro Val Asp Tyr
```

-continued

```
                740                 745                 750
Ala Ser His Ser Ala His Val Glu Thr Ile Glu Asn Glu Leu Ala Asp
            755                 760                 765

Val Leu Ala Gly Leu Ser Pro Gln Thr Pro Gln Val Pro Phe Phe Ser
770                 775                 780

Thr Leu Glu Gly Thr Trp Ile Thr Glu Pro Ala Leu Asp Gly Gly Tyr
785                 790                 795                 800

Trp Tyr Arg Asn Leu Arg His Arg Val Gly Phe Ala Pro Ala Val Glu
                805                 810                 815

Thr Leu Ala Thr Asp Glu Gly Phe Thr His Phe Ile Glu Val Ser Ala
                820                 825                 830

His Pro Val Leu Thr Met Thr Leu Pro Asp Lys Val Thr Gly Leu Ala
                835                 840                 845

Thr Leu Arg Arg Glu Asp Gly Gly Gln His Arg Leu Thr Thr Ser Leu
                850                 855                 860

Ala Glu Ala Trp Ala Asn Gly Leu Ala Leu Asp Trp Ala Ser Leu Leu
865                 870                 875                 880

Pro Ala Thr Gly Ala Leu Ser Pro Ala Val Pro Asp Leu Pro Thr Tyr
                885                 890                 895

Ala Phe Gln His Arg Ser Tyr Trp Ile Ser Pro Ala Gly Pro Gly Glu
                900                 905                 910

Ala Pro Ala His Thr Ala Ser Gly Arg Glu Ala Val Ala Glu Thr Gly
                915                 920                 925

Leu Ala Trp Gly Pro Gly Ala Glu Asp Leu Asp Glu Glu Gly Arg Arg
            930                 935                 940

Ser Ala Val Leu Ala Met Val Met Arg Gln Ala Ala Ser Val Leu Arg
945                 950                 955                 960

Cys Asp Ser Pro Glu Glu Val Pro Val Asp Arg Pro Leu Arg Glu Ile
                965                 970                 975

Gly Phe Asp Ser Leu Thr Ala Val Asp Phe Arg Asn Arg Val Asn Arg
            980                 985                 990

Leu Thr Gly Leu Gln Leu Pro Pro Thr Val Val Phe Glu His Pro Thr
            995                 1000                1005

Pro Val Ala Leu Ala Glu Arg Ile Ser Asp Glu Leu Ala Glu Arg Asn
    1010                1015                1020

Trp Ala Val Ala Glu Pro Ser Asp His Glu Gln Ala Glu Glu Glu Lys
1025                1030                1035                1040

Ala Ala Ala Pro Ala Gly Ala Arg Ser Gly Ala Asp Thr Gly Ala Gly
                1045                1050                1055

Ala Gly Met Phe Arg Ala Leu Phe Arg Gln Ala Val Glu Asp Asp Arg
            1060                1065                1070

Tyr Gly Glu Phe Leu Asp Val Leu Ala Glu Ala Ser Ala Phe Arg Pro
    1075                1080                1085

Gln Phe Ala Ser Pro Glu Ala Cys Ser Glu Arg Leu Asp Pro Val Leu
    1090                1095                1100

Leu Ala Gly Gly Pro Thr Asp Arg Ala Glu Gly Arg Ala Val Leu Val
1105                1110                1115                1120

Gly Cys Thr Gly Thr Ala Ala Asn Gly Gly Pro His Glu Phe Leu Arg
                1125                1130                1135

Leu Ser Thr Ser Phe Gln Glu Glu Arg Asp Phe Leu Ala Val Pro Leu
                1140                1145                1150

Pro Gly Tyr Gly Thr Gly Thr Gly Thr Gly Thr Ala Leu Leu Pro Ala
                1155                1160                1165
```

-continued

```
Asp Leu Asp Thr Ala Leu Asp Ala Gln Ala Arg Ala Ile Leu Arg Ala
    1170                1175                1180

Ala Gly Asp Ala Pro Val Val Leu Leu Gly His Ser Gly Gly Ala Leu
1185                1190                1195                1200

Leu Ala His Glu Leu Ala Phe Arg Leu Glu Arg Ala His Gly Ala Pro
            1205                1210                1215

Pro Ala Gly Ile Val Leu Val Asp Pro Tyr Pro Pro Gly His Gln Glu
        1220                1225                1230

Pro Ile Glu Val Trp Ser Arg Gln Leu Gly Gly Leu Phe Ala Gly
        1235                1240                1245

Glu Leu Glu Pro Met Ser Asp Ala Arg Leu Leu Ala Met Gly Arg Tyr
    1250                1255                1260

Ala Arg Phe Leu Ala Gly Pro Arg Pro Gly Arg Ser Ser Ala Pro Val
1265                1270                1275                1280

Leu Leu Val Arg Ala Ser Glu Pro Leu Gly Asp Trp Gln Glu Glu Arg
            1285                1290                1295

Gly Asp Trp Arg Ala His Trp Asp Leu Pro His Thr Val Ala Asp Val
        1300                1305                1310

Pro Gly Asp His Phe Thr Met Met Arg Asp His Ala Pro Ala Val Ala
        1315                1320                1325

Glu Ala Val Leu Ser Trp Leu Asp Ala Ile Glu Gly Ile Glu Gly Ala
    1330                1335                1340

Gly Lys
1345

<210> SEQ ID NO 6
<211> LENGTH: 281
<212> TYPE: PRT
<213> ORGANISM: Streptomyces venezuelae

<400> SEQUENCE: 6

Val Thr Asp Arg Pro Leu Asn Val Asp Ser Gly Leu Trp Ile Arg Arg
  1               5                  10                  15

Phe His Pro Ala Pro Asn Ser Ala Val Arg Leu Val Cys Leu Pro His
              20                  25                  30

Ala Gly Gly Ser Ala Ser Tyr Phe Phe Arg Phe Ser Glu Glu Leu His
          35                  40                  45

Pro Ser Val Glu Ala Leu Ser Val Gln Tyr Pro Gly Arg Gln Asp Arg
      50                  55                  60

Arg Ala Glu Pro Cys Leu Glu Ser Val Glu Leu Ala Glu His Val
 65                  70                  75                  80

Val Ala Ala Thr Glu Pro Trp Trp Gln Glu Gly Arg Leu Ala Phe Phe
              85                  90                  95

Gly His Ser Leu Gly Ala Ser Val Ala Phe Glu Thr Ala Arg Ile Leu
          100                 105                 110

Glu Gln Arg His Gly Val Arg Pro Glu Gly Leu Tyr Val Ser Gly Arg
      115                 120                 125

Arg Ala Pro Ser Leu Ala Pro Asp Arg Leu Val His Gln Leu Asp Asp
130                 135                 140

Arg Ala Phe Leu Ala Glu Ile Arg Leu Ser Gly Thr Asp Glu Arg
145                 150                 155                 160

Phe Leu Gln Asp Asp Glu Leu Leu Arg Leu Val Leu Pro Ala Leu Arg
              165                 170                 175

Ser Asp Tyr Lys Ala Ala Glu Thr Tyr Leu His Arg Pro Ser Ala Lys
```

-continued

```
                180                 185                 190
Leu Thr Cys Pro Val Met Ala Leu Ala Gly Asp Arg Asp Pro Lys Ala
            195                 200                 205

Pro Leu Asn Glu Val Ala Glu Trp Arg Arg His Thr Ser Gly Pro Phe
        210                 215                 220

Cys Leu Arg Ala Tyr Ser Gly Gly His Phe Tyr Leu Asn Asp Gln Trp
225                 230                 235                 240

His Glu Ile Cys Asn Asp Ile Ser Asp His Leu Leu Val Thr Arg Gly
                245                 250                 255

Ala Pro Asp Ala Arg Val Val Gln Pro Pro Thr Ser Leu Ile Glu Gly
            260                 265                 270

Ala Ala Lys Arg Trp Gln Asn Pro Arg
        275                 280
```

<210> SEQ ID NO 7
<211> LENGTH: 382
<212> TYPE: PRT
<213> ORGANISM: Streptomyces venezuelae

<400> SEQUENCE: 7

```
Val Ala Asp Arg Glu Leu Gly Thr His Leu Leu Glu Thr Arg Gly Ile
1               5                   10                  15

His Trp Ile His Ala Ala Asn Gly Asp Pro Tyr Ala Thr Val Leu Arg
                20                  25                  30

Gly Gln Ala Asp Asp Pro Tyr Pro Ala Tyr Glu Arg Val Arg Ala Arg
            35                  40                  45

Gly Ala Leu Ser Phe Ser Pro Thr Gly Ser Trp Val Thr Ala Asp His
        50                  55                  60

Ala Leu Ala Ala Ser Ile Leu Cys Ser Thr Asp Phe Gly Val Ser Gly
65                  70                  75                  80

Ala Asp Gly Val Pro Val Pro Gln Gln Val Leu Ser Tyr Gly Glu Gly
                85                  90                  95

Cys Pro Leu Glu Arg Glu Gln Val Leu Pro Ala Ala Gly Asp Val Pro
            100                 105                 110

Glu Gly Gly Gln Arg Ala Val Val Glu Gly Ile His Arg Glu Thr Leu
        115                 120                 125

Glu Gly Leu Ala Pro Asp Pro Ser Ala Ser Tyr Ala Phe Glu Leu Leu
    130                 135                 140

Gly Gly Phe Val Arg Pro Ala Val Thr Ala Ala Ala Ala Val Leu
145                 150                 155                 160

Gly Val Pro Ala Asp Arg Arg Ala Asp Phe Ala Asp Leu Leu Glu Arg
                165                 170                 175

Leu Arg Pro Leu Ser Asp Ser Leu Leu Ala Pro Gln Ser Leu Arg Thr
            180                 185                 190

Val Arg Ala Ala Asp Gly Ala Leu Ala Glu Leu Thr Ala Leu Leu Ala
        195                 200                 205

Asp Ser Asp Asp Ser Pro Gly Ala Leu Leu Ser Ala Leu Gly Val Thr
    210                 215                 220

Ala Ala Val Gln Leu Thr Gly Asn Ala Val Leu Ala Leu Leu Ala His
225                 230                 235                 240

Pro Glu Gln Trp Arg Glu Leu Cys Asp Arg Pro Gly Leu Ala Ala Ala
                245                 250                 255

Ala Val Glu Glu Thr Leu Arg Tyr Asp Pro Pro Val Gln Leu Asp Ala
            260                 265                 270
```

-continued

Arg Val Val Arg Gly Glu Thr Glu Leu Ala Gly Arg Arg Leu Pro Ala
            275                 280                 285

Gly Ala His Val Val Leu Thr Ala Ala Thr Gly Arg Asp Pro Glu
        290                 295                 300

Val Phe Thr Asp Pro Glu Arg Phe Asp Leu Ala Arg Pro Asp Ala Ala
305                 310                 315                 320

Ala His Leu Ala Leu His Pro Ala Gly Pro Tyr Gly Pro Val Ala Ser
                325                 330                 335

Leu Val Arg Leu Gln Ala Glu Val Ala Leu Arg Thr Leu Ala Gly Arg
                340                 345                 350

Phe Pro Gly Leu Arg Gln Ala Gly Asp Val Leu Arg Pro Arg Arg Ala
                355                 360                 365

Pro Val Gly Arg Gly Pro Leu Ser Val Pro Val Ser Ser Ser
        370                 375                 380

<210> SEQ ID NO 8
<211> LENGTH: 426
<212> TYPE: PRT
<213> ORGANISM: Streptomyces venezuelae

<400> SEQUENCE: 8

Met Arg Val Leu Leu Thr Ser Phe Ala His His Thr His Tyr Tyr Gly
1               5                   10                  15

Leu Val Pro Leu Ala Trp Ala Leu Leu Ala Ala Gly His Glu Val Arg
                20                  25                  30

Val Ala Ser Gln Pro Ala Leu Thr Asp Thr Ile Thr Gly Ser Gly Leu
            35                  40                  45

Ala Ala Val Pro Val Gly Thr Asp His Leu Ile His Glu Tyr Arg Val
    50                  55                  60

Arg Met Ala Gly Glu Pro Arg Pro Asn His Pro Ala Ile Ala Phe Asp
65                  70                  75                  80

Glu Ala Arg Pro Glu Pro Leu Asp Trp Asp His Ala Leu Gly Ile Glu
                85                  90                  95

Ala Ile Leu Ala Pro Tyr Phe Tyr Leu Leu Ala Asn Asn Asp Ser Met
                100                 105                 110

Val Asp Asp Leu Val Asp Phe Ala Arg Ser Trp Gln Pro Asp Leu Val
            115                 120                 125

Leu Trp Glu Pro Thr Thr Tyr Ala Gly Ala Val Ala Ala Gln Val Thr
    130                 135                 140

Gly Ala Ala His Ala Arg Val Leu Trp Gly Pro Asp Val Met Gly Ser
145                 150                 155                 160

Ala Arg Arg Lys Phe Val Ala Leu Arg Asp Arg Gln Pro Pro Glu His
                165                 170                 175

Arg Glu Asp Pro Thr Ala Glu Trp Leu Thr Trp Thr Leu Asp Arg Tyr
                180                 185                 190

Gly Ala Ser Phe Glu Glu Glu Leu Leu Thr Gly Gln Phe Thr Ile Asp
            195                 200                 205

Pro Thr Pro Pro Ser Leu Arg Leu Asp Thr Gly Leu Pro Thr Val Gly
    210                 215                 220

Met Arg Tyr Val Pro Tyr Asn Gly Thr Ser Val Val Pro Asp Trp Leu
225                 230                 235                 240

Ser Glu Pro Pro Ala Arg Pro Arg Val Cys Leu Thr Leu Gly Val Ser
                245                 250                 255

Ala Arg Glu Val Leu Gly Gly Asp Gly Val Ser Gln Gly Asp Ile Leu
                260                 265                 270

-continued

```
Glu Ala Leu Ala Asp Leu Asp Ile Glu Leu Val Ala Thr Leu Asp Ala
            275                 280                 285
Ser Gln Arg Ala Glu Ile Arg Asn Tyr Pro Lys His Thr Arg Phe Thr
        290                 295                 300
Asp Phe Val Pro Met His Ala Leu Leu Pro Ser Cys Ser Ala Ile Ile
305                 310                 315                 320
His His Gly Gly Ala Gly Thr Tyr Ala Thr Ala Val Ile Asn Ala Val
                325                 330                 335
Pro Gln Val Met Leu Ala Glu Leu Trp Asp Ala Pro Val Lys Ala Arg
            340                 345                 350
Ala Val Ala Glu Gln Gly Ala Gly Phe Phe Leu Pro Pro Ala Glu Leu
        355                 360                 365
Thr Pro Gln Ala Val Arg Asp Ala Val Val Arg Ile Leu Asp Asp Pro
    370                 375                 380
Ser Val Ala Thr Ala Ala His Arg Leu Arg Glu Thr Phe Gly Asp
385                 390                 395                 400
Pro Thr Pro Ala Gly Ile Val Pro Glu Leu Glu Arg Leu Ala Ala Gln
                405                 410                 415
His Arg Arg Pro Pro Ala Asp Ala Arg His
            420                 425
```

<210> SEQ ID NO 9
<211> LENGTH: 2401
<212> TYPE: DNA
<213> ORGANISM: Streptomyces venezuelae

<400> SEQUENCE: 9

```
cgtggcggcc gccgctcccg gcgccgccga cacggccaat gttcagtaca cgagccgggc     60
ggcggagctc gtcgcccaga tgacgctcga cgagaagatc agcttcgtcc actgggcgct    120
ggaccccgac cggcagaacg tcggctacct tcccggcgtg ccgcgtctgg gcatcccgga    180
gctgcgtgcc gccgacggcc cgaacggcat ccgcctggtg gggcagaccg ccaccgcgct    240
gcccgcgccg gtcgccctgg ccagcacctt cgacgacacc atggccgaca gctacggcaa    300
ggtcatgggc cgcgacggtc gcgcgctcaa ccaggacatg gtcctgggcc cgatgatgaa    360
caacatccgg gtgccgcacg gcggccggaa ctacgagacc ttcagcgagg accccctggt    420
ctcctcgcgc accgcggtcg cccagatcaa gggcatccag ggtgcgggtc tgatgaccac    480
ggccaagcac ttcgcggcca acaaccagga gaacaaccgc ttctccgtga cgccaatgt     540
cgacgagcag acgctccgcg agatcgagtt cccggcgttc gaggcgtcct ccaaggccgg    600
cgcgggctcc ttcatgtgtg cctacaacgg cctcaacggg aagccgtcct gcggcaacga    660
cgagctcctc aacaacgtgc tgcgcacgca gtggggcttc cagggctggg tgatgtccga    720
ctggctcgcc accccgggca ccgacgccat caccaagggc ctcgaccagg agatgggcgt    780
cgagctcccc ggcgacgtcc gaagggcga gccctcgccg ccggccaagt tcttcggcga    840
ggcgctgaag acgccgtcc tgaacggcac ggtccccgag gcggccgtga cgcggtcggc    900
ggagcggatc gtcggccaga tggagaagtt cggtctgctc ctcgccactc cggcgccgcg    960
gcccgagcgc gacaaggcgg gtgcccaggc ggtgtcccgc aaggtcgccg agaacggcgc   1020
ggtgctcctg cgcaacgagg ccaggcccct gccgctcgcc ggtgacgccg gcaagagcat   1080
cgcggtcatc ggcccgacgg ccgtcgaccc caaggtcacc ggcctgggca cgcccacgt    1140
cgtcccggac tcggcggcgg cgccactcga caccatcaag gcccgcgcgg gtgcgggtgc   1200
```

-continued

```
gacggtgacg tacgagacgg gtgaggagac cttcgggacg cagatcccgg cggggaacct    1260
cagcccggcg ttcaaccagg gccaccagct cgagccgggc aaggcggggg cgctgtacga    1320
cggcacgctg accgtgcccg ccgacggcga gtaccgcatc gcggtccgtg ccaccggtgg    1380
ttacgccacg gtgcagctcg gcagccacac catcgaggcc ggtcaggtct acggcaaggt    1440
gagcagcccc ctcctcaagc tgaccaaggg cacgcacaag ctcacgatct cgggcttcgc    1500
gatgagtgcc accccgctct ccctggagct gggctgggtn acgccggcgg cggccgacgc    1560
gacgatcgcg aaggccgtgg agtcggcgcg gaaggcccgt acggcggtcg tcttcgccta    1620
cgacgacggc accgagggcg tcgaccgtcc gaacctgtcg ctgccgggta cgcaggacaa    1680
gctgatctcg gctgtcgcgg acgccaaccc gaacacgatc gtggtcctca acaccggttc    1740
gtcggtgctg atgccgtggc tgtccaagac ccgcgcggtc ctggacatgt ggtacccggg    1800
ccaggcgggc gccgaggcca ccgccgcgct gctctacggt gacgtcaacc cgagcggcaa    1860
gctcacgcag agcttcccgg ccgccgagaa ccagcacgcg gtcgccggcg acccgaccag    1920
ctacccgggc gtcgacaacc agcagacgta ccgcgagggc atccacgtcg ggtaccgctg    1980
gttcgacaag gagaacgtca gccgctgtt cccgttcggg cacggcctgt cgtacacctc    2040
gttcacgcag agcgccccga ccgtcgtgcg tacgtccacg ggtggtctga aggtcacggt    2100
cacggtccgc aacagcggga agcgcgccgg ccaggaggtc gtccaggcgt acctcggtgc    2160
cagcccgaac gtgacggctc cgcaggcgaa gaagaagctc gtgggctaca cgaaggtctc    2220
gctcgccgcg ggcgaggcga agacggtgac ggtgaacgtc gaccgccgtc agctgcagtt    2280
ctgggatgcc gccacggaca actggaagac gggaacgggc aaccgcctcc tgcagaccgg    2340
ttcgtcctcc gccgacctgc ggggcagcgc cacggtcaac gtctggtgac gtgacgccgt    2400
g                                                                    2401
```

<210> SEQ ID NO 10
<211> LENGTH: 769
<212> TYPE: PRT
<213> ORGANISM: Streptomyces venezuelae

<400> SEQUENCE: 10

```
Met Thr Leu Asp Glu Lys Ile Ser Phe Val His Trp Ala Leu Asp Pro
 1               5                  10                  15

Asp Arg Gln Asn Val Gly Tyr Leu Pro Gly Val Pro Arg Leu Gly Ile
             20                  25                  30

Pro Glu Leu Arg Ala Ala Asp Gly Pro Asn Gly Ile Arg Leu Val Gly
         35                  40                  45

Gln Thr Ala Thr Ala Leu Pro Ala Pro Val Ala Leu Ala Ser Thr Phe
     50                  55                  60

Asp Asp Thr Met Ala Asp Ser Tyr Gly Lys Val Met Gly Arg Asp Gly
 65                  70                  75                  80

Arg Ala Leu Asn Gln Asp Met Val Leu Gly Pro Met Met Asn Asn Ile
                 85                  90                  95

Arg Val Pro His Gly Gly Arg Asn Tyr Glu Thr Phe Ser Glu Asp Pro
            100                 105                 110

Leu Val Ser Ser Arg Thr Ala Val Ala Gln Ile Lys Gly Ile Gln Gly
        115                 120                 125

Ala Gly Leu Met Thr Thr Ala Lys His Phe Ala Ala Asn Asn Gln Glu
    130                 135                 140

Asn Asn Arg Phe Ser Val Asn Ala Asn Val Asp Glu Gln Thr Leu Arg
145                 150                 155                 160
```

```
Glu Ile Glu Phe Pro Ala Phe Glu Ala Ser Ser Lys Ala Gly Ala Gly
            165                 170                 175

Ser Phe Met Cys Ala Tyr Asn Gly Leu Asn Gly Lys Pro Ser Cys Gly
            180                 185                 190

Asn Asp Glu Leu Leu Asn Asn Val Leu Arg Thr Gln Trp Gly Phe Gln
            195                 200                 205

Gly Trp Val Met Ser Asp Trp Leu Ala Thr Pro Gly Thr Asp Ala Ile
            210                 215                 220

Thr Lys Gly Leu Asp Gln Glu Met Gly Val Glu Leu Pro Gly Asp Val
225                 230                 235                 240

Pro Lys Gly Glu Pro Ser Pro Ala Lys Phe Phe Gly Glu Ala Leu
            245                 250                 255

Lys Thr Ala Val Leu Asn Gly Thr Val Pro Glu Ala Ala Val Thr Arg
            260                 265                 270

Ser Ala Glu Arg Ile Val Gly Gln Met Glu Lys Phe Gly Leu Leu Leu
            275                 280                 285

Ala Thr Pro Ala Pro Arg Pro Glu Arg Asp Lys Ala Gly Ala Gln Ala
            290                 295                 300

Val Ser Arg Lys Val Ala Glu Asn Gly Ala Val Leu Leu Arg Asn Glu
305                 310                 315                 320

Gly Gln Ala Leu Pro Leu Ala Gly Asp Ala Gly Lys Ser Ile Ala Val
            325                 330                 335

Ile Gly Pro Thr Ala Val Asp Pro Lys Val Thr Gly Leu Gly Ser Ala
            340                 345                 350

His Val Val Pro Asp Ser Ala Ala Ala Pro Leu Asp Thr Ile Lys Ala
            355                 360                 365

Arg Ala Gly Ala Gly Ala Thr Val Thr Tyr Glu Thr Gly Glu Glu Thr
370                 375                 380

Phe Gly Thr Gln Ile Pro Ala Gly Asn Leu Ser Pro Ala Phe Asn Gln
385                 390                 395                 400

Gly His Gln Leu Glu Pro Gly Lys Ala Gly Ala Leu Tyr Asp Gly Thr
            405                 410                 415

Leu Thr Val Pro Ala Asp Gly Glu Tyr Arg Ile Ala Val Arg Ala Thr
            420                 425                 430

Gly Gly Tyr Ala Thr Val Gln Leu Gly Ser His Thr Ile Glu Ala Gly
            435                 440                 445

Gln Val Tyr Gly Lys Val Ser Ser Pro Leu Leu Lys Leu Thr Lys Gly
            450                 455                 460

Thr His Lys Leu Thr Ile Ser Gly Phe Ala Met Ser Ala Thr Pro Leu
465                 470                 475                 480

Ser Leu Glu Leu Gly Trp Val Thr Pro Ala Ala Ala Asp Ala Thr Ile
            485                 490                 495

Ala Lys Ala Val Glu Ser Ala Arg Lys Ala Arg Thr Ala Val Val Phe
            500                 505                 510

Ala Tyr Asp Asp Gly Thr Glu Gly Val Asp Arg Pro Asn Leu Ser Leu
            515                 520                 525

Pro Gly Thr Gln Asp Lys Leu Ile Ser Ala Val Ala Asp Ala Asn Pro
            530                 535                 540

Asn Thr Ile Val Val Leu Asn Thr Gly Ser Ser Val Leu Met Pro Trp
545                 550                 555                 560

Leu Ser Lys Thr Arg Ala Val Leu Asp Met Trp Tyr Pro Gly Gln Ala
            565                 570                 575
```

-continued

```
Gly Ala Glu Ala Thr Ala Ala Leu Leu Tyr Gly Asp Val Asn Pro Ser
            580                 585                 590
Gly Lys Leu Thr Gln Ser Phe Pro Ala Ala Glu Asn Gln His Ala Val
        595                 600                 605
Ala Gly Asp Pro Thr Ser Tyr Pro Gly Val Asp Asn Gln Gln Thr Tyr
    610                 615                 620
Arg Glu Gly Ile His Val Gly Tyr Arg Trp Phe Asp Lys Glu Asn Val
625                 630                 635                 640
Lys Pro Leu Phe Pro Phe Gly His Gly Leu Ser Tyr Thr Ser Phe Thr
                645                 650                 655
Gln Ser Ala Pro Thr Val Val Arg Thr Ser Thr Gly Gly Leu Lys Val
            660                 665                 670
Thr Val Thr Val Arg Asn Ser Gly Lys Arg Ala Gly Gln Glu Val Val
        675                 680                 685
Gln Ala Tyr Leu Gly Ala Ser Pro Asn Val Thr Ala Pro Gln Ala Lys
    690                 695                 700
Lys Lys Leu Val Gly Tyr Thr Lys Val Ser Leu Ala Ala Gly Glu Ala
705                 710                 715                 720
Lys Thr Val Thr Val Asn Val Asp Arg Arg Gln Leu Gln Phe Trp Asp
                725                 730                 735
Ala Ala Thr Asp Asn Trp Lys Thr Gly Thr Gly Asn Arg Leu Leu Gln
            740                 745                 750
Thr Gly Ser Ser Ser Ala Asp Leu Arg Gly Ser Ala Thr Val Asn Val
        755                 760                 765
Trp

<210> SEQ ID NO 11
<211> LENGTH: 5970
<212> TYPE: DNA
<213> ORGANISM: Streptomyces venezuelae

<400> SEQUENCE: 11
ggcgagaagt aggcgcgggt gtgcacgcct tcggccttca ggacctccat gacgaggtcg      60
cggtggatgc cggtggtggc ctcgtcgatc tcgacgatca cgtactggtg gttgttgagg     120
ccgtggcggt cgtggtcggc gacgaggacg ccggggaggt ccgcgaggtg ctcgcggtag     180
scggcgtggt tgcgccggtt ccggtcgatg acctcgggaa acgcgtcgag ggaggtgagg     240
cccatggcgg cggcggcctc gctcatcttg gcgttggtcc cgccggcggg gctgccgccg     300
ggcaggtcga agccgaagtt gtggagggcg cggatccggg cggcgaggtc ggcgtcgtcg     360
gtgacgacgg cgccgccctc gaaggcgttg acggccttgg tggcgtggaa gctgaagacc     420
tcggcgtcgc cgaggctgcc ggcgggccgg ccgtcgaccg cgcagccgag ggcgtgcgcg     480
gcgtcgaagt acagccgcag gccgtgctcg tcggcgacct tccgcagctg gtcggcggcg     540
caggggcggc cccagaggtg gacgccgacg acggccgagg tgcggggtgt gaccgcggcg     600
gccacctggt ccgggtcgag gttgccggtg tccgggtcga tgtcggcgaa gaccggggtg     660
aggccgatcc agcgcagtgc gtgcgggtg gcggcgaacg tcatcgacgg catgatcact     720
tcgccggtga ggccggcggc gtgcgcgagg agctggagcc cggccgtggc gttgcaggtg     780
gccacggcat gccggacccc ggcgagcccg gcgacgcgct cctcgaactc gcggacgagc     840
gggccgccgt tggacagcca ctggctgtcg agggcccggt cgagccgctc gtacagcctg     900
gcgcggtcga tgcggttggg ccgccccacg aggagcggct ggtcgaaagc ggcggggccg     960
ccgaagaatg cgaggtcgga taaggcgctt ttcacggatg ttccctccgg gccaccgtca    1020
```

-continued

```
cgaaatgatt cgccgatccg ggaatcccga acgaggtcgc cgcgctccac cgtgacgtac      1080
gacgagatgg tcgattgtgg tggtcgattt cgggggggact ctaatccgcg cggaacggga      1140
ccgacaagag cacgctatgc gctctcgatg tgcttcggat cacatccgcc tccggggtat      1200
tccatcggcg gcccgaatgt gatgatcctt gacaggatcc gggaatcagc cgagccgccg      1260
ggagggccgg ggcgcgctcc gcggaagagt acgtgtgaga agtcccgttc ctcttcccgt      1320
ttccgttccg cttccggccc ggtctggagt tctccgtgcg ccgtacccag cagggaacga      1380
ccgcttctcc cccggtactc gacctcgggg ccctggggca ggatttcgcg gccgatccgt      1440
atccgacgta cgcgagactg cgtgccgagg gtccggccca ccgggtgcgc acccccgagg      1500
gggacgaggt gtggctggtc gtcggctacg accgggcgcg ggcggtcctc gccgatcccc      1560
ggttcagcaa ggactggcgc aactccacga ctcccctgac cgaggccgag gccgcgctca      1620 accacaaacat gctggagtcc gacccgccgc ggcacacccg gctgcgcaag ctggtggccc      1680
gtgagttcac catgcgccgg gtcgagttgc tgcggccccg ggtccaggag atcgtcgacg      1740
ggctcgtgga cgccatgctg gcggcgcccg acggccgcgc cgatctgatg gagtccctgg      1800
cctggccgct gccgatcacc gtgatctccg aactcctcgg cgtgcccgag ccggaccgcg      1860
ccgccttccg cgtctggacc gacgccttcg tcttcccgga cgatcccgcc caggcccaga      1920
ccgccatggc cgagatgagc ggctatctct cccggctcat cgactccaag cgcgggcagg      1980
acggcgagga cctgctcagc gcgctcgtgc ggaccagcga cgaggacggc tcccggctga      2040
cctccgagga gctgctcggt atggcccaca tcctgctcgt cgcggggcac gagaccacgg      2100
tcaatctgat cgccaacggc atgtacgcgc tgctctcgca ccccgaccag ctggccgccc      2160
tgcgggccga catgacgctc ttggacggcg cggtggagga gatgttgcgc tacgagggcc      2220
cggtggaatc cgcgacctac cgcttcccgg tcgagcccgt cgacctggac ggcacggtca      2280
tcccggccgg tgacacggtc ctcgtcgtcc tggccgacgc ccaccgcacc cccgagcgct      2340
tcccggaccc gcaccgcttc gacatccgcc gggacaccgc cggccatctc gccttcggcc      2400
acggcatcca cttctgcatc ggcgcccct tggcccggtt ggaggccgcgg atcgccgtcc      2460 gcgcccttct cgaacgctgc ccggacctcg ccctggacgt ctccccccggc gaactcgtgt      2520 ggtatccgaa cccgatgatc cgcgggctca aggccctgcc gatccgctgg cggcgaggac      2580
gggaggcggg ccgccgtacc ggttgaaccc gcacgtcacc cattacgact ccttgtcacg      2640
gaagccccgg atcggtcccc cctcgccgta acaagacctg gttagagtga tggaggacga      2700
cgaagggttc ggcgcccgga cgaggggga cttccgcgat gaatctggtg gaacgcgacg      2760
gggagatagc ccatctcagg gccgttcttg acgcatccgc cgcaggtgac gggacgctct      2820
tactcgtctc cggaccggcc ggcagcggga agacggagct gctgcggtcg ctccgccggc      2880
tggccgccga gcgggagacc cccgtctggt cggtccgggc gctgccgggt gaccgcgaca      2940
tccccctggg cgtcctctgc cagttactcc gcagcgccga caacacggt gccgacacct      3000 ccgccgtccg cgacctgctg gacgccgcct cgcggcgggc cggaacctca cctcccccgc      3060
cgacgcgccg ctccgcgtcg acgagacaca ccgcctgcac gactggctgc tctccgtctc      3120
ccgccggcac cccgttcctc gtcgccgtcg acgacctgac ccacgccgac accgcgtccc      3180
tgaggttcct cctgtactgc gccgcccacc acgaccaggg cggcatcggc ttcgtcatga      3240
ccgagcgggc ctcgcagcgc gccggatacc gggtgttccg cgccgagctg ctccgccagc      3300
cgcactgccg caacatgtgg ctctccgggc ttccccccag cggggtacgc cagttactcg      3360
```

```
cccactacta cggccccgag gccgccgagc ggcgggcccc cgcgtaccac gcgacgaccg    3420
gcgggaaccc gctgctcctg cgggcgctga cccaggaccg gcaggcctcc cacaccaccc    3480
tcggcgcggc cggcggcgac gagcccgtcc acggcgacgc cttcgcccag gccgtcctcg    3540
actgcctgca ccgcagcgcc gagggcacac tggagaccgc ccgctggctc gcggtcctcg    3600
aacagtccga cccgctcctg gtggagcggg tcacgggaac gaccgccgcc gccgtcgagc    3660
gccacatcca ggagctcgcc gccatcggcc tcctggacga ggacggcacc ctgggacagc    3720
ccgcgatccg cgaggccgcc ctccaggacc tgccggccgg cgagcgcacc gaactgcacc    3780
ggcgcgccgc ggagcagctg caccgggacg cgccgacga ggacaccgtg gcccgccacc    3840
tgctggtcgg cggcgccccc gacgctccct gggcgctgcc cctgctcgaa cggggcgcgc    3900
agcaggccct gttcgacgac cgactcgacg acgccttccg gatcctcgag ttcgccgtgc    3960
ggtcgagcac cgacaacacc cagctggccc gcctcgcccc acacctggtc gcggcctcct    4020
ggcggatgaa cccgcacatg acgacccggg ccctcgcact cttcgaccgg ctcctgagcg    4080
gtgaactgcc gccagccac ccggtcatgg ccctgatccg ctgcctcgtc tggtacggnc    4140
ggctgcccga ggccgccgac gcgctgtccc ggctgcggcc cagctccgac aacgatgcct    4200
tggagctgtc gctcacccgg atgtggctcg cggcgctgtg cccgccgctc ctggagtccc    4260
tgccggccac gccggagccg gagcggggtc ccgtccccgt acggctcgcg ccgcggacga    4320
ccgcgctcca ggcccaggcc ggcgtcttcc agcggggccc ggacaacgcc tcggtcgcgc    4380
aggccgaaca gatcctgcag ggctgccggc tgtcggagga gacgtacgag gccctggaga    4440
cggccctctt ggtcctcgtc cacgccgacc ggctcgaccg ggcgctgttc tggtcggacg    4500
ccctgctcgc cgaggccgtg gagcggcggt cgctcggctg ggaggcggtc ttcgccgcga    4560
cccgggcgat gatcgcgatc cgctgcggcg acctcccgac ggcgcgggag cgggccgagc    4620
tggcgctctc ccacgcggcg ccggagagct ggggcctcgc cgtgggcatg ccctctccg    4680
cgctgctgct cgcctgcacg gaggccggcg agtacgaaca ggcggagcgg gtcctgcggc    4740
agccggtgcc ggacgcgatg ttcgactcgc ggcacggcat ggagtacatg cacgcccggg    4800
gccgctactg gctggcgganc ggccggctgc acgcggcgct gggcgagttc atgctctgcg    4860
gggagatcct gggcagctgg aacctcgacc agccctcgat cgtgccctgg cggacctccg    4920
ccgccgaggt gtacctgcgg ctcggcaacc gccagaaggc cagggcgctg ccgaggcccc    4980
agctcgccct ggtgcggccc gggcgctccc gcacccgggg tctcaccctg cgggtcctgg    5040
cggcggcggt ggacggccag caggcggagc ggctgcacgc cgaggcggtc gacatgctgc    5100
acgacagcgg cgaccggctc gaacacgccc gcgcgctcgc cgggatgagc cgccaccagc    5160
aggcccaggg ggacaactac cgggcgagga tgacggcgcg gctcgccggc gacatggcgt    5220
gggcctgcgg cgccgtacccg ctggccgagg agatcgtgcc gggccgcggc ggccgccggg    5280
cgaaggcggt gagcacggag ctggaactgc cgggcggccc ggacgtcggc ctgctctcgg    5340
aggccgaacg ccgggtggcg gccctggcag cccgaggatt gacgaaccgc cagatagcgc    5400
gccggctctg cgtcaccgcg agcacggtcg aacagcacct gacgcgcgtc taccgcaaac    5460
tgaacgtgac ccgccagca gacctcccga tcagcctcgc ccaggacaag tccgtcacgg    5520
cctgagccac cccggtgtc cccgtgcgac gaccgccgc acgggccacc gggcccgccg    5580
ggacacgccg gtgcgacacg ggggcgcgcc aggtgccatg ggacctccg tgaccgcccg    5640
aggcgcccga ggcgccggt gcggcacccg gagacgccga gaccgccggg accaccggag    5700
acgccaggga ccgctgggga caccgggacc tcagggaccg ccgggaccgc ccgagttgca    5760
```

```
cccggtgcgc ccggggacac cagaccgccg ggaccacccg agggtgcccg gtgtggcccc    5820
ggcggccggg gtgtccttca tcggtgggcc ttcatcggca ggaggaagcg accgtgagac    5880
ccgtcgtgcc gtcggcgatc agccgcctgt acgggcgtcg gactccctgg cggtcccgga    5940
cccgtcgtac gggctcgcgg gacccggtgc                                     5970
```

<210> SEQ ID NO 12
<211> LENGTH: 331
<212> TYPE: PRT
<213> ORGANISM: Streptomyces venezuelae

<400> SEQUENCE: 12

```
Val Lys Ser Ala Leu Ser Asp Leu Ala Phe Phe Gly Gly Pro Ala Ala
 1               5                  10                  15

Phe Asp Gln Pro Leu Leu Val Gly Arg Pro Asn Arg Ile Asp Arg Ala
                20                  25                  30

Arg Leu Tyr Glu Arg Leu Asp Arg Ala Leu Asp Ser Gln Trp Leu Ser
            35                  40                  45

Asn Gly Gly Pro Leu Val Arg Glu Phe Glu Arg Val Ala Gly Leu
        50                  55                  60

Ala Gly Val Arg His Ala Val Ala Thr Cys Asn Ala Thr Ala Gly Leu
 65                  70                  75                  80

Gln Leu Leu Ala His Ala Ala Gly Leu Thr Gly Glu Val Ile Met Pro
                85                  90                  95

Ser Met Thr Phe Ala Ala Thr Pro His Ala Leu Arg Trp Ile Gly Leu
                100                 105                 110

Thr Pro Val Phe Ala Asp Ile Asp Pro Asp Thr Gly Asn Leu Asp Pro
            115                 120                 125

Asp Gln Val Ala Ala Ala Val Thr Pro Arg Thr Ser Ala Val Val Gly
        130                 135                 140

Val His Leu Trp Gly Arg Pro Cys Ala Ala Asp Gln Leu Arg Lys Val
145                 150                 155                 160

Ala Asp Glu His Gly Leu Arg Leu Tyr Phe Asp Ala Ala His Ala Leu
                165                 170                 175

Gly Cys Ala Val Asp Gly Arg Pro Ala Gly Ser Leu Gly Asp Ala Glu
            180                 185                 190

Val Phe Ser Phe His Ala Thr Lys Ala Val Asn Ala Phe Glu Gly Gly
        195                 200                 205

Ala Val Val Thr Asp Asp Ala Asp Leu Ala Ala Arg Ile Arg Ala Leu
    210                 215                 220

His Asn Phe Gly Phe Asp Leu Pro Gly Gly Ser Pro Ala Gly Gly Thr
225                 230                 235                 240

Asn Ala Lys Met Ser Glu Ala Ala Ala Met Gly Leu Thr Ser Leu
                245                 250                 255

Asp Ala Phe Pro Glu Val Ile Asp Arg Asn Arg Arg Asn His Ala Xaa
            260                 265                 270

Tyr Arg Glu His Leu Ala Asp Leu Pro Gly Val Leu Val Ala Asp His
        275                 280                 285

Asp Arg His Gly Leu Asn Asn His Gln Tyr Val Ile Val Glu Ile Asp
    290                 295                 300

Glu Ala Thr Thr Gly Ile His Arg Asp Leu Val Met Glu Val Leu Lys
305                 310                 315                 320

Ala Glu Gly Val His Thr Arg Ala Tyr Phe Ser
                325                 330
```

<210> SEQ ID NO 13
<211> LENGTH: 416
<212> TYPE: PRT
<213> ORGANISM: Streptomyces venezuelae

<400> SEQUENCE: 13

```
Val Arg Arg Thr Gln Gln Gly Thr Thr Ala Ser Pro Pro Val Leu Asp
  1               5                  10                  15

Leu Gly Ala Leu Gly Gln Asp Phe Ala Ala Asp Pro Tyr Pro Thr Tyr
             20                  25                  30

Ala Arg Leu Arg Ala Glu Gly Pro Ala His Arg Val Arg Thr Pro Glu
         35                  40                  45

Gly Asp Glu Val Trp Leu Val Gly Tyr Asp Arg Ala Arg Ala Val
     50                  55                  60

Leu Ala Asp Pro Arg Phe Ser Lys Asp Trp Arg Asn Ser Thr Thr Pro
 65                  70                  75                  80

Leu Thr Glu Ala Glu Ala Ala Leu Asn His Asn Met Leu Glu Ser Asp
                 85                  90                  95

Pro Pro Arg His Thr Arg Leu Arg Lys Leu Val Ala Arg Glu Phe Thr
            100                 105                 110

Met Arg Arg Val Glu Leu Leu Arg Pro Arg Val Gln Glu Ile Val Asp
        115                 120                 125

Gly Leu Val Asp Ala Met Leu Ala Ala Pro Asp Gly Arg Ala Asp Leu
    130                 135                 140

Met Glu Ser Leu Ala Trp Pro Leu Pro Ile Thr Val Ile Ser Glu Leu
145                 150                 155                 160

Leu Gly Val Pro Glu Pro Asp Arg Ala Ala Phe Arg Val Trp Thr Asp
                165                 170                 175

Ala Phe Val Phe Pro Asp Asp Pro Ala Gln Ala Gln Thr Ala Met Ala
            180                 185                 190

Glu Met Ser Gly Tyr Leu Ser Arg Leu Ile Asp Ser Lys Arg Gly Gln
        195                 200                 205

Asp Gly Glu Asp Leu Leu Ser Ala Leu Val Arg Thr Ser Asp Glu Asp
    210                 215                 220

Gly Ser Arg Leu Thr Ser Glu Glu Leu Leu Gly Met Ala His Ile Leu
225                 230                 235                 240

Leu Val Ala Gly His Glu Thr Thr Val Asn Leu Ile Ala Asn Gly Met
                245                 250                 255

Tyr Ala Leu Leu Ser His Pro Asp Gln Leu Ala Ala Leu Arg Ala Asp
            260                 265                 270

Met Thr Leu Leu Asp Gly Ala Val Glu Glu Met Leu Arg Tyr Glu Gly
        275                 280                 285

Pro Val Glu Ser Ala Thr Tyr Arg Phe Pro Val Glu Pro Val Asp Leu
    290                 295                 300

Asp Gly Thr Val Ile Pro Ala Gly Asp Thr Val Leu Val Leu Ala
305                 310                 315                 320

Asp Ala His Arg Thr Pro Glu Arg Phe Pro Asp Pro His Arg Phe Asp
                325                 330                 335

Ile Arg Arg Asp Thr Ala Gly His Leu Ala Phe Gly His Gly Ile His
            340                 345                 350

Phe Cys Ile Gly Ala Pro Leu Ala Arg Leu Glu Ala Arg Ile Ala Val
        355                 360                 365

Arg Ala Leu Leu Glu Arg Cys Pro Asp Leu Ala Leu Asp Val Ser Pro
```

-continued

```
                370             375             380
Gly Glu Leu Val Trp Tyr Pro Asn Pro Met Ile Arg Gly Leu Lys Ala
385                 390                 395                 400

Leu Pro Ile Arg Trp Arg Arg Gly Arg Glu Ala Gly Arg Arg Thr Gly
                405                 410                 415

<210> SEQ ID NO 14
<211> LENGTH: 928
<212> TYPE: PRT
<213> ORGANISM: Streptomyces venezuelae

<400> SEQUENCE: 14

Met Asn Leu Val Glu Arg Asp Gly Glu Ile Ala His Leu Arg Ala Val
  1               5                  10                  15

Leu Asp Ala Ser Ala Ala Gly Asp Gly Thr Leu Leu Leu Val Ser Gly
                 20                  25                  30

Pro Ala Gly Ser Gly Lys Thr Glu Leu Leu Arg Ser Leu Arg Arg Leu
             35                  40                  45

Ala Ala Glu Arg Glu Thr Pro Val Trp Ser Val Arg Ala Leu Pro Gly
         50                  55                  60

Asp Arg Asp Ile Pro Leu Gly Val Leu Cys Gln Leu Leu Arg Ser Ala
 65                  70                  75                  80

Glu Gln His Gly Ala Asp Thr Ser Ala Val Arg Asp Leu Leu Asp Ala
                 85                  90                  95

Ala Ser Arg Arg Ala Gly Thr Ser Pro Pro Pro Thr Arg Arg Ser
            100                 105                 110

Ala Ser Thr Arg His Thr Ala Cys Thr Thr Gly Cys Ser Pro Ser Pro
            115                 120                 125

Ala Gly Thr Pro Phe Leu Val Ala Val Asp Asp Leu Thr His Ala Asp
        130                 135                 140

Thr Ala Ser Leu Arg Phe Leu Leu Tyr Cys Ala Ala His His Asp Gln
145                 150                 155                 160

Gly Gly Ile Gly Phe Val Met Thr Glu Arg Ala Ser Gln Arg Ala Gly
                165                 170                 175

Tyr Arg Val Phe Arg Ala Glu Leu Leu Arg Gln Pro His Cys Arg Asn
            180                 185                 190

Met Trp Leu Ser Gly Leu Pro Pro Ser Gly Val Arg Gln Leu Leu Ala
        195                 200                 205

His Tyr Tyr Gly Pro Glu Ala Ala Glu Arg Arg Ala Pro Ala Tyr His
    210                 215                 220

Ala Thr Thr Gly Gly Asn Pro Leu Leu Leu Arg Ala Leu Thr Gln Asp
225                 230                 235                 240

Arg Gln Ala Ser His Thr Thr Leu Gly Ala Ala Gly Gly Asp Glu Pro
                245                 250                 255

Val His Gly Asp Ala Phe Ala Gln Ala Val Leu Asp Cys Leu His Arg
            260                 265                 270

Ser Ala Glu Gly Thr Leu Glu Thr Ala Arg Trp Leu Ala Val Leu Glu
        275                 280                 285

Gln Ser Asp Pro Leu Leu Val Glu Arg Leu Thr Gly Thr Thr Ala Ala
    290                 295                 300

Ala Val Glu Arg His Ile Gln Glu Leu Ala Ala Ile Gly Leu Leu Asp
305                 310                 315                 320

Glu Asp Gly Thr Leu Gly Gln Pro Ala Ile Arg Glu Ala Ala Leu Gln
                325                 330                 335
```

```
Asp Leu Pro Ala Gly Glu Arg Thr Glu Leu His Arg Arg Ala Glu
        340                 345                 350

Gln Leu His Arg Asp Gly Ala Asp Glu Asp Thr Val Ala Arg His Leu
        355                 360                 365

Leu Val Gly Gly Ala Pro Asp Ala Pro Trp Ala Leu Pro Leu Leu Glu
        370                 375                 380

Arg Gly Ala Gln Gln Ala Leu Phe Asp Asp Arg Leu Asp Asp Ala Phe
385                 390                 395                 400

Arg Ile Leu Glu Phe Ala Val Arg Ser Ser Thr Asp Asn Thr Gln Leu
                405                 410                 415

Ala Arg Leu Ala Pro His Leu Val Ala Ala Ser Trp Arg Met Asn Pro
        420                 425                 430

His Met Thr Thr Arg Ala Leu Ala Leu Phe Asp Arg Leu Leu Ser Gly
        435                 440                 445

Glu Leu Pro Pro Ser His Pro Val Met Ala Leu Ile Arg Cys Leu Val
        450                 455                 460

Trp Tyr Gly Arg Leu Pro Glu Ala Ala Asp Ala Leu Ser Arg Leu Arg
465                 470                 475                 480

Pro Ser Ser Asp Asn Asp Ala Leu Glu Leu Ser Leu Thr Arg Met Trp
                485                 490                 495

Leu Ala Ala Leu Cys Pro Pro Leu Leu Glu Ser Leu Pro Ala Thr Pro
        500                 505                 510

Glu Pro Glu Arg Gly Pro Val Pro Val Arg Leu Ala Pro Arg Thr Thr
        515                 520                 525

Ala Leu Gln Ala Gln Ala Gly Val Phe Gln Arg Gly Pro Asp Asn Ala
        530                 535                 540

Ser Val Ala Gln Ala Glu Gln Ile Leu Gln Gly Cys Arg Leu Ser Glu
545                 550                 555                 560

Glu Thr Tyr Glu Ala Leu Glu Thr Ala Leu Leu Val Leu Val His Ala
                565                 570                 575

Asp Arg Leu Asp Arg Ala Leu Phe Trp Ser Asp Ala Leu Leu Ala Glu
        580                 585                 590

Ala Val Glu Arg Arg Ser Leu Gly Trp Glu Ala Val Phe Ala Ala Thr
        595                 600                 605

Arg Ala Met Ile Ala Ile Arg Cys Gly Asp Leu Pro Thr Ala Arg Glu
        610                 615                 620

Arg Ala Glu Leu Ala Leu Ser His Ala Ala Pro Glu Ser Trp Gly Leu
625                 630                 635                 640

Ala Val Gly Met Pro Leu Ser Ala Leu Leu Ala Cys Thr Glu Ala
                645                 650                 655

Gly Glu Tyr Glu Gln Ala Glu Arg Val Leu Arg Gln Pro Val Pro Asp
        660                 665                 670

Ala Met Phe Asp Ser Arg His Gly Met Glu Tyr Met His Ala Arg Gly
        675                 680                 685

Arg Tyr Trp Leu Ala Xaa Gly Arg Leu His Ala Leu Gly Glu Phe
690                 695                 700

Met Leu Cys Gly Glu Ile Leu Gly Ser Trp Asn Leu Asp Gln Pro Ser
705                 710                 715                 720

Ile Val Pro Trp Arg Thr Ser Ala Ala Glu Val Tyr Leu Arg Leu Gly
                725                 730                 735

Asn Arg Gln Lys Ala Arg Ala Leu Ala Glu Ala Gln Leu Ala Leu Val
        740                 745                 750

Arg Pro Gly Arg Ser Arg Thr Arg Gly Leu Thr Leu Arg Val Leu Ala
```

```
                755              760              765
    Ala Ala Val Asp Gly Gln Gln Ala Glu Arg Leu His Ala Glu Ala Val
            770              775              780
    Asp Met Leu His Asp Ser Gly Asp Arg Leu Glu His Ala Arg Ala Leu
    785              790              795              800
    Ala Gly Met Ser Arg His Gln Gln Ala Gln Gly Asp Asn Tyr Arg Ala
                    805              810              815
    Arg Met Thr Ala Arg Leu Ala Gly Asp Met Ala Trp Ala Cys Gly Ala
                820              825              830
    Tyr Pro Leu Ala Glu Glu Ile Val Pro Gly Arg Gly Arg Arg Ala
                    835              840              845
    Lys Ala Val Ser Thr Glu Leu Glu Leu Pro Gly Gly Pro Asp Val Gly
        850              855              860
    Leu Leu Ser Glu Ala Glu Arg Arg Val Ala Ala Leu Ala Ala Arg Gly
    865              870              875              880
    Leu Thr Asn Arg Gln Ile Ala Arg Arg Leu Cys Val Thr Ala Ser Thr
                    885              890              895
    Val Glu Gln His Leu Thr Arg Val Tyr Arg Lys Leu Asn Val Thr Arg
                900              905              910
    Arg Ala Asp Leu Pro Ile Ser Leu Ala Gln Asp Lys Ser Val Thr Ala
                    915              920              925

<210> SEQ ID NO 15
<211> LENGTH: 3292
<212> TYPE: DNA
<213> ORGANISM: Streptomyces venezuelae

<400> SEQUENCE: 15 acccccaaa ggggtggtga cactccccct gcgcagcccc tagcgccccc ctaactcgcc      60
acgccgaccg ttatcaccgg cgccctgctg ctagtttccg agaatgaagg gaatagtcct    120
ggccggcggg agcggaactc ggctgcatcc ggcgacctcg gtcatttcga agcagattct    180
tccggtctac aacaaaccga tgatctacta tccgctgtcg gttctcatgc tcggcggtat    240
tcgcgagatt caaatcatct cgacccccca gcacatcgaa ctcttccagt cgcttctcgg    300
aaacggcagg cacctgggaa tagaactcga ctatgcggtc cagaaagagc cgcaggaat    360
cgcggacgca cttctcgtcg gagccgagca catcggcgac gacacctgcg ccctgatcct    420
gggcgacaac atcttccacg ggcccggcct ctacacgctc ctgcgggaca gcatcgcgcg    480
cctcgacggc tgcgtgctct cggctaccc ggtcaaggac cccgagcggt acggcgtcgc    540
cgaggtggac gcgacgggcc ggctgaccga cctcgtcgag aagcccgtca gccgcgctc    600
caacctcgcc gtcaccggcc tctacctcta cgacaacgac gtcgtcgaca tcgccaagaa    660
catccggccc tcgccgcgcg cgagctgga gatcaccgac gtcaaccgcg tctacctgga    720
gcggggccgg gccgaactcg tcaacctggg ccgcggcttc gcctggctgg acaccggcac    780
ccacgactcg ctcctgcggg ccgcccagta cgtccaggtc ctggaggagc ggcagggcgt    840
ctggatcgcg ggccttgagg agatcgcctt ccgcatgggc ttcatcgacg ccgaggcctg    900
tcacggcctg ggagaaggcc tctcccgcac cgagtacggc agctatctga tggagatcgc    960
cggccgcgag ggagccccgt gagggcacct cgcggccgac gcgttccac gaccgacagc   1020
gccaccgaca gtgcgaccca caccgcgacc cgcaccgcca ccgacagtgc gacccacacc   1080
gcgacctaca gcgcgaccga aaggaagacg gcagtgcggc ttctggtgac cggaggtgcg   1140
ggcttcatcg gctcgcactt cgtgcggcag ctcctcgccg ggcgtacccc gacgtgccc   1200
```

```
gccgatgagg tgatcgtcct ggacagcctc acctacgcgg gcaaccgcgc caacctcgcc   1260
ccggtggacg cggacccgcg actgcgcttc gtccacggcg acatccgcga cgccggcctc   1320
ctcgcccggg aactgcgcgg cgtggacgcc atcgtccact tcgcggccga gagccacgtg   1380
gaccgctcca tcgcgggcgc gtccgtgttc accgagacca acgtgcaggg cacgcagacg   1440
ctgctccagt gcgccgtcga cgccggcgtc ggccgggtcg tgcacgtctc caccgacgag   1500
gtgtacgggt cgatcgactc cggctcctgg accgagagca gcccgctgga gcccaactcg   1560
ccctacgcgg cgtccaaggc cggctccgac ctcgttgccc gcgcctacca ccggacgtac   1620
ggcctcgacg tacggatcac ccgctgctgc aacaactacg ggccgtacca gcaccccgag   1680
aagctcatcc ccctcttcgt gacgaacctc ctcgacggcg ggacgctccc gctgtacggc   1740
gacggcgcga acgtccgcga gtgggtgcac accgacgacc actgccgggg catcgcgctc   1800
gtcctcgcgg gcggccgggc cggcgagatc taccacatcg gcggcggcct ggagctgacc   1860
aaccgcgaac tcaccggcat cctcctggac tcgctcggcg ccgactggtc ctcggtccgg   1920 aagtcgccg accgcaaggg ccacgacctg cgctactccc tcgacggcgg caagatcgag   1980
cgcgagctcg gctaccgccc gcaggtctcc ttcgcggacg gcctcgcgcg gaccgtccgc   2040
tggtaccggg agaaccgcgg ctggtgggag ccgctcaagg cgaccgcccc gcagctgccc   2100
gccaccgccg tggaggtgtc cgcgtgagca gccgcgccga gaccccccgc gtccccttcc   2160
tcgacctcaa ggccgcctac gaggagctcc gcgcggagac cgacgccgcg atcgcccgcg   2220
tcctcgactc ggggcgctac ctcctcggac ccgaactcga aggattcgag gcggagttcg   2280
ccgcgtactg cgagacggac cacgccgtcg gcgtgaacag cgggatggac gccctccagc   2340
tcgccctccg cggcctcggc atcggacccg gggacgaggt gatcgtcccc tcgcacacgt   2400
acatcgccag ctggctcgcg gtgtccgcca ccggcgcgac cccgtgccc gtcgagccgc   2460 acgaggacca ccccaccctg gaccgctgc tcgtcgagaa ggcgatcacc ccccgcaccc   2520
gggcgctcct ccccgtccac ctctacgggc acccgccga catggacgcc ctccgcgagc   2580
tcgcggaccg gcacggcctg cacatcgtcg aggacgccgc gcaggccac ggcgcccgct   2640 accggggccg gcggatcggc gccgggtcgt cggtggccgc gttcagcttc tacccgggca   2700
agaacctcgg ctgcttcggc gacggcggcg ccgtcgtcac cggcgacccc gagctcgccg   2760
aacggctccg gatgctccgc aactacggct cgcggcagaa gtacagccac gagacgaagg   2820
gcaccaactc ccgcctggac gagatgcagg ccgccgtgct gcggatccgg ctcgnccacc   2880
tggacagctg gaacgccgc aggtcggcgc tggccgcgga gtacctctcc gggctcgccg   2940
gactgcccgg catcggcctg ccggtgaccg cgcccgacac cgacccggtc tggcacctct   3000
tcaccgtgcg caccgagcgc cgcgacgagc tgcgcagcca cctcgacgcc cgcggcatcg   3060
acaccctcac gcactacccg gtaccgtgc acctctcgcc cgcctacgcg ggcgaggcac   3120
cgccggaagg ctcgctcccg cgggccgaga gcttcgcgcg gcaggtcctc agcctgccga   3180
tcggcccgca cctggagcgc ccgcaggcgc tgcgggtgat cgacgccgtg cgcgaatggg   3240
ccgagcgggt cgaccaggcc tagtcaggtg gtccggtaga cccagcaggc cg           3292
```

<210> SEQ ID NO 16
<211> LENGTH: 292
<212> TYPE: PRT
<213> ORGANISM: Streptomyces venezuelae

<400> SEQUENCE: 16

-continued

```
Met Lys Gly Ile Val Leu Ala Gly Gly Ser Gly Thr Arg Leu His Pro
  1               5                  10                  15

Ala Thr Ser Val Ile Ser Lys Gln Ile Leu Pro Val Tyr Asn Lys Pro
             20                  25                  30

Met Ile Tyr Tyr Pro Leu Ser Val Leu Met Leu Gly Gly Ile Arg Glu
             35                  40                  45

Ile Gln Ile Ile Ser Thr Pro Gln His Ile Glu Leu Phe Gln Ser Leu
 50                  55                  60

Leu Gly Asn Gly Arg His Leu Gly Ile Glu Leu Asp Tyr Ala Val Gln
 65                  70                  75                  80

Lys Glu Pro Ala Gly Ile Ala Asp Ala Leu Leu Val Gly Ala Glu His
             85                  90                  95

Ile Gly Asp Asp Thr Cys Ala Leu Ile Leu Gly Asp Asn Ile Phe His
            100                 105                 110

Gly Pro Gly Leu Tyr Thr Leu Leu Arg Asp Ser Ile Ala Arg Leu Asp
            115                 120                 125

Gly Cys Val Leu Phe Gly Tyr Pro Val Lys Asp Pro Glu Arg Tyr Gly
130                 135                 140

Val Ala Glu Val Asp Ala Thr Gly Arg Leu Thr Asp Leu Val Glu Lys
145                 150                 155                 160

Pro Val Lys Pro Arg Ser Asn Leu Ala Val Thr Gly Leu Tyr Leu Tyr
            165                 170                 175

Asp Asn Asp Val Val Asp Ile Ala Lys Asn Ile Arg Pro Ser Pro Arg
            180                 185                 190

Gly Glu Leu Glu Ile Thr Asp Val Asn Arg Val Tyr Leu Glu Arg Gly
            195                 200                 205

Arg Ala Glu Leu Val Asn Leu Gly Arg Gly Phe Ala Trp Leu Asp Thr
210                 215                 220

Gly Thr His Asp Ser Leu Leu Arg Ala Ala Gln Tyr Val Gln Val Leu
225                 230                 235                 240

Glu Glu Arg Gln Gly Val Trp Ile Ala Gly Leu Glu Glu Ile Ala Phe
            245                 250                 255

Arg Met Gly Phe Ile Asp Ala Glu Ala Cys His Gly Leu Gly Glu Gly
            260                 265                 270

Leu Ser Arg Thr Glu Tyr Gly Ser Tyr Leu Met Glu Ile Ala Gly Arg
            275                 280                 285

Glu Gly Ala Pro
            290
```

<210> SEQ ID NO 17
<211> LENGTH: 337
<212> TYPE: PRT
<213> ORGANISM: Streptomyces venezuelae

<400> SEQUENCE: 17

```
Val Arg Leu Leu Val Thr Gly Gly Ala Gly Phe Ile Gly Ser His Phe
  1               5                  10                  15

Val Arg Gln Leu Leu Ala Gly Ala Tyr Pro Asp Val Pro Ala Asp Glu
             20                  25                  30

Val Ile Val Leu Asp Ser Leu Thr Tyr Ala Gly Asn Arg Ala Asn Leu
             35                  40                  45

Ala Pro Val Asp Ala Asp Pro Arg Leu Arg Phe Val His Gly Asp Ile
 50                  55                  60

Arg Asp Ala Gly Leu Leu Ala Arg Glu Leu Arg Gly Val Asp Ala Ile
 65                  70                  75                  80
```

```
Val His Phe Ala Ala Glu Ser His Val Asp Arg Ser Ile Ala Gly Ala
                85                  90                  95

Ser Val Phe Thr Glu Thr Asn Val Gln Gly Thr Gln Thr Leu Leu Gln
            100                 105                 110

Cys Ala Val Asp Ala Gly Val Gly Arg Val His Val Ser Thr Asp
            115                 120                 125

Glu Val Tyr Gly Ser Ile Asp Ser Gly Ser Trp Thr Glu Ser Ser Pro
        130                 135                 140

Leu Glu Pro Asn Ser Pro Tyr Ala Ala Ser Lys Ala Gly Ser Asp Leu
145                 150                 155                 160

Val Ala Arg Ala Tyr His Arg Thr Tyr Gly Leu Asp Val Arg Ile Thr
                165                 170                 175

Arg Cys Cys Asn Asn Tyr Gly Pro Tyr Gln His Pro Glu Lys Leu Ile
                180                 185                 190

Pro Leu Phe Val Thr Asn Leu Leu Asp Gly Gly Thr Leu Pro Leu Tyr
            195                 200                 205

Gly Asp Gly Ala Asn Val Arg Glu Trp Val His Thr Asp Asp His Cys
        210                 215                 220

Arg Gly Ile Ala Leu Val Leu Ala Gly Gly Arg Ala Gly Glu Ile Tyr
225                 230                 235                 240

His Ile Gly Gly Gly Leu Glu Leu Thr Asn Arg Glu Leu Thr Gly Ile
                245                 250                 255

Leu Leu Asp Ser Leu Gly Ala Asp Trp Ser Ser Val Arg Lys Val Ala
            260                 265                 270

Asp Arg Lys Gly His Asp Leu Arg Tyr Ser Leu Asp Gly Gly Lys Ile
            275                 280                 285

Glu Arg Glu Leu Gly Tyr Arg Pro Gln Val Ser Phe Ala Asp Gly Leu
        290                 295                 300

Ala Arg Thr Val Arg Trp Tyr Arg Glu Asn Arg Gly Trp Trp Glu Pro
305                 310                 315                 320

Leu Lys Ala Thr Ala Pro Gln Leu Pro Ala Thr Ala Val Glu Val Ser
                325                 330                 335

Ala

<210> SEQ ID NO 18
<211> LENGTH: 379
<212> TYPE: PRT
<213> ORGANISM: Streptomyces venezuelae

<400> SEQUENCE: 18

Val Ser Ser Arg Ala Glu Thr Pro Arg Val Pro Phe Leu Asp Leu Lys
1               5                   10                  15

Ala Ala Tyr Glu Glu Leu Arg Ala Glu Thr Asp Ala Ala Ile Ala Arg
                20                  25                  30

Val Leu Asp Ser Gly Arg Tyr Leu Leu Gly Pro Glu Leu Glu Gly Phe
            35                  40                  45

Glu Ala Glu Phe Ala Ala Tyr Cys Glu Thr Asp His Ala Val Gly Val
        50                  55                  60

Asn Ser Gly Met Asp Ala Leu Gln Leu Ala Leu Arg Gly Leu Gly Ile
65                  70                  75                  80

Gly Pro Gly Asp Glu Val Ile Val Pro Ser His Thr Tyr Ile Ala Ser
                85                  90                  95

Trp Leu Ala Val Ser Ala Thr Gly Ala Thr Pro Val Pro Val Glu Pro
            100                 105                 110
```

His Glu Asp His Pro Thr Leu Asp Pro Leu Leu Val Glu Lys Ala Ile
            115                 120                 125

Thr Pro Arg Thr Arg Ala Leu Leu Pro Val His Leu Tyr Gly His Pro
    130                 135                 140

Ala Asp Met Asp Ala Leu Arg Glu Leu Ala Asp Arg His Gly Leu His
145                 150                 155                 160

Ile Val Glu Asp Ala Ala Gln Ala His Gly Ala Arg Tyr Arg Gly Arg
                165                 170                 175

Arg Ile Gly Ala Gly Ser Ser Val Ala Ala Phe Ser Phe Tyr Pro Gly
            180                 185                 190

Lys Asn Leu Gly Cys Phe Gly Asp Gly Gly Ala Val Val Thr Gly Asp
        195                 200                 205

Pro Glu Leu Ala Glu Arg Leu Arg Met Leu Arg Asn Tyr Gly Ser Arg
    210                 215                 220

Gln Lys Tyr Ser His Glu Thr Lys Gly Thr Asn Ser Arg Leu Asp Glu
225                 230                 235                 240

Met Gln Ala Ala Val Leu Arg Ile Arg Leu Xaa His Leu Asp Ser Trp
                245                 250                 255

Asn Gly Arg Arg Ser Ala Leu Ala Ala Glu Tyr Leu Ser Gly Leu Ala
            260                 265                 270

Gly Leu Pro Gly Ile Gly Leu Pro Val Thr Ala Pro Asp Thr Asp Pro
        275                 280                 285

Val Trp His Leu Phe Thr Val Arg Thr Glu Arg Arg Asp Glu Leu Arg
    290                 295                 300

Ser His Leu Asp Ala Arg Gly Ile Asp Thr Leu Thr His Tyr Pro Val
305                 310                 315                 320

Pro Val His Leu Ser Pro Ala Tyr Ala Gly Glu Ala Pro Pro Glu Gly
                325                 330                 335

Ser Leu Pro Arg Ala Glu Ser Phe Ala Arg Gln Val Leu Ser Leu Pro
            340                 345                 350

Ile Gly Pro His Leu Glu Arg Pro Gln Ala Leu Arg Val Ile Asp Ala
        355                 360                 365

Val Arg Glu Trp Ala Glu Arg Val Asp Gln Ala
    370                 375

<210> SEQ ID NO 19
<211> LENGTH: 1693
<212> TYPE: DNA
<213> ORGANISM: Streptomyces venezuelae

<400> SEQUENCE: 19
atgcggcacc ccttggcgcc gagcgtggtg atccaggtgc cgacccgggc gagcacctcc      60
tgctcggtcc agcccgtctt gctgagcagc agcgcccgct cgtaggcgtt cgtgaacagc     120
agctcggctc cgtcgacgag ctcccggacg ctgtcgccct ccagccgggc gagctgctgc     180
gaggggtccg cggcccggcg gaggcccagc tcgcggcaga cccgcgtgtg ccgcaccatc     240 gcctcgggt cgtccgcgcc gacgaggacg aggtcgatcc cgccgggccg gccggccgtc     300
tcgcccaggt cgatgtcgcg cgcctcggcc atcgcgcccg cgtagaacga ggcgagctga     360
ttgccgtcct cgtcggtggt gcacatgaag cgggcggtgt gctgacggtc cgacacccgc     420
acggagtcgg tgtcgacgcc cgcggcgcgg agcagctgcc cgtacccgtc gaagtccttg     480
ccgacggcgc cgacgaggac ggggcggcga ccgagcaggc cgaggccgta cgcgatgttg     540
gcggcgacgc cgccgtgccg gatgtccagg tgtcgacga ggaacgacag ggacacgtgg      600

```
gcgagctggt ccggcaggat ctgctcggcg aagcggcccg ggaaggtcat caggtggtcg      660
gtggcgatcg acccggtgac ggctatacgc atgtcagagc cccgcggcct tcttcagggc      720
gtccacgcgg tcggtgcgct cccaggtgaa gtccggcagc tcgcggccga agtggccgta      780
ggcggcggtc tgggagtaga tcgggcggag caggtcgagg tcgcggatga tcgcggccgg      840
gcggaggtcg aagacctcgc cgatggcgtt ctcgatcttc tcggtctcga tcttgtgggt      900
gccgaaggtc tcgacgaaga ggccgacggg ctcggccttg ccgatcgcgt acgcgacctg      960
gacctcgcag cgcgaggcga daccggcggc gacgacgttc ttcgccaccc agcgcatcgc     1020
gtacgcggcg gagcggtcga ccttcgacgg gtccttgccg agaaggcgc cgccaccgtg     1080
gcgggccatg ccgccgtagg tgtcgatgat gatcttgcgg ccggtgaggc cggcgtcgcc     1140
catcgggccg ccgatctcga agcgaccggt cgggttcacg agcaggcggt agccgtcggt     1200
gtcgagcttg atgccgtcct cgacgagctg cgcaagcacg tgctcgacga cgaacttccg     1260
cacgtcgggg gcgagcagcg actccaggtc gatgtccgag gcgtgctgcg aggagacgac     1320
gaccgtgtcg agacggaccg ccctgtcgcc gtcgtactcg atggtgacct gggtcttgcc     1380
gtcgggacgc aggtacggga tggtcccgtt cttgcggacc tcggtcaggc ggcgcgagag     1440
acggtgcgcg aggtggatcg gcagcggcat cagctcgggc gtctcgtccg aggcatagcc     1500
gaacatcagg ccctggtcac cggcgccctg cttgtcgagc tcgtccccct cgtcccgctg     1560
ggaggcaccc tcgacccgct tctcgtacgc ggtgtcgaca ccctgggcga tgtccgggga     1620
ctgcgacccg atggacaccg acacgccgca ggaggcgccg tcgaagccct tcttcgagga     1680
gtcgtacccg atc                                                        1693
```

<210> SEQ ID NO 20
<211> LENGTH: 332
<212> TYPE: PRT
<213> ORGANISM: Streptomyces venezuelae

<400> SEQUENCE: 20

```
Ile Gly Tyr Asp Ser Ser Lys Lys Gly Phe Asp Gly Ala Ser Cys Gly
  1               5                  10                  15

Val Ser Val Ser Ile Gly Ser Gln Ser Pro Asp Ile Ala Gln Gly Val
             20                  25                  30

Asp Thr Ala Tyr Glu Lys Arg Val Glu Gly Ala Ser Gln Arg Asp Glu
         35                  40                  45

Gly Asp Glu Leu Asp Lys Gln Gly Ala Gly Asp Gln Gly Leu Met Phe
     50                  55                  60

Gly Tyr Ala Ser Asp Glu Thr Pro Glu Leu Met Pro Leu Pro Ile His
 65                  70                  75                  80

Leu Ala His Arg Leu Ser Arg Arg Leu Thr Glu Val Arg Lys Asn Gly
                 85                  90                  95

Thr Ile Pro Tyr Leu Arg Pro Asp Gly Lys Thr Gln Val Thr Ile Glu
            100                 105                 110

Tyr Asp Gly Asp Arg Ala Val Arg Leu Asp Thr Val Val Ser Ser
        115                 120                 125

Gln His Ala Ser Asp Ile Asp Leu Glu Ser Leu Leu Ala Pro Asp Val
    130                 135                 140

Arg Lys Phe Val Val Glu His Val Leu Ala Gln Leu Val Glu Asp Gly
145                 150                 155                 160

Ile Lys Leu Asp Thr Asp Gly Tyr Arg Leu Val Asn Pro Thr Gly
                165                 170                 175
```

-continued

```
Arg Phe Glu Ile Gly Gly Pro Met Gly Asp Ala Gly Leu Thr Gly Arg
            180                 185                 190
Lys Ile Ile Ile Asp Thr Tyr Gly Gly Met Ala Arg His Gly Gly Gly
        195                 200                 205
Ala Phe Ser Gly Lys Asp Pro Ser Lys Val Asp Arg Ser Ala Ala Tyr
    210                 215                 220
Ala Met Arg Trp Val Ala Lys Asn Val Val Ala Ala Gly Leu Ala Ser
225                 230                 235                 240
Arg Cys Glu Val Gln Val Ala Tyr Ala Ile Gly Lys Ala Glu Pro Val
                245                 250                 255
Gly Leu Phe Val Glu Thr Phe Gly Thr His Lys Ile Glu Thr Glu Lys
            260                 265                 270
Ile Glu Asn Ala Ile Gly Glu Val Phe Asp Leu Arg Pro Ala Ala Ile
        275                 280                 285
Ile Arg Asp Leu Asp Leu Leu Arg Pro Ile Tyr Ser Gln Thr Ala Ala
    290                 295                 300
Tyr Gly His Phe Gly Arg Glu Leu Pro Asp Phe Thr Trp Glu Arg Thr
305                 310                 315                 320
Asp Arg Val Asp Ala Leu Lys Lys Ala Ala Gly Leu
                325                 330

<210> SEQ ID NO 21
<211> LENGTH: 230
<212> TYPE: PRT
<213> ORGANISM: Streptomyces venezuelae

<400> SEQUENCE: 21

Met Arg Ile Ala Val Thr Gly Ser Ile Ala Thr Asp His Leu Met Thr
  1               5                  10                  15
Phe Pro Gly Arg Phe Ala Glu Gln Ile Leu Pro Asp Gln Leu Ala His
             20                  25                  30
Val Ser Leu Ser Phe Leu Val Asp Thr Leu Asp Ile Arg His Gly Gly
         35                  40                  45
Val Ala Ala Asn Ile Ala Tyr Gly Leu Gly Leu Leu Gly Arg Arg Pro
     50                  55                  60
Val Leu Val Gly Ala Val Gly Lys Asp Phe Asp Gly Tyr Gly Gln Leu
 65                  70                  75                  80
Leu Arg Ala Ala Gly Val Asp Thr Asp Ser Val Arg Val Ser Asp Arg
                 85                  90                  95
Gln His Thr Ala Arg Phe Met Cys Thr Thr Asp Glu Asp Gly Asn Gln
            100                 105                 110
Leu Ala Ser Phe Tyr Ala Gly Ala Met Ala Glu Ala Arg Asp Ile Asp
        115                 120                 125
Leu Gly Glu Thr Ala Gly Arg Pro Gly Gly Ile Asp Leu Val Leu Val
    130                 135                 140
Gly Ala Asp Asp Pro Glu Ala Met Val Arg His Thr Arg Val Cys Arg
145                 150                 155                 160
Glu Leu Gly Leu Arg Arg Ala Ala Asp Pro Ser Gln Gln Leu Ala Arg
                165                 170                 175
Leu Glu Gly Asp Ser Val Arg Glu Leu Val Asp Gly Ala Glu Leu Leu
            180                 185                 190
Phe Thr Asn Ala Tyr Glu Arg Ala Leu Leu Ser Lys Thr Gly Trp
        195                 200                 205
Thr Glu Gln Glu Val Leu Ala Arg Val Gly Thr Trp Ile Thr Thr Leu
```

Gly Ala Lys Gly Cys Arg
225                 230

<210> SEQ ID NO 22
<211> LENGTH: 1565
<212> TYPE: DNA
<213> ORGANISM: Streptomyces venezuelae

<400> SEQUENCE: 22

| | | | | | |
|---|---|---|---|---|---|
| ccccgctcgc | ggccccccag | acatccacgc | ccacgattgg | acgctcccga | tgaccgcccc | 60 |
| cgccctctcc | gccaccgccc | cggccgaacg | ctgcgcgcac | cccggagccg | atctgggggc | 120 |
| ggcggtccac | gccgtcggcc | agaccctcgc | cgccggcggc | ctcgtgccgc | cgacgaggc | 180 |
| cggaacgacc | gcccgccacc | tcgtccggct | cgccgtgcgc | tacggcaaca | gccccttcac | 240 |
| cccgctggag | gaggcccgcc | acgacctggg | cgtcgaccgg | gacgccttcc | ggcgcctcct | 300 |
| cgccctgttc | gggcaggtcc | cggagctccg | caccgcggtc | gagaccggcc | ccgccggggc | 360 |
| gtactggaag | aacaccctgc | tcccgctcga | cagcgcggt | gtcttcgacg | cggcgctcgc | 420 |
| caggaagccc | gtcttcccgt | acagcgtcgg | cctctacccc | ggcccgacct | gcatgttccg | 480 |
| ctgccacttc | tgcgtccgtg | tgaccggcgc | ccgctacgac | ccgtccgccc | tcgacgccgg | 540 |
| caacgccatg | ttccggtcgg | tcatcgacga | gataccccgcg | ggcaaccct | cggcgatgta | 600 |
| cttctccggc | ggcctggagc | cgctcaccaa | ccccggcctc | gggagcctgg | ccgcgcacgc | 660 |
| caccgaccac | ggcctgcggc | ccaccgtcta | cacgaactcc | ttcgcgctca | ccgagcgcac | 720 |
| cctggagcgc | cagcccggcc | tctgggggcct | gcacgccatc | cgcacctcgc | tctacggcct | 780 |
| caacgacgag | gagtacgagc | agaccaccgg | caagaaggcc | gccttccgcc | gcgtccgcga | 840 |
| gaacctgcgc | cgcttccagc | agctgcgcgc | cgagcgcgag | tcgccgatca | acctcggctt | 900 |
| cgcctacatc | gtgctcccgg | gccgtgcctc | ccgcctgctc | gacctggtcg | acttcatcgc | 960 |
| cgacctcaac | gacgccgggc | agggcaggac | gatcgacttc | gtcaacattc | gcaggacta | 1020 |
| cagcggccgt | gacgacggca | agctgccgca | ggaggagcgg | gccgagctcc | aggaggccct | 1080 |
| caacgccttc | gaggagcggg | tccgcgagcg | caccccgga | ctccacatcg | actacggcta | 1140 |
| cgccctgaac | agcctgcgca | ccggggccga | cgccgaactg | ctgcggatca | gcccgccac | 1200 |
| catgcggccc | accgcgcacc | cgcaggtcgc | ggtgcaggtc | gatctcctcg | gcgacgtgta | 1260 |
| cctgtaccgc | gaggccggct | tccccgacct | ggacggcgca | acccgctaca | tcgcgggccg | 1320 |
| cgtgaccccc | gacacctccc | tcaccgaggt | cgtcagggac | ttcgtcgagc | gcggcggcga | 1380 |
| ggtggcggcc | gtcgacggcg | acgagtactt | catgacggc | ttcgatcagg | tcgtcaccgc | 1440 |
| ccgcctgaac | cagctggagc | gcgacgccgc | ggacggctgg | gaggaggccc | gcggcttcct | 1500 |
| gcgctgaccc | gcaccgccc | cgatccccc | gatccccccc | ccacgatccc | cccacctgag | 1560 |
| ggccc | | | | | 1565 |

<210> SEQ ID NO 23
<211> LENGTH: 485
<212> TYPE: PRT
<213> ORGANISM: Streptomyces venezuelae

<400> SEQUENCE: 23

Met Thr Ala Pro Ala Leu Ser Ala Thr Ala Pro Ala Glu Arg Cys Ala
 1               5                  10                  15

His Pro Gly Ala Asp Leu Gly Ala Ala Val His Ala Val Gly Gln Thr

-continued

```
                    20                  25                  30
Leu Ala Ala Gly Gly Leu Val Pro Pro Asp Glu Ala Gly Thr Thr Ala
             35                  40                  45
Arg His Leu Val Arg Leu Ala Val Arg Tyr Gly Asn Ser Pro Phe Thr
 50                  55                  60
Pro Leu Glu Glu Ala Arg His Asp Leu Gly Val Asp Arg Asp Ala Phe
 65                  70                  75                  80
Arg Arg Leu Leu Ala Leu Phe Gly Gln Val Pro Glu Leu Arg Thr Ala
                 85                  90                  95
Val Glu Thr Gly Pro Ala Gly Ala Tyr Trp Lys Asn Thr Leu Leu Pro
             100                 105                 110
Leu Glu Gln Arg Gly Val Phe Asp Ala Leu Ala Arg Lys Pro Val
             115                 120                 125
Phe Pro Tyr Ser Val Gly Leu Tyr Pro Gly Pro Thr Cys Met Phe Arg
 130                 135                 140
Cys His Phe Cys Val Arg Val Thr Gly Ala Arg Tyr Asp Pro Ser Ala
 145                 150                 155                 160
Leu Asp Ala Gly Asn Ala Met Phe Arg Ser Val Ile Asp Glu Ile Pro
                 165                 170                 175
Ala Gly Asn Pro Ser Ala Met Tyr Phe Ser Gly Gly Leu Glu Pro Leu
             180                 185                 190
Thr Asn Pro Gly Leu Gly Ser Leu Ala Ala His Ala Thr Asp His Gly
             195                 200                 205
Leu Arg Pro Thr Val Tyr Thr Asn Ser Phe Ala Leu Thr Glu Arg Thr
 210                 215                 220
Leu Glu Arg Gln Pro Gly Leu Trp Gly Leu His Ala Ile Arg Thr Ser
 225                 230                 235                 240
Leu Tyr Gly Leu Asn Asp Glu Glu Tyr Glu Gln Thr Thr Gly Lys Lys
                 245                 250                 255
Ala Ala Phe Arg Arg Val Arg Glu Asn Leu Arg Arg Phe Gln Gln Leu
             260                 265                 270
Arg Ala Glu Arg Glu Ser Pro Ile Asn Leu Gly Phe Ala Tyr Ile Val
             275                 280                 285
Leu Pro Gly Arg Ala Ser Arg Leu Leu Asp Leu Val Asp Phe Ile Ala
 290                 295                 300
Asp Leu Asn Asp Ala Gly Gln Gly Arg Thr Ile Asp Phe Val Asn Ile
 305                 310                 315                 320
Arg Glu Asp Tyr Ser Gly Arg Asp Asp Gly Lys Leu Pro Gln Glu Glu
                 325                 330                 335
Arg Ala Glu Leu Gln Glu Ala Leu Asn Ala Phe Glu Glu Arg Val Arg
             340                 345                 350
Glu Arg Thr Pro Gly Leu His Ile Asp Tyr Gly Tyr Ala Leu Asn Ser
             355                 360                 365
Leu Arg Thr Gly Ala Asp Ala Glu Leu Leu Arg Ile Lys Pro Ala Thr
 370                 375                 380
Met Arg Pro Thr Ala His Pro Gln Val Ala Val Gln Val Asp Leu Leu
 385                 390                 395                 400
Gly Asp Val Tyr Leu Tyr Arg Glu Ala Gly Phe Pro Asp Leu Asp Gly
                 405                 410                 415
Ala Thr Arg Tyr Ile Ala Gly Arg Val Thr Pro Asp Thr Ser Leu Thr
             420                 425                 430
Glu Val Val Arg Asp Phe Val Glu Arg Gly Gly Glu Val Ala Ala Val
             435                 440                 445
```

```
Asp Gly Asp Glu Tyr Phe Met Asp Gly Phe Asp Gln Val Val Thr Ala
        450                 455                 460
Arg Leu Asn Gln Leu Glu Arg Asp Ala Ala Asp Gly Trp Glu Glu Ala
465                 470                 475                 480
Arg Gly Phe Leu Arg
                485

<210> SEQ ID NO 24
<211> LENGTH: 37
<212> TYPE: DNA
<213> ORGANISM: Streptomyces venezuelae

<400> SEQUENCE: 24
ttgcatgcat atgcgccgta cccagcaggg aacgacc                        37

<210> SEQ ID NO 25
<211> LENGTH: 38
<212> TYPE: DNA
<213> ORGANISM: Streptomyces venezuelae

<400> SEQUENCE: 25
ttgaattctc aactagtacg gcggcccgcc tcccgtcc                       38

<210> SEQ ID NO 26
<211> LENGTH: 18
<212> TYPE: DNA
<213> ORGANISM: Streptomyces venezuelae

<400> SEQUENCE: 26
tcctctagac gtttccgt                                             18

<210> SEQ ID NO 27
<211> LENGTH: 21
<212> TYPE: DNA
<213> ORGANISM: Streptomyces venezuelae

<400> SEQUENCE: 27
tgaagcttga attcaaccgg t                                         21

<210> SEQ ID NO 28
<211> LENGTH: 31
<212> TYPE: DNA
<213> ORGANISM: Streptomyces venezuelae

<400> SEQUENCE: 28
ccctgcagcg gcaaggaagg acacgacgcc a                              31

<210> SEQ ID NO 29
<211> LENGTH: 32
<212> TYPE: DNA
<213> ORGANISM: Streptomyces venezuelae

<400> SEQUENCE: 29
aggtctagag ctcagtgccg ggcgtcggcc gg                             32

<210> SEQ ID NO 30
<211> LENGTH: 27
<212> TYPE: DNA
<213> ORGANISM: Streptomyces venezuelae

<400> SEQUENCE: 30
tttatgcatc ccgcgggtcc cggcgag                                   27
```

```
<210> SEQ ID NO 31
<211> LENGTH: 27
<212> TYPE: DNA
<213> ORGANISM: Streptomyces venezuelae

<400> SEQUENCE: 31
tcagaattct gtcggtcact tgcccgc                                              27
```

POLYKETIDE SYNTHASE GENES FROM STREPTOMYCES VENEZUELAE

CROSS-REFERENCE TO RELATED APPLICATIONS

This application claims benefit under 35 USC 119(e) to U.S. Provisional application No. 60/087,080 filed May 28, 1998, the disclosure of which is incorporated herein by reference.

REFERENCE TO GOVERNMENT FUNDING

This work was supported at least in part by U.S, government under SBIR grant 1R43 CA 75792-01. The U.S. government has certain rights in this invention.

TECHNICAL FIELD

The invention relates to the field of novel polyketides and antibiotics and to methods to prepare them. More particularly, it concerns construction of new polyketides and to libraries of polyketides synthesized by polyketide synthases derived from the picromycin PKS and other enzymes derived from Streptomyces venezuelae.

BACKGROUND ART

Polyketides represent a large family of diverse compounds ultimately synthesized from 2-carbon units through a series of Claisen-type condensations and subsequent modifications. Members of this group include antibiotics such as tetracyclines, anticancer agents such as daunomycin, and immunosuppressants such as FK506 and rapamycin. Polyketides occur in many types of organisms including fungi and mycelial bacteria, in particular, the actinomycetes.

The polyketides are synthesized in vivo by polyketide synthases (PKS). This group of enzymatically active proteins is considered in a different category from the fatty acid synthases which also catalyze condensation of 2-carbon units to result in, for example, fatty acids and prostaglandins. Two major types of PKS are known which are vastly different in their construction and mode of synthesis. These are commonly referred to as Type I or "modular" and Type II, "aromatic."

The PKS scaffold that is one subject of the present invention is a member of the group designated Type I or "modular" PKS. In this type, a set of separate active sites exists for each step of carbon chain assembly and modification, but the individual proteins contain a multiplicity of such separate active sites. There may be only one multifunctional protein of this type, such as the "fungal" type required for the biosynthesis of 6-methyl salicylic acid (Beck, J. et al., *Eur J Biochem* (1990) 192:487–498; Davis, R. et al., *Abstracts of Genetics of Industrial Microorganism Meeting*, Montreal, Abstract P288 (1994)). More commonly, and in bacterial-derived Type I PKS assemblies, there are several such multifunctional proteins assembled to result in the end product polyketide. (Cortes, J. et al., *Nature* (1990) 348:176; Donadio, S. et al., *Science* (1991) 252:675; MacNeil, D. J. et al., *Gene* (1992) 115:119.)

A number of modular PKS genes have been cloned. U.S. Pat. No. 5,252,474 describes cloning of genes encoding the synthase for avermectin; U.S. Pat. No. 5,098,837 describes the cloning of genes encoding the synthase for spiramycin; European application 791,655 and European application 791,656 describe the genes encoding the synthases for tylosin and platenolide respectively.

The PKS for erythromycin, used as an illustrative system is a modular PKS. Erythromycin was originally isolated from *S. erythraeus* (since reclassified as *Saccharopolyspora erythrea*) which was found in a soil sample from the Philippine archipelago. Cloning the genes was described by Donadio, S. et al., *Science* (1991) 252:675. The particulars have been reviewed by Perun, T. J. in *Drug Action and Drug Resistance in Bacteria*, Vol. 1, S. Mitsuhashi (ed.) University Park Press, Baltimore, 1977. The antibiotic occurs in various glycosylated forms, designated A, B and C during various stages of fermentation. The entire erythromycin biosynthetic gene cluster from *S. erythraeus* has been mapped and sequenced by Donadio et al. in *Industrial Microorganisms: Basic and Applied Molecular Genetics* (1993) R. H. Baltz, G. D. Hegeman, and P. L. Skatrud (eds.) (*Amer Soc Microbiol*) and the entire PKS is an assembly of three such multifunctional proteins usually designated DEBS-1, DEBS-2, and DEBS-3, encoded by three separate genes.

Expression of the genes encoding the PKS complex may not be sufficient to permit the production by the synthase enzymes of polyketides when the genes are transformed into host cells that do not have the required auxiliary phosphopantetheinyl transferase enzymes which posttranslationally modify the ACP domains of the PKS. Genes encoding some of these transferases are described in WO97/13845. In addition, enzymes that mediate glycosylation of the polyketides synthesized are described in WO97/23630. U.S. Ser. No. 08/989,332 filed Dec. 11, 1997 describes the production of polyketides in hosts that normally do not produce them by supplying appropriate phosphopantetheinyl transferase expression systems. The contents of this application are incorporated herein by reference.

There have been attempts to alter the polyketide synthase pathway of modular PKS clusters. For example, European application 238,323 describes a process for enhancing production of polyketides by introducing a rate-limiting synthase gene and U.S. Pat. No. 5,514,544 describes use of an activator protein for the synthase in order to enhance production. U.S. Pat. Nos. 4,874,748 and 5,149,639 describe shuttle vectors that are useful in cloning modular PKS genes in general. Methods of introducing an altered gene into a microorganism chromosome are described in WO93/13663. Modification of the loading module for the DEBS-1 protein of the erythromycin-producing polyketide synthase to substitute the loading module for the avermectin-producing polyketide synthase in order to vary the starter unit was described by Marsden, Andrew F. A. et al. *Science* (1998) 279:199–202 and Oliynyk, M. et al. *Chemistry and Biology* (1996) 3:833–839. WO 98/01571, published Jan. 15, 1998, describes manipulation of the erythromycin PKS and polyketides resulting from such manipulation. In addition, WO 98/01546, also published Jan. 15, 1998 describes a hybrid modular PKS gene for varying the nature of the starter and extender units to synthesize polyketides.

In addition, U.S. Pat. Nos. 5,063,155 and 5,168,052 describe preparation of antibiotics using modular PKS systems.

Type II PKS, in contrast to modular PKS, include several proteins, each of which is simpler than those found in Type I polyketide synthases. The active sites in these enzymes are used iteratively so that the proteins themselves are generally monofunctional or bifunctional. For example, the aromatic PKS complexes derived from Streptomyces have so far been found to contain three proteins encoded in three open reading frames. One protein provides ketosynthase (KS) and acyltransferase (AT) activities, a second provides a chain length determining factor (CLDF) and a third is an acyl carrier protein (ACP).

The present invention is concerned with PKS systems derived from the modular PKS gene clusters which results in the production of narbomycin in *Streptomyces narbonensis* and of picromycin in *S. venezuelae*. Glycosylation of the C5 hydroxyl group of the polyketide precursor, narbonolide, is achieved through an endogenous desosamino transferase. In *S. venezuelae*, narbomycin is then converted to picromycin by the endogenously produced narbomycin hydroxylase. Thus, as in the case of other macrolide antibiotics, the macrolide product of the PKS is further modified by hydroxylation and glycosylation. The nature of these clusters and their manipulation are further described below.

DISCLOSURE OF THE INVENTION

The invention provides recombinant materials for the production of libraries of polyketides wherein the polyketide members of the library are synthesized by PKS systems derived from picromycin by using this system as a scaffold or by inserting portions of the picromycin PKS into other PKS scaffolds, and by providing recombinant forms of enzymes that further modify the resulting macrolides. Further, recombinant hosts that are modified to provide only certain activities involved in producing the endogenous antibiotic are described. Generally, many members of these libraries may themselves be novel compounds, and the invention further includes novel polyketide members of these libraries. The invention methods may thus be directed to the preparation of an individual polyketide. The individual polyketide may or may not be novel; in any case the invention provides a more convenient method of preparing it. The resulting polyketides may be further modified to convert them to antibiotics, typically through hydroxylation and/or glycosylation. Modified macrolides that are useful intermediates in the preparation of synthetic antibiotics are of particular interest. The invention also includes methods to recover novel polyketides with desired binding activities by screening the libraries of the invention.

The invention provides for the first time, the complete PKS gene cluster which ultimately results, in *S. venezuelae*, in the production of picromycin. The ketolide product of this PKS is narbonolide which is glycosylated to obtain narbomycin and then hydroxylated at C12 to obtain picromycin. The enzymes responsible for the glycosylation and hydroxylation are also provided.

Thus, in one aspect, the invention is directed to recombinant materials useful in the production of ketolides and their corresponding antibiotics which contain nucleotide sequences encoding at least one activity, or at least one module, or at least one protein encoded by an open reading frame of the picromycin PKS. The invention is directed also to recombinant materials useful for conversion of ketolides to antibiotics which comprise nucleotide sequences encoding the 12-hydroxylase (the picK gene) and the glycosylation enzyme which provides a glycoside residue at position 5 which enzyme is present in *S. narbonensis* and *S. venezuelae*. This aspect also provides methods to obtain the corresponding proteins, ketolides and antibiotics.

These materials are also useful as scaffolds and auxiliary reagents in preparing individual polyketides and combinatorial libraries thereof.

Thus, in another aspect, the invention is directed to a method to prepare a nucleic acid which contains a nucleotide sequence encoding a modified polyketide synthase which method comprises using the picromycin PKS encoding sequence as a scaffold and modifying the portions of the nucleotide sequence that encode enzymatic activities, either by mutagenesis, inactivation, or replacement. The thus modified picromycin PKS encoding nucleotide sequence can then be used to modify a suitable host cell and the cell thus modified employed to produce a polyketide different from that produced by the picromycin PKS. In addition, portions of the picromycin PKS can be inserted into other host scaffolds to modify the products thereof. Portions of the picromycin PKS can be hybridized to portions of other PKS-encoding nucleotide sequences to obtain novel nucleotide sequences with one or more reading frames encoding additional PKS alternatives. The picromycin PKS can itself be manipulated, for example, by fusing two or more of its open reading frames in order to make more efficient the production of the intended macrolide.

In another aspect, the invention relates to conversions effected by the product of the pick gene and by the product of the gene encoding glycosylation enzymes for narbonolide. The invention is also directed to polyketides thus produced and the antibiotics to which they may then be converted.

In another aspect, the invention is directed to a multiplicity of cell colonies comprising a library of colonies wherein each colony of the library contains an expression vector for the production of a different modular PKS, but derived from picromycin PKS. By "derived from" picromycin PKS means simply that at least a portion of the modular PKS is identical to that found in the PKS which results the production of narbonolide and is recognizable as such. The derived portion may, of course, be prepared synthetically as well as prepared directly from DNA that originates in organisms which natively produce narbonolide. In a preferred embodiment, PKS derived from the picromycin PKS is used as a scaffold. The library of different modular PKS is in this case obtained by modifying one or more of the regions of the picromycin PKS gene cluster encoding an enzymatic activity so as to alter that activity, leaving intact the scaffold portions of picromycin PKS gene. If desired, an additional scaffold source may be used creating a hybrid scaffold. In another aspect, the invention is directed to a multiplicity of cell colonies comprising a library of colonies wherein each colony of the library contains a different modular PKS derived from the PKS gene clusters as described above. The invention is also directed to methods to produce libraries of PKS complexes and to produce libraries of polyketides and their corresponding antibiotics by culturing these colonies, as well as to the polyketide and antibiotic libraries so produced. In addition, the invention is directed to methods to screen the resulting polyketide and antibiotic libraries and to novel polyketides and antibiotics contained therein.

BRIEF DESCRIPTION OF THE DRAWINGS

FIG. 6 shows a diagram of the cosmid KOS023-26, a list of the open reading frames contained therein, and the nucleotide sequence and deduced amino acid sequences associated with these reading frames SEQ ID NOs:9–23).

MODES OF CARRYING OUT THE INVENTION

It may be helpful to review the nature of the erythromycin PKS complex and the gene cluster that encodes it as a model for modular PKS, in general. To clarify the terminology, the product of the PKS gene cluster is generally termed a ketolide or macrolide and may or may not have antibiotic activity. It is converted to an antibiotic by additional enzymes not considered part of the PKS cluster. These additional enzymes, in general, provide additional hydroxylation and/or glycosylation of the ketolide PKS product.

Figure 1A:
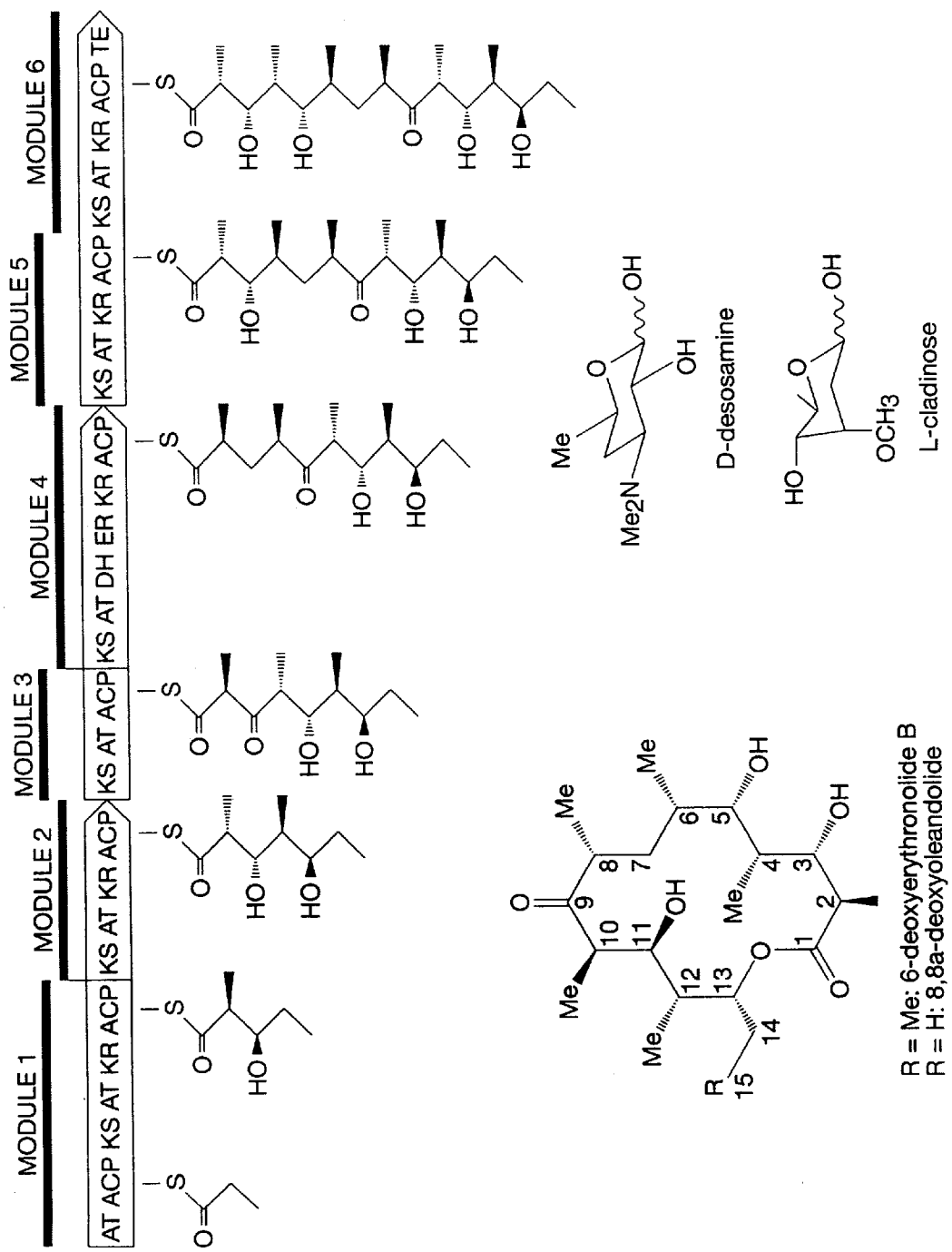
FIG. 1A is a diagram of the erythromycin PKS complex from *S. erythraeus* showing the function of each multifunctional protein, and also shows the structure of the ketolide product, 6 dEB and of D-desosamine and L-cladinose.

FIG. 1A is a diagrammatic representation of the gene cluster encoding the synthase for the polyketide backbone of the antibiotic erythromycin. The erythromycin PKS protein assembly contains three high-molecular-weight proteins (>200 kD) designated DEBS-1, DEBS-2 and DEBS-3, each encoded by a separate gene (Caffrey et al., *FEBS Lett* (1992) 304:225). The diagram in FIG. 1A shows that each of the three proteins contains two modules of the synthase—a module being that subset of reactivities required to provide an additional 2-carbon unit to the molecule. As shown in FIG. 1A, modules 1 and 2 reside on DEBS-1; modules 3 and 4 on DEBS-2 and modules 5 and 6 on DEBS-3. The minimal module is typified in module 3 which contains a ketosynthase (KS), an acyltransferase (AT) and an acyl carrier protein (ACP). These three functions are sufficient to activate an extender unit and attach it to the remainder of the growing molecule. Additional activities that may be included in a module relate to reactions other than the Claisen condensation, and include a dehydratase activity (DH), an enoylreductase activity (ER) and a ketoreductase activity (KR). Preceding the first module is a loading domain which contains the AT and ACP activities which catalyze the initial condensation and determine the nature of the starter unit. Although not shown, module 3 has a KR region which has been inactivated (in the native PKS gene cluster) by mutation. The "finishing" of the molecule is regulated by the thioesterase activity (TE) in module 6. This thioesterase appears to catalyze cyclization of the macrolide ring thereby increasing the yield of the polyketide product.

The product in this case is 6 dEB; the structure and numbering system for this molecule are shown in FIG. 1A. Conversion to the antibiotics erythromycin A, B, C and D requires two types of reactions, hydroxylation at C-6 and, for erythromycins C and A, at C-12, and glycosylation, generally by D-desosamine or L-mycarose, which may ultimately be converted to cladinose at appropriate locations.

Figure 1B:
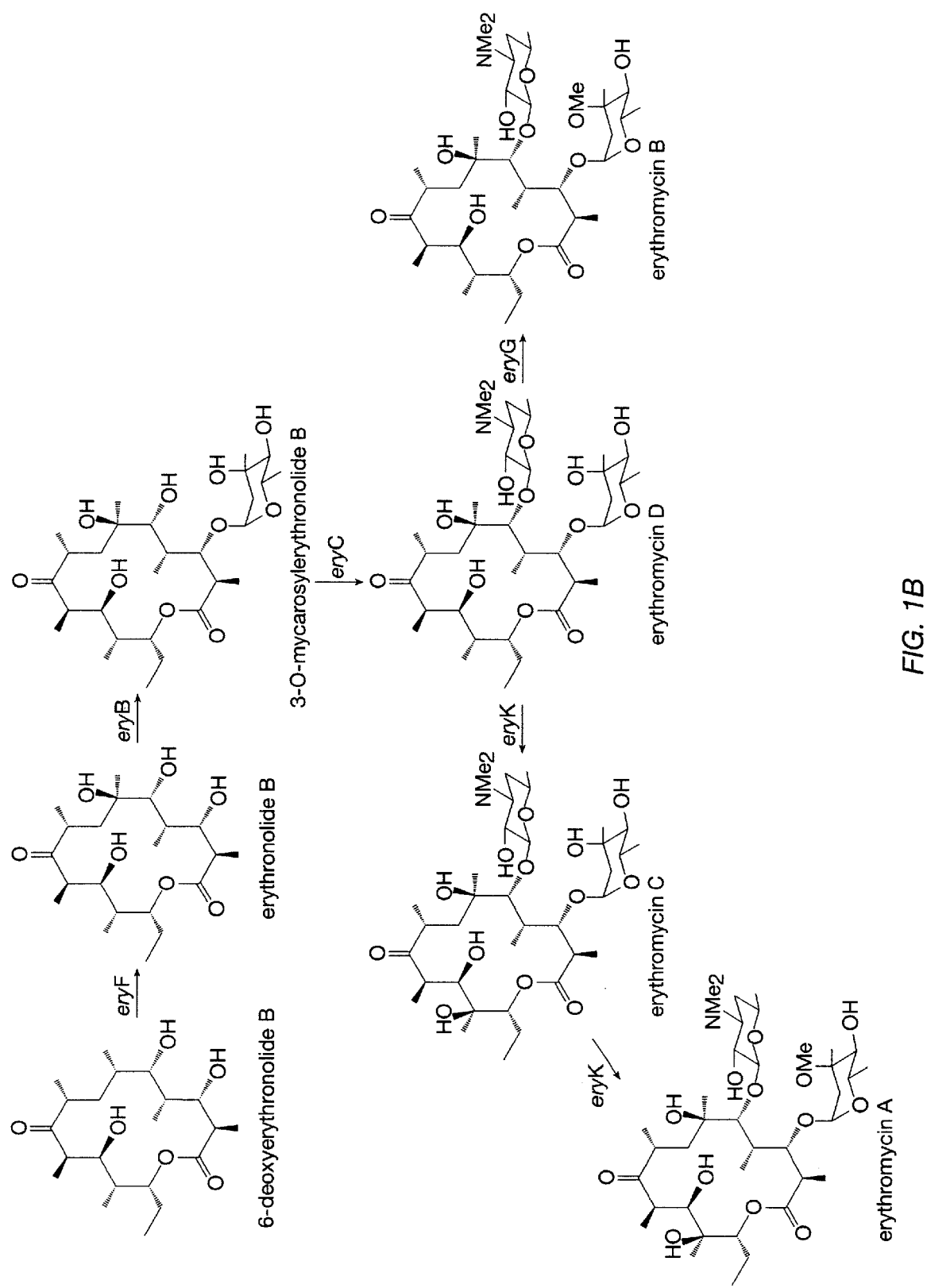
FIG. 1B shows a diagram of the post-PKS biosynthesis of erythromycins A–D.

FIG. 1B diagrams the post-PKS biosynthesis of the erythromycins through hydroxylation and addition of glycosyl groups. As shown, 6 dEB is converted by the product of the gene eryF to erythronolide B. Erythronolide B (eryB) is hydroxylated at C6. It is believed that this hydroxylation enhances the antibiotic activity. The hydroxylase is not part of the PKS per se; it is nevertheless endogenous to *S. erythraeus*. Erythronolide B is glycosylated by the product of the eryB gene to obtain 3-O-mycarosylerythronolide B which contains L-mycarose at position 3. This product, 3-O-mycarosylerythronolide B serves as a precursor for all of the erythromycin antibiotics. It is first converted to erythromycin D by the enzyme encoded by eryC by glycosylation with D-desosamine at position 5. Erythromycin D, therefore, differs from 6 dEB through glycosylation and by the addition of a hydroxyl group at position 6. Erythromycin D can be converted to erythromycin B in a reaction catalyzed by the product of the eryG gene by methylating the L-mycarose residue at position 3. Erythromycin D is converted to erythromycin C by the addition of a hydroxyl group at position 12. This conversion is catalyzed by a hydroxylase that is the product of the eryK gene. The analogous picK gene is provided by the present invention. Erythromycin A is obtained from erythromycin C by methylation of the mycarose residue catalyzed by the product of the eryG gene. The series of erythromycin antibiotics, then, differs in the level of hydroxylation of the polyketide framework and by the methylation status of the glycosyl residues.

Figure 2:
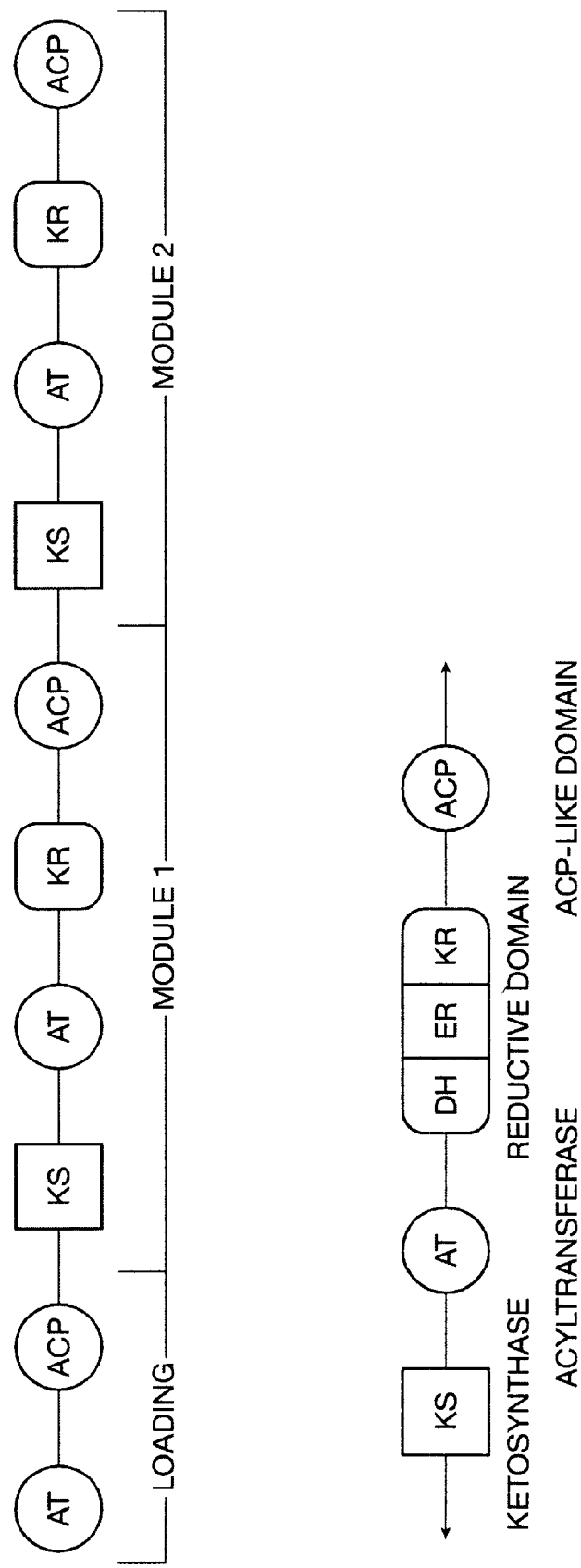
FIG. 2 is a diagram of DEBS-1 from *S. erythraeus* showing the functional regions separated by linker regions.

FIG. 2 shows a detailed view of the regions in the first two modules of the erythromycin PKS which comprise the first open reading frame encoding DEBS-1. The regions that encode enzymatic activities are separated by linker or "scaffold"-encoding regions. These scaffold regions encode amino acid sequences that space the enzymatic activities at the appropriate distances and in the correct order. Thus, these linker regions collectively can be considered to encode a scaffold into which the various activities are placed in a particular order and spatial arrangement. This organization is similar in the remaining modules, as well as in other naturally occurring modular PKS gene clusters.

The three DEBS-1, 2 and 3 proteins are encoded by the genetic segments ery-AI, ery-AII and ery-AIII, respectively. These reading frames are located on the bacterial chromosome starting at about 10 kb distant from the erythromycin resistance gene (ermE or eryR).

The detailed description above referring to erythromycin is typical for modular PKS in general. Thus, rather than the illustrated erythromycin, the polyketide synthases making up the libraries of the invention can be derived from the synthases of other modular PKS, such as those which result in the production of rapamycin, avermectin, FK-506, FR-008, monensin, rifamycin, soraphen-A, spinocyn, squalestatin, or tylosin, and the like.

Figure 3:
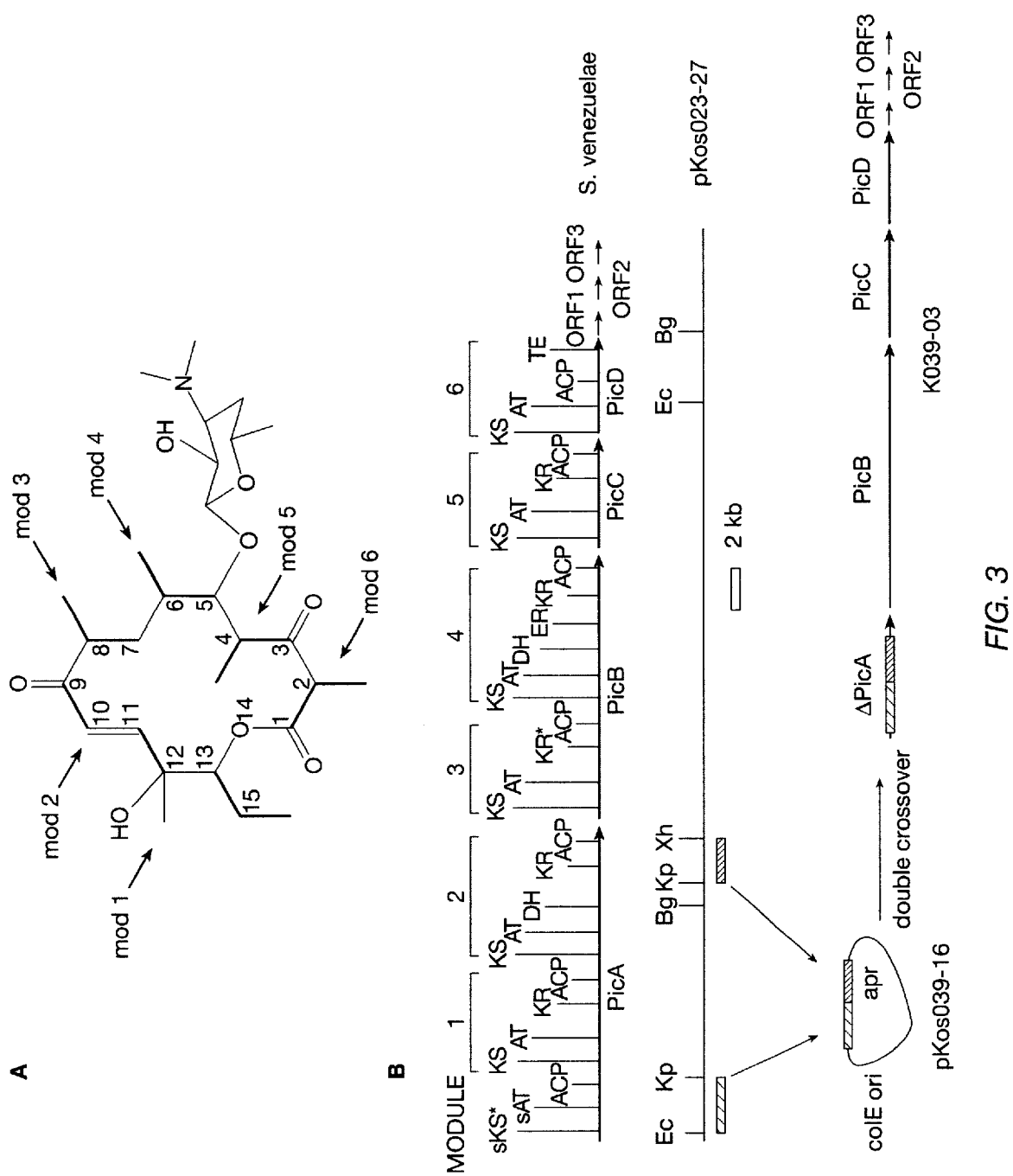
FIG. 3 is a diagram of the picromycin PKS.

A focus of the present invention is the provision of the nucleotide sequences of the picromycin PKS as well as the nucleotide sequences of genes encoding enzymes which catalyze the further modification of the ketolides produced by the picromycin PKS. FIG. 3 shows a diagram of the picromycin PKS provided by the invention. As compared to the erythromycin PKS, there are many similarities. Both encode enzymes that result in 14-member macrolides; therefore, each contains six modules. The six modules of the picromycin PKS, however, reside on four, rather than three reading frames; modules 5 and 6 are encoded on separate reading frames. As shown in FIG. 3, the activities associated with each module of the picromycin PKS are similar to erythromycin, but there are some important differences.

The loading domain of the picromycin PKS, unlike that of erythromycin, contains an inactivated ketosynthase (KS) domain. Sequence analysis indicates that this domain is enzymatically inactivated as a critical cysteine residue in the motif TVDACSSSL, which is highly conserved among KS domains, is replaced by a glutamine. Such inactivated KS domains are also found in the 16-membered macrolides carbomycin, spiromycin, tylosin and nidamycin. Thus, in effect, the loading domains of the picromycin and erythromycin PKS appear functionally similar. Modules 1, 3, 4, and 6 are also functionally similar. In both cases, module 3 contains a ketoreductase-encoding region which is inactive. The major functional differences between the two PKS nucleotide sequences occur in modules 2 and 5. This results in structural differences in the resulting ketolides at carbons 10, 11 (module 2) and carbon 3 (module 5). The acyl transferase in module 2 of the picromycin PKS is specific for malonyl CoA, rather than methylmalonyl CoA and thus results in the lack of a methyl group at position 10. Further, the presence of a dehydrase (DH) activity in module 2 results in a double bond between carbons 10 and 11; the ketoreductase present in module 2 in the erythromycin PKS results in a hydroxyl group at position 11.

Figure 4:
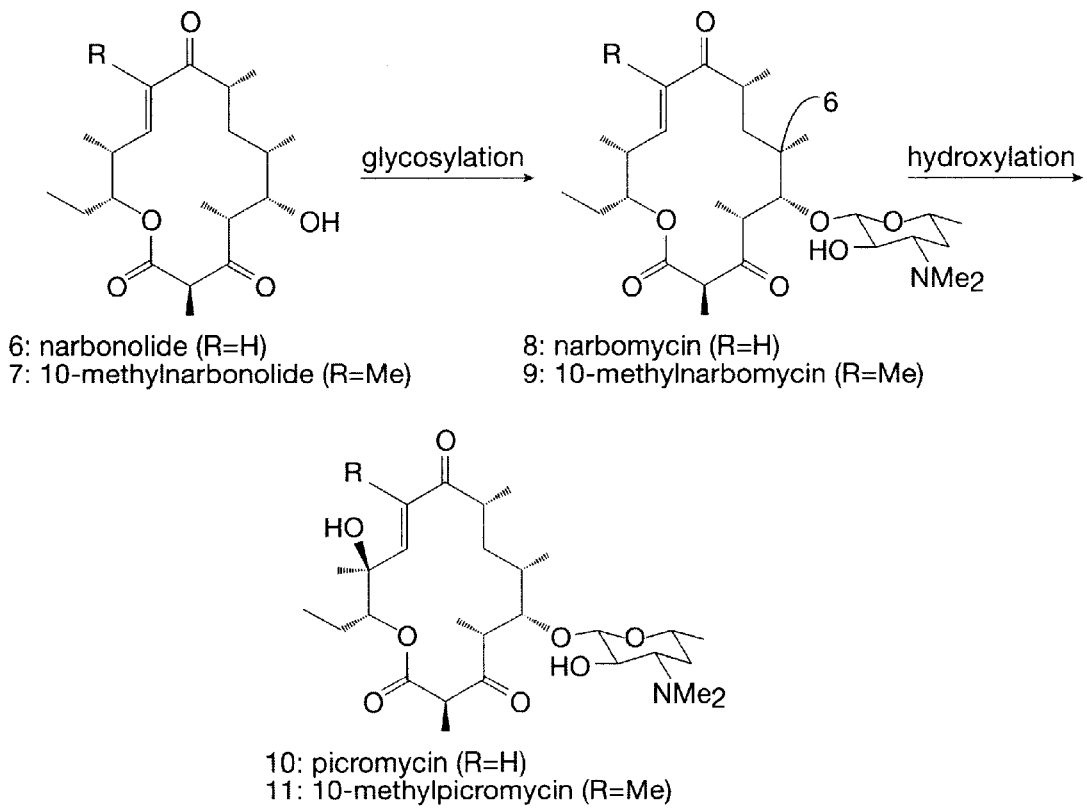
FIG. 4 shows the postsynthesis conversion of the ketolide product of the picromycin PKS, narbonolide.
Figure 4:
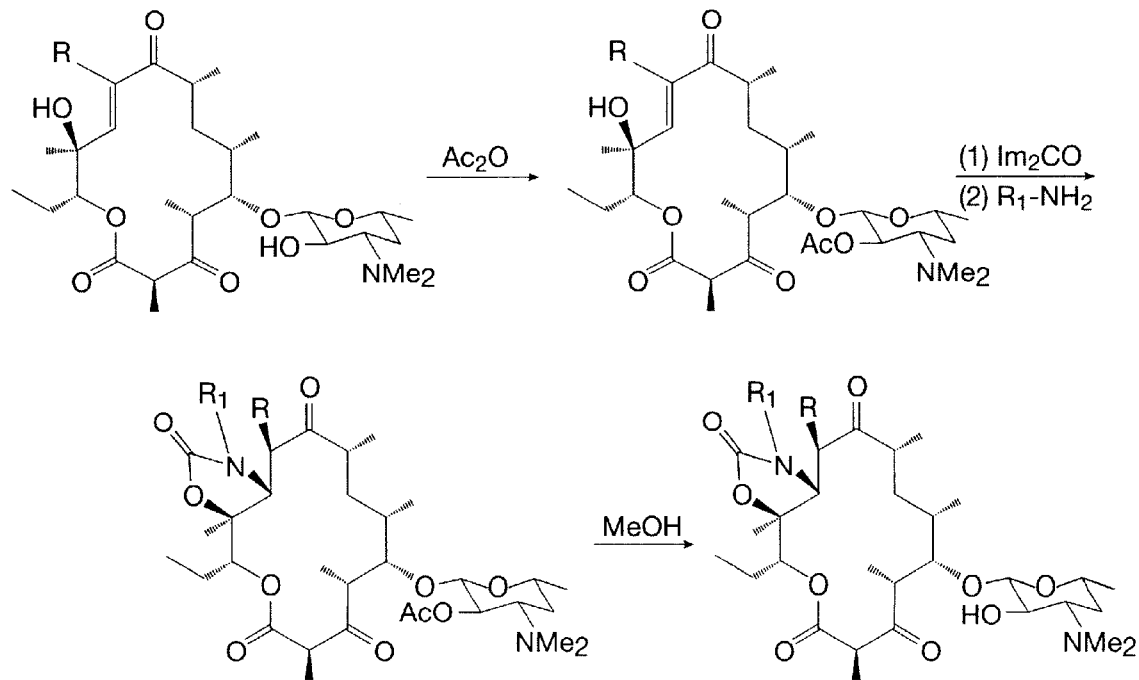

Like erythromycin, picromycin itself results from further modifications catalyzed by enzymes not part of the PKS. This series of reactions is shown in FIG. 4. As shown, the product ketolide, narbonolide, is converted to narbomycin by glycosylation with desosamine and then hydroxylated at the 12-position by the product of the picK (nucleotides 1356–2606 of SEQ ID NO:11) gene.

The present invention provides all of the necessary nucleotide sequences for manipulating the picromycin PKS as well as the postmacrolide synthesis enzymes. These materials are contained on pKOS023-27 (SEQ ID NO:1) and pKOS023-26 (SEQ ID NOs:9, 11, 15, 19 and 22) both deposited at the ATCC under the terms of the Budapest Convention on Aug. 20, 1998, and provided accession numbers ATCC203141 and ATCC203142 respectively.

Figure 5:
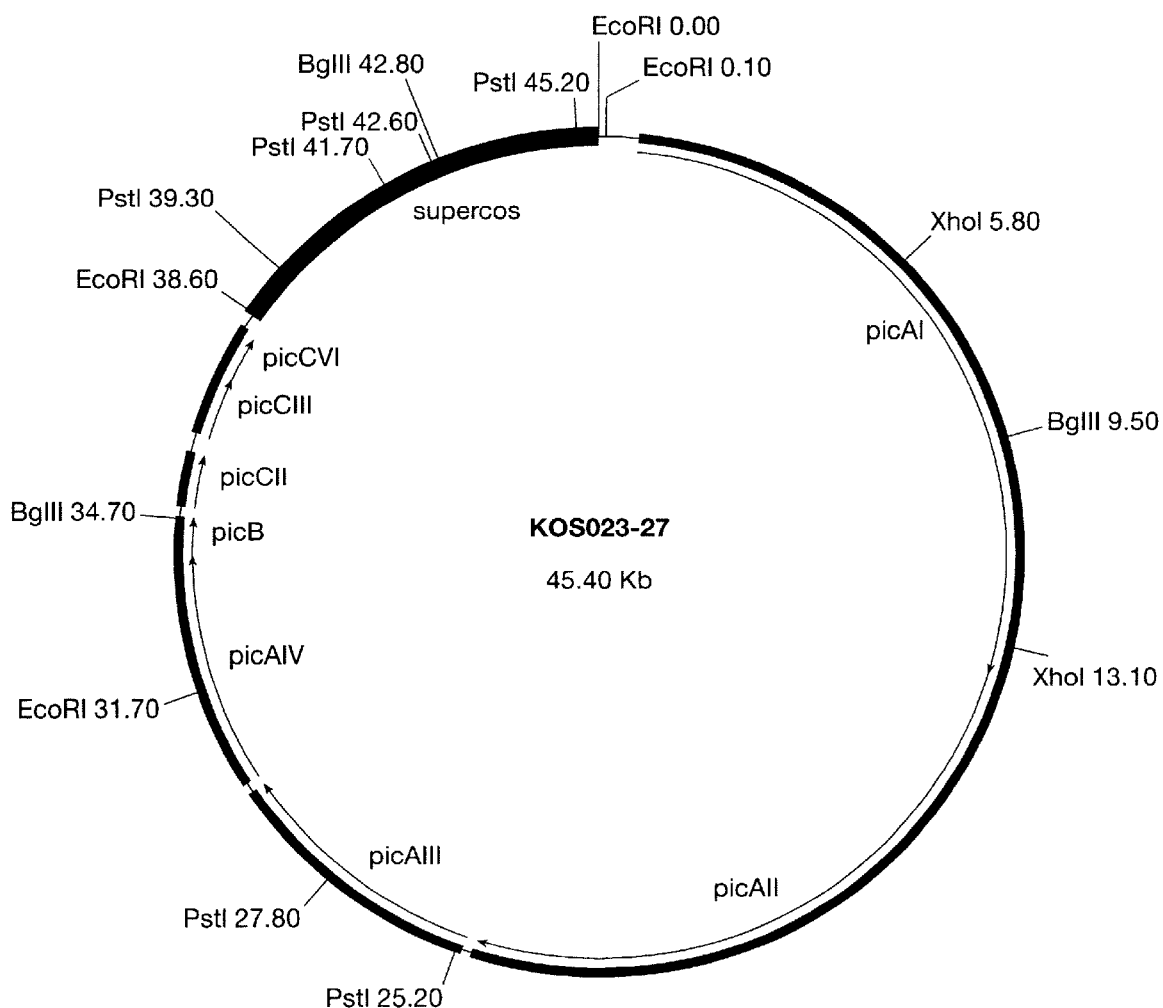
FIG. 5 shows a diagram of the cosmid KOS023-27, a list of the open reading frames contained therein, and the nucleotide sequence and deduced amino acid sequences associated with these reading frames. The nucleotide sequence for the entire cosmid insert is included (SEQ ID NO:1).

FIG. 5 shows a diagram of pKOS023-27 (SEQ ID NO:1) which contains the entire picromycin PKS along with three additional open reading frames at the C-terminus. The gene product of ORF1 (pic AI SEQ ID NO:2) shows a high degree of similarity to all of the non-PKS thioesterases; with an identity of 51%, 49%, 45% and 40% as compared to those of *Amycolatopsis mediterranae*, *S. griseus*, *S. fradiae* and *Saccharopolyspora erythreae*, respectively. The product of ORF2, (pic AII SEQ ID NO:3) shows 48% identity to the dnrQ gene product of *S. peucetius*. The product of ORF2 (pic AII SEQ ID NO:3) is the desosamino transferase which converts narbonolide to narbomycin. The product of ORF3 (pic AIII SEQ ID NO:4) also has 50% identity to a glycotransferase.

FIG. 5 also provides the complete nucleotide sequence of pKOS023-27 (SEQ ID NO:1) on pages 3–14 thereof. Pages 15–23 contain the deduced amino acid sequences of the four open reading frames of the PKS and the additional open reading frames at the C-terminus.

FIG. 6 shows the structure of pKOS023-26 (SEQ ID NOs:9, 11, 15, 16 and 22) which contains a region of overlap with pKOS023-27 (SEQ ID NO:1) representing nucleotides 14252 to nucleotides 38506 of pKOS023-27 (SEQ ID NO:1). The nucleotide sequences of five contigs contained in pKOS023-26 (SEQ ID NOs:9, 11, 15, 19 and 22) are provided in FIG. 6 along with the translations of open reading frames contained therein. Pages 2–3 show contig 1 (SEQ ID NO:9) and a translation of the reading frame contained therein; pages 4–8 provide the corresponding information for contig 2 (SEQ ID NO:11); pages 9–13 for contig 3 (SEQ ID NO:15); pages 14–16 for contig 4 (SEQ ID NO:19); and pages 17–18 for contig 5 (SEQ ID NO:22). These open reading frames have been assigned as follows:

In contig 001 (SEQ ID NO:9), one reading frame, ORF11 (nucleotides 80–2389 of SEQ ID NO:9) encodes a glucosidase.

In contig 2 (SEQ ID NO:11), the three reading frames include a reading frame encoding a 3,4-dehydratase designated picClIV pic CIV (nucleotides 1–995 of SEQ ID NO:11) which is a homolog of eryCIV. A second reading frame is the picK gene (nucleotide 1356–2606 og SEQ ID NO:11 which is a cytochrome p450 hydroxylase responsible for hydroxylating C12 of glycosylated narbomycin. The third reading frame designated ORF12 (nucleotide 2739–55–25 of SEQ ID NO:11) is putatively a regulatory gene.

In contig 003 (SEQ ID NO:15), one reading frame, designated ORF13 (nucleotide 104–982 of SEQ ID NO:15) is an NDP glucose synthase and a second gene, designated ORF14 (nucleotides 1114–2127 of SEQ ID NO:15) encodes an NDP glucose 4,6-dehydratase. The third open reading frame has been designated picCI (nucleotides 2124–3263 of SEQ ID NO:15) as it appears to be homologous to the eryC1 gene.

In contig 004 (SEQ ID NO:19), the two open reading frames are ORF15 (nucleotides 694–1692 of SEQ ID NO:19) which encodes an S-adenosyl methionine synthase and ORF16 (nucleotides 1–692 of SEQ ID NO19) which is a homolog of the *M. tuberculosis* cbhK gene. Contig 5 (SEQ ID NO:22) contains one reading frame which is designated picCV (nueceltiodes 50–1507 of SEQ ID NO:22) a homolog to the eryCV gene which encodes a protein that catalyzes desosamine synthesis.

Thus, nucleotide sequences encoding the entire picromycin PKS have been provided, along with those encoding the enzymes for essential further modification of the resulting ketolide. picK is included in pKOS023–26 (SEQ ID NOs.:9, 11,15,19, and 22) contig 002 and the gene encoding the glycosylation enzyme for conversion of narbonolide to narbomycin is shown as ORF2 in FIG. 5.

The availability of these nucleotide sequences permits their use in recombinant procedures for production of desired portions of the picromycin PKS and for production of the proteins useful in postmacrolide conversions. A portion of the PKS which encodes a particular activity can be isolated and manipulated, for example, by replacing the corresponding region in a different modular PKS. In addition, individual modules of the PKS may be ligated into suitable expression systems and used to produce the encoded portion of the protein encoded by the open reading frame which may be isolated and purified, or which may be employed in situ to effect polyketide synthesis. Depending on the host for the recombinant production of the module or an entire open reading frame, or combination of open reading frames, suitable control sequences such as promoters, termination sequences, enhancers, and the like are ligated to the nucleotide sequence encoding the desired protein. Suitable control sequences for a variety of hosts are well known in the art.

If the hosts ordinarily produce polyketides, it may be desirable to modify them so as to prevent the production of endogenous polyketides by these hosts. Such hosts have been described, for example, in U.S. Pat. No. 5,672,491, incorporated herein by reference. In such hosts, however, it may not be necessary to provide enzymatic activity for posttranslational modification of the enzymes that make up the recombinantly produced polyketide synthase. In particular, these hosts generally contain suitable enzymes, designated holo-ACP synthases, for providing a pantotheinyl residue needed for functionality of the synthase. However, in hosts such as yeasts, plants, or mammalian cells which ordinarily do not produce polyketides, it may be necessary to provide, also typically by recombinant means, suitable holo-ACP synthases to convert the recombinantly produced PKS to functionality. Provision of such enzymes is described, for example, in PCT application WO 98/27203, incorporated herein by reference.

Thus, included within the scope of the invention in addition to isolated nucleic acids containing the desired nucleotide sequences encoding activities, modules or open reading frames of PKS as well as glycosylation and hydroxylation enzymes, are recombinant expression systems containing these nucleotide sequences wherein the encoding nucleotide sequences are operably linked to promoters, enhancers, and/or termination sequences which operate to effect expression of the encoding nucleotide sequence in host cells compatible with these sequences; host cells modified to contain these sequences either as extrachromosomal elements or vectors or integrated into the chromosome, and methods to produce PKS and post-PKS enzymes as well as polyketides and antibiotics using these modified host cells.

The availability of these nucleotide sequences also expands the possibility for the production of novel polyketides and their corresponding antibiotics using host cells modified to contain suitable expression systems for the appropriate enzymes. By manipulating the various activity-encoding regions of a donor PKS by replacing them into a scaffold of a different PKS or by forming hybrids instead of or in addition to such replacements or other mutagenizing alterations, a wide variety of polyketides and corresponding antibiotics may be obtained.

The availability of the hydroxylase encoded by the picK gene (nucleotides 1356–2606 of SEQ ID NO:11) in recombinant form is of great significance in this regard as the enzyme appears to accept a wide variety of substrates. Thus, additional hydroxylation reactions can be carried out with respect to large numbers of polyketides.

Thus, in addition to the novel polyketides described in parent application U.S. Ser. No. 09/073,538, filed May 6, 1998, the invention includes novel hydroxylated polyketides of the formula

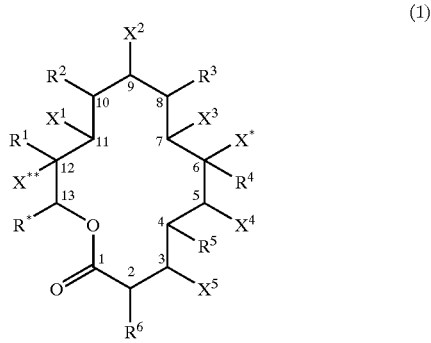

(1)

including the glycosylated and isolated stereoisomeric forms thereof, wherein R* is a straight-chain, branched or cyclic saturated or unsaturated substituted or unsubstituted hydrocarbyl of 1–15C;

each of $R^1$–$R^6$ is independently H or alkyl (1–4C);

each of $X^1$–$X^5$ is independently $H_2$, HOH or =O; or each of $X^1$–$X^5$ is independently H and the compound of formula (1) contains a π-bond in the ring adjacent to the position of said X at 2–3, 4–5, 6–7, 8–9 and/or 10–11; and wherein at least one of X* and X** is OH; and wherein at least two of $R^1$–$R^6$ are alkyl.

Hydroxylated forms at the C6 and C12 positions are facilitated by the availability of the relevant hydroxylases.

As mentioned above, the C12 hydroxylase encoded by the picK gene is particularly advantageous as it will accept a wide variety of polyketide precursors wherein X** is H.

Hydroxylation can be achieved by a number of approaches. First, the hydroxylation may be performed in vitro using purified hydroxylase or the relevant hydroxylase produced recombinantly from its retrieved gene. Alternatively, hydroxylation may be effected by supplying the nonhydroxylated precursor to a cell which provides the appropriate hydroxylase, either natively, or by virtue of recombinant modification. The availability of the 12-hydroxylase encoded by the picK gene is helpful in providing a cellular environment with the appropriate hydroxylase produced recombinantly. Alternatively, a native source of the hydroxylase, such as *S. venezuelae* may conveniently be used, either by providing the unhydroxylated ketolide to the cells, or preferably by generating the desired ketolide through recombinant modification of these cells, preferably concomitantly with deleting the ability of the host cell to produce its own polyketide.

The invention provides libraries or individual modified forms, ultimately of polyketides, by generating modifications in the picromycin PKS or other naturally occurring PKS gene cluster so that the protein complexes produced by the cluster have altered activities in one or more respects, and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities. As will be further described below, the metes and bounds of this derivation can be described on both the protein level and the encoding nucleotide sequence level.

As described above, a modular PKS "derived from" the picromycin or other naturally occurring PKS includes a modular polyketide synthase (or its corresponding encoding gene(s)) that retains the scaffolding of all of the utilized portion of the naturally occurring gene. (Not all modules need be included in the constructs.) On the constant scaffold, at least one enzymatic activity is mutated, deleted or replaced, so as to alter the activity. Alteration results when these activities are deleted or are replaced by a different version of the activity, or simply mutated in such a way that a polyketide other than the natural product results from these collective activities. This occurs because there has been a resulting alteration of the starter unit and/or extender unit, and/or stereochemistry, and/or chain length or cyclization and/or reductive or dehydration cycle outcome at a corresponding position in the product polyketide. Where a deleted activity is replaced, the origin of the replacement activity may come from a corresponding activity in a different naturally occurring polyketide synthase or from a different region of the picromycin PKS. Any or all of the pic AI, pic AII, pic AIII, and pic AIV genes (nucleotides 70–13725, 13830–25049, 25133–29821, and 29924–33964 of SEQ ID NO:1) referred to as picA, picB, picC and picD genes respectively (see FIG. 3) may be included in the derivative or portions of any of these may be included; but the scaffolding of the resulting PKS protein is retained in whatever derivative is considered.

The derivative may contain preferably at least a thioesterase activity from the picromycin or other naturally occurring PKS gene cluster.

In summary, a polyketide synthase "derived from" the picromycin PKS includes those which contain the scaffolding encoded by all or the portion employed of the picromycin synthase gene, contains at least two modules that are functional, preferably three modules, and more preferably four or more modules and contains mutations, deletions, or replacements of one or more of the activities of these functional modules so that the nature of the resulting polyketide is altered. This definition applies both at the protein and genetic levels. Particular preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized.

Conversely, also included within the definition of PKS "derived from the picromycin PKS" are functional PKS modules or their encoding genes wherein at least one portion, preferably two portions, of the picromycin activities have been inserted. Exemplary, for example, is the use of the picromycin acyl transferase (AT) for module 2 which accepts a malonyl CoA extender unit rather than methyl malonyl CoA. Other examples include insertion of portions of noncondensation cycle enzymatic activities, or other regions of picromycin synthase activity. Again, the "derived from" definition applies to the PKS at both the genetic and protein levels.

Thus, there are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, or ethyl malonyl, etc. Third, the loading domain specificity will also have an effect on the resulting carbon skeleton of the polyketide. Thus, the loading domain may use a different starter unit, such as acetyl, propionyl, butyryl and the like. Fourth, the oxidation state at various positions of the polyketide will be determined by the dehydratase and reductase portions of the modules. This will determine the presence and location of ketone, alcohol, double bonds or single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Second, the specificity of the ketoreductase will determine the chirality of any β-OH. Finally, the enoyl reductase specificity for substituted malonyls as extender units will influence the result when there is a complete KR/DH/ER available.

In the working examples below, in manipulating the foregoing variables for varying loading domain specificity which controls the starter unit, a useful approach is to modify the KS activity in module 1 which results in the ability to incorporate alternative starter units as well as module 1 extended units. This approach was illustrated in PCT application US/96/11317, incorporated herein by reference, wherein the KS-I activity was inactivated through mutation. Polyketide synthesis is then initiated by feeding chemically synthesized analogs of module 1 diketide products. Working examples of this aspect are also presented hereinbelow.

Thus, the modular PKS systems, and in particular, the picromycin PKS system, permit a wide range of polyketides to be synthesized. As compared to the aromatic PKS systems, a wider range of starter units including aliphatic monomers (acetyl, propionyl, butyryl, isovaleryl, etc.), aromatics (aminohydroxybenzoyl), alicyclics (cyclohexanoyl), and heterocyclics (thiazolyl) are found in various macrocyclic polyketides. Recent studies have shown that modular PKSs have relaxed specificity for their starter units (Kao et al. *Science* (1994), supra). Modular PKSs also exhibit considerable variety with regard to the choice of extender units in each condensation cycle. The degree of β-ketoreduction following a condensation reaction has also been shown to be altered by genetic manipulation (Donadio et al. *Science* (1991), supra; Donadio, S. et al. *Proc Natl Acad Sci USA* (1993) 90:7119–7123). Likewise, the size of the polyketide product can be varied by designing mutants with the appropriate number of modules (Kao, C. M. et al. *J Am Chem Soc* (1994) 116:11612–11613). Lastly, these enzymes are particularly well-known for generating an impressive range of asymmetric centers in their products in a highly controlled manner. The polyketides and antibiotics produced by the methods of the present invention are typically single stereoisomeric forms. Although the compounds of the invention can occur as mixtures of stereoisomers, it is more practical to generate individual stereoisomers using this system. Thus, the combinatorial potential within modular PKS pathways based on any naturally occurring modular, such as the erythromycin, PKS scaffold is virtually unlimited.

In addition, the nature of the acyl transferase (AT) appears to determine the nature of the extended unit which is added by the module in question. As noted, picromycin module 2 contains an AT which uses malonyl CoA as an extender; the remaining modules utilize methyl malonyl CoA. This results in the absence of a methyl group at C10. By substituting AT activity-encoding regions from various PKS genes, or by mutagenizing the AT unit in a module of a host scaffolding PKS gene, the nature of the extender unit, and thus the nature of $R^1$–$R^6$ may readily be varied.

In general, the polyketide products of the PKS must be further modified, typically by hydroxylation and glycosylation, in order to exhibit antibiotic activity. As described above, hydroxylation results in the novel polyketides of the present invention which contain hydroxyl groups at C6 and/or C12. The presence of hydroxyl groups at these positions is thought to enhance the antibiotic activity. It is clear that glycosylation is important in antibiotic activity as well.

Methods for glycosylating the polyketides are generally known in the art; the glycosylation may be effected intracellularly by providing the appropriate glycosylation enzymes or may be effected in vitro using chemical synthetic means as described in parent application U.S. Ser. No. 09/073,538.

The antibiotic modular polyketides may contain any of a number of different sugars, although D-desosamine, or a close analog thereof, is most common. Erythromycin, picromycin, narbomycin and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al. *J Am Chem Soc* (1975) 97:3512, 3513. Other, apparently more stable, donors include glycosyl fluorides, thioglycosides, and trichloroacetimidates; Woodward, R. B. et al. *J Am Chem Soc* (1981) 103:3215; Martin, S. F. et al. *Am Chem Soc* (1997)

119:3193; Toshima, K. et al. *J Am Chem Soc* (1995) 117:3717; Matsumoto, T. et al. *Tetrahedron Lett* (1988) 29:3575. Glycosylation can also be effected using the macrolides as starting materials and using mutants of *S. erythraea* that are unable to synthesize the macrolides to make the conversion.

In general, the approaches to effecting glycosylation mirror those described above with respect to hydroxylation. The purified enzymes, isolated from native sources or recombinantly produced may be used in vitro. Alternatively, glycosylation may be effected intracellularly using endogenous or recombinantly produced intracellular glycosylases. In addition, synthetic chemical methods may be employed.

Methods to Construct Multiple Modular PKS Derived from a Naturally Occurring PKS The derivatives of a naturally occurring PKS can be prepared by manipulation of the relevant genes. A large number of modular PKS gene clusters have been mapped and/or sequenced, including erythromycin, soraphen A, rifamycin, and rapamycin, which have been completely mapped and sequenced, and FK506 and oleandomycin which have been partially sequenced, and candicidin, avermectin, and nemadectin which have been mapped and partially sequenced. Additional modular PKS gene clusters are expected to be available as time progresses. The present invention provides the picromycin PKS. These genes can be manipulated using standard techniques to delete or inactivate activity encoding regions, insert regions of genes encoding corresponding activities form the same or different PKS system, or otherwise mutated using standard procedures for obtaining genetic alterations. Of course, portions of, or all of, the desired derivative coding sequences can be synthesized using standard solid phase synthesis methods such as those described by Jaye et al., *J Biol Chem* (1984) 259:6331 and which are available commercially from, for example, Applied Biosystems, Inc.

In order to obtain nucleotide sequences encoding a variety of derivatives of the naturally occurring PKS, and thus a variety of polyketides for construction of a library, a desired number of constructs can be obtained by "mixing and matching" enzymatic activity-encoding portions, and mutations can be introduced into the native host PKS gene cluster or portions thereof. Components of the picromycin PKS are made available by the present invention.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *BioTechniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc Natl Acad Sci USA* (1982) 79:6409. PCR mutagenesis will also find use for effecting the desired mutations.

Random mutagenesis of selected portions of the nucleotide sequences encoding enzymatic activities can be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT application WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Suitable control sequences include those which function in eucaryotic and procaryotic host cells. Preferred host include fungal systems such as yeast and procaryotic hosts, but single cell cultures of, for example, mammalian cells could also be used. There is no particular advantage, however, in using such systems. Particularly preferred are yeast and procaryotic hosts which use control sequences compatible with Streptomyces spp. Suitable controls sequences for single cell cultures of various types of organisms are well known in the art. Control systems for expression in yeast, including controls which effect secretion are widely available are routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as tryptophan (trp), the β-lactamase (bla), bacteriophage lambda PL, and T5. In addition, synthetic promoters, such as the tac promoter (U.S. Pat. No. 4,551,433), can be used.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for screening cells successfully transformed by the present constructs.

The various PKS nucleotide sequences, or a cocktail of such sequences, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

As described above, particularly useful control sequences are those which themselves, or using suitable regulatory systems, activate expression during transition from growth to stationary phase in the vegetative mycelium. The system contained in the illustrative plasmid pRM5, i.e., the actI/actIII promoter pair and the actII-ORF4, an activator gene, is particularly preferred. Particularly preferred hosts are those which lack their own means for producing polyketides so that a cleaner result is obtained. Illustrative host cells of this type include the modified *S. coelicolor* CH999 culture described in PCT application WO 96/40968 and similar strains of *S. lividans*.

The expression vectors containing nucleotide sequences encoding a variety of PKS systems for the production of different polyketides are then transformed into the appropriate host cells to construct the library. In one straightforward approach, a mixture of such vectors is transformed into the selected host cells and the resulting cells plated into individual colonies and selected for successful transformants. Each individual colony will then represent a colony with the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

As disclosed in copending application Ser. No. 08/989, 332 filed Dec. 11, 1997, incorporated herein by reference, a wide variety of hosts can be used, even though some hosts natively do not contain the appropriate post-translational mechanisms to activate the acyl carrier proteins of the synthases. These hosts can be modified with the appropriate recombinant enzymes to effect these modifications.

The polyketide producing colonies can be identified and isolated using known techniques and the produced polyketides further characterized. The polyketides produced by these colonies can be used collectively in a panel to represent a library or may be assessed individually for activity.

The libraries can thus be considered at four levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; (3) the polyketides produced; and (4) antibiotics derived from the polyketides. Of course, combination libraries can also be constructed wherein members of a library derived, for example, from the erythromycin PKS can be considered as a part of the same library as those derived from, for example, the rapamycin PKS cluster.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art.

Alternatively, individual polyketide members of the library can be tested against a desired target. In this event, screens wherein the biological response of the target is measured can more readily be included.

The parent application herein describes the preparation of a large number of polyketides. These polyketides are useful intermediates in formation of compounds with antibiotic activity through hydroxylation and glycosylation reactions as described above. As indicated above, the individual polyketides are reacted with suitable sugar derivatives to obtain compounds of antibiotic activity. Antibiotic activity can be verified using typical screening assays such as those set forth in Lehrer, R. et al. *J Immunol Meth* (1991) 137:167–173.

New polyketides which are the subject of the invention are hydroxylated forms of those described in the parent application.

New antibiotics which are the subject of the invention include the hydroxylated and glycosylated forms of the polyketides described in the parent application.

The compounds of the present invention are thus optionally glycosylated forms of the polyketide set forth in formula (2) below which are hydroxylated at either the 6-carbon or the 12-carbon or both. The compounds of formula (2) can be prepared using six modules of a modular polyketide synthase, modified or prepared in hybrid form as herein described. These polyketides have the formula

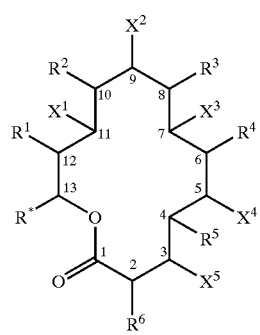

(2)

including the glycosylated and isolated stereoisomeric forms thereof;

wherein R* is a straight chain, branched or cyclic, saturated or unsaturated substituted or unsubstituted hydrocarbyl of 1–15C;

each of $R^1$–$R^6$ is independently H or alkyl (1–4C) wherein any alkyl at $R^1$ may optionally be substituted;

each of $X^1$–$X^5$ is independently $H_2$, HOH or =O; or each of $X^1$–$X^5$ is independently H and the compound of formula (2) contains a π-bond in the ring adjacent to the position of said X at 2–3, 4–5, 6–7, 8–9 and/or 10–11;

with the proviso that:

at least two of $R^1$–$R^6$ are alkyl (1–4C).

Preferred compounds comprising formula (2) are those wherein at least three of $R^1$–$R^5$ are alkyl (1–4C), preferably methyl or ethyl; more preferably wherein at least four of $R^1$–$R^5$ are alkyl (1–4C), preferably methyl or ethyl.

Also preferred are those wherein $X^2$ is $H_2$, =O or H▸ ... OH, and/or $X^3$ is H, and/or $X^1$ is OH and/or $X^4$ is OH and/or $X^5$ is OH.

Also preferred are compounds with variable R* when $R^1$–$R^5$ are methyl, $X^2$ is =O, and $X^1$, $X^4$ and $X^5$ are OH. The glycosylated forms of the foregoing are also preferred.

The following examples are intended to illustrate, but not to limit the invention.

Materials and Methods

General Techniques

Bacterial strains, plasmids, and culture conditions. *S. coelicolor* CH999 described in WO 95/08548, published Mar. 30, 1995 was used as an expression host. DNA manipulations were performed in *Escherichia coli* MC1061. Plasmids were passaged through *E. coli* ET12567 (dam dcm hsdS Cm$^r$) (MacNeil, D. J. *J Bacteriol* (1988) 170:5607) to generate unmethylated DNA prior to transformation of *S. coelicolor*. *E. coli* strains were grown under standard conditions. *S. coelicolor* strains were grown on R2YE agar plates (Hopwood, D. A. et al. *Genetic manipulation of Streptomyces. A laboratory manual*. The John Innes Foundation: Norwich, 1985). pRM5, also described in WO 95/08548, includes a colEI replicon, an appropriately truncated SCP2* Streptomyces replicon, two act-promoters to allow for bidirectional cloning, the gene encoding the actII-ORF4 activator which induces transcription from act promoters during the transition from growth phase to stationary phase, and appropriate marker genes. Engineered restriction sites facilitate the combinatorial construction of PKS gene clusters starting from cassettes encoding individual domains of naturally occurring PKSs.

When pRM5 is used for expression of PKS, (i) all relevant biosynthetic genes are plasmid-borne and therefore amenable to facile manipulation and mutagenesis in *E. coli*, (ii) the entire library of PKS gene clusters can be expressed in the same bacterial host which is genetically and physiologically well-characterized and presumably contains most, if not all, ancillary activities required for in vivo production of polyketides, (iii) polyketides are produced in a secondary metabolite-like manner, thereby alleviating the toxic effects of synthesizing potentially bioactive compounds in vivo, and (iv) molecules thus produced undergo fewer side reactions than if the same pathways were expressed in wild-type organisms or blocked mutants.

Manipulation of DNA and organisms. Polymerase chain reaction (PCR) was performed using Taq polymerase (Perkin Elmer Cetus) under conditions recommended by the enzyme manufacturer. Standard in vitro techniques were used for DNA manipulations (Sambrook, et al. *Molecular Cloning: A Laboratory Manual* (Current Edition)). *E. coli* was transformed with a Bio-Rad *E. Coli* Pulsing apparatus using protocols provided by Bio-Rad. *S. coelicolor* was transformed by standard procedures (Hopwood, D. A. et al. *Genetic manipulation of streptomyces. A laboratory manual*. The John Innes Foundation: Norwich, 1985) and transformants were selected using 2 mL of a 500 μg/ml thiostrepton overlay.

EXAMPLE 1

Construction of the Complete Picromycin PKS

Cosmid pKOS023-27 (SEQ ID NO:1) was isolated from a genomic library of *S. venezuelae*. The structure of pKOS023-27 (SEQ ID NO:1) is shown in FIG. 5 and confirms that this contains the complete set of open reading frames corresponding to the picromycin PKS.

The identity of the sequences in this cosmid with those encoding the picromycin PKS was confirmed by using the 2.4 kb EcoRI/KpnI fragment and the 2.1 kb KpnI/XhoI fragment isolated from the cosmid ligated together and cloned into pLitmus 28 to give pKOS039-07. The 4.5 kb HindIII/SpeI fragment from this plasmid was cloned into the 2.5 kb HindIII/NheI fragment of pSet 152 which contains the *E. coli* origins for replication and an apramycin-resistant gene to obtain pKOS039-16. This vector was used to transform *S. venezuelae* to apramycin-resistance. The transformed *S. venezuelae* lost its ability to produce picromycin indicating that the plasmid was integrated into the appropriate location on the chromosome. Either loss of the integrated vector or introduction of the picA gene on pWHM3 under the control of the ermE* on plasmid pKOS039-27 were able to restore picromycin synthesis, although at a lower level.

EXAMPLE 2

Cloning of picK, the Narbomycin 12-Hydroxylase Gene from *S. venezuelae*

Genomic DNA isolated from *Streptomyces venezuelae* ATCC15439 using standard procedures (100 µg) was partially digested with Sau3AI endonuclease to generate fragments ca. 40-kbp in length. SuperCosI (Stratagene) DNA cosmid arms were prepared as directed by the manufacturer. A cosmid library was prepared by ligating 2.5 µg of the digested genomic DNA with 1.5 µg of cosmid arms in a 20 µL reaction. One microliter of the ligation mixture was propagated in *E. coli* XL 1-Blue MR (Stratagene) using a GigapackIII XL packaging extract kit (Stratagene). The resulting library of ca. 3000 colonies was plated on a 10×150 mm agar plate and replicated to a nylon membrane.

The library was initially screened by direct colony hybridization with a DNA probe specific for ketosynthase domains of polyketide synthases. Colonies were alkaline lysed, and the DNA was crosslinked to the membrane using UV irradiation. After overnight incubation with the probe at 42° C., the membrane was washed twice at 25° C. in 2×SSC buffer+0.1% SDS for 15 minutes, followed by two 15 minutes washes with 2×SSC buffer at 55° C. Approximately 30 colonies gave positive hybridization signals. Several candidate cosmids were selected and divided into two classes based on restriction digestion patterns. A representative cosmid was selected from each class for further analysis.

Each cosmid was probed by Southern hybridization using a labeled DNA fragment amplified by PCR from the *Saccharopolyspora erythraea* 12-hydroxylase gene, eryK. The cosmids were digested with BamHI endonuclease and electrophoresed on a 1% agarose gel, and the resulting fragments were transferred to a nylon membrane. The membrane was incubated with the eryK probe overnight at 42° C., washed twice at 25° C. in 2×SSC buffer+0.1% SDS for 15 minutes, followed by two 15 minutes washes with 2×SSC buffer at 50° C. One cosmid, pKOS023-26 (SEQ ID NO:9,11,15,19 and 22) produced a 3.0-kbp fragment which hybridized with the probe under these conditions. This fragment was subcloned into the PCRscript (Stratagene) cloning vector to yield plasmid pKOS023-28, and sequenced. A ca. 1.2-kbp gene, designated pick, was found having homology to eryK and other known macrolide cytochrome P450 hydroxylases.

The complete sequence of the open reading frame and the deduced amino acid sequence are shown in FIG. 6, pages 4–5 (nucleotide sequence nt 1356–2606 of SEQ ID NO:9) and page 7 (amino acid sequence SEQ ID NO:13).

In addition, the glycosylase was retrieved on the cosmid KOS023-26 and the open reading frame and deduced amino acid sequence are shown in FIG. 5, page 13 (nucleotide sequence, nt 36159–37439 (SEQ ID NO:9)) and page 23 (amino acid sequence (SEQ ID NO:8))

EXAMPLE 3

Construction of picK Expression Plasmids for *E. coli*

A. The picK gene was PCR amplified using oligonucleotide primers (forward 5'-TTGCATGCATATGCGCCGTACC CAGCAGGGAACGACC (SEQ ID NO:24); reverse 5'-TTGAATTCTCAACTAGTACGGCGGCCCGCCTCCC GTCC) (SEQ ID NO:25).

These primers alter the Streptomyces GTG start codon to ATG and introduce a SpeI site at the C-terminal end of the gene, resulting in the substitution of a serine for the terminal glycine amino acid residue. Following subcloning of the PCR product, the 1.3 kb gene fragment was cloned into the NdeI/XhoI sites of the T7 expression vector pET22b (Novagen, Madison, Wis.) to generate pKOS023-61. A short linker fragment encoding 6 histidine residues and a stop codon was introduced into the SpeI site to obtain pKOS023-68.

Alternatively, the PCR product was cloned into the SrfI site of PCRscript (Stratagene) to generate pKOS023-60. This plasmid was digested with NdeI/XhoI and the resulting 1.3 kb fragment ligated with correspondingly restricted pET22V vector (Invitrogen) to obtain pKOS023-61.

EXAMPLE 4

Hydroxylation of Narbomycin by Narbomycin 12-Hydroxylase

Narbomycin was converted to picromycin with a crude cell-free extract from *E. coli* expressing picK. Narbomycin was purified from a culture of *S. narbonensis*, and upon LC/MS analysis gave a single peak of $[M+H]^+$=510. Plasmid pKOS023-61 (See Example 3) was transformed into *E. coli* BL21-DE3. Successful transformants were grown in LB-containing carbenicillin (100 µg/ml) at 37° C. to an $OD_{600}$ of 0.6. Isopropyl-b-D-thiogalactopyranoside (IPTG) was added to a final concentration of 1 mM and the cells were grown for an additional 3 hours before harvesting. The cells were collected by centrifugation and frozen at −80° C. A control culture of BL21 -DE3 containing the vector plasmid pET21c (Invitrogen) was prepared in parallel.

The frozen BL21-DE3/pKOS023-61 cells were thawed, suspended in 2 µL of cold cell disruption buffer (5 mM imidazole, 500 mM NaCl, 20 mM Tris/HCl, pH 8.0) and sonicated to facilitate lysis. Cellular debris and supernatant were separated by centrifugation and subjected to SDS-PAGE on 10–15% gradient gels, with Coomassie Blue staining, using a Pharmacia Phast Gel Electrophoresis system. the soluble crude extract from BL21-DE3/pKOS023-61 contained a Coomassie stained band of $M_r$~46 kDa which was absent in the control strain BL21-DE3/pET21c.

The hydroxylase activity of the picK protein was assayed as follows. The crude supernatant (20 µl) was added to a reaction mixture (100 µl total volume) containing 50 mM Tris/HCl (pH 7.5), 20 µM spinach ferredoxin, 0.025 Unit of spinach ferredoxin:$NADP^+$ oxidoreductase, 0.8 Unit of glucose-6-phosphate dehydrogenase, 1.4 mM $NADP^+$, 7.6 mM glucose-6phosphate, and 20 nmol of narbomycin. The reaction was allowed to proceed for 105 minutes at 30° C. Half of the reaction mixture was loaded onto an HPLC, and the effluent was analyzed by evaporative light scattering (ELSD) and mass spectrometry. The control extract (BL21-DE3/pET21c) was processed identically. The BL21-DE3/pKOS023-61 reaction contained a compound not present in the control having the same retention time, molecular weight and mass fragmentation pattern as picromycin ([M+H]$^+$= 526). The conversion of narbormycin to picromycin under these conditions was estimated to be greater than 90% by ELSD peak area.

EXAMPLE 5

Preparation of Cell Extracts and Purification of PicK/6-His

To produce His-tailed hydroxylase, pKOS023-68, described in Example 3, was transfected into *E. coli* BL21 (DE3) and cultured as described in Example 4. The cells were harvested and the picK protein purified.

All purification steps were performed at 4° C. *E. coli* cell pellets were suspended in 32 μL of cold binding buffer (20 mM Tris/HCl, pH 8.0, 5 mM imidazole, 500 mM NaCl) per mL of culture and lysed by sonication. For analysis of *E. coli* cell-free extracts, the cellular debris was removed by low-speed centrifugation and the supernatant was used directly in assays. For purification of PicK/6-His, the supernatant was loaded (0.5 mL/min.) onto a 5 mL HiTrap Chelating column (Pharmacia, Piscataway, N.J.), equilibrated with binding buffer. The column was washed with 25 μL of binding buffer and the protein was eluted with a 35 μL linear gradient (5–500 mM imidazole in binding buffer). Column effluent was monitored at 280 nm and 416 nm. Fractions corresponding to the 416 nm absorbance peak were pooled and dialyzed against storage buffer (45 mM Tris/HCl, pH 7.5, 0.1 mM EDTA, 0.2 mM DTT, 10% glycerol). The purified 46 kDa protein was analyzed by SDS-PAGE using coomassie blue staining, and enzyme concentration and yield were determined.

EXAMPLE 6

6-Hydroxylation of 3.6-dideoxy-3-oxoerythronolide B Using the eryF Hydroxylase The 6-hydroxylase encoded by eryF was expressed in *E. coli*, and partially purified.

The hydroxylase (100 pmol in 10 μL) was added to a reaction mixture (100 μl total volume) containing 50 mM Tris/HCl (pH 7.5), 20 μM spinach ferredoxin, 0.025 Unit of spinach ferredoxin:NADP$^+$ oxidoreductase, 0.8 Unit of glucose-6-phosphate dehydrogenase, 1.4 mM NADP$^+$, 7.6 mM glucose-6-phosphate, and 10 nmol 6-deoxyerythronolide B. The reaction was allowed to proceed for 90 minutes at 30° C. Half of the reaction mixture was loaded onto an HPLC, and the effluent was analyzed by mass spectrometry. This revealed production of erythronolide B as evidenced by a new peak eluting earlier in the gradient and showing [M+H]$^+$=401. Conversion was estimated at 50% based on relative total ion counts.

EXAMPLE 7

Kinetic Assays with Narbomycin

Narbomycin was purified from a culture of *Streptomyces narbonensis* ATCC19790. reactions for kinetic assays (100 μL) consisted of 50 mM Tris/HCl (pH 7.5), 100 μM spinach ferredoxin, 0.025 Unit of spinach ferredoxin:NADP$^+$ oxidoreductase, 0.8 U glucose-6-phosphate dehydrogenase, 1.4 mM NADP$^+$, 7.6 mM glucose-6-phosphate, 20–500 μM narbomycin substrate, and 50–500 nM of picK. The reaction proceeded at 30° C. and samples were withdrawn for analysis at 5, 10, 15, and 90 minutes. Reactions were stopped by heating to 100° C. for 1 minute and denatured protein was removed by centrifugation. Depletion of narbomycin and formation of picromycin were determined by high performance liquid chromatography (HPLC, Beckman C-18 0.46× 15 cm column) coupled to atmosphere pressure chemical ionization (APCI) mass spectroscopic detection (Perkin Elmer/Sciex API 100) and evaporative light scattering detection (Alltech 500 ELSD).

EXAMPLE 8

Measurement of Antibacterial Activity

Antibacterial activity was determined using either disk diffusion assays with *Bacillus cereus* as the test organism or by measurement of minimum inhibitory concentrations (MIC) in liquid culture against sensitive and resistant strains of *Staphylococcus pneumoniae*.

EXAMPLE 9

Expression of the picK Gene Encoding the Hydroxylase in *S. narbonensis*

In order to improve the yield and purity of picromycin produced in *S. narbonensis*, the picK gene was expressed in this host.

The picK gene was amplified from pKOS023-26 (SEQ ID NOs:9, 11, 15, 19 and 22) using the primers:

N3903: 5'-TCCTCTAGACGTTTCCGT-3'
N3904: 5'-TGAAGCTTGAATTCAACCGGT-3' to obtain a 1.29 kb product. The product was treated with XbaI/HindIII and cloned into similarly treated with pWHMM1104 to provide pKOS039-01 placing the gene under the ermE* promoter. The resulting plasmid was transformed into purified stocks of *S. narbonensis* by protoplast fusion and electroporation. The transformants were grown in suitable media and shown to convert narbomycin to picromycin at a yield of over 95%.

EXAMPLE 10

Expression of Desosaminyl Transferase into *S. erythraea*

To provide *S. erythraea* with suitable additional enzymes for glycosylation, the picG gene (desosaminyl transferase) was amplified from pKOS023-27 (SEQ ID NO:1) using the primers:

N3917: 5'-CCCTGCAGCGGCAAGGAAGGACACG ACGCCA-3' (SEQ ID NO:28)
N3918: 5'-AGGTCTAGAGCTCAGTGCCGGGCGTC GGCCGG-3' (SEQ ID NO:29)

to give a 1.5 kb product which was treated with PstI/XbaI and ligated into similarly treated pKOS039-06 along with the PstI/HindIII fragment of pWHM1104 to provide pKOS039-14 placing the picG gene after DEBS module 2 and under the control of the ermE* promoter. The vector was then transformed into *S. erythraea* by treating the protoplast with the plasmid.

EXAMPLE 11

Construction of Hybrid Erythromycin/Picromycin PKS

Table 1 shows a summary of constructs which are hybrids of portions of the picromycin PKS and portions of rapamycin and/or erythromycin PKS. In the first constructs, pKOS039-18 and pKOS039-19, the picromycin module 6ACP and thioesterase replaced the corresponding region as well as the KR in the erythromycin cluster; in pKOS039-19 the erythromycin cluster further contains a KS1 knock-out—i.e., the ketosynthase in module 1 was disabled. The KS1 knock-out is described in detail in PCT application no. US96/11317, the disclosure of which is incorporated herein by reference. To construct pKOS039-18, the 2.33 kb BamHI/EcoRI fragment of pKOS023-27 which contains the desired sequence was subcloned on pUC 19 and used as the template for PCR. The primers were
N3905: 5'-TTTATGCATCCCGCGGGTCCCGGCGAG-3' (SEQ ID NO:30)
N3906: 5'-TCAGAATTCTGTCGGTCACTTGCCCGC-3' (SEQ ID NO:31)

The 1.6 kb PCR product was digested with PstI/EcoRI and cloned into the corresponding sites of pKOS015-52 and pLitmus 28 to provide pKOS039-12 and pKOS039-13, respectively. The BglII/EcoRI fragment of pKOS039-12 was cloned into pKOS011-77 which contains wild-type erythromycin gene cluster and into JRJ2 which corresponds to this plasmid that contains the KSI knock-out. pKOS039-18 and pKOS039-19, respectively, were obtained.

These two plasmids were transfected into *S. coelicolor* CH999 by protoplast fusion.

The resulting cells were cultured under conditions whereby expression was obtained and the expected polyketides were obtained from this culture. From pKOS039-18, the product was 3-keto-6 dEB. From pKOS039-19, when activated isobutyrate was used as the starting material, propyl-3-keto-6 dEB was obtained.

Table 1 shows additional constructs and the nature of the expected product. When CH999 is used as a host, the product is the unconverted polyketide; when cultured in strain K39-03, which contains the required hydroxylase and glycosylation enzymes, the corresponding antibiotics were obtained.

TABLE 1

| # | Substrate | 1 | 2 | 3 | 4 | 5 | 6 | Host | Product |
|---|---|---|---|---|---|---|---|---|---|
| 1 | — | ery | ery | ery | ery | ery | ery KR-ACP-TE → pic-ACP-TE | CH999 | 3-keto-6-dEB |
| 2 | butyrate | ery KSI* | ery | ery | ery | ery | ery KR-ACP-TE → pic-ACP-TE | CH999 | propyl-3-keto-6-dEB |
| 3 | — | pic | pic AT → ery AT | ery | ery | ery | ery KR-ACP-TE → pic-ACP-TE | CH999 | 10-methyl narbonolide |
| 4 | butyrate | pic KSI* | pic AT → ery AT | ery | ery | ery | ery KR-ACP-TE → pic-ACP-TE | CH999 | propyl-10-methyl narbonolide |
| 5 | — | ery | ery KR → rap DH/KR | ery | ery | ery | ery KR-ACP-TE → pic-ACP-TE | CH999 | 10-methyl narbonolide |
| 6 | butyrate | ery KSI* | ery KR → rap DH/KR | ery | ery | ery | ery KR-ACP-TE → pic-ACP-TE | CH999 | propyl-10-methyl narbonolide |
| 7 | butyrate | pic KSI* | pic AT → ery AT | ery | ery | ery | ery | CH999 | propyl-10,11-dehydro 6dEB |
| 8 | butyrate | pic KSI* | pic AT → ery AT | pic | pic | pic | pic | K3903 | propyl-10-methyl picromycin |
| 9 | — | pic | pic AT → ery AT | pic | pic | pic | pic | K3903 | 10-methyl picromycin |
| 10 | — | ery | ery | ery | ery | ery | ery KR-ACP-TE → pic ACP-TE | K3903 | 5-sugar-3-keto-6-dEB |

In Table 1 "ery" refers to the numbered module from the erythromycin PKS; "pic" refers to the relevant module on the picromycin PKS. The notations under the designations indicate any alterations that were made in the module. Thus, embodiment #1 that described hereinabove where the KR-ACP-TE of module 6 of erythromycin was replaced by the ACP-TE corresponding portion of module 6 of the picromycin PKS. The CH999 host does not glycosylate the corresponding ketolides, but K39-03 has this ability. When module 1 has a KS1 knock-out (symbolized KS1*) butyrate was supplied as the substrate, leading to the corresponding ketolide or antibiotic with a propyl chain at on 13.

What is claimed is:

1. An isolated nucleic acid which comprises a nucleotide sequence encoding at least one activity selected from a group consisting of ketosynthase (KS), acyltransferase (AT), acyl carrier protein (ACP), dehydratase (DH), enoyl reductase (ER), and ketoreductase (KR) activity of a picromycin polyketide synthase (PKS) from Streptomyces venezuelae encoded by a nucleic acid sequence of SEQ ID NO:1.

2. The isolated nucleic acid of claim 1 which comprises the nucleotide sequence encoding at least one module of the picromycin PKS from Streptomyces venezuelae.

3. The isolated nucleic acid of claim 2 which comprises the nucleotide sequence encoding at least one open reading frame of a gene cluster in Streptomyces venezuelae that encodes a picromycin PKS of SEQ ID NO:1.

4. A recombinant nucleic acid molecule which comprises a first nucleotide sequence encoding at least one activity selected from a group consisting of ketosynthase (KS), acyltransferase (AT), acyl carrier protein (ACP), dehydratase (DH), enoyl reductase (ER), and ketoreductase (KR) activity of a picromycin polyketide synthase (PKS) from Streptomyces venezuelae encoded by a nucleic acid sequence of SEQ ID NO:1 operably linked to at least one second nucleotide sequence that effects the expression of said first nucleotide sequence in a recombinant host.

5. The recombinant nucleic acid molecule of claim 4 wherein the first nucleotide sequence encodes at least one module of the picromycin PKS from Streptomyces venezuelae.

6. The recombinant nucleic acid molecule of claim 4 wherein the first nucleotide sequence encodes the protein encoded by at least one open reading frame selected from a gene cluster in Streptomyces venezuelae that encodes a picromycin PKS.

7. The nucleic acid molecule of claim 4 wherein said second nucleotide sequence is capable of effecting expression in yeast, E coli or Streptomyces host cells.

8. The nucleic acid molecule of claim 5 wherein said second nucleotide sequence is capable of effecting expression in yeast, E. coli or Streptomyces host cells.

9. The nucleic acid molecule of claim 6 wherein said second nucleotide sequence is capable of effecting expression in yeast, E. coli or Streptomyces host cells.

10. Recombinant host cells containing the recombinant nucleic acid molecule of claim 4.

11. Recombinant host cells containing the recombinant nucleic acid molecule of claim 5.

12. Recombinant host cells containing the recombinant nucleic acid molecule of claim 6.

13. A method to produce a protein having at least one activity of a picromycin PKS from Streptomyces venezuelae which method comprises culturing the cells of claim 11 under conditions wherein a protein having such activity is produced.

14. The recombinant nucleic acid molecule of claim 5 that encodes a hybrid modular PKS composed of a portion of an erythromycin PKS and a portion of the picromycin PKS.

15. A host cell modified to contain the recombinant nucleic acid molecule of claim 14.

16. A method to prepare a functional polyketide synthase which method comprises culturing the cells of claim 15 under conditions wherein said polyketide synthase is produced.

* * * * *